US010987324B2

(12) United States Patent
Nguyen et al.

(10) Patent No.: US 10,987,324 B2
(45) Date of Patent: Apr. 27, 2021

(54) METHODS AND COMPOSITIONS FOR THE TREATMENT OF SEIZURE-RELATED DISORDERS

(71) Applicant: Adamas Pharmaceuticals, Inc., Emeryville, CA (US)

(72) Inventors: Jack Nguyen, Berkeley, CA (US); David Chernoff, Sausalito, CA (US); Sangita Ghosh, Foster City, CA (US); Gregory T. Went, Mill Valley, CA (US); Timothy J. Fultz, Jasper, GA (US)

(73) Assignee: Adamas Pharmaceuticals, Inc., Emeryville, CA (US)

( * ) Notice: Subject to any disclaimer, the term of this patent is extended or adjusted under 35 U.S.C. 154(b) by 0 days.

(21) Appl. No.: 15/863,746

(22) Filed: Jan. 5, 2018

(65) Prior Publication Data

US 2018/0161282 A1    Jun. 14, 2018

Related U.S. Application Data

(62) Division of application No. 15/396,161, filed on Dec. 30, 2016.
(Continued)

(51) Int. Cl.
*A61K 31/165* (2006.01)
*A61K 9/16* (2006.01)
(Continued)

(52) U.S. Cl.
CPC .......... *A61K 31/165* (2013.01); *A61K 9/0053* (2013.01); *A61K 9/16* (2013.01);
(Continued)

(58) Field of Classification Search
CPC ... A61K 31/165; A61K 9/1635; A61K 9/5026
See application file for complete search history.

(56) References Cited

U.S. PATENT DOCUMENTS

| 3,642,775 A | 2/1972 | Schindler |
| 4,369,172 A | 1/1983 | Schor et al. |

(Continued)

FOREIGN PATENT DOCUMENTS

| DE | 10-2008-059-155 A1 | 6/2010 |
| EP | 0 524 968 A1 | 2/1993 |

(Continued)

OTHER PUBLICATIONS https://www.pharmpress.com/files/docs/ft_pharmaceutics_drug_delivery_sample.pdf, sample chapter from "Pharmaceuticals—Drug Delivery and Targeting," published Jun. 2012, website visited Feb. 4, 2019. (Year: 2012).*

(Continued)

*Primary Examiner* — Craig D Ricci
*Assistant Examiner* — Janet L Coppins
(74) *Attorney, Agent, or Firm* — Cooley LLP

(57) ABSTRACT

Compositions and methods are provided for administering a pharmaceutical composition to a human patient. Compositions are administered to a human patient orally, once daily, at a therapeutically effective dose. The pharmaceutical compositions comprise a drug selected from the group consisting of brivaracetam, divalproex, lacosamide, levetiracetam, oxcarbazepine, vigabatrin, and pharmaceutically acceptable salts of any of the foregoing, and at least one excipient. At least one of said at least one excipients modifies the release of said drug to provide an extended release form. The pharmaceutical composition have pharmacokinetic properties recited in the claims.

18 Claims, 20 Drawing Sheets

Related U.S. Application Data

(60) Provisional application No. 62/273,187, filed on Dec. 30, 2015.

(51) Int. Cl.

| | |
|---|---|
| *A61K 9/50* | (2006.01) |
| *A61K 31/4015* | (2006.01) |
| *A61K 9/00* | (2006.01) |
| *A61K 31/19* | (2006.01) |
| *A61K 31/192* | (2006.01) |
| *A61P 25/08* | (2006.01) |

(52) U.S. Cl.
CPC .......... *A61K 9/5026* (2013.01); *A61K 9/5042* (2013.01); *A61K 9/5047* (2013.01); *A61K 9/5078* (2013.01); *A61K 31/19* (2013.01); *A61K 31/192* (2013.01); *A61K 31/4015* (2013.01); *A61P 25/08* (2018.01); *A61K 9/1635* (2013.01)

(56) References Cited

U.S. PATENT DOCUMENTS

| | | | |
|---|---|---|---|
| 4,837,223 A | 6/1989 | Gobert et al. |
| 4,897,268 A | 6/1990 | Tice et al. |
| 4,943,639 A | 7/1990 | Gobert et al. |
| 4,988,731 A | 1/1991 | Meade |
| 5,212,326 A | 5/1993 | Meade |
| 5,358,721 A | 10/1994 | Guittard et al. |
| 5,378,729 A | 1/1995 | Kohn et al. |
| 5,395,626 A | 3/1995 | Kotwal et al. |
| 5,422,120 A | 6/1995 | Kim |
| 5,422,123 A | 6/1995 | Conte et al. |
| 5,601,845 A | 2/1997 | Buxton et al. |
| 5,654,301 A | 8/1997 | Kohn et al. |
| 5,773,475 A | 6/1998 | Kohn |
| 5,863,558 A | 1/1999 | Jao et al. |
| 5,876,750 A | 3/1999 | Jao et al. |
| 5,906,832 A | 5/1999 | Jao et al. |
| 5,912,013 A | 6/1999 | Rudnic et al. |
| 5,955,103 A | 9/1999 | Jao et al. |
| 6,048,899 A | 4/2000 | Kohn et al. |
| 6,107,492 A | 8/2000 | Futagawa et al. |
| 6,194,000 B1 | 2/2001 | Smith et al. |
| 6,210,712 B1 | 4/2001 | Edgren et al. |
| 6,217,905 B1 | 4/2001 | Edgren et al. |
| 6,511,678 B2 | 1/2003 | Qiu et al. |
| 6,528,090 B2 | 3/2003 | Qin et al. |
| 6,627,223 B2 | 9/2003 | Percel et al. |
| 6,713,086 B2 | 3/2004 | Qiu et al. |
| 6,713,635 B2 | 3/2004 | Surtees et al. |
| 6,720,004 B2 | 4/2004 | Qiu et al. |
| RE38,551 E | 7/2004 | Kohn |
| 6,784,197 B2 | 8/2004 | Differding et al. |
| 6,911,461 B2 | 6/2005 | Differding et al. |
| 6,913,768 B2 | 7/2005 | Couch et al. |
| 6,919,373 B1 | 7/2005 | Lam et al. |
| 6,923,800 B2 | 8/2005 | Chen et al. |
| 6,929,803 B2 | 8/2005 | Wong et al. |
| 6,930,128 B2 | 8/2005 | D'Amato et al. |
| 6,939,556 B2 | 9/2005 | Lautenbach |
| 7,037,525 B2 | 5/2006 | Schliitermann |
| 7,358,276 B2 | 4/2008 | Differding et al. |
| 7,692,028 B2 | 4/2010 | Differding et al. |
| 7,718,161 B2 | 5/2010 | Stoehr |
| 7,858,122 B2 | 12/2010 | Kshirsagar et al. |
| 7,863,316 B2 | 1/2011 | Kshirsagar et al. |
| 7,884,134 B2 | 2/2011 | Riedner et al. |
| 8,119,148 B2 | 2/2012 | Sigg et al. |
| 8,389,578 B2 | 3/2013 | Went et al. |
| 8,435,564 B2 | 5/2013 | Eeckman et al. |
| 8,440,861 B2 | 5/2013 | Duran Lopez et al. |
| 8,460,712 B2 | 6/2013 | Fanara et al. |
| 8,604,075 B2 | 12/2013 | Gallagher et al. |
| 8,809,585 B2 | 8/2014 | Riedner et al. |
| 10,149,818 B2 | 12/2018 | Cawello et al. |
| 2005/0277579 A1 | 12/2005 | Krishnan et al. |
| 2006/0100157 A1 | 5/2006 | Rauschkolb-Loffler et al. |
| 2006/0135437 A1 | 6/2006 | Stoehr et al. |
| 2006/0142398 A1 | 6/2006 | Went et al. |
| 2006/0165745 A1 | 7/2006 | Chew et al. |
| 2006/0189694 A1 | 8/2006 | Went et al. |
| 2006/0252788 A1 | 11/2006 | Went et al. |
| 2007/0042969 A1 | 2/2007 | Rauschkolb-Loffler et al. |
| 2007/0043120 A1 | 2/2007 | Beyreuther et al. |
| 2007/0048372 A1 | 3/2007 | Beyreuther et al. |
| 2007/0071819 A1 | 3/2007 | Kesarwani et al. |
| 2007/0197657 A1 | 8/2007 | Beyreuther et al. |
| 2008/0227743 A1 | 9/2008 | Nguyen et al. |
| 2008/0280835 A1 | 11/2008 | Beyreuther et al. |
| 2009/0131508 A1 | 5/2009 | Verdru |
| 2009/0298947 A1 | 12/2009 | Mundorfer et al. |
| 2010/0120906 A1 | 5/2010 | Nadjsombati |
| 2010/0240576 A1 | 9/2010 | Stoehr |
| 2010/0256179 A1 | 10/2010 | Stöhr |
| 2010/0260716 A1 | 10/2010 | Stöhr et al. |
| 2010/0324144 A1 | 12/2010 | Heers et al. |
| 2011/0021786 A1 | 1/2011 | Schenkel et al. |
| 2011/0091547 A1 | 4/2011 | Eeckman et al. |
| 2011/0189273 A1 | 8/2011 | Went et al. |
| 2011/0250282 A1 | 10/2011 | Fanara et al. |
| 2011/0275693 A1 | 11/2011 | Cuypers et al. |
| 2011/0281929 A1 | 11/2011 | Cuypers et al. |
| 2012/0040006 A1 | 2/2012 | Eeckman et al. |
| 2012/0219631 A1 | 8/2012 | Kulkarni et al. |
| 2012/0225119 A1 | 9/2012 | Beyreuther et al. |
| 2013/0039957 A1 | 2/2013 | Kasu et al. |
| 2013/0251803 A1* | 9/2013 | Cawello .............. A61K 9/1635 424/474 |
| 2013/0251813 A1 | 9/2013 | Cawello et al. |
| 2014/0066515 A1 | 3/2014 | Heers et al. |
| 2014/0128377 A1 | 5/2014 | Stöhr |
| 2014/0128378 A1 | 5/2014 | Stöhr |
| 2014/0142140 A1 | 5/2014 | Bird |
| 2015/0104507 A1 | 4/2015 | Cawello et al. |
| 2017/0189342 A1 | 7/2017 | Nguyen et al. |
| 2019/0029968 A1 | 1/2019 | Kulkarni et al. |

FOREIGN PATENT DOCUMENTS

| | | |
|---|---|---|
| JP | 2006-124385 A | 5/2006 |
| WO | WO-91/14445 A1 | 10/1991 |
| WO | WO-95/13796 A1 | 5/1995 |
| WO | WO-2006/036007 A2 | 4/2006 |
| WO | WO-2006/036007 A3 | 4/2006 |
| WO | WO-2006/131322 A2 | 12/2006 |
| WO | WO-2006/131322 A3 | 12/2006 |
| WO | WO-2007/120485 A2 | 10/2007 |
| WO | WO-2007/120485 A3 | 10/2007 |
| WO | WO-2008/086492 A1 | 7/2008 |
| WO | WO-2009/146325 A1 | 12/2009 |
| WO | WO-2010/009433 A1 | 1/2010 |
| WO | WO-2010/018408 A2 | 2/2010 |
| WO | WO-2010/018408 A3 | 2/2010 |
| WO | WO-2010/060624 A2 | 6/2010 |
| WO | WO-2010/060624 A3 | 6/2010 |
| WO | WO-2010/089372 A1 | 8/2010 |
| WO | WO-2011/055385 A1 | 5/2011 |
| WO | WO-2011/101863 A2 | 8/2011 |
| WO | WO-2011/101863 A3 | 8/2011 |
| WO | WO-2011/135430 A1 | 11/2011 |
| WO | WO-2012/072256 A2 | 6/2012 |
| WO | WO-2012/072256 A3 | 6/2012 |
| WO | WO-2013/036224 A1 | 3/2013 |
| WO | WO-2014/163314 A1 | 10/2014 |
| WO | WO-2014/180895 A1 | 11/2014 |
| WO | WO-2014/180912 A1 | 11/2014 |
| WO | WO-2014/180920 A1 | 11/2014 |
| WO | WO-2015/079010 A2 | 6/2015 |

(56) References Cited

FOREIGN PATENT DOCUMENTS

WO    WO-2015/079010 A3    6/2015
WO    WO-2017/117569 A1    7/2017

OTHER PUBLICATIONS

Declaration of Prior Invention Under 37 C.F.R. §1.131 submitted in U.S. Appl. No. 13/990,861 with Exhibits A-D, 29 total pages.
Hedaya, M.A. (2012). "Drug pharmacokinetics following single oral drug administration: The rate of drug absorption," Chapter 9 in *Basic Pharmacokinetics*, Second Edition, CRC Press Pharmacy Education Series, pp. 125-136.
International Search Report dated May 11, 2017, for PCT Application No. PCT/US2016/069581, filed on Dec. 30, 2016, 5 pages.
Written Opinion of the International Searching Authority dated May 11, 2017, for PCT Application No. PCT/US2016/069581, filed on Dec. 30, 2016, 6 pages.
Hofstra, W.A. et al. (2009). "Temporal distribution of clinical seizures over the 24-h day: A retrospective observational study in a tertiary epilepsy clinic," *Epilepsia* 50:2019-2026.
Non-Final Office Action dated Mar. 20, 2018, for U.S. Appl. No. 15/396,161, filed Dec. 30, 2016, 11 pages.
Siepmann, F. et al. (2008). "Polymer blends for controlled release coatings," Journal of Controlled Release 125:1-15.
Final Office Action dated Jan. 23, 2019, for U.S. Appl. No. 15/396,161, filed Dec. 30, 2016, 12 pages.
Non-Final Office Action dated Oct. 3, 2019, for U.S. Appl. No. 15/396,161, filed Dec. 30, 2016, 12 pages.
Ummadi, S. et al. (2013). "Overview on controlled release dosage form," Int. J. Pharma Sciences 3:258-269.
Beyreuther, B.K. et al. (2007). "Lacosamide: A review of preclinical properties," CNS Drug Reviews 13:21-42.
Craig, P.N. (1953). "Synthesis of ion exchange resins," Annals of the New York academy of sciences 57:67-78.
Errington, A.C. et al. (2008). "The investigational anticonvulsant lacosamide selectively enhances slow inactivation of voltage—Gated sodium channels," Mol. Pharmacol. 73:157-169.
Final Office Action dated Jun. 23, 2020, for U.S. Appl. No. 15/396,161, filed Dec. 30, 2016, 12 pages.
Halford, J. et al. (2009). "Clinical perspectives on lacosamide," Epilepsy Currents 9:1-9.
Hiremath, P.S. et al. (2008). "Controlled Release Hydrophilic Matrix Tablet Formulations of Isoniazid: Design and In Vitro Studies," AAPS PharmSciTech. 9:1171-1178.
Li, C.L. et al. (2005). "The use of hypromellose in oral drug delivery," J. Pharmacy and Pharmacology 57:533-546.
Ranade, V.V. et al. (2004). "Drug delivery systems," Second Edition, CRC Press, p. 167.
The Editors of Encyclopaedia Britannica (2012). "Ion-exchange resin," Encyclopaedia Britannica, Inc., 2 total pages.
Vimpat® film coated tablet. European Medicine Agency, 2008. Summary of Product Characteristics, 156 total pages.
Vimpat® film coated tablet (2008). Highlights of Prescribing Information, Approved labeling—NDA 22-253 and 22-254, 29 total pages.
Wikipedia (2020). "Ion-exchange resin," located at https://en.wikipedia.org/wiki/Ion-exchange_resin, 6 total pages.
Notice of Allowance dated Jan. 25, 2021, for U.S. Appl. No. 15/396,161, filed Dec. 30, 2016, 14 pages.

\* cited by examiner

METHODS AND COMPOSITIONS FOR THE TREATMENT OF SEIZURE-RELATED DISORDERS

CROSS REFERENCE TO RELATED APPLICATIONS

This application is a divisional application of U.S. patent application Ser. No. 15/396,161, filed Dec. 30, 2016, which claims priority to U.S. Provisional Patent Application No. 62/273,187, filed on Dec. 30, 2015, the subject matter of which applications is incorporated herein by reference in their entireties.

FIELD OF THE INVENTION

The field of the invention relates to extended release compositions of anti-epileptic compounds for the treatment of seizure-related disorders and methods of using same.

BACKGROUND

Epilepsy and seizure-related disorders affect nearly 3 million people in the US annually, at an estimated annual cost of $17.6 billion in direct and indirect costs. 200,000 new cases of seizures are reported annually in the US, and approximately 10% of the American population will experience at least one seizure in their lifetime. Seizures dramatically affect the quality of life and activities of daily living, especially activities that occur during the day like cooking, cleaning, and driving.

Numerous anticonvulsant drugs exist in the market today to treat the symptoms or manage epilepsy and other seizure disorders, including lacosamide, lamotrigine, levetiracetam, topiramate, valproate, and zonisamide. These agents have modest or limited efficacy and only about one-third of patients respond to monotherapy.

Data on the distribution of seizures during the human sleep-wake cycle or on the temporal distribution of seizures over the 24-hour day have been scarce and variable. Based on a large retrospective study in a tertiary epilepsy and sleep center, 176 patients (76 children, 100 adults) had continuous electroencephalography (EEG) and video monitoring. More than 800 seizures were recorded. Significantly more seizures occurred between 11 AM and 5 PM than at any other time of day, whereas significantly fewer seizures were detected between 11 PM and 5 AM. The results suggest that seizures have a tendency to occur in a diurnal pattern, characterized by a peak during midday and lower frequency in the nighttime (Hofstra et al., 2009). A once daily modified release formulation of an antiepileptic drug (AED) that has a PK profile that is synchronous with the diurnal pattern of seizures could be clinically advantageous.

Improved therapeutics and methods for treatment of these diseases and disorders are needed. Currently approved AEDs (both immediate and extended release forms) do not match the peak plasma concentrations to the times of highest seizure susceptibility, resulting in suboptimal seizure control. For instance, immediate release products with short half-lives (e.g. lacosamide and levetiracetam) are expected to have relatively low plasma concentrations throughout long periods of the day when there is a high seizure burden. Furthermore, currently approved AEDs with long half-lives are associated with safety concerns, including black box warnings (e.g. lamotrigine and zonisamide) and the risk of increased bleeding and epistaxis (e.g. topiramate).

The ideal product for treating seizures should have demonstrated efficacy in reducing the frequency of seizures, be relatively well tolerated, and have a PK profile that is synchronous with the daily impact of seizures. Thus, a novel formulation for an AED that provides sustained and high plasma levels between 9 AM and 6 PM would provide better seizure control.

Additionally, many of the approved AEDs in clinical use have limiting side effects which are related to the rapid rate in which the drug is absorbed into plasma, as opposed to the $C_{max}$ or AUC. By slowing the initial release of the AED and decreasing the initial rate of rise of plasma concentration, it is possible to improve the tolerability of the AED without compromising the effectiveness of the drug. Furthermore, by slowing the initial rate of rise of plasma concentration and improving tolerability, it is possible to reduce or eliminate titration and administer higher strengths of the AED compared to existing commercial immediate release formulations, thereby providing greater efficacy and better seizure control.

Anti-Epileptic Drugs (AEDs)

A large number of drugs have shown anti-epileptic activity, including, but not limited to, carbamazepine, divalproex sodium, eslicarbazepine acetate, ethotoin, ezogabine, felbamate, gabapentin, lacosamide, lamotrigine, levetiracetam, oxcarbazepine, perampanel, phenytoin, pregabalin, primidone, tiagabine, topiramate, valproic acid, vigabatrin, and zonisamide.

Lacosamide

Lacosamide, also known as R-2-acetamido-N-benzyl-3-methoxypropionamide, is a functionalized amino acid with the molecular formula C13H18N20 3 and a molecular weight of 250.30. The chemical structure is:

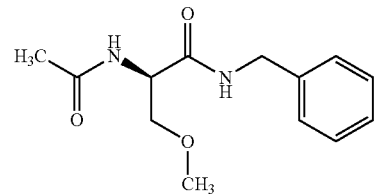 [SMILES: COC[C@@H](NC(C)=O)C(=O)NCc1ccccc1]

Lacosamide was approved for use in the US in 2008 by the FDA as adjunctive therapy in the treatment of partial-onset seizures in patients with epilepsy aged 17 years and older. In 2014, lacosamide was approved for monotherapy in patients with partial onset seizures. It was also approved for use in the European Union in 2008. It is marketed as "Vimpat" (UCB Pharmaceuticals).

Lacosamide immediate release ("IR") is currently available in the form of 50 mg, 100 mg, 150 mg, and 200 mg tablets for oral administration, as well as a 200 mg/20 mL solution for intravenous administration ("IV"). Typical oral dosages are 200-400 mg daily administered in two divided doses daily.

Lacosamide IR is completely absorbed after oral administration with negligible first-pass effect with a bioavailability of approximately 100%. The $T_{max}$ for an immediate release form is 1 to 4 hours for oral dosing, with an elimination half-life of approximately 13 hours. Steady state plasma concentrations are achieved after 3 days of twice-daily repeated administration. Pharmacokinetics of lacosamide are proportional to dose within a range of 100 to 800 mg with low inter- and intra-subject variability. Compared to lacosamide, the major metabolite, O-desmethyl metabolite, has a longer $T_{max}$ (0.5 to 12 hours) and elimination half-life (15 to 23 hours).

Cytochrome P450 2C19 (CYP2C19) a member of the cytochrome P450 mixed-function oxidase system, is involved in the metabolism of many antiepileptic drugs. There is no significant effect of CYP2C 19 polymorphism on the pharmacokinetics of lacosamide. There are reports that there no clinically relevant differences in the pharmacokinetics between CYP2C 19 poor metabolizers and extensive metabolizers, but concentrations and the amount excreted into urine of the O-desmethyl metabolite were about 70% reduced in the former as compared to the latter.

Lacosamide can be associated with a number of adverse side effects. For example, lacosamide is implicated to increase the risks of suicidal thoughts and behavior. Users are warned that lacosamide may cause dizziness, headache, ataxia, somnolence, tremor, nystagmus, balance disorder, cardiac complications including cardiac rhythm and conduction abnormalities, atrial fibrillation and atrial flutter, and syncope. Other adverse events associated with lacosamide at higher incidence than placebo in clinical trials include, but are not limited to, vertigo, diplopia, blurred vision, nausea, vomiting, diarrhea, fatigue, gait disturbance, asthenia, depression and pruritus.

Adverse reactions in patients with partial-onset seizures reported in clinical trials include neutropenia, anemia, cardiac palpitations, tinnitus, constipation, dehydration, dry mouth, oral hypoaesthesia, irritability, pyrexia, increased incidence of falls, muscle spasms, paresthesia, cognitive disorder, hypoaesthesia, dysarthria, disturbance in attention, cerebellar syndrome, confusion, mood disorders, and depressed mood. In adjunctive therapy controlled clinical trials, the adverse reactions most commonly leading to discontinuation were dizziness, ataxia, vomiting, diplopia, nausea, vertigo, and blurred vision. The most common adverse reactions in adjunctive therapy controlled clinical trials include dizziness (31%), headache (13%), and diplopia (11%).

In a long term (up to five years exposure) open-label extension clinical trial to study long term safety and efficacy of lacosamide, 10.7% of patients withdrew due to treatment emergent adverse events (TEAEs). However, the authors noted that it was difficult to attribute the TEAES solely to lacosamide therapy due to trial design, length of study, and the use of concomitant AEDs, and/or the addition of new AEDs. TEAEs reported included dizziness, headache, contusion, nausea, convulsion, nasopharyngitis, fall, vomiting, and diplopia. TEAEs that most commonly resulted in discontinuation of lacosamide treatment were dizziness and convulsion.

The lacosamide composition is described in U.S. Pat. No. 5,378,729, RE38,551 (from U.S. Pat. No. 5,773,475), and U.S. Pat. No. 5,654,301. These patents, along with U.S. Pat. No. 6,048,899 discuss the use of lacosamide for treating CNS conditions. U.S. Pat. No. 7,884,134 is directed to lacosamide synthesis. U.S. Pat. No. 7,718,161 discusses the use of lacosamide for treating motor neuron disease. US 20070043120, 20070048372, US 20070197657, US 20080280835, US 20100256179, US 20120225119, and US 20100260716 are directed to the use of lacosamide for treatment, inhibition, alleviation or prevention of a number of conditions including pain, non-inflammatory osteoarthritic pain, musculoskeletal pain associated with fibromyalgia, muscle pain associated with myofascial pain syndrome, back pain, neck pain, and demyelination conditions. US 20100324144 is directed to methods for alleviating or treating myotonia. US 20140128377 is directed to methods of treating repetitive seizures and seizure clusters. US 20140066515 is directed to methods of alleviating or treating channelopathies using lacosamide. US 20140128378 is directed to methods of alleviating or treating epileptogenesis.

Other US applications, including US 20130251813 and US 20130251803 by Cawello et al., are based on the development of controlled release oral lacosamide formulations. US 20120219631 by Kulkarni et al., describes a modified release formulation of lacosamide with minimal $C_{max}$ to $C_{min}$ peak to trough variation. These compositions are characterized as having a decreased Cmax and delayed Tmax, a decreased peak-trough fluctuation (PTF), and an increased $C_{min}$ in comparison to IR formulations. WO 2011/101863 (Roy) is based on extended release lacosamide compositions comprising modified release polymers.

Levetiracetam

Levetiracetam, also known as (S)-alpha-ethyl-2-oxo-pyrrolidine acetamide, is an S-enantiomer of etiracetam and has the chemical structure $C_8H_{14}N_2O_2$ and a molecular weight of 170.209. The chemical structure is:

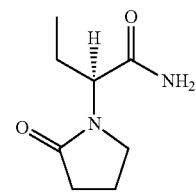

Levetiracetam was approved by the FDA in 1999 as an adjunctive therapy for the treatment of partial onset seizures in adults. The FDA later extended the use to children four years of age and older in 2012, and to children one month of age or older in 2012. Levetiracetam is marketed as Keppra by UCB Pharmaceuticals.

Levetiracetam is approved for use in some regions as adjunctive therapy in the treatment of myoclonic seizures in adults and adolescents 12 years of age or older with juvenile myoclonic epilepsy, as adjunctive therapy in the treatment of primary generalized tonic-clonic seizures in patients with idiopathic generalized epilepsy, and for partial onset seizures in adults and children as young as one moth of age.

Levetiracetam (immediate release) is marketed as Keppra IR is available as 250 mg, 500 mg, and 750 mg tablets, as well as 100 mg/ml oral solution. Typical dosing is 500 mg twice daily, which can be increased with 1000 mg increments to 3000 mg/day.

Levetiracetam has a $T_{max}$ of approximately one hour in fasted subjects, which can be delayed by 1.5 hours by food. It has a plasma half-life of 6-8 hours, an $AUC_{0-24}$ (µg*h/mL) of 300-350, and is excreted renally mostly in an unmetabolized form at a rate of 0.6 mL/min/kg.

Adverse events associated with levetiracetam use include somnolence in 14.8% of patients (compared to 8% in patients taking a placebo). Approximately 45% of patients taking 4000 mg levetiracetam daily reported somnolence in one untitrated study.

Besides somnolence, other common adverse events associated with levetiracetam use include asthenia, ataxia, psychosis, psychotic depression, behavioral symptoms including aggression, agitation, anger, anxiety, apathy, depersonalization, depression, emotional lability, hostility, irritability, and suicidal behavior. Adverse events reported in pediatric patients include somnolence, fatigue and behavior abnormalities.

An extended release formulation of levetiracetam is marketed as Keppra XR by UCB Pharmaceuticals. It is available as 500 mg and 750 mg tablets. Like the IR formulation, the Keppra XR doses are typically between 1000-3000 mg daily, but are taken as a single dose per day.

Adverse events associated with the XR formulation of levetiracetam at levels higher than in corresponding patients taking a placebo include suicidal behavior and ideation, somnolence, dizziness, depression, nervousness, fatigue, nausea, anxiety, amnesia irritability, hostility, paresthesia, ataxia, vertigo, emotional lability, and diplopia.

The levetiracetam composition is described U.S. Pat. Nos. 4,837,223, 4,943,639 and 6,107,492. Extended release levetiracetam is described in U.S. Pat. Nos. 7,858,122 and 7,863,316. U.S. Pat. No. 8,604,075 is directed to the methods for treating age-related cognitive function using levetiracetam.

Brivaracetam

Brivaracetam (Briva) is the 4-n-propyl analog of levetiracetam. It is also known as (2S)-2-[(4R)-2-oxo-4-propylpyrrolidin-1-yl]butanamide. It has the chemical formula $C_{11}H_2ON_2O_2$, and has a molecular weight of 212.29. The chemical structure is:

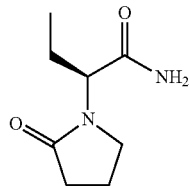

In one clinical study, brivaracetam had a $T_{max}$ of approximately 2 hours and a plasma half-life of 7-8 hrs. Unlike levetiracetam, only a small fraction of the brivaracetam dose administered (5-8%) is unchanged in urine; the remaining drug appears to be excreted as metabolites, indicating metabolic clearance.

In clinical trials, dose-dependent AEs included sedation and decreased alertness. Another trial showed that somnolence, dizziness, and decreased attention, alertness, and motor control were dose-related in healthy adult males.

Brivaracetam synthesis, compositions, and methods are described in U.S. Pat. Nos. 6,911,461, 6,713,635, 6,784,197, 7,358,276, and 7,692,028; 8,435,564 is based on the development of brivaracetam sustained release tablets; U.S. Pat. No. 8,460,712 and US 20110250282 describe compositions covering brivaracetam granules coated for sustained release; US 20120040006 and US 20110091547 are directed to brivaracetam sustained release solid dosage forms; 20130039957 is directed to controlled release formulations of brivaracetam; US 20110281929 and US 20110275693 are directed to immediate release brivaracetam formulations, US 20110021786 is directed to stable brivaracetam aqueous solutions; US 20100240576 is directed to therapeutic compounds comprising, in some embodiments, lacosamide and a racetam selected from a group comprising levetiracetam, and brivaracetam. WO 2006/131322 and US2009131508 are directed to methods for treating myoclonic epilepsies using brivaracetam-based compounds.

Oxcarbazepine

Oxcarbazepine, also known as 10,11-dihydro-10-oxo-5H-dibenz(b,f)azepine-5-carboxamide is a structural derivative of the anti-epileptic agent carbamazepine. It has the chemical formula $C_{15}H_{12}N_2O_2$, and a molecular weight of 252.268 g/mol. It is marketed under the name Trileptal. The chemical structure is:

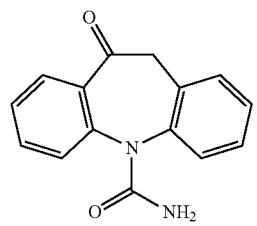 [SMILES: NC(=O)N1c2ccccc2CC(=O)c2ccccc21]

Oxcarbazepine is metabolized by liver enzymes into 10-monohydroxy metabolite (MHD), the active form of the drug, as well as small amounts of an inactive metabolite, 10,11-dihydroxy metabolite (DHD). Although the precise mechanism of action is unknown, the drug is thought to act by blocking voltage-sensitive sodium channels, thereby stabilizing hyperexcited neural membranes, inhibiting repetitive neuronal firing, and reducing propagation of synaptic firing. Additionally, the drug is thought to modulation of high-voltage CA+2 channels and increase potassium conductance, contributing to anti-epileptic activity.

Oxcarbazepine has a half-life of approximately 2 hours, while the metabolite (MDH) has a half-life of 9 hours. The $T_{max}$ is approximately 3 hours, the $C_{max}$ (µg/mL) of 2.72 for 600 mg IR BID, and an $AUC_{0-24}$ (µg*h/mL) of 16.8 for 600 mg IR BID. Per the Trileptal label, oxcarbazepine and the MDH metabolite share similar bioavailability. No food effects are displayed with either oxcarbazepine or its metabolite.

Seven multicenter, randomized, controlled clinical trials established the effectiveness of Trileptal as adjunctive and monotherapy for partial seizures in adults, and as adjunctive therapy in children aged 2-16 years. AEs identified in the clinical trials include cognitive symptoms including psychomotor slowing, difficulty with concentration, speech and language problems, somnolence and fatigue, and coordination abnormalities including ataxia and gait disturbances. Patents covering Trileptal include U.S. Pat. No. 7,037,525, covering methods of treatment using oxcarbazepine, and U.S. Pat. No. 8,119,148, covering an oxcarbazepine suspension. Other patents directed to oxcarbazepine include U.S. Pat. No. 3,642,775, covering the composition, and U.S. Pat. Nos. 5,863,558, 5,876,750, 5,906,832, 5,955,103, 6,210,712, covering osmotic forms of the drug for release of active ingredient in the GI tract.

Divalproex Sodium/Valproic Acid

Divalproex sodium, is the sodium salt of valproic acid, which is also known as 2-propylpentanoic acid. It has the chemical formula $C_8H_{16}O_2$, and the chemical structure:

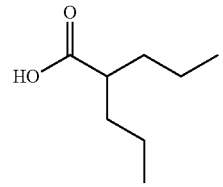

Sold under a number of brand names including Depakote, Convulex, Epilim, Valparin, Valpro, Vilapro, and Stavzor, divalproex dissociates into the valproate ion in the gastrointestinal tract. The mechanism of action is not fully characterized, but its anti-epileptic activity has been associated with increased GABA concentrations in the brain. Immediate release (IR) and extended release forms of the drugs are available. Divalproex sodium ER has a half-life of 16±3 hours, a $T_{max}$ of 7.7 hours for 1000 mg ER, and an $AUC_{0-24}$ (µg*h/mL) of 1970 for 1000 mg ER.

Adverse events associated with valproic acid therapy include abdominal pain, accidental injury, alopecia, amblyopia/blurred vision, amnesia, anorexia, asthenia, ataxia, back pain, bronchitis, constipation, depression, diarrhea, diplopia, dizziness, dyspepsia, dyspnea, ecchymosis, emotional lability, fever, flu syndrome, headache, increased appetite, infection, insomnia, nausea, nervousness, nystagmus, peripheral edema, pharyngitis, rash, rhinitis, somnolence, thinking abnormal, thrombocytopenia, tinnitus, tremor, vomiting, weight gain, and weight loss.

U.S. patents directed to divalproex sodium/valproic acid include U.S. Pat. Nos. 4,988,731, 5,212,326, 6,511,678, 6,528,090, 6,713,086, and 6,720,004.

Vigabatrin

Vigabatrin, also known as (RS)-4-aminohex-5-enoic acid and as gamma-vinyl-GABA is a GABA analog. It has the chemical formula $C6H_{11}NO_2$, and a molecular weight of 129.157 g/mol. It is marketed under the name Sabril. The chemical structure is:

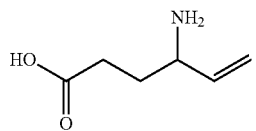

Vigabatrin irreversibly inhibits gamma-aminobutyric acid transaminase (GABA-T), the enzyme responsible for GABA catabolism. It has a $T_{1/2}$ of 7.5 hrs at steady state, a $T_{max}$ of approximately 1 hour, a $C_{max}$ 61 (µg/mL) at steady state.

Vigabatrin is indicated as monotherapy for pediatric patients one month to two years of age with infantile spasms for whom the potential benefits outweigh the potential risk of vision loss, and as adjunctive (add-on) therapy for adult patients with refractory complex partial seizures (CPS) who have inadequately responded to several alternative treatments and for whom the potential benefits outweigh the risk of vision loss. Vigabatrin may cause permanent vision loss in a high percentage of patients. This effect may occur within weeks or sooner after starting treatment. It may also occur after months or years. The risk may increase with higher doses and prolonged use, but it may occur with any dose or length of use. Vision loss may continue to worsen after stopping vigabatrin. Commonly reported side effects of vigabatrin include confusion, fatigue, diplopia, weight gain, arthralgia, blurred vision, depression, cough, diarrhea, memory impairment, drowsiness, tremor, ataxia, abnormal gait, irritability, and pharyngolaryngeal pain. Other side effects include urinary tract infection, status epilepticus, pulmonary congestion, depressed mood, muscle twitching, paresthesia, weakness, dysmenorrhea, eye pain, erectile dysfunction, sinus headache, abnormality in thinking, peripheral edema, nystagmus, lethargy, sedation, back pain, abnormal behavior, constipation, myalgia, fever, nervousness, vertigo, anemia, chest pain, bronchitis, hyporeflexia, upper abdominal pain, toothache, hypoesthesia, sensory disturbance, peripheral neuropathy, malaise, increased appetite, bruise, and abnormal dreams.

SUMMARY OF THE INVENTION

The inventors have found that certain AED pharmaceutical compounds may be formulated to provide more effective treatment of seizures, particularly partial onset seizures, and other indications for which these compounds are used. Generally, the invention relates to an extended release composition of an anti-epilepsy drug, that provides pharmacokinetic characteristics as further defined herein, and its use in a method of treating seizure-related disorders by administration as defined herein.

In some embodiments, compositions of these AED pharmaceutical compounds comprise an extended release form that, upon oral ingestion by a subject (or subjects) of a fasted, single dose, human pharmacokinetic study provides a $T_{max}$ that is greater than the $T_{max}$ provided by ingestion of an immediate release, oral form of the same pharmaceutical compound to a subject (or subjects) in the same or similar fasted, single dose, human pharmacokinetic study. In some embodiments, compositions of these compounds comprise an extended release form that, upon oral dosing to a subject of a fasted, single dose, human pharmacokinetic study provides a $T_{max}$ that is greater than the $T_{max}$ provided by oral dosing of an immediate release, oral form of the same pharmaceutical compound at the same strength to said subject in the same fasted, single dose, human pharmacokinetic study; preferably the $T_{max}$ is 5 to 20 hours, more preferably, the $T_{max}$ is 10 to 20 hours, even more preferably, the $T_{max}$ is 12 to 20 hours, and most preferably, the $T_{max}$ is 14 to 20 hours. The plasma concentration profiles provided by compositions described herein are designed to achieve one or more of the following objectives: increased diurnal variation, peak steady state plasma concentration chronosynchronous with the need for therapy (i.e., higher concentration when seizures are most prevalent), reduced adverse events (including those adverse events which may lead to discontinuation or lower adherence), reduced dosing frequency, increased daily dose, increased efficacy. In some embodiments, two or more of these objectives are achieved; in some embodiments, at least three of the objectives are achieved. Formulations may be designed for administration at specific times to achieve the aforementioned objectives. In some embodiments, the compositions may be designed to provide a reduced rate of rise in drug plasma concentration during the first 2, 3, 4, 5, or 6 hours of administration as compared to a commercially available, oral, immediate release form of the same amount of the same active pharmaceutical ingredient, yet provide bioavailability comparable to that for a commercially available, oral, immediate release form of the same active pharmaceutical ingredient (e.g., 80% to 125% of the $AUC_{0-inf}$ of the commercially available, oral, immediate release form of the same active pharmaceutical ingredient). For example, an extended release composition of lacosamide may be designed (as exemplified below) to release the drug much more slowly than an immediate release formulation; certain such formulations may be administered in the evening, before bedtime, and upon multiple administrations, the steady state plasma concentration profile will be characterized by a higher plasma concentration profile during the daytime hours (and lower concentrations during the night) such that the peak concentrations are chronosynchronous with the peak seizure activity in a patient. Furthermore, such formulations enable a full day's dosing to be administered orally, once daily. In some embodiments, the total daily dose of the active pharmaceutical ingredient may be administered orally, once daily at a higher daily dose than typically employed for the same active pharmaceutical ingredient in an immediate release form in divided doses (e.g., BID, TID). In some embodiments, the once daily administration of the pharmaceutical composition provides a plasma concentration profile of the active pharmaceutical ingredient characterized by a diurnal variation that is increased such that the swing (i.e., $(C_{max,ss}-C_{min,ss})/C_{min,ss} \times 100\%$) is greater than 90%, 100%, 110%, or 120%.

In some embodiments, the AED drug is one or more members of the group consisting of brivaracetam, divalproex, lacosamide, levetiracetam, oxcarbazepine, vigabatrin, and pharmaceutically acceptable salts of brivaracetam, divalproex, lacosamide, levetiracetam, oxcarbazepine, and vigabatrin.

Additionally, many of the approved AEDs in clinical use have limiting side effects which are related to the rapid rate in which the drug is absorbed into plasma, as opposed to the $C_{max}$ or AUC. By slowing the initial release of the AED and decreasing the initial rate of rise of plasma concentration, it is possible to improve the tolerability of the AED without compromising the effectiveness of the drug. Furthermore, by slowing the initial rate of rise of plasma concentration and improving tolerability, it is possible to reduce or eliminate titration and administer higher strengths of the AED compared to existing commercial immediate release formulations, thereby providing greater efficacy and better seizure control. Some embodiments provide an anti-epileptic formulation that is administered once daily and has a pharmacokinetic profile with diurnal variations, with a $T_{1/2}$ between 4 and 15 hours, preferably between 4 and 12 hours. These embodiments include, but are not limited to, formulations of brivaracetam, divalproex sodium, valproic acid, felbamate, lacosamide, lamotrigine, levetiracetam, oxcarbazepine, pregabalin, tiagabine, and vigabatrin. Preferred are formulations of brivaracetam, divalproex sodium, valproic acid, lacosamide, levetiracetam, oxcarbazepine, pregabalin, tiagabine, and vigabatrin. Most preferred are formulations of levetiracetam, brivaracetam, lacosamide, oxcarbazepine and valproic acid for administration once daily.

Some embodiments described herein provide a method of administering a pharmaceutical composition to a human, comprising administering to a human orally, once daily, a therapeutically effective dose of a pharmaceutical composition comprising (i) a drug selected from the group consisting of brivaracetam, divalproex, lacosamide, levetiracetam, oxcarbazepine, vigabatrin, and pharmaceutically acceptable salts thereof, and mixtures of any of the foregoing, and (ii) one or more excipients, wherein at least one of said one or more excipients modifies the release of the drug to provide an extended release form. In some embodiments the pharmaceutical composition comprises one or more additional active pharmaceutical ingredients. In a preferred embodiment, no other drugs are included in the pharmaceutical composition.

Some embodiments described herein provide a method of administering a pharmaceutical composition to a human, comprising administering to a human orally, once daily, a therapeutically effective dose of a pharmaceutical composition comprising (i) a drug selected from the group consisting of brivaracetam, lacosamide, levetiracetam, oxcarbazepine, and pharmaceutically acceptable salts thereof, and mixtures of any of the foregoing, and (ii) one or more excipients, wherein at least one of said one or more excipients modifies the release of the drug to provide an extended release form.

Some embodiments described herein provide a method of administering a pharmaceutical composition to a human, comprising administering to a human orally, once daily, a therapeutically effective dose of a pharmaceutical composition comprising (i) a drug selected from the group consisting of lacosamide and pharmaceutically acceptable salts thereof, and mixtures of any of the foregoing, and (ii) one or more excipients, wherein at least one of said one or more excipients modifies the release of the drug to provide an extended release form.

Some aspects of any of the embodiments described herein provide a method of administering a pharmaceutical composition to a human, orally, once daily, wherein said composition comprises at least one or more excipients with modifies the release of the drug to provide a delayed release form.

Some aspects of any of the embodiments described herein provide a method of administering a pharmaceutical composition to a human, orally, once daily, wherein said composition provides a dissolution profile characterized by at least two of the following: (i) release of less than 8% in 2 hours, (ii) release of less than 17% in 4 hours, (iii) release of less than 45% at 6 hours, and wherein the dissolution profile of said pharmaceutical composition is characterized by release of at least 45% at 12 hours, wherein the dissolution is performed in a USP type 1 (basket) apparatus rotating at 100 rpm using 900 ml simulated gastric fluid (pH 1.2) at 37.0±0.5° C. for 2 hours, followed by dissolution in the same apparatus and speed using 900 ml simulated intestinal fluid (pH 6.8) at 37.0±0.5° C. for the subsequent 4 hours, followed by dissolution in the same apparatus and speed using 900 ml phosphate buffer (pH 7.5) at 37.0±0.5° C. for the subsequent 18 hours. In a preferred aspect of this embodiment, all three of said release criteria are met. In a preferred aspect of this embodiment, the release of drug at 4 hours is less than 10%.

Some aspects of any of the embodiments described herein provide a method of administering a pharmaceutical composition to a human, orally, once daily, wherein said composition provides a dissolution profile characterized by at least three of the following: (i) less than 10% release at 1 hour, (ii) less than 15% release at 2 hours, (iii) less than 25% release at 4 hours, (iv) at least 35% release at 9 hours, (v) at least 65% release at 12 hours, wherein the dissolution is performed in a USP type 1 (basket) apparatus rotating at 100 rpm using 900 ml simulated gastric fluid (pH 1.2) at 37.0±0.5° C. for 2 hours, followed by dissolution in the same apparatus and speed using 900 ml simulated intestinal fluid (pH 6.8) at 37.0±0.5° C. for the subsequent 4 hours, followed by dissolution in the same apparatus and speed using 900 ml phosphate buffer (pH 7.5) at 37.0±0.5° C. for the subsequent 18 hours.

Some aspects of any of the embodiments described herein provide a method of administering a pharmaceutical composition to a human, orally, once daily, wherein said composition provides a dissolution profile characterized by a release at 2 hours of not more than 18%, and wherein the dissolution profile of said pharmaceutical composition is characterized by release of at least 45% at 12 hours, wherein the dissolution is performed in a USP type 1 (basket) apparatus rotating at 100 rpm using 900 ml simulated gastric fluid (pH 1.2) at 37.0±0.5° C. for 2 hours, followed by dissolution in the same apparatus and speed using 900 ml simulated intestinal fluid (pH 6.8) at 37.0±0.5° C. for the subsequent 4 hours, followed by dissolution in the same apparatus and speed using 900 ml phosphate buffer (pH 7.5) at 37.0±0.5° C. for the subsequent 18 hours. In a preferred aspect of this embodiment, all three of said release criteria are met. In a preferred aspect of this embodiment, all three of said release criteria are met. In a preferred aspect, the release of drug at 2 hours is less than 12%. In a preferred aspect, the release of drug at 2 hours is less than 9%. In a preferred aspect, the release of drug at 2 hours is less than 6%. In a preferred aspect, the release of drug at 2 hours is less than 3%. In a preferred aspect, the release of drug at 2 hours is less than 2%.

Some aspects of any of the embodiments described herein provide a method of administering a pharmaceutical composition to a human, orally, once daily, wherein said composition provides a dissolution profile characterized by a release at 4 hours of not more than 25%, and wherein the dissolution profile of said pharmaceutical composition is characterized by release of at least 45% at 12 hours, wherein the dissolution is performed in a USP type 1 (basket) apparatus rotating at 100 rpm using 900 ml simulated gastric fluid (pH 1.2) at 37.0±0.5° C. for 2 hours, followed by dissolution in the same apparatus and speed using 900 ml simulated intestinal fluid (pH 6.8) at 37.0±0.5° C. for the subsequent 4 hours, followed by dissolution in the same apparatus and speed using 900 ml phosphate buffer (pH 7.5) at 37.0±0.5° C. for the subsequent 18 hours. In a preferred aspect, the release of drug at 4 hours is less than 20%. In a preferred aspect, the release of drug at 4 hours is less than 15%. In a preferred aspect, the release of drug at 4 hours is less than 10%. In a preferred aspect, the release of drug at 4 hours is less than 7.5%. In a preferred aspect, the release of drug at 4 hours is less than 5%.

Some aspects of any of the embodiments described herein provide a method of administering a pharmaceutical composition to a human, orally, once daily, wherein said composition provides a dissolution profile characterized by a release at 6 hours of not more than 30%, and wherein the dissolution profile of said pharmaceutical composition is characterized by release of at least 45% at 12 hours, wherein the dissolution is performed in a USP type 1 (basket) apparatus rotating at 100 rpm using 900 ml simulated gastric fluid (pH 1.2) at 37.0±0.5° C. for 2 hours, followed by dissolution in the same apparatus and speed using 900 ml simulated intestinal fluid (pH 6.8) at 37.0±0.5° C. for the subsequent 4 hours, followed by dissolution in the same apparatus and speed using 900 ml phosphate buffer (pH 7.5) at 37.0±0.5° C. for the subsequent 18 hours. In a preferred aspect, the release of drug at 6 hours is less than 25%. In a preferred aspect, the release of drug at 6 hours is less than 20%. In a preferred aspect, the release of drug at 6 hours is less than 15%. In a preferred aspect, the release of drug at 4 hours is less than 12%. In a preferred aspect, the release of drug at 6 hours is less than 9%.

Some aspects of any of the embodiments described herein provide a method of administering a pharmaceutical composition to a human, orally, once daily, wherein said composition provides a dissolution profile characterized by a release at 9 hours of at least 35%, and wherein the dissolution profile of said pharmaceutical composition is characterized by release of at least 45% at 12 hours, wherein the dissolution is performed in a USP type 1 (basket) apparatus rotating at 100 rpm using 900 ml simulated gastric fluid (pH 1.2) at 37.0±0.5° C. for 2 hours, followed by dissolution in the same apparatus and speed using 900 ml simulated intestinal fluid (pH 6.8) at 37.0±0.5° C. for the subsequent 4 hours, followed by dissolution in the same apparatus and speed using 900 ml phosphate buffer (pH 7.5) at 37.0±0.5° C. for the subsequent 18 hours. In a preferred aspect, the release of drug at 9 hours is at least 40% and the release at 12 hours is at least 65%. In a preferred aspect, the release of drug at 9 hours is at least 45% and the release at 12 hours is at least 65%. In a preferred aspect, the release of drug at 9 hours is at least 50% and the release at 12 hours is at least 65%.

Some aspects of any of the embodiments described herein provide a method of administering a pharmaceutical composition to a human, orally, once daily, wherein oral ingestion of a dose of said pharmaceutical composition by a subject of a fasted, single dose, human pharmacokinetic study provides a plasma concentration profile for the drug of said pharmaceutical composition characterized by a $T_{max}$ of 5 to 20 hours. In a preferred aspect, said $T_{max}$ is 5 to 10 hours. In a preferred aspect, said $T_{max}$ is 8 to 20 hours. In a preferred aspect, said $T_{max}$ is 10 to 20 hours. In a preferred aspect, said $T_{max}$ is 10 to 14 hours. In a preferred aspect, said $T_{max}$ is 12 to 20 hours. In a more preferred aspect, said $T_{max}$ is 13 to 20 hours.

Some aspects of any of the embodiments described herein provide a method of administering a pharmaceutical composition to a human, orally, once daily, wherein oral ingestion of a dose of said pharmaceutical composition by a subject of a fasted, single dose, human pharmacokinetic study provides a plasma concentration profile for the drug of said pharmaceutical composition characterized by a $T_{lag}$ of 0.25 to 9 hours. In a preferred aspect, said $T_{lag}$ is 0.25 to 5 hours. In a preferred aspect, said $T_{lag}$ is 1 to 9 hours. In a preferred aspect, said $T_{lag}$ is 2 to 9 hours. In a preferred aspect, said $T_{lag}$ is 3 to 8 hours. In a preferred aspect, said $T_{lag}$ is 0.5 to 5 hours. In a preferred aspect, said $T_{lag}$ is 1 to 5 hours. In a preferred aspect, said $T_{lag}$ is 2 to 5 hours.

Some aspects of any of the embodiments described herein provide a method of administering a pharmaceutical composition to a human, orally, once daily, wherein oral ingestion of a dose of said pharmaceutical composition by a subject of a fasted, single dose, human pharmacokinetic study provides a plasma concentration profile for the drug of said pharmaceutical composition characterized by an $AUC_{0-\infty}$ that provides AUC equivalence to IR. Some aspects of any of the embodiments described herein provide a method of administering a pharmaceutical composition to a human, orally, once daily, wherein oral ingestion of a dose of said pharmaceutical composition by a subject of a fasted, single dose, human pharmacokinetic study provides a plasma concentration profile for the drug of said pharmaceutical composition characterized by an $AUC_{0-\infty}$ that is 100% to 150% of the $AUC_{0-\infty}$ determined for an equivalent dose of the drug of said pharmaceutical composition in an immediate release form after ingestion by a subject of said fasted, single dose, human pharmacokinetic study.

Some aspects of any of the embodiments described herein provide a method of administering a pharmaceutical composition to a human, orally, once daily, wherein oral ingestion of a dose of said pharmaceutical composition by a subject of a fasted, single dose, human pharmacokinetic study provides a plasma concentration profile for the drug of said pharmaceutical composition characterized by a dC/dt over the first 1.4 hours after ingestion that is less than 10% of the dC/dt determined for an equivalent dose of the drug of said pharmaceutical composition in an immediate release form over the first 1.4 hours after ingestion by a subject of said fasted, single dose, human pharmacokinetic study. In a preferred aspect, the dC/dt determined for said composition is less than 5% of the dC/dt determined for an equivalent dose of the drug of said pharmaceutical composition in an immediate release form over the first 1.4 hours after ingestion by a subject of said fasted, single dose, human pharmacokinetic study.

Some aspects of any of the embodiments described herein provide a method of administering a pharmaceutical composition to a human, orally, once daily, wherein oral ingestion of a dose of said pharmaceutical composition by a subject of a fasted, single dose, human pharmacokinetic study provides a plasma concentration profile for the drug of said pharmaceutical composition characterized by a dC/dt over the first 2 hours after ingestion that is less than 15% of the dC/dt determined for an equivalent dose of the drug of said pharmaceutical composition in an immediate release form over the first 2 hours after ingestion by a subject of said fasted, single dose, human pharmacokinetic study. In a preferred aspect, the dC/dt determined for said composition is less than 10% of the dC/dt determined for an equivalent dose of the drug of said pharmaceutical composition in an immediate release form over the first 2 hours after ingestion by a subject of said fasted, single dose, human pharmacokinetic study. In a preferred aspect, the dC/dt determined for said composition is less than 5% of the dC/dt determined for an equivalent dose of the drug of said pharmaceutical composition in an immediate release form over the first 2 hours after ingestion by a subject of said fasted, single dose, human pharmacokinetic study.

Some aspects of any of the embodiments described herein provide a method of administering a pharmaceutical composition to a human, orally, once daily, wherein oral ingestion of a dose of said pharmaceutical composition by a subject of a fasted, single dose, human pharmacokinetic study provides a plasma concentration profile for the drug of said pharmaceutical composition characterized by a dC/dt over the first 3 hours after ingestion that is less than 25% of the dC/dt determined for an equivalent dose of the drug of said pharmaceutical composition in an immediate release form over the first 3 hours after ingestion by a subject of said fasted, single dose, human pharmacokinetic study. In a preferred aspect, the dC/dt determined for said composition is less than 20% of the dC/dt determined for an equivalent dose of the drug of said pharmaceutical composition in an immediate release form over the first 3 hours after ingestion by a subject of said fasted, single dose, human pharmacokinetic study. In a preferred aspect, the dC/dt determined for said composition is less than 10% of the dC/dt determined for an equivalent dose of the drug of said pharmaceutical composition in an immediate release form over the first 3 hours after ingestion by a subject of said fasted, single dose, human pharmacokinetic study.

Some aspects of any of the embodiments described herein provide a method of administering a pharmaceutical composition to a human, orally, once daily, wherein oral ingestion of a dose of said pharmaceutical composition by a subject of a fasted, single dose, human pharmacokinetic study provides a plasma concentration profile for the drug of said pharmaceutical composition characterized by a dC/dt over the first 4 hours after ingestion that is less than 30% of the dC/dt determined for an equivalent dose of the drug of said pharmaceutical composition in an immediate release form over the first 4 hours after ingestion by a subject of said fasted, single dose, human pharmacokinetic study. In a preferred aspect, the dC/dt determined for said composition is less than 20% of the dC/dt determined for an equivalent dose of the drug of said pharmaceutical composition in an immediate release form over the first 4 hours after ingestion by a subject of said fasted, single dose, human pharmacokinetic study. In a preferred aspect, the dC/dt determined for said composition is less than 10% of the dC/dt determined for an equivalent dose of the drug of said pharmaceutical composition in an immediate release form over the first 4 hours after ingestion by a subject of said fasted, single dose, human pharmacokinetic study.

Some aspects of any of the embodiments described herein provide a method of administering a pharmaceutical composition to a human, orally, once daily, wherein oral ingestion of a dose of said pharmaceutical composition by a subject of a fasted, single dose, human pharmacokinetic study provides a plasma concentration profile for the drug of said pharmaceutical composition characterized by a dC/dt over the first 2 hours after ingestion that is less than 1 µg/ml/hr. In a preferred aspect, said dC/dt over the first 2 hours after ingestion is less than 0.6 µg/ml/hr. In a preferred aspect, said dC/dt over the first 2 hours after ingestion is less than 0.45 µg/ml/hr. In a preferred aspect, said dC/dt over the first 2 hours after ingestion is less than 0.3 µg/ml/hr. In a preferred aspect, said dC/dt over the first 2 hours after ingestion is less than 0.1 µg/ml/hr.

Some aspects of any of the embodiments described herein provide a method of administering a pharmaceutical composition to a human, orally, once daily, wherein oral ingestion of a dose of said pharmaceutical composition by a subject of a fasted, single dose, human pharmacokinetic study provides a plasma concentration profile for the drug of said pharmaceutical composition characterized by a dC/dt over the first 3 hours after ingestion that is less than 0.8 µg/ml/hr. In a preferred aspect, said dC/dt over the first 3 hours after ingestion is less than 0.6 µg/ml/hr. In a preferred aspect, said dC/dt over the first 3 hours after ingestion is less than 0.4 µg/ml/hr. In a preferred aspect, said dC/dt over the first 3 hours after ingestion is less than 0.25 µg/ml/hr. In a preferred aspect, said dC/dt over the first 3 hours after ingestion is less than 0.1 µg/ml/hr.

Some aspects of any of the embodiments described herein provide a method of administering a pharmaceutical composition to a human, orally, once daily, wherein oral ingestion of a dose of said pharmaceutical composition by a subject of a fasted, single dose, human pharmacokinetic study provides a plasma concentration profile for the drug of said pharmaceutical composition characterized by a dC/dt over the first 4 hours after ingestion that is less than 0.6 µg/ml/hr. In a preferred aspect, said dC/dt over the first 4 hours after ingestion is less than 0.5 µg/ml/hr. In a preferred aspect, said dC/dt over the first 4 hours after ingestion is less than 0.4 µg/ml/hr. In a preferred aspect, said dC/dt over the first 4 hours after ingestion is less than 0.25 µg/ml/hr. In a preferred aspect, said dC/dt over the first 4 hours after ingestion is less than 0.1 µg/ml/hr.

Some aspects of any of the embodiments described herein provide a method of administering a pharmaceutical composition to a human, orally, once daily, wherein oral ingestion of a dose of said pharmaceutical composition by a subject of a fasted, single dose, human pharmacokinetic study provides a plasma concentration profile for the drug of said pharmaceutical composition characterized by a dC/dt over the first 2 hours after ingestion that is less than 2.2 ng/ml/hr per mg of the drug of said pharmaceutical composition. In a preferred aspect, said dC/dt over the first 2 hours after ingestion is less than 1.8 ng/ml/hr per mg of the drug of said pharmaceutical composition. In a preferred aspect, said dC/dt over the first 2 hours after ingestion is less than 1.4 ng/ml/hr per mg of the drug of said pharmaceutical composition. In a preferred aspect, said dC/dt over the first 2 hours after ingestion is less than 1 ng/ml/hr per mg of the drug of said pharmaceutical composition. In a preferred aspect, said dC/dt over the first 2 hours after ingestion is less than 0.5 ng/ml/hr per mg of the drug of said pharmaceutical composition.

Some aspects of any of the embodiments described herein provide a method of administering a pharmaceutical composition to a human, orally, once daily, wherein oral ingestion of a dose of said pharmaceutical composition by a subject of a fasted, single dose, human pharmacokinetic study provides a plasma concentration profile for the drug of said pharmaceutical composition characterized by a dC/dt over the first 3 hours after ingestion that is less than 2 ng/ml/hr per mg of the drug of said pharmaceutical composition. In a preferred aspect, said dC/dt over the first 3 hours after ingestion is less than 1.6 ng/ml/hr per mg of the drug of said pharmaceutical composition. In a preferred aspect, said dC/dt over the first 3 hours after ingestion is less than 1.2 ng/ml/hr per mg of the drug of said pharmaceutical composition. In a preferred aspect, said dC/dt over the first 3 hours after ingestion is less than 0.8 ng/ml/hr per mg of the drug of said pharmaceutical composition. In a preferred aspect, said dC/dt over the first 3 hours after ingestion is less than 0.4 ng/ml/hr per mg of the drug of said pharmaceutical composition.

Some aspects of any of the embodiments described herein provide a method of administering a pharmaceutical composition to a human, orally, once daily, wherein oral ingestion of a dose of said pharmaceutical composition by a subject of a fasted, single dose, human pharmacokinetic study provides a plasma concentration profile for the drug of said pharmaceutical composition characterized by a dC/dt over the first 4 hours after ingestion that is less than 1.6 ng/ml/hr per mg of the drug of said pharmaceutical composition. In a preferred aspect, said dC/dt over the first 4 hours after ingestion is less than 1.2 ng/ml/hr per mg of the drug of said pharmaceutical composition. In a preferred aspect, said dC/dt over the first 4 hours after ingestion is less than 0.8 ng/ml/hr per mg of the drug of said pharmaceutical composition. In a preferred aspect, said dC/dt over the first 4 hours after ingestion is less than 0.4 ng/ml/hr per mg of the drug of said pharmaceutical composition. In a preferred aspect, said dC/dt over the first 4 hours after ingestion is less than 0.2 ng/ml/hr per mg of the drug of said pharmaceutical composition.

Some aspects of any of the embodiments described herein provide a method of administering a pharmaceutical composition to a human, orally, once daily, wherein oral ingestion of a dose of said pharmaceutical composition by a subject of a fasted, single dose, human pharmacokinetic study provides a plasma concentration profile for the drug of said pharmaceutical composition characterized by a $pAUC_{0-4}$ that is less than 12% of $AUC_{0-\infty}$ determined for the drug of said pharmaceutical composition from said plasma concentration profile. In a preferred aspect, said $pAUC_{0-4}$ is less than 10% of $AUC_{0-\infty}$ determined for the drug of said pharmaceutical composition from said plasma concentration profile. In a preferred aspect, said $pAUC_{0-4}$ is less than 8% of $AUC_{0-\infty}$ determined for the drug of said pharmaceutical composition from said plasma concentration profile. In a preferred aspect, said $pAUC_{0-4}$ is less than 6% of $AUC_{0-\infty}$ determined for the drug of said pharmaceutical composition from said plasma concentration profile. In a preferred aspect, said $pAUC_{0-4}$ is less than 4% of $AUC_{0-\infty}$ determined for the drug of said pharmaceutical composition from said plasma concentration profile. In a preferred aspect, said $pAUC_{0-4}$ is less than 2% of $AUC_{0-\infty}$ determined for the drug of said pharmaceutical composition from said plasma concentration profile. In a preferred aspect, said $pAUC_{0-4}$ is less than 1% of $AUC_{0-\infty}$ determined for the drug of said pharmaceutical composition from said plasma concentration profile.

Some aspects of any of the embodiments described herein provide a method of administering a pharmaceutical composition to a human, orally, once daily, wherein oral ingestion of a dose of said pharmaceutical composition by a subject of a fasted, single dose, human pharmacokinetic study provides a plasma concentration profile for the drug of said pharmaceutical composition characterized by a $pAUC_{0-8}$ that is less than 12% of $AUC_{0-\infty}$ determined for the drug of said pharmaceutical composition from said plasma concentration profile. In a preferred aspect, said $pAUC_{0-8}$ is less than 10% of $AUC_{0-\infty}$ determined for the drug of said pharmaceutical composition from said plasma concentration profile. In a preferred aspect, said $pAUC_{0-8}$ is less than 7.5% of $AUC_{0-\infty}$ determined for the drug of said pharmaceutical composition from said plasma concentration profile. In a preferred aspect, said $pAUC_{0-8}$ is less than 5% of $AUC_{0-\infty}$ determined for the drug of said pharmaceutical composition from said plasma concentration profile. In a preferred aspect, said $pAUC_{0-8}$ is less than 3% of $AUC_{0-\infty}$ determined for the drug of said pharmaceutical composition from said plasma concentration profile.

Some aspects of any of the embodiments described herein provide a method of administering a pharmaceutical composition to a human, orally, once daily, wherein oral ingestion of a dose of said pharmaceutical composition by a subject of a fasted, single dose, human pharmacokinetic study provides a plasma concentration profile for the drug of said pharmaceutical composition characterized by a $pAUC_{4-8}$ that is less than 14% of $AUC_{0-\infty}$ determined for the drug of said pharmaceutical composition from said plasma concentration profile. In a preferred aspect, said $pAUC_{4-8}$ is less than 12% of $AUC_{0-\infty}$ determined for the drug of said pharmaceutical composition from said plasma concentration profile. In a preferred aspect, said $pAUC_{4-8}$ is less than 10% of $AUC_{0-\infty}$ determined for the drug of said pharmaceutical composition from said plasma concentration profile. In a preferred aspect, said $pAUC_{4-8}$ is less than 8% of $AUC_{0-\infty}$ determined for the drug of said pharmaceutical composition from said plasma concentration profile. In a preferred aspect, said $pAUC_{4-8}$ is less than 7% of $AUC_{0-\infty}$ determined for the drug of said pharmaceutical composition from said plasma concentration profile. In a preferred aspect, said $pAUC_{4-8}$ is less than 6% of $AUC_{0-\infty}$ determined for the drug of said pharmaceutical composition from said plasma concentration profile. In a preferred aspect, said $pAUC_{4-8}$ is less than 4% of $AUC_{0-\infty}$ determined for the drug of said pharmaceutical composition from said plasma concentration profile. In a preferred aspect, said $pAUC_{4-8}$ is less than 2.5% of $AUC_{0-\infty}$ determined for the drug of said pharmaceutical composition from said plasma concentration profile.

Some aspects of any of the embodiments described herein provide a method of administering a pharmaceutical composition to a human, orally, once daily, wherein once daily oral dosing of said pharmaceutical composition to a subject of a fasted, human pharmacokinetic study provides a steady state plasma concentration profile for the drug of said pharmaceutical composition characterized by a $T_{max,ss}$ that is 5 to 20 hours. In a preferred aspect, said $T_{max,ss}$ is 5 to 10 hours. In a preferred aspect, said $T_{max,ss}$ is 10 to 20 hours. In a preferred aspect, said $T_{max,ss}$ is 12 to 20 hours. In a preferred aspect, said $T_{max,ss}$ is 11 to 18 hours. In a preferred aspect, said $T_{max,ss}$ is 12 to 18 hours. In a preferred aspect, said $T_{max,ss}$ is 13 to 18 hours. In a preferred aspect, said $T_{max,ss}$ is 14 to 18 hours.

Some aspects of any of the embodiments described herein provide a method of administering a pharmaceutical composition to a human, orally, once daily, wherein once daily oral dosing of said pharmaceutical composition to a subject of a fasted, human pharmacokinetic study provides a steady state plasma concentration profile for the drug of said pharmaceutical composition characterized by a $C_{max,ss}$ that is 12 to 36 ng/ml per mg of drug. In a preferred aspect, said $C_{max,ss}$ is 16 to 32 ng/ml per mg of drug. In a preferred aspect, said $C_{max,ss}$ is 20 to 30 ng/ml per mg of drug. In a preferred aspect, said $C_{max,ss}$ is 22 to 30 ng/ml per mg of drug. In a preferred aspect, said $C_{max,ss}$ is 23 to 30 ng/ml per mg of drug. In a preferred aspect, said $C_{max,ss}$ is 24 to 32 ng/ml per mg of drug.

Some aspects of any of the embodiments described herein provide a method of administering a pharmaceutical composition to a human, orally, once daily, wherein once daily oral dosing of said pharmaceutical composition to a subject of a fasted, human pharmacokinetic study provides a steady state plasma concentration profile for the drug of said pharmaceutical composition characterized by a $C_{min,ss}$ that is 6 to 15 ng/ml per mg of drug. In a preferred aspect, said $C_{min,ss}$ is 8 to 12.5 ng/ml per mg of drug. In a preferred aspect, said $C_{min,ss}$ is 9 to 12 ng/ml per mg of drug.

Some aspects of any of the embodiments described herein provide a method of administering a pharmaceutical composition to a human, orally, once daily, wherein once daily oral dosing of said pharmaceutical composition at a predetermined administration time to a subject of a fasted, human pharmacokinetic study provides a steady state plasma concentration profile for the drug of said pharmaceutical composition characterized by a C-ave-day that is 20 to 100% greater than C-ave-night. In a preferred aspect, said steady state plasma concentration profile for the drug of said pharmaceutical composition is characterized by a C-ave-day that is 30% to 100% greater than C-ave-night. In a preferred aspect, C-ave-day is determined from the steady state plasma concentration profile over the period of 9 am to 6 pm and C-ave-night is determined from the steady state plasma concentration profile over the period of 11 pm to 8 am and said predetermined time is 5 am. In a preferred aspect, C-ave-day is determined from the steady state plasma concentration profile over the period of 9 am to 6 pm and C-ave-night is determined from the steady state plasma concentration profile over the period of 11 pm to 8 am and said predetermined time is 6 am. In a preferred aspect, C-ave-day is determined from the steady state plasma concentration profile over the period of 9 am to 6 pm and C-ave-night is determined from the steady state plasma concentration profile over the period of 11 pm to 8 am and said predetermined time is 7 am. In a preferred aspect, C-ave-day is determined from the steady state plasma concentration profile over the period of 9 am to 6 pm and C-ave-night is determined from the steady state plasma concentration profile over the period of 11 pm to 8 am and said predetermined time is 8 am. In a preferred aspect, C-ave-day is determined from the steady state plasma concentration profile over the period of 9 am to 6 pm and C-ave-night is determined from the steady state plasma concentration profile over the period of 11 pm to 8 am and said predetermined time is 8 pm. In a preferred aspect, C-ave-day is determined from the steady state plasma concentration profile over the period of 9 am to 6 pm and C-ave-night is determined from the steady state plasma concentration profile over the period of 11 pm to 8 am and said predetermined time is 9 pm. In a preferred aspect, C-ave-day is determined from the steady state plasma concentration profile over the period of 9 am to 6 pm and C-ave-night is determined from the steady state plasma concentration profile over the period of 11 pm to 8 am and said predetermined time is 10 pm. In a preferred aspect, C-ave-day is determined from the steady state plasma concentration profile over the period of 9 am to 6 pm and C-ave-night is determined from the steady state plasma concentration profile over the period of 11 pm to 8 am and said predetermined time is 11 pm. In a preferred aspect, C-ave-day is determined from the steady state plasma concentration profile over the period of 9 am to 6 pm and C-ave-night is determined from the steady state plasma concentration profile over the period of 11 pm to 8 am and said predetermined time is 12 am. In a preferred aspect, C-ave-day is determined from the steady state plasma concentration profile over the period of 9 am to 4 pm and C-ave-night is determined from the steady state plasma concentration profile over the period of 11 pm to 8 am and said predetermined time is 6 am. In a preferred aspect, C-ave-day is determined from the steady state plasma concentration profile over the period of 9 am to 4 pm and C-ave-night is determined from the steady state plasma concentration profile over the period of 11 pm to 8 am and said predetermined time is 10 pm. As used herein, 100%* ((C-ave-day/C-ave-night)−1) is equivalent to the percentage increase recited in this paragraph; for example a C-ave-day/C-ave-night ratio of 1.3 is equivalent to a 30% increase in C-ave-day from C-ave-night.

Some aspects of any of the embodiments described herein provide a method of administering a pharmaceutical composition to a human, orally, once daily, wherein once daily oral dosing of said pharmaceutical composition at a predetermined administration time to a subject of a fasted, human pharmacokinetic study provides a steady state plasma concentration profile for the drug of said pharmaceutical composition characterized by a C-ave-day that is 40 to 120% greater than C-ave-night. In a preferred aspect, C-ave-day is determined from the steady state plasma concentration profile over the period of 9 am to 6 pm and C-ave-night is determined from the steady state plasma concentration profile over the period of 11 pm to 8 am and said predetermined time is 5 am. In a preferred aspect, C-ave-day is determined from the steady state plasma concentration profile over the period of 9 am to 6 pm and C-ave-night is determined from the steady state plasma concentration profile over the period of 11 pm to 8 am and said predetermined time is 6 am. In a preferred aspect, C-ave-day is determined from the steady state plasma concentration profile over the period of 9 am to 6 pm and C-ave-night is determined from the steady state plasma concentration profile over the period of 11 pm to 8 am and said predetermined time is 7 am. In a preferred aspect, C-ave-day is determined from the steady state plasma concentration profile over the period of 9 am to 6 pm and C-ave-night is determined from the steady state plasma concentration profile over the period of 11 pm to 8 am and said predetermined time is 8 am. In a preferred aspect, C-ave-day is determined from the steady state plasma concentration profile over the period of 9 am to 6 pm and C-ave-night is determined from the steady state plasma concentration profile over the period of 11 pm to 8 am and said predetermined time is 8 pm. In a preferred aspect, C-ave-day is determined from the steady state plasma concentration profile over the period of 9 am to 6 pm and C-ave-night is determined from the steady state plasma concentration profile over the period of 11 pm to 8 am and said predetermined time is 9 pm. In a preferred aspect, C-ave-day is determined from the steady state plasma concentration profile over the period of 9 am to 6 pm and C-ave-night is determined from the steady state plasma concentration profile over the period of 11 pm to 8 am and said predetermined time is 10 pm. In a preferred aspect, C-ave-day is determined from the steady state plasma concentration profile over the period of 9 am to 6 pm and C-ave-night is determined from the steady state plasma concentration profile over the period of 11 pm to 8 am and said predetermined time is 11 pm. In a preferred aspect, C-ave-day is determined from the steady state plasma concentration profile over the period of 9 am to 6 pm and C-ave-night is determined from the steady state plasma concentration profile over the period of 11 pm to 8 am and said predetermined time is 12 am. In a preferred aspect, C-ave-day is determined from the steady state plasma concentration profile over the period of 9 am to 4 pm and C-ave-night is determined from the steady state plasma concentration profile over the period of 11 pm to 8 am and said predetermined time is 6 am. In a preferred aspect, C-ave-day is determined from the steady state plasma concentration profile over the period of 9 am to 4 pm and C-ave-night is determined from the steady state plasma concentration profile over the period of 11 pm to 8 am and said predetermined time is 10 pm. As used herein, 100%*((C-ave-day/C-ave-night)−1) is equivalent to the percentage increase recited in this paragraph; for example a C-ave-day/C-ave-night ratio of 1.55 is equivalent to a 55% increase in C-ave-day from C-ave-night.

Some aspects of any of the embodiments described herein provide a method of administering a pharmaceutical composition to a human, orally, once daily, wherein once daily oral dosing of said pharmaceutical composition to a subject of a fasted, human pharmacokinetic study provides a steady state plasma concentration profile for the drug of said pharmaceutical composition characterized by a swing that is 40% to 200%. In a preferred aspect, said swing is 60% to 200%. In a preferred aspect, said swing is 75% to 200%. In a preferred aspect, said swing is 80% to 180%. In a preferred aspect, said swing is 85% to 160%. In a preferred aspect, said swing is 80% to 150%. In a preferred aspect, said swing is 100% to 150%. In a preferred aspect, said swing is 50% to 100%.

Some aspects of any of the embodiments described herein provide a method of administering a pharmaceutical composition to a human, orally, once daily, wherein once daily oral dosing of said pharmaceutical composition to a subject of a fasted, human pharmacokinetic study provides a steady state plasma concentration profile for the drug of said pharmaceutical composition characterized by a PTF that is 50% to 100%. In a preferred aspect, said PTF is 50% to 90%. In a preferred aspect, said PTF is 55% to 85%. In a preferred aspect, said PTF is 60% to 80%. In a preferred aspect, said PTF is 45% to 85%. In a preferred aspect, said PTF is 40% to 80%.

Some aspects of any of the embodiments described herein provide a method of administering a pharmaceutical composition to a human, orally, once daily, wherein said pharmaceutical composition comprises a delayed release coating.

Some aspects of any of the embodiments described herein provide a method of administering a pharmaceutical composition to a human, orally, once daily, wherein the daily dose of the drug of said pharmaceutical composition is 50 mg to 900 mg. In a preferred aspect, the daily dose of the drug of said composition is 100 mg to 900 mg. In a preferred aspect, the daily dose of the drug of said composition is 150 mg to 900 mg. In a preferred aspect, the daily dose of the drug of said composition is 300 mg to 900 mg. In a preferred aspect, the daily dose of the drug of said composition is 200 mg to 850 mg. In a preferred aspect, the daily dose of the drug of said composition is 250 mg to 850 mg. In a preferred aspect, the daily dose of the drug of said composition is 300 mg to 850 mg. In a preferred aspect, the daily dose of the drug of said composition is 350 mg to 850 mg. In a preferred aspect, the daily dose of the drug of said composition is 400 mg to 850 mg. In a preferred aspect, the daily dose of the drug of said composition is 450 mg to 850 mg. In a preferred aspect, the daily dose of the drug of said composition is 500 mg to 850 mg. In a preferred aspect, the daily dose of the drug of said composition is 550 mg to 850 mg. In a preferred aspect, the daily dose of the drug of said composition is 600 mg to 850 mg. In a preferred aspect, the daily dose of the drug of said composition is 650 mg to 850 mg. In a preferred aspect, the daily dose of the drug of said composition is 400 mg to 800 mg. In a preferred aspect, the daily dose of the drug of said composition is 450 mg to 800 mg.

Some aspects of any of the embodiments described herein provide a method of administering a pharmaceutical composition to a human, orally, once daily, 0 to 4 hours before bedtime; preferably 0 to 3 hours before bedtime; more preferably 0 to 2 hours before bedtime.

Some aspects of any of the embodiments described herein provide a method of administering a pharmaceutical composition to a human, orally, once daily, at 8 pm, 9 pm, 10 pm, 11 pm, or 12 am; preferably at 8 pm, 9 pm, 10 pm, or 11 pm. In a preferred aspect the composition is administered at 10 pm. In a preferred aspect, the composition is administered at 11 pm. These administration times are examples of preferred predetermined administration times.

Some aspects of any of the embodiments described herein provide a method of administering a pharmaceutical composition to a human, orally, once daily, 0 to 4 hours after waking for the day; preferably 0 to 3 hours after waking for the day; more preferably 0 to 2 hours after waking for the day.

Some aspects of any of the embodiments described herein provide a method of administering a pharmaceutical composition to a human, orally, once daily, at 5 am, 6 am, 7 am, 8 am, or 9 am; preferably at 6 am, 7 am, or 8 am. In a preferred aspect the composition is administered at 6 am. In a preferred aspect, the composition is administered at 7 am. These administration times are examples of preferred predetermined administration times.

Some embodiments described herein provide a pharmaceutical composition for oral administration to a human comprising (i) a drug selected from the group consisting of brivaracetam, divalproex, lacosamide, levetiracetam, oxcarbazepine, vigabatrin, and pharmaceutically acceptable salts thereof, and mixtures of any of the foregoing, and (ii) one or more excipients, wherein at least one of said one or more excipients modifies the release of the drug to provide an extended release form. In some embodiments the pharmaceutical composition comprises one or more additional active pharmaceutical ingredients. In a preferred embodiment, no other drugs are included in the pharmaceutical composition.

Some embodiments described herein provide a pharmaceutical composition for oral administration to a human comprising (i) a drug selected from the group consisting of brivaracetam, lacosamide, levetiracetam, oxcarbazepine, and pharmaceutically acceptable salts thereof, and mixtures of any of the foregoing, and (ii) one or more excipients, wherein at least one of said one or more excipients modifies the release of the drug to provide an extended release form.

Some embodiments described herein provide a pharmaceutical composition for oral administration to a human comprising (i) a drug selected from the group consisting of lacosamide and pharmaceutically acceptable salts thereof, and mixtures of any of the foregoing, and (ii) one or more excipients, wherein at least one of said one or more excipients modifies the release of the drug to provide an extended release form.

Some aspects of any of the embodiments described herein provide a pharmaceutical composition wherein said pharmaceutical composition comprises at least one or more excipients which modifies the release of the drug to provide a delayed release form.

Some aspects of any of the embodiments described herein provide a pharmaceutical composition for oral administration to a human, wherein said composition provides a dissolution profile characterized by at least two of the following: (i) release of less than 8% in 2 hours, (ii) release of less than 17% in 4 hours, (iii) release of less than 45% at 6 hours, and wherein the dissolution profile of said pharmaceutical composition is characterized by release of at least 45% at 12 hours, wherein the dissolution is performed in a USP type 1 (basket) apparatus rotating at 100 rpm using 900 ml 0.1 N simulated gastric fluid (pH 1.2) at 37.0±0.5° C. for 2 hours, followed by dissolution in the same apparatus and speed using 900 ml simulated intestinal fluid (pH 6.8) at 37.0±0.5° C. for the subsequent 4 hours, followed by dissolution in the same apparatus and speed using 900 ml phosphate buffer (pH 7.5) at 37.0±0.5° C. for the subsequent 18 hours. In a preferred aspect of this embodiment, all three of said release criteria are met. In a preferred aspect of this embodiment, the release of drug at 4 hours is less than 10%.

Some aspects of any of the embodiments described herein provide a pharmaceutical composition to a human, wherein said composition provides a dissolution profile characterized by at least three of the following: (i) less than 10% release at 1 hour, (ii) less than 15% release at 2 hours, (iii) less than 25% release at 4 hours, (iv) at least 35% release at 9 hours, (v) at least 65% release at 12 hours, wherein the dissolution is performed in a USP type 1 (basket) apparatus rotating at 100 rpm using 900 ml simulated gastric fluid (pH 1.2) at 37.0±0.5° C. for 2 hours, followed by dissolution in the same apparatus and speed using 900 ml simulated intestinal fluid (pH 6.8) at 37.0±0.5° C. for the subsequent 4 hours, followed by dissolution in the same apparatus and speed using 900 ml phosphate buffer (pH 7.5) at 37.0±0.5° C. for the subsequent 18 hours.

Some aspects of any of the embodiments described herein provide a pharmaceutical composition for oral administration to a human, wherein oral ingestion of a dose of said pharmaceutical composition by a subject of a fasted, single dose, human pharmacokinetic study provides a plasma concentration profile for the drug of said pharmaceutical composition characterized by a $T_{max}$ of 5 to 20 hours. In a preferred aspect, said $T_{max}$ is 5 to 10 hours. In a preferred aspect, said $T_{max}$ is 8 to 20 hours. In a preferred aspect, $T_{max}$ is 10 to 20 hours. In a preferred aspect, said $T_{max}$ is 10 to 14 hours. In a preferred aspect, said $T_{max}$ is 12 to 20 hours. In a more preferred aspect, said $T_{max}$ is 13 to 20 hours.

Some aspects of any of the embodiments described herein provide a pharmaceutical composition for oral administration to a human, wherein oral ingestion of a dose of said pharmaceutical composition by a subject of a fasted, single dose, human pharmacokinetic study provides a plasma concentration profile for the drug of said pharmaceutical composition characterized by a $T_{lag}$ of 0.25 to 9 hours. In a preferred aspect, said $T_{lag}$ is 0.25 to 5 hours. In a preferred aspect, said $T_{lag}$ is 1 to 9 hours. In a preferred aspect, said $T_{lag}$ is 2 to 9 hours. In a preferred aspect, said $T_{lag}$ is 3 to 8 hours. In a preferred aspect, said $T_{lag}$ is 0.5 to 5 hours. In a preferred aspect, said $T_{lag}$ is 1 to 5 hours. In a preferred aspect, said $T_{lag}$ is 2 to 5 hours.

Some aspects of any of the embodiments described herein provide a pharmaceutical composition for oral administration to a human, wherein oral ingestion of a dose of said pharmaceutical composition by a subject of a fasted, single dose, human pharmacokinetic study provides a plasma concentration profile for the drug of said pharmaceutical composition characterized by an $AUC_{0-\infty}$ provides AUC equivalence to IR.

Some aspects of any of the embodiments described herein provide a pharmaceutical composition for oral administration to a human, wherein oral ingestion of a dose of said pharmaceutical composition by a subject of a fasted, single dose, human pharmacokinetic study provides a plasma concentration profile for the drug of said pharmaceutical composition characterized by a dC/dt over the first 1.4 hours after ingestion that is less than 10% of the dC/dt determined for an equivalent dose of the drug of said pharmaceutical composition in an immediate release form over the first 1.4 hours after ingestion by a subject of said fasted, single dose, human pharmacokinetic study. In a preferred aspect, the dC/dt determined for said composition is less than 5% of the dC/dt determined for an equivalent dose of the drug of said pharmaceutical composition in an immediate release form over the first 1.4 hours after ingestion by a subject of said fasted, single dose, human pharmacokinetic study.

Some aspects of any of the embodiments described herein provide a pharmaceutical composition for oral administration to a human, wherein oral ingestion of a dose of said pharmaceutical composition by a subject of a fasted, single dose, human pharmacokinetic study provides a plasma concentration profile for the drug of said pharmaceutical composition characterized by a dC/dt over the first 2 hours after ingestion that is less than 15% of the dC/dt determined for an equivalent dose of the drug of said pharmaceutical composition in an immediate release form over the first 2 hours after ingestion by a subject of said fasted, single dose, human pharmacokinetic study. In a preferred aspect, the dC/dt determined for said composition is less than 10% of the dC/dt determined for an equivalent dose of the drug of said pharmaceutical composition in an immediate release form over the first 2 hours after ingestion by a subject of said fasted, single dose, human pharmacokinetic study. In a preferred aspect, the dC/dt determined for said composition is less than 5% of the dC/dt determined for an equivalent dose of the drug of said pharmaceutical composition in an immediate release form over the first 2 hours after ingestion by a subject of said fasted, single dose, human pharmacokinetic study.

Some aspects of any of the embodiments described herein provide a pharmaceutical composition for oral administration to a human, wherein oral ingestion of a dose of said pharmaceutical composition by a subject of a fasted, single dose, human pharmacokinetic study provides a plasma concentration profile for the drug of said pharmaceutical composition characterized by a dC/dt over the first 3 hours after ingestion that is less than 25% of the dC/dt determined for an equivalent dose of the drug of said pharmaceutical composition in an immediate release form over the first 3 hours after ingestion by a subject of said fasted, single dose, human pharmacokinetic study. In a preferred aspect, the dC/dt determined for said composition is less than 20% of the dC/dt determined for an equivalent dose of the drug of said pharmaceutical composition in an immediate release form over the first 3 hours after ingestion by a subject of said fasted, single dose, human pharmacokinetic study. In a preferred aspect, the dC/dt determined for said composition is less than 10% of the dC/dt determined for an equivalent dose of the drug of said pharmaceutical composition in an immediate release form over the first 3 hours after ingestion by a subject of said fasted, single dose, human pharmacokinetic study.

Some aspects of any of the embodiments described herein provide a pharmaceutical composition for oral administration to a human, wherein oral ingestion of a dose of said pharmaceutical composition by a subject of a fasted, single dose, human pharmacokinetic study provides a plasma concentration profile for the drug of said pharmaceutical composition characterized by a dC/dt over the first 4 hours after ingestion that is less than 30% of the dC/dt determined for an equivalent dose of the drug of said pharmaceutical composition in an immediate release form over the first 4 hours after ingestion by a subject of said fasted, single dose, human pharmacokinetic study. In a preferred aspect, the dC/dt determined for said composition is less than 20% of the dC/dt determined for an equivalent dose of the drug of said pharmaceutical composition in an immediate release form over the first 4 hours after ingestion by a subject of said fasted, single dose, human pharmacokinetic study. In a preferred aspect, the dC/dt determined for said composition is less than 10% of the dC/dt determined for an equivalent dose of the drug of said pharmaceutical composition in an immediate release form over the first 4 hours after ingestion by a subject of said fasted, single dose, human pharmacokinetic study.

Some aspects of any of the embodiments described herein provide a pharmaceutical composition for oral administration to a human, wherein oral ingestion of a dose of said pharmaceutical composition by a subject of a fasted, single dose, human pharmacokinetic study provides a plasma concentration profile for the drug of said pharmaceutical composition characterized by a dC/dt over the first 2 hours after ingestion that is less than 1 µg/ml/hr. In a preferred aspect, said dC/dt over the first 2 hours after ingestion is less than 0.6 µg/ml/hr. In a preferred aspect, said dC/dt over the first 2 hours after ingestion is less than 0.45 µg/ml/hr. In a preferred aspect, said dC/dt over the first 2 hours after ingestion is less than 0.3 µg/ml/hr. In a preferred aspect, said dC/dt over the first 2 hours after ingestion is less than 0.1 µg/ml/hr.

Some aspects of any of the embodiments described herein provide a pharmaceutical composition for oral administration to a human, wherein oral ingestion of a dose of said pharmaceutical composition by a subject of a fasted, single dose, human pharmacokinetic study provides a plasma concentration profile for the drug of said pharmaceutical composition characterized by a dC/dt over the first 3 hours after ingestion that is less than 0.8 µg/ml/hr. In a preferred aspect, said dC/dt over the first 3 hours after ingestion is less than 0.6 µg/ml/hr. In a preferred aspect, said dC/dt over the first 3 hours after ingestion is less than 0.4 µg/ml/hr. In a preferred aspect, said dC/dt over the first 3 hours after ingestion is less than 0.25 µg/ml/hr. In a preferred aspect, said dC/dt over the first 3 hours after ingestion is less than 0.1 µg/ml/hr.

Some aspects of any of the embodiments described herein provide a pharmaceutical composition for oral administration to a human, wherein oral ingestion of a dose of said pharmaceutical composition by a subject of a fasted, single dose, human pharmacokinetic study provides a plasma concentration profile for the drug of said pharmaceutical composition characterized by a dC/dt over the first 4 hours after ingestion that is less than 0.6 µg/ml/hr. In a preferred aspect, said dC/dt over the first 4 hours after ingestion is less than 0.5 µg/ml/hr. In a preferred aspect, said dC/dt over the first 4 hours after ingestion is less than 0.4 µg/ml/hr. In a preferred aspect, said dC/dt over the first 4 hours after ingestion is less than 0.25 µg/ml/hr. In a preferred aspect, said dC/dt over the first 4 hours after ingestion is less than 0.1 µg/ml/hr.

Some aspects of any of the embodiments described herein provide a pharmaceutical composition for oral administration to a human, wherein oral ingestion of a dose of said pharmaceutical composition by a subject of a fasted, single dose, human pharmacokinetic study provides a plasma concentration profile for the drug of said pharmaceutical composition characterized by a dC/dt over the first 2 hours after ingestion that is less than 2.2 ng/ml/hr per mg of the drug of said pharmaceutical composition. In a preferred aspect, said dC/dt over the first 2 hours after ingestion is less than 1.8 ng/ml/hr per mg of the drug of said pharmaceutical composition. In a preferred aspect, said dC/dt over the first 2 hours after ingestion is less than 1.4 ng/ml/hr per mg of the drug of said pharmaceutical composition. In a preferred aspect, said dC/dt over the first 2 hours after ingestion is less than 1 ng/ml/hr per mg of the drug of said pharmaceutical composition. In a preferred aspect, said dC/dt over the first 2 hours after ingestion is less than 0.5 ng/ml/hr per mg of the drug of said pharmaceutical composition.

Some aspects of any of the embodiments described herein provide a pharmaceutical composition for oral administration to a human, wherein oral ingestion of a dose of said pharmaceutical composition by a subject of a fasted, single dose, human pharmacokinetic study provides a plasma concentration profile for the drug of said pharmaceutical composition characterized by a dC/dt over the first 3 hours after ingestion that is less than 2 ng/ml/hr per mg of said pharmaceutical composition. In a preferred aspect, said dC/dt over the first 3 hours after ingestion is less than 1.6 ng/ml/hr per mg of the drug of said pharmaceutical composition. In a preferred aspect, said dC/dt over the first 3 hours after ingestion is less than 1.2 ng/ml/hr per mg of the drug of said pharmaceutical composition. In a preferred aspect, said dC/dt over the first 3 hours after ingestion is less than 0.8 ng/ml/hr per mg of the drug of said pharmaceutical composition. In a preferred aspect, said dC/dt over the first 3 hours after ingestion is less than 0.4 ng/ml/hr per mg of the drug of said pharmaceutical composition.

Some aspects of any of the embodiments described herein provide a pharmaceutical composition for oral administration to a human, wherein oral ingestion of a dose of said pharmaceutical composition by a subject of a fasted, single dose, human pharmacokinetic study provides a plasma concentration profile for the drug of said pharmaceutical composition characterized by a dC/dt over the first 4 hours after ingestion that is less than 1.6 ng/ml/hr per mg of the drug of said pharmaceutical composition. In a preferred aspect, said dC/dt over the first 4 hours after ingestion is less than 1.2 ng/ml/hr per mg of the drug of said pharmaceutical composition. In a preferred aspect, said dC/dt over the first 4 hours after ingestion is less than 0.8 ng/ml/hr per mg of the drug of said pharmaceutical composition. In a preferred aspect, said dC/dt over the first 4 hours after ingestion is less than 0.4 ng/ml/hr per mg of the drug of said pharmaceutical composition. In a preferred aspect, said dC/dt over the first 4 hours after ingestion is less than 0.2 ng/ml/hr per mg of the drug of said pharmaceutical composition.

Some aspects of any of the embodiments described herein provide a pharmaceutical composition for oral administration to a human, wherein oral ingestion of a dose of said pharmaceutical composition by a subject of a fasted, single dose, human pharmacokinetic study provides a plasma concentration profile for the drug of said pharmaceutical composition characterized by a $pAUC_{0-4}$ that is less than 12% of $AUC_{0-\infty}$ determined for the drug of said pharmaceutical composition from said plasma concentration profile. In a preferred aspect, said $pAUC_{0-4}$ is less than 10% of $AUC_{0-\infty}$ determined for the drug of said pharmaceutical composition from said plasma concentration profile. In a preferred aspect, said $pAUC_{0-4}$ is less than 8% of $AUC_{0-\infty}$ determined for the drug of said pharmaceutical composition from said plasma concentration profile. In a preferred aspect, said $pAUC_{0-4}$ is less than 6% of $AUC_{0-\infty}$ determined for the drug of said pharmaceutical composition from said plasma concentration profile. In a preferred aspect, said $pAUC_{0-4}$ is less than 4% of $AUC_{0-\infty}$ determined for the drug of said pharmaceutical composition from said plasma concentration profile. In a preferred aspect, said $pAUC_{0-4}$ is less than 2% of $AUC_{0-\infty}$ determined for the drug of said pharmaceutical composition from said plasma concentration profile. In a preferred aspect, said $pAUC_{0-4}$ is less than 1% of $AUC_{0-\infty}$ determined for the drug of said pharmaceutical composition from said plasma concentration profile.

Some aspects of any of the embodiments described herein provide a pharmaceutical composition for oral administration to a human, wherein oral ingestion of a dose of said pharmaceutical composition by a subject of a fasted, single dose, human pharmacokinetic study provides a plasma concentration profile for the drug of said pharmaceutical composition characterized by a $pAUC_{0-8}$ that is less than 12% of $AUC_{0-\infty}$ determined for the drug of said pharmaceutical composition from said plasma concentration profile. In a preferred aspect, said $pAUC_{0-8}$ is less than 10% of $AUC_{0-\infty}$ determined for the drug of said pharmaceutical composition from said plasma concentration profile. In a preferred aspect, said $pAUC_{0-8}$ is less than 7.5% of $AUC_{0-\infty}$ determined for the drug of said pharmaceutical composition from said plasma concentration profile. In a preferred aspect, said $pAUC_{0-8}$ is less than 5% of $AUC_{0-\infty}$ determined for the drug of said pharmaceutical composition from said plasma concentration profile. In a preferred aspect, said $pAUC_{0-8}$ is less than 3% of $AUC_{0-\infty}$ determined for the drug of said pharmaceutical composition from said plasma concentration profile.

Some aspects of any of the embodiments described herein provide a pharmaceutical composition for oral administration to a human, wherein oral ingestion of a dose of said pharmaceutical composition by a subject of a fasted, single dose, human pharmacokinetic study provides a plasma concentration profile for the drug of said pharmaceutical composition characterized by a $pAUC_{4-8}$ that is less than 14% of $AUC_{0-\infty}$ determined for the drug of said pharmaceutical composition from said plasma concentration profile. In a preferred aspect, said $pAUC_{4-8}$ is less than 12% of $AUC_{0-\infty}$ determined for the drug of said pharmaceutical composition from said plasma concentration profile. In a preferred aspect, said $pAUC_{4-8}$ is less than 10% of $AUC_{0-\infty}$ determined for the drug of said pharmaceutical composition from said plasma concentration profile. In a preferred aspect, said $pAUC_{4-8}$ is less than 8% of $AUC_{0-\infty}$ determined for the drug of said pharmaceutical composition from said plasma concentration profile. In a preferred aspect, said $pAUC_{4-8}$ is less than 7% of $AUC_{0-\infty}$ determined for the drug of said pharmaceutical composition from said plasma concentration profile. In a preferred aspect, said $pAUC_{4-8}$ is less than 6% of $AUC_{0-\infty}$ determined for the drug of said pharmaceutical composition from said plasma concentration profile. In a preferred aspect, said $pAUC_{4-8}$ is less than 4% of $AUC_{0-\infty}$ determined for the drug of said pharmaceutical composition from said plasma concentration profile. In a preferred aspect, said $pAUC_{4-8}$ is less than 2.5% of $AUC_{0-\infty}$ determined for the drug of said pharmaceutical composition from said plasma concentration profile.

Some aspects of any of the embodiments described herein provide a pharmaceutical composition for oral administration to a human, wherein once daily oral dosing of said pharmaceutical composition to a subject of a fasted, human pharmacokinetic study provides a steady state plasma concentration profile for the drug of said pharmaceutical composition characterized by a $T_{max,ss}$ that is 5 to 20 hours. In a preferred aspect, said $T_{max,ss}$ is 5 to 10 hours. In a preferred aspect, said $T_{max,ss}$ is 10 to 20 hours. In a preferred aspect, said $T_{max,ss}$ is 12 to 20 hours. In a preferred aspect, said $T_{max,ss}$ is 11 to 18 hours. In a preferred aspect, said $T_{max,ss}$ is 12 to 18 hours. In a preferred aspect, said $T_{max,ss}$ is 13 to 18 hours. In a preferred aspect, said $T_{max,ss}$ is 14 to 18 hours.

Some aspects of any of the embodiments described herein provide a pharmaceutical composition for oral administration to a human, wherein once daily oral dosing of said pharmaceutical composition to a subject of a fasted, human pharmacokinetic study provides a steady state plasma concentration profile for the drug of said pharmaceutical composition characterized by a $C_{max,ss}$ that is 12 to 36 ng/ml per mg of drug. In a preferred aspect, said $C_{max,ss}$ is 16 to 32 ng/ml per mg of drug. In a preferred aspect, said $C_{max,ss}$ is 20 to 30 ng/ml per mg of drug. In a preferred aspect, said $C_{max,ss}$ is 22 to 30 ng/ml per mg of drug. In a preferred aspect, said $C_{max,ss}$ is 23 to 30 ng/ml per mg of drug. In a preferred aspect, said $C_{max,ss}$ is 24 to 32 ng/ml per mg of drug.

Some aspects of any of the embodiments described herein provide a pharmaceutical composition for oral administration to a human, wherein once daily oral dosing of said pharmaceutical composition to a subject of a fasted, human pharmacokinetic study provides a steady state plasma concentration profile for the drug of said pharmaceutical composition characterized by a $C_{min,ss}$ that is 6 to 15 ng/ml per mg of drug. In a preferred aspect, said $C_{min,ss}$ is 8 to 12.5 ng/ml per mg of drug. In a preferred aspect, said $C_{min,ss}$ is 9 to 12 ng/ml per mg of drug.

Some aspects of any of the embodiments described herein provide a pharmaceutical composition for oral administration to a human, wherein once daily oral dosing of said pharmaceutical composition to a subject of a fasted, human pharmacokinetic study provides a steady state plasma concentration profile for the drug of said pharmaceutical composition characterized by a swing that is 40% to 200%. In a preferred aspect, said swing is 60% to 200%. In a preferred aspect, said swing is 75% to 200%. In a preferred aspect, said swing is 80% to 180%. In a preferred aspect, said swing is 85% to 160%. In a preferred aspect, said swing is 80% to 150%. In a preferred aspect, said swing is 100% to 150%. In a preferred aspect, said swing is 50% to 100%. Some aspects of any of the embodiments described herein provide a pharmaceutical composition for oral administration to a human, wherein once daily oral dosing of said pharmaceutical composition to a subject of a fasted, human pharmacokinetic study provides a steady state plasma concentration profile for the drug of said pharmaceutical composition characterized by a PTF that is 50% to 100%. In a preferred aspect, said PTF is 50% to 90%. In a preferred aspect, said PTF is 55% to 85%. In a preferred aspect, said PTF is 60% to 80%. In a preferred aspect, said PTF is 45% to 85%. In a preferred aspect, said PTF is 40% to 80%.

Some aspects of any of the embodiments described herein provide a pharmaceutical composition for oral administration to a human comprising a delayed release coating.

Some aspects of any of the embodiments described herein provide a pharmaceutical composition for oral administration to a human, wherein the wherein the drug of said pharmaceutical composition is 50 mg to 900 mg. In a preferred aspect, the drug of said composition is 100 mg to 900 mg. In a preferred aspect, the drug of said composition is 150 mg to 900 mg. In a preferred aspect, the drug of said composition is 300 mg to 900 mg. In a preferred aspect, the drug of said composition is 200 mg to 850 mg. In a preferred aspect, the drug of said composition is 250 mg to 850 mg. In a preferred aspect, the drug of said composition is 300 mg to 850 mg. In a preferred aspect, the drug of said composition is 350 mg to 850 mg. In a preferred aspect, the drug of said composition is 400 mg to 850 mg. In a preferred aspect, the drug of said composition is 450 mg to 850 mg. In a preferred aspect, the drug of said composition is 500 mg to 850 mg. In a preferred aspect, the drug of said composition is 550 mg to 850 mg. In a preferred aspect, the drug of said composition is 600 mg to 850 mg. In a preferred aspect, the drug of said composition is 650 mg to 850 mg. In a preferred aspect, the drug of said composition is 200 mg to 800 mg. In a preferred aspect, the drug of said composition is 225 mg to 800 mg. In a preferred aspect, the drug of said composition is 250 mg to 800 mg. In a preferred aspect, the drug of said composition is 400 mg to 800 mg. In a preferred aspect, the drug of said composition is 450 mg to 800 mg.

Some embodiments described herein provide a method of administering a pharmaceutical composition to a human, comprising administering to a human orally, once daily, a dose of the pharmaceutical compositions described herein comprising a drug selected from the group consisting of brivaracetam, divalproex, lacosamide, levetiracetam, oxcarbazepine, vigabatrin, and pharmaceutically acceptable salts thereof, and one or more excipients, and mixtures of any of the foregoing, wherein at least one of said one or more excipients modifies the release of the drug to provide an extended release form, and wherein administration of said pharmaceutical composition preferably provides one or more of the following: a $T_{max}$ of 5 to 20 hours, an $AUC_{0-inf}$ of 80% to 125% of that for an equivalent dose of the drug in an immediate release form, and/or a dC/dt over the period of 0 to 1.4 hours after administration that is less than 10% of the dC/dt of an equivalent dose of the drug in an immediate release form over the same time period as determined from a single dose, fasted, human pharmacokinetic study.

In some aspects of these embodiments, partial AUCs of the compositions are from 8 am to 10 am, 10 am to 12 pm, 12 pm to 2 pm, 2 pm to 4 pm, and 4 pm to 8 pm and are 80% to 125% of the partial AUCs for an equivalent total daily dose of the drug in an immediate release form of said drug administered in equal portions at 8 am and 8 pm.

In some embodiments, oral administration of said pharmaceutical composition to a subject of a fasted, single dose, human pharmaceutical composition provides a drug plasma concentration profile characterized by one or both of the following: a $pAUC_{0-4}$ for at least one active pharmaceutical ingredient of the composition that is less than 2%, 4%, 6%, 8%, 10%, or 12% of the $AUC_{0-inf}$ for said active pharmaceutical ingredient of the composition (e.g. <4%), or a $pAUC_{4-8}$ for at least one active pharmaceutical ingredient of the composition that is less than 3%, 5%, 7%, 9%, 12%, or 15% of the $AUC_{0-inf}$ for said active pharmaceutical ingredient of the composition (e.g. <7%). In preferred aspects the active pharmaceutical ingredient of the composition is selected from the group consisting of brivaracetam, lacosamide, and levetiracetam. In more preferred aspects, the active pharmaceutical ingredient of the composition is lacosamide.

In some embodiments of the invention, the method is directed to orally administering, to a human once daily, a dose of said pharmaceutical composition consisting of a drug selected from the group consisting of brivaracetam, divalproex, lacosamide, levetiracetam, oxcarbazepine, vigabatrin, and pharmaceutically acceptable salts thereof, and one or more excipients, and mixtures of any of the foregoing, wherein at least one of said one or more excipients modifies the release of the drug to provide an extended release form, and wherein administration of said pharmaceutical composition preferably provides one or more of the following: a $T_{max}$ of 12 to 20 hours, AUC equivalence to IR, and/or a dC/dt over the period of 0 to 1.4 hours after administration that is less than 10% of the dC/dt of an equivalent dose of the drug in an immediate release form over the same time period as determined from a single dose, fasted, human pharmacokinetic study.

In other embodiments of the invention, the method of administering, to a human orally, once daily, a dose of said pharmaceutical composition consisting of a drug selected from the group consisting of brivaracetam, divalproex, lacosamide, levetiracetam, oxcarbazepine, vigabatrin, and pharmaceutically acceptable salts thereof, and one or more excipients, wherein at least one of said one or more excipients modifies the release of the drug to provide an extended release form, wherein the dissolution profile of said pharmaceutical composition is characterized by 2 or more of the following: (i) release of less than 8% in 2 hours, (ii) release of less than 17% in 4 hours, (iii) release of less than 45% at 6 hours, and/or (iv) release of at least 45% at 12 hours; wherein the dissolution is typically performed in a USP type 1 (basket) apparatus rotating at 100 rpm using 900 ml 0.1 N HCl at 37.0±0.5° C. for 2 hours followed by dissolution in the same apparatus and speed using 900 ml USP phosphate buffer pH 6.8 at 37.0±0.5° C., and wherein administration of said pharmaceutical composition provides one or more of the following: a $T_{max}$ of 12 to 20 hours, AUC equivalence to IR, and/or a dC/dt over the period of 0 to 1.4 hours after administration that is less than 10% of the dC/dt of an equivalent dose of the drug in an immediate release form over the same time period as determined from a single dose, fasted, human pharmacokinetic study.

In another embodiment of the invention, the pharmaceutical composition is administered 0 to 4 hours before bedtime, and said pharmaceutical composition comprising an AED selected from the group consisting of brivaracetam, divalproex, lacosamide, levetiracetam, oxcarbazepine, vigabatrin, and pharmaceutically acceptable salts thereof, provides a $T_{max}$ of 12 to 20 hours, AUC equivalence to IR, and a dC/dt over the period of 0 to 1.4 hours after administration that is less than 10% of the dC/dt of an equivalent dose of the drug in an immediate release form over the same time period as determined from a single dose, fasted, human pharmacokinetic study.

In some embodiments of the invention, the method of administering a pharmaceutical composition to a human, comprising orally administering to a human, once daily, a dose of said pharmaceutical composition consisting of a drug selected from the group consisting of brivaracetam, divalproex, lacosamide, levetiracetam, oxcarbazepine, vigabatrin, and pharmaceutically acceptable salts thereof, and one or more excipients, wherein at least one of said one or more excipients modifies the release of the drug to provide an extended release form, and wherein administration of said pharmaceutical composition provides a $T_{max}$ of 5 to 10 hours, AUC equivalence to IR, and a dC/dt over the period of 0 to 1.4 hours after administration that is less than 10% of the dC/dt of an equivalent dose of the drug in an immediate release form over the same time period as determined from a single dose, fasted, human pharmacokinetic study. In some aspects of this embodiment, the drug is administered 0 to 3 hours after waking for the day, preferably between 5:00 am and 9:00 am.

Another embodiment is directed to a method of administering a pharmaceutical composition to a human, comprising administering to said human orally, once daily, a dose of said pharmaceutical composition consisting of a drug selected from the group consisting of brivaracetam, lacosamide, levetiracetam, oxcarbazepine, divalproex, vigabatrin, and pharmaceutically acceptable salts thereof, and one or more excipients, wherein at least one of said one or more excipients modifies the release of the drug to provide an extended release form, and wherein administration of said pharmaceutical composition provides a $T_{max}$ of 5 to 20 hours, AUC equivalence to IR, and a C-ave-day that is 20% to 100% greater than C-ave-night as determined from a fasted human pharmacokinetic study. In a preferred aspect of this embodiment, C-ave-day is the average plasma concentration at steady state determined over the period from 9 am to 6 pm and C-ave-night is the average plasma concentration at steady state determined over the period from 11 pm to 8 am. In a preferred aspect of this embodiment, the C-ave-day and C-ave-night determinations are from a WinNonLin model or a GastroPlus model of the steady state plasma concentration profile for a once daily orally administered composition of said drug. In another preferred aspect of this embodiment, the C-ave-day is 30%, 40%, 50%, 60% to 60%, 70%, 80%, 90%, or 100% greater than C-ave-night.

Some embodiments are directed to a method of administering a pharmaceutical composition to a human, comprising administering to said human orally, once daily, a dose of said pharmaceutical composition consisting of (i) a drug selected from the group consisting of brivaracetam, lacosamide, levetiracetam, oxcarbazepine, divalproex, vigabatrin, and pharmaceutically acceptable salts thereof, and (ii) one or more excipients, wherein at least one of said one or more excipients modifies the release of the drug to provide an extended release form, and wherein administration of said pharmaceutical composition provides a) a $T_{max}$ of 12 to 20 hours and b) AUC equivalence to IR, and a C-ave-day that is 20% to 100% greater than C-ave-night as determined from a fasted human pharmacokinetic study.

In some embodiments, administration of the pharmaceutical composition is 0 to 4 hours before bedtime and provides a $T_{max}$ of 12 to 20 hours as determined from a single dose, fasted, human pharmacokinetic study. In some embodiments, the pharmaceutical composition is administered once daily 0 to 4 hours before bedtime. In some aspects of these embodiments, the C-ave-day is 20 to 100% greater than the C-ave-night wherein C-ave-day is determined over the period from 9 am to 6 pm and C-ave-night is determined over the period from 11 pm to 8 am.

Some embodiments are directed to a method of administering a pharmaceutical composition to a human, comprising administering to said human orally, once daily, a dose of said pharmaceutical composition consisting of (i) a drug selected from the group consisting of brivaracetam, lacosamide, levetiracetam, oxcarbazepine, divalproex, vigabatrin, and pharmaceutically acceptable salts thereof, and (ii) one or more excipients, wherein at least one of said one or more excipients modifies the release of the drug to provide an extended release form, and wherein administration of said pharmaceutical composition provides a) a $T_{max}$ of 5 to 10 hours and b) AUC equivalence to IR, and a C-ave-day that is 20% to 100% greater than C-ave-night as determined from a fasted human pharmacokinetic study.

Some embodiments are directed to a method of administering a pharmaceutical composition to a human, comprising administering to said human orally, once daily 0 to 3 hours after waking, a dose of said pharmaceutical composition consisting of (i) a drug selected from the group consisting of brivaracetam, lacosamide, levetiracetam, oxcarbazepine, divalproex, vigabatrin, and pharmaceutically acceptable salts thereof, and (ii) one or more excipients, wherein at least one of said one or more excipients modifies the release of the drug to provide an extended release form, and wherein administration of said pharmaceutical composition provides a) a $T_{max}$ of 5 to 10 hours; and b) AUC equivalence to IR, and a C-ave-day that is 20% to 100% greater than C-ave-night as determined from a fasted human pharmacokinetic study.

Some embodiments are directed to a method of administering a pharmaceutical composition to a human, comprising administering to said human orally, once daily, a dose of said pharmaceutical composition consisting of (i) a drug selected from the group consisting of brivaracetam, lacosamide, levetiracetam, oxcarbazepine, divalproex, vigabatrin, and pharmaceutically acceptable salts thereof, and (ii) one or more excipients, wherein at least one of said one or more excipients modifies the release of the drug to provide an extended release form, and wherein oral dosing of said composition to a subject of a fasted, single dose, human pharmacokinetic study provides a plasma profile characterized by one or more of the following elements: (i) a $T_{max}$ of 5 to 20 hours, (ii) AUC equivalence to IR, (iii) a dC/dt over the period of 0 to 2 hours that is less than 1 µg/ml/hr, (iv) a dC/dt over the period of 0-2 hours that is less than 2 ng/ml/hr per mg of drug, (v) a $pAUC_{0-4}$ that is less than 4% of $AUC_{0-inf}$ for the drug, (vi) a $pAUC_{4-8}$ that is less than 8% of $AUC_{0-inf}$ for the drug. In some embodiments, the plasma profile is characterized by two or more of these elements. In some embodiments, the plasma profile is characterized by three or more of these elements. In some embodiments, the plasma profile is characterized by four or more of these elements. In some of these embodiments, the plasma concentration profile is characterized by a $T_{max}$ of 12 to 20 hours. In some of these embodiments, the plasma concentration profile is characterized by a $T_{max}$ of 5 to 10 hours.

Some embodiments are directed to a method of administering a pharmaceutical composition to a human, comprising administering to said human orally, once daily, a dose of said pharmaceutical composition consisting of (i) a drug selected from the group consisting of brivaracetam, lacosamide, levetiracetam, oxcarbazepine, divalproex, vigabatrin, and pharmaceutically acceptable salts thereof, and (ii) one or more excipients, wherein at least one of said one or more excipients modifies the release of the drug to provide an extended release form, and wherein oral dosing of said composition to a subject of a fasted, single dose, human pharmacokinetic study provides a plasma profile characterized by one or more of the following elements: (i) a $T_{max}$ of 5 to 20 hours, (ii) AUC equivalence to IR, (iii) a dC/dt over the period of 0 to 2 hours that is less than 1 µg/ml/hr, (iv) a dC/dt over the period of 0-2 hours that is less than 2 ng/ml/hr per mg of drug, (v) a $pAUC_{0-4}$ that is less than 4% of $AUC_{0-inf}$ for the drug, (vi) a $pAUC_{4-8}$ that is less than 8% of $AUC_{0-inf}$ for the drug, and (iii) one or more additional drugs selected from the group consisting of brivaracetam, lacosamide, levetiracetam, oxcarbazepine, divalproex, vigabatrin, and pharmaceutically acceptable salts thereof. In some embodiments, the plasma profile is characterized by two or more of these elements. In some embodiments, the plasma profile is characterized by three or more of these elements. In some embodiments, the plasma profile is characterized by four or more of these elements. In some of these embodiments, the plasma concentration profile is characterized by a $T_{max}$ of 12 to 20 hours. In some of these embodiments, the plasma concentration profile is characterized by a $T_{max}$ of 5 to 10 hours.

Some embodiments are directed to methods of administering a pharmaceutical composition to a human, comprising administering to said human orally, once daily, a dose of said pharmaceutical composition consisting of a drug selected from the group consisting of brivaracetam, lacosamide, levetiracetam, oxcarbazepine, divalproex, vigabatrin, and pharmaceutically acceptable salts thereof, and one or more excipients, wherein at least one of said one or more excipients modifies the release of the drug to provide an extended release form, wherein the dissolution profile of said pharmaceutical composition is less than 8% in 2 hours, less than 17% in 4 hours, less than 45% at 6 hours, and at least 45% at 12 hours, wherein the dissolution is performed in a USP type 1 (basket) apparatus rotating at 100 rpm using 900 ml 0.1 N HCl at 37.0±0.5° C. for 2 hours followed by dissolution in the same apparatus and speed using 900 ml USP phosphate buffer pH 6.8 at 37.0±0.5° C., and wherein administration of said pharmaceutical composition provides a $T_{max}$ of 5 to 20 hours, AUC equivalence to IR, and a C-ave-day that is 20% to 100% greater than C-ave-night as determined from a fasted human pharmacokinetic study.

Some embodiments are directed to methods of administering a pharmaceutical composition to a human, comprising administering to said human orally, once daily, a dose of said pharmaceutical composition consisting of a drug selected from the group consisting of brivaracetam, lacosamide, levetiracetam, oxcarbazepine, divalproex, vigabatrin, and pharmaceutically acceptable salts thereof, and one or more excipients, wherein at least one of said one or more excipients modifies the release of the drug to provide an extended release form, wherein the dissolution profile of said pharmaceutical composition characterized by at least two of the following: (i) release of less than 8% in 2 hours, (ii) release of less than 17% in 4 hours, (iii) release of less than 45% at 6 hours, and wherein the dissolution profile of said pharmaceutical composition is characterized by release of at least 45% at 12 hours, wherein the dissolution is performed in a USP type 1 (basket) apparatus rotating at 100 rpm using 900 ml 0.1 N simulated gastric fluid (pH 1.2) at 37.0±0.5° C. for 2 hours, followed by dissolution in the same apparatus and speed using 900 ml simulated intestinal fluid (pH 6.8) at 37.0±0.5° C. for the subsequent 4 hours, followed by dissolution in the same apparatus and speed using 900 ml phosphate buffer (pH 7.5) at 37.0±0.5° C. for the subsequent 18 hours, and wherein oral dosing of said pharmaceutical composition to a subject of a fasted, single dose, human pharmacokinetic study provides plasma concentration profile characterized by a $T_{max}$ of 5 to 20 hours. In some aspects of this embodiment, said plasma concentration profile provides AUC equivalence to IR. In some aspects of this embodiment, said plasma concentration profile is characterized by one or more of the following: (i) a dC/dt over the period of 0 to 2 hours that is less than 1 µg/ml/hr, (ii) a dC/dt over the period of 0-2 hours that is less than 2 ng/ml/hr per mg of drug, (iii) a $pAUC_{0-4}$ that is less than 4% of $AUC_{0-inf}$ for the drug, (iv) a $pAUC_{4-8}$ that is less than 8% of $AUC_{0-inf}$ for the drug. In some aspects, the plasma profile is characterized by two or more of these elements. In some aspects, the plasma profile is characterized by three or more of these elements. In some aspects, the drug is selected from the group consisting of brivaracetam, lacosamide, and levetiracetam. In some aspects, the drug is lacosamide.

In some aspects of any of the previous embodiments, oral dosing of the composition to a subject of a fasted, human pharmacokinetic study provides a steady state plasma concentration profile for once daily oral dosing characterized by one or more of the following: (i) a $T_{max,ss}$ of 10 to 20 hours, (ii) a $T_{max,ss}$ of 12 to 20 hours, (iii) a C-ave-day that is 20% to 100% greater than C-ave-night (iii) a swing of 70% to 200%, (iv) a swing of 75% to 160%, (v) a PTF of 50% to 100%, preferably. In some aspects, the steady state plasma profile is characterized by two or more of these elements. In some aspects, the steady state plasma profile is characterized by three or more of these elements. In some aspects, the C-ave-day is determined over the period from 9 am to 4 pm. In some aspects, the C-ave-day is determined over the period from 9 am to 6 pm. In some aspects, the C-ave-night is determined over the period from 11 pm to 8 am. In some aspects, the steady state plasma concentration profile is adjusted to a predetermined administration time to provide a C-ave-day that is 20% to 100% greater than the C-ave-night. In some aspects, the steady state plasma concentration profile is adjusted to a predetermined administration time to provide a C-ave-day that is 40% to 100% greater than the C-ave-night.

Some embodiments are directed to a method of administering a pharmaceutical composition to a human, comprising administering to said human orally, once daily, a dose of said pharmaceutical composition consisting of: a drug selected from the group consisting of brivaracetam, lacosamide, levetiracetam, oxcarbazepine, divalproex, vigabatrin, and pharmaceutically acceptable salts thereof; and one or more excipients, wherein at least one of said one or more excipients modifies the release of the drug to provide an extended release form, and wherein administration of said pharmaceutical composition provides a $T_{max}$ of 5 to 20 hours, an $AUC_{0-inf}$ of 80% to 125% of that for an equivalent dose of the drug in an immediate release form, wherein the partial AUCs from 8 am to 10 am, 10 am to 12 pm, 12 pm to 2 pm, 2, pm to 4 pm, and 4 pm to 8 pm are 80% to 125% of the partial AUCs for an equivalent total daily dose of the drug in an immediate release form of said drug administered in equal portions at 8 am and 8 pm, and wherein C-ave-day that is 20% to 100% greater than C-ave-night as determined from a fasted human pharmacokinetic study.

Some embodiments are directed to a method of administering a pharmaceutical composition to a human, comprising administering to said human orally, once daily, a dose of said pharmaceutical composition consisting of a drug selected from the group consisting of brivaracetam, lacosamide, levetiracetam, oxcarbazepine, divalproex, vigabatrin, and pharmaceutically acceptable salts thereof, and one or more excipients, wherein at least one of said one or more excipients modifies the release of the drug to provide an extended release form, and wherein said pharmaceutical composition provides a plasma concentration profile characterized by a $T_{max}$ of 5 to 20 hours and/or (i) an $AUC_{0-4}$ for the drug of less than 2%, 4%, 6%, 8%, 10%, 12% (preferably less than 4%) of the $AUC_{0-inf}$ for said drug or (ii) an $AUC_4$-8 for the drug of less than 3%, 5%, 7%, 9%, 12%, 15% (preferably less than 7%) of the $AUC_{0-inf}$ for said drug, wherein $T_{max}$ and AUC values are determined from the plasma concentration for said drug upon oral administration of the pharmaceutical composition to a subject of a fasted, single dose human pharmacokinetic study. In some embodiments, the $AUC_{0-inf}$ for said drug of the composition is 80% to 125% of the $AUC_{0-inf}$ for said drug when administered in an oral, immediate release form to said subject of said fasted, single dose, human pharmacokinetic study. In some embodiments, said drug is selected from the group consisting of brivaracetam, lacosamide, and levetiracetam. In some embodiments, said drug is lacosamide.

Another embodiment is a pharmaceutical composition consisting of a drug selected from the group consisting of brivaracetam, lacosamide, levetiracetam, oxcarbazepine, divalproex, vigabatrin, and pharmaceutically acceptable salts thereof, and one or more excipients, wherein at least one of said one or more excipients modifies the release of the drug to provide an extended release form, and wherein administration of said pharmaceutical composition provides a $T_{max}$ of 5 to 20 hours, AUC equivalence to IR, and a dC/dt over the period of 0 to 1.4 hours after administration that is less than 10% of the dC/dt of an equivalent dose of the drug in an immediate release form over the same time period as determined from a single dose, fasted, human pharmacokinetic study.

Another embodiment is a pharmaceutical composition consisting of a drug selected from the group consisting of brivaracetam, lacosamide, levetiracetam, oxcarbazepine, divalproex, vigabatrin, and pharmaceutically acceptable salts thereof, and one or more excipients, wherein at least one of said one or more excipients modifies the release of the drug to provide an extended release form, and wherein administration of said pharmaceutical composition provides a $T_{max}$ of 12 to 20 hours, AUC equivalence to IR, and a dC/dt over the period of 0 to 1.4 hours after administration that is less than 10% of the dC/dt of an equivalent dose of the drug in an immediate release form over the same time period as determined from a single dose, fasted, human pharmacokinetic study.

Additional embodiments provide a pharmaceutical composition consisting of a drug selected from the group consisting of brivaracetam, lacosamide, levetiracetam, oxcarbazepine, divalproex, vigabatrin, and pharmaceutically acceptable salts thereof, and one or more excipients, wherein at least one of said one or more excipients modifies the release of the drug to provide an extended release form, and wherein administration of said pharmaceutical composition provides a $T_{max}$ of 5 to 20 hours, AUC equivalence to IR, and one or more of the following: (i) a dC/dt over the period of 0 to 2 hours after administration that is less than 5%, 10%, 15% of the dC/dt of an equivalent dose of the drug in an immediate release form over the same time period, (ii) a dC/dt over the period of 0 to 3 hours after administration that is less than 10%, 15%, 20% of the dC/dt of an equivalent dose of the drug in an immediate release form over the period of 0 to 3 hours after administration, and (iii) a dC/dt over the period of 0 to 4 hours after administration that is less than 10%, 15%, 20%, 25%, 30% of the dC/dt of an equivalent dose of the drug in an immediate release form over the period of 0 to 4 hours after administration, wherein the dC/dt values are determined from a fasted, single dose, human pharmacokinetic study.

In a preferred aspect of this embodiment, the drug is selected from the group consisting of brivaracetam, lacosamide, levetiracetam, and pharmaceutically acceptable salts thereof. In a more preferred aspect of this embodiment, the drug is lacosamide.

Another embodiment is a pharmaceutical composition consisting of a drug selected from the group consisting of lacosamide and pharmaceutically acceptable salts thereof, and one or more excipients, wherein at least one of said one or more excipients modifies the release of the drug to provide an extended release form, and wherein administration of said pharmaceutical composition provides a $T_{max}$ of 5 to 20 hours, and one or more of the following: (i) a dC/dt over the period of 0 to 2 hours after administration that is less than 0.5, 1.0, 1.5, 2.0 ng/ml/hr per mg of drug, (ii) a dC/dt over the period of 0 to 3 hours after administration that is less than 0.25, 0.5, 1.0, 1.5, 2.0 ng/ml/hr per mg of drug, (iii) a dC/dt over the period of 0 to 4 hours after administration that is less than 0.25, 0.50, 0.75, 1.00, 1.25, 1.50 ng/ml/hr per mg of drug, (iv) a dC/dt over the period of 0 to 2 hours after administration that is less than 0.2, 0.4, 0.6, 0.8 µg/ml/hr, (v) a dC/dt over the period of 0 to 3 hours after administration that is less than 0.2, 0.4, 0.6, 0.8 µg/ml/hr, (vi) a dC/dt over the period of 0 to 4 hours after administration that is less than 0.1, 0.2, 0.3, 0.4, 0.5, 0.6 µg/ml/hr, wherein $T_{max}$ and dC/dt values for the drug are determined from a fasted, oral, single dose, human pharmacokinetic study.

In some embodiments, administration of the pharmaceutical composition provides a $T_{max}$ of 5 to 10 hours as determined from a single dose, fasted, human pharmacokinetic study.

In another embodiment the pharmaceutical composition consisting of a drug selected from the group consisting of brivaracetam, lacosamide, levetiracetam, oxcarbazepine, divalproex, vigabatrin, and pharmaceutically acceptable salts thereof, and one or more excipients, wherein at least one of said one or more excipients modifies the release of the drug to provide an extended release form, the pharmaceutical composition having a dissolution profile of said pharmaceutical composition is less than 8% in 2 hours, less than 17% in 4 hours, less than 45% at 6 hours, and at least 45% at 12 hours, wherein the dissolution is performed in a USP type 1 (basket) apparatus rotating at 100 rpm using 900 ml 0.1 N HCl at 37.0±0.5° C. for 2 hours followed by dissolution in the same apparatus and speed using 900 ml USP phosphate buffer pH 6.8 at 37.0±0.5° C., and wherein administration of said pharmaceutical composition provides a $T_{max}$ of 5 to 20 hours, AUC equivalence to IR, and a dC/dt over the period of 0 to 1.4 hours after administration that is less than 10% of the dC/dt of an equivalent dose of the drug in an immediate release form over the same time period as determined from a single dose, fasted, human pharmacokinetic study.

In some embodiments described herein, a pharmaceutical composition consists of a drug selected from the group consisting of brivaracetam, lacosamide, levetiracetam, oxcarbazepine, divalproex, vigabatrin, and pharmaceutically acceptable salts thereof, and one or more excipients, wherein at least one of said one or more excipients modifies the release of the drug to provide an extended release form, and wherein administration of said pharmaceutical composition provides a $T_{max}$ of 5 to 20 hours and b) AUC equivalence to IR, wherein the partial AUCs from 8 am to 10 am, 10 am to 12 pm, 12 pm to 2 pm, 2, pm to 4 pm, and 4 pm to 8 pm are 80% to 125% of the partial AUCs for an equivalent total daily dose of the drug in an immediate release form of said drug administered in equal portions at 8 am and 8 pm, a dC/dt over the period of 0 to 1.4 hours after administration that is less than 10% of the dC/dt of an equivalent dose of the drug in an immediate release form over the same time period as determined from a single dose, fasted, human pharmacokinetic study.

In yet another embodiment, the pharmaceutical composition consists of a drug selected from the group consisting of brivaracetam, lacosamide, levetiracetam, oxcarbazepine, divalproex, vigabatrin, and pharmaceutically acceptable salts thereof, and one or more excipients, wherein at least one of said one or more excipients modifies the release of the drug to provide an extended release form, and wherein administration of said pharmaceutical composition provides a) a $T_{max}$ of 5 to 20 hours and b) AUC equivalence to IR, and a C-ave-day that is 20% to 100% greater than C-ave-night as determined from a fasted human pharmacokinetic study.

In another embodiment, the pharmaceutical composition consists of a drug selected from the group consisting of brivaracetam, lacosamide, levetiracetam, oxcarbazepine, divalproex, vigabatrin, and pharmaceutically acceptable salts thereof, and one or more excipients, wherein at least one of said one or more excipients modifies the release of the drug to provide an extended release form, and wherein administration of said pharmaceutical composition provides a) a $T_{max}$ of 12 to 20 hours and b) AUC equivalence to IR, and a C-ave-day that is 20% to 100% greater than C-ave-night as determined from a fasted human pharmacokinetic study.

In yet another embodiment, the pharmaceutical composition consists of a drug selected from the group consisting of brivaracetam, lacosamide, levetiracetam, oxcarbazepine, divalproex, vigabatrin, and pharmaceutically acceptable salts thereof, and one or more excipients, wherein at least one of said one or more excipients modifies the release of the drug to provide an extended release form, and wherein administration of said pharmaceutical composition provides a) a $T_{max}$ of 5 to 10 hours and b) AUC equivalence to IR, and a C-ave-day that is 20% to 100% greater than C-ave-night as determined from a fasted human pharmacokinetic study.

Another embodiment is directed to a the pharmaceutical composition consists of a drug selected from the group consisting of brivaracetam, lacosamide, levetiracetam, oxcarbazepine, divalproex, vigabatrin, and pharmaceutically acceptable salts thereof, and one or more excipients, wherein at least one of said one or more excipients modifies the release of the drug to provide an extended release form, wherein the dissolution profile of said pharmaceutical composition is less than 8% in 2 hours, less than 17% in 4 hours, less than 45% at 6 hours, and at least 45% at 12 hours, wherein the dissolution is performed in a USP type 1 (basket) apparatus rotating at 100 rpm using 900 ml 0.1 N HCl at 37.0±0.5° C. for 2 hours followed by dissolution in the same apparatus and speed using 900 ml USP phosphate buffer pH 6.8 at 37.0±0.5° C., and wherein administration of said pharmaceutical composition provides a) a $T_{max}$ of 5 to 20 hours; and b) an $AUC_{0-inf}$ of 80% to 125% of that for an equivalent dose of the drug in an immediate release form, and a C-ave-day that is 20% to 100% greater than C-ave-night as determined from a fasted human pharmacokinetic study.

Some embodiments are directed to a pharmaceutical composition selected from a group consisting of a drug selected from the group consisting of brivaracetam, lacosamide, levetiracetam, oxcarbazepine, divalproex, vigabatrin, and pharmaceutically acceptable salts thereof, and one or more excipients, wherein at least one of said one or more excipients modifies the release of the drug to provide an extended release form, wherein administration of said pharmaceutical composition provides a $T_{max}$ of 5 to 20 hours and AUC equivalence to IR, wherein the partial AUCs from 8 am to 10 am, 10 am to 12 pm, 12 pm to 2 pm, 2, pm to 4 pm, and 4 pm to 8 pm are 80% to 125% of the partial AUCs for an equivalent total daily dose of the drug in an immediate release form of said drug administered in equal portions at 8 am and 8 pm and wherein a C-ave-day that is 20% to 100% greater than C-ave-night as determined from a fasted human pharmacokinetic study.

Some embodiments are directed to a method of administering a pharmaceutical composition to a human, comprising administering to said human orally, once daily, a dose of said pharmaceutical composition consisting of (i) a drug selected from the group consisting of brivaracetam, divalproex, lacosamide, levetiracetam, oxcarbazepine, vigabatrin, and pharmaceutically acceptable salts thereof, and (ii) at least one excipient, wherein at least one of said excipients modifies the release of the drug to provide an extended release form, and wherein administration of said pharmaceutical composition provides a) a Tmax of 5 to 20 hours and b) AUC equivalence to IR, and c) a dC/dt over the period of 0 to 1.4 hours after administration that is less than 10% of the dC/dt of an equivalent dose of the drug in an immediate release form over the same time period as determined from a single dose, fasted, human pharmacokinetic study.

In some aspects of that embodiment, the administration of the pharmaceutical composition provides a Tmax of 12 to 20 hours as determined from a single dose, fasted, human pharmacokinetic study.

In some aspects of that embodiment, the administration is 0 to 4 hours before bedtime.

In some aspects of that embodiment, administration of said pharmaceutical composition provides a Tmax of 5 to 10 hours as determined from a single dose, fasted, human pharmacokinetic study. In some aspects of that embodiment, administration is 0 to 3 hours after waking.

In some embodiments of the invention providing a composition with a Tmax of 12 to 20 hours as determined from a single dose, fasted, human pharmacokinetic study, the dissolution profile of the pharmaceutical composition is less than 8% in 2 hours, less than 17% in 4 hours, less than 45% at 6 hours, and at least 45% at 12 hours, wherein the dissolution is performed in a USP type 1 (basket) apparatus rotating at 100 rpm using 900 ml 0.1 N HCl at 37.0±0.5° C. for 2 hours followed by dissolution in the same apparatus and speed using 900 ml USP phosphate buffer pH 6.8 at 37.0±0.5° C.

In some embodiments of the pharmaceutical composition consisting of (i) a drug selected from the group consisting of brivaracetam, divalproex, lacosamide, levetiracetam, oxcarbazepine, vigabatrin, and pharmaceutically acceptable salts thereof, and (ii) at least one excipient, wherein at least one of said excipients modifies the release of the drug to provide an extended release form, and wherein administration of said pharmaceutical composition provides a) a Tmax of 5 to 20 hours and b) AUC equivalence to IR, and c) a dC/dt over the period of 0 to 1.4 hours after administration that is less than 10% of the dC/dt of an equivalent dose of the drug in an immediate release form over the same time period as determined from a single dose, fasted, human pharmacokinetic study, the partial AUCs from 8 am to 10 am, 10 am to 12 pm, 12 pm to 2 pm, 2, pm to 4 pm, and 4 pm to 8 pm are 80% to 125% of the partial AUCs for an equivalent total daily dose of the drug in an immediate release form of said drug administered in equal portions at 8 am and 8 pm.

Some embodiments of the invention are directed to methods of administering a pharmaceutical composition to a human, comprising administering to said human orally, once daily, a dose of said pharmaceutical composition consisting of (i) a drug selected from the group consisting of brivaracetam, lacosamide, levetiracetam, oxcarbazepine, divalproex, vigabatrin, and pharmaceutically acceptable salts thereof, and (ii) at least one excipient, wherein at least one of said excipients modifies the release of the drug to provide an extended release form, and wherein administration of said pharmaceutical composition provides a) a Tmax of 5 to 20 hours and b) AUC equivalence to IR, and a C-ave-day that is 20% to 100% greater than C-ave-night as determined from a fasted human pharmacokinetic study.

In some aspects of the above embodiment, the administration of said pharmaceutical composition provides a Tmax of 12 to 20 hours as determined from a single dose, fasted, human pharmacokinetic study. In some of these embodiments, administration is 0 to 4 hours before bedtime.

In other aspects of the above embodiment, administration of said pharmaceutical composition provides a Tmax of 5 to 10 hours as determined from a single dose, fasted, human pharmacokinetic study. In some of these embodiments, administration is 0 to 3 hours after waking.

Some embodiments of the invention are directed to a dose of a pharmaceutical composition consisting of (i) a drug selected from the group consisting of brivaracetam, lacosamide, levetiracetam, oxcarbazepine, divalproex, vigabatrin, and pharmaceutically acceptable salts thereof, and (ii) at least one excipient, wherein at least one of said excipients modifies the release of the drug to provide an extended release form, and wherein administration of said pharmaceutical composition provides a) a Tmax of 5 to 20 hours and b) AUC equivalence to IR, and a C-ave-day that is 20% to 100% greater than C-ave-night as determined from a fasted human pharmacokinetic study, wherein the dissolution profile of said pharmaceutical composition is less than 8% in 2 hours, less than 17% in 4 hours, less than 45% at 6 hours, and at least 45% at 12 hours, wherein the dissolution is performed in a USP type 1 (basket) apparatus rotating at 100 rpm using 900 ml 0.1 N HCl at 37.0±0.5° C. for 2 hours followed by dissolution in the same apparatus and speed using 900 ml USP phosphate buffer pH 6.8 at 37.0±0.5° C.

In some aspects of the above embodiment, the partial AUCs from 8am to 10 am, 10 am to 12 pm, 12 pm to 2 pm, 2, pm to 4 pm, and 4 pm to 8 pm are 80% to 125% of the partial AUCs for an equivalent total daily dose of the drug in an immediate release form of said drug administered in equal portions at 8 am and 8 pm.

Some embodiments of the invention are directed to a pharmaceutical composition consisting of (i) a drug selected from the group consisting of brivaracetam, lacosamide, levetiracetam, oxcarbazepine, divalproex, vigabatrin, and pharmaceutically acceptable salts thereof, and (ii) at least one excipient, wherein at least one of said excipients modifies the release of the drug to provide an extended release form, and wherein administration of said pharmaceutical composition provides a) a Tmax of 5 to 20 hours and b) AUC equivalence to IR, and c) a dC/dt over the period of 0 to 1.4 hours after administration that is less than 10% of the dC/dt of an equivalent dose of the drug in an immediate release form over the same time period as determined from a single dose, fasted, human pharmacokinetic study.

In some of these embodiments, the partial AUCs from 8am to 10 am, 10 am to 12 pm, 12 pm to 2 pm, 2, pm to 4 pm, and 4 pm to 8 pm are 80% to 125% of the partial AUCs for an equivalent total daily dose of the drug in an immediate release form of said drug administered in equal portions at 8 am and 8 pm.

In some aspects of the embodiment, administration of said pharmaceutical composition provides a Tmax of 12 to 20 hours or of 5 to 10 hours as determined from a single dose, fasted, human pharmacokinetic study.

In some aspects of the embodiment, the dissolution profile of said pharmaceutical composition is less than 8% in 2 hours, less than 17% in 4 hours, less than 45% at 6 hours, and at least 45% at 12 hours, wherein the dissolution is performed in a USP type 1 (basket) apparatus rotating at 100 rpm using 900 ml 0.1 N HCl at 37.0±0.5° C. for 2 hours followed by dissolution in the same apparatus and speed using 900 ml USP phosphate buffer pH 6.8 at 37.0±0.5° C. In some of these embodiments, Some embodiments of the invention are directed to a pharmaceutical composition consisting of (i) a drug selected from the group consisting of brivaracetam, lacosamide, levetiracetam, oxcarbazepine, divalproex, vigabatrin, and pharmaceutically acceptable salts thereof, and (ii) at least one excipient, wherein at least one of said excipients modifies the release of the drug to provide an extended release form, and wherein administration of said pharmaceutical composition provides a) a Tmax of 5 to 20 hours and b) AUC equivalence to IR, and a C-ave-day that is 20% to 100% greater than C-ave-night as determined from a fasted human pharmacokinetic study. In some of these embodiments, the dissolution profile of the pharmaceutical composition is less than 8% in 2 hours, less than 17% in 4 hours, less than 45% at 6 hours, and at least 45% at 12 hours, wherein the dissolution is performed in a USP type 1 (basket) apparatus rotating at 100 rpm using 900 ml 0.1 N HCl at 37.0±0.5° C. for 2 hours followed by dissolution in the same apparatus and speed using 900 ml USP phosphate buffer pH 6.8 at 37.0±0.5° C.

In some embodiments of the invention, administration of said pharmaceutical composition provides a Tmax of 12 to 20 hours as determined from a single dose, fasted, human pharmacokinetic study. In other embodiments, the Tmax is 5 to 10 hours as determined from a single dose, fasted, human pharmacokinetic study.

In some aspects of the above embodiments, the pharmaceutical composition provides partial AUCs from 8 am to 10 am, 10 am to 12 pm, 12 pm to 2 pm, 2, pm to 4 pm, and 4 pm to 8 pm are 80% to 125% of the partial AUCs for an equivalent total daily dose of the drug in an immediate release form of said drug administered in equal portions at 8 am and 8 pm.

In some of the embodiments of pharmaceutical compositions described in the preceding paragraphs, the drug is lacosamide.

In some method embodiments described in the preceding paragraphs, the drug is lacosamide.

An embodiment of the invention is a method of administering a pharmaceutical composition to a human patient, comprising administering to the human patient orally, once daily, a therapeutically effective dose of the pharmaceutical composition wherein the pharmaceutical composition comprises (i) a drug selected from the group consisting of brivaracetam, divalproex, lacosamide, levetiracetam, oxcarbazepine, vigabatrin, and pharmaceutically acceptable salts of any of the foregoing, and (ii) at least one excipient, wherein at least one of the at least one excipients modifies the release of the drug to provide an extended release form wherein the pharmaceutical composition has a plasma concentration profile for the drug characterized by a $pAUC_{0-4}$ that is less than 4% of $AUC_{0-inf}$ for the drug as determined by dosing the pharmaceutical composition to a subject of a fasted, single dose, human pharmacokinetic study. In some aspects of the embodiment, the drug is selected from the group consisting of brivaracetam, lacosamide, levetiracetam, and pharmaceutically acceptable salts of any of the foregoing. In some embodiments the drug is lacosamide. In some aspects of the embodiment, the pharmaceutical composition has a plasma concentration profile for the drug characterized by a $pAUC_{4-8}$ that is less than 14% of $AUC_{0-inf}$ for the drug as determined by dosing the pharmaceutical composition to a subject of a fasted, single dose, human pharmacokinetic study. In some embodiments, the therapeutically effective dose of is 300 to 900 mg, 400 to 800 mg, or 450 to 800 mg of the drug. In some embodiments of the invention, at least one of the at least one excipients modifies the release of the drug to provide a delayed release form.

In some aspects of the embodiment pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted pharmacokinetic study. In some aspects of the embodiment, plasma concentration profile for said drug is further characterized by an $AUC_{0-inf}$ that provides AUC equivalence to IR Another embodiment of the invention is directed to a method of administering a pharmaceutical composition to a human patient, comprising administering to the human patient orally, once daily, a therapeutically effective dose of the pharmaceutical composition, wherein the pharmaceutical composition comprises (i) a drug selected from the group consisting of brivaracetam, divalproex, lacosamide, levetiracetam, oxcarbazepine, vigabatrin, and pharmaceutically acceptable salts of any of the foregoing, and (ii) at least one excipient, wherein at least one of the at least one excipients modifies the release of the drug to provide an extended release form, wherein the pharmaceutical composition has a plasma concentration profile for the drug characterized by a $pAUC_{4-8}$ that is less than 8% of $AUC_{0-inf}$ for the drug as determined by dosing pharmaceutical composition to a subject of a fasted, single dose, human pharmacokinetic study. In some aspects of the embodiment, the drug is selected from the group consisting of brivaracetam, lacosamide, levetiracetam, and pharmaceutically acceptable salts of any of the foregoing. In some embodiments of the method, the drug is lacosamide. In some aspects of the embodiment, the therapeutically effective dose is 300 to 900 mg, 400 to 800 mg, or 450 to 800 mg of said drug. In some embodiments of the method, at least one of said at least one excipients modifies the release of said drug to provide a delayed release form. In some aspects of the embodiment, the said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted human pharmacokinetic study. In some aspects of the embodiment, said plasma concentration profile for said drug is further characterized by an $AUC_{0-inf}$ that provides AUC equivalence to IR Some embodiments of the invention are directed to a method of administering a pharmaceutical composition to a human patient, comprising administering to the human patient orally, once daily, a therapeutically effective dose of the pharmaceutical composition, wherein the pharmaceutical composition comprises (i) a drug selected from the group consisting of brivaracetam, divalproex, lacosamide, levetiracetam, oxcarbazepine, vigabatrin, and pharmaceutically acceptable salts of any of the foregoing, and (ii) at least one excipient, wherein at least one of the excipients modifies the release of the drug to provide an extended release form, wherein the pharmaceutical composition has a plasma concentration profile for the drug characterized by a $T_{max}$ of 8 to 20 hours as determined by dosing the pharmaceutical composition to a subject of a fasted, single dose, human pharmacokinetic study, and wherein said pharmaceutical composition has a steady state plasma concentration profile for said drug upon once daily dosing of said pharmaceutical composition characterized by a swing of 40% to 200%, as determined by dosing said pharmaceutical composition to a subject of a fasted human pharmacokinetic study.

In some aspects of the embodiment, the drug is selected from the group consisting of brivaracetam, lacosamide, levetiracetam, and pharmaceutically acceptable salts of any of the foregoing. In some embodiments of the method, the drug is lacosamide. In some aspects of the embodiment, the therapeutically effective dose is 300 to 900 mg, 400 to 800 mg, or 450 to 800 mg of said drug. In some embodiments of the method, at least one of said at least one excipients modifies the release of said drug to provide a delayed release form. In some aspects of the embodiment, the pharmaceutical composition has a plasma concentration profile for said drug characterized by a $T_{max}$ of 12 to 20 hours as determined by dosing said pharmaceutical composition to a subject of a fasted, single dose, human pharmacokinetic study. In other aspects of the embodiment, said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted pharmacokinetic study. In some aspects of the embodiment, said pharmaceutical composition has a steady state plasma concentration profile for said drug upon once daily dosing of said pharmaceutical composition characterized by a swing of 50% to 100%, as determined by dosing said pharmaceutical composition to a subject of a fasted pharmacokinetic study. In some aspects of the embodiment, said pharmaceutical composition has a steady state plasma concentration profile for said drug upon once daily dosing of said pharmaceutical composition characterized by a swing of 60% to 200%, as determined by dosing said pharmaceutical composition to a subject of a fasted human pharmacokinetic study. In some aspects of the embodiment, said drug is further characterized by an $AUC_{0-inf}$ that provides AUC equivalence to IR. Some embodiments of the invention are directed to a method of administering a pharmaceutical composition to a human patient, comprising administering to the human patient orally, once daily, a therapeutically effective dose of the pharmaceutical composition, wherein said pharmaceutical composition comprises (i) a drug selected from the group consisting of brivaracetam, divalproex, lacosamide, levetiracetam, oxcarbazepine, vigabatrin, and pharmaceutically acceptable salts of any of the foregoing, and (ii) at least one excipient, wherein at least one of the at least one excipients modifies the release of the drug to provide an extended release form, wherein the pharmaceutical composition has a plasma concentration profile for the drug characterized by a $T_{max}$ of 8 to 20 hours and a dC/dT of less than 2.2 ng/ml/hr per mg of the drug over the first 2 hours after dosing, both as determined by dosing the pharmaceutical composition to a subject of a fasted, single dose, human pharmacokinetic study. In some aspects of the embodiment, the drug is selected from the group consisting of brivaracetam, lacosamide, levetiracetam, and pharmaceutically acceptable salts of any of the foregoing. In some embodiments of the method, the drug is lacosamide. In some aspects of the embodiment, the therapeutically effective dose is 300 to 900 mg, 400 to 800 mg, or 450 to 800 mg of drug. In some embodiments of the method, at least one of said at least one excipients modifies the release of said drug to provide a delayed release form. In some aspects of the embodiment, the pharmaceutical composition has a plasma concentration profile for said drug characterized by a $T_{max}$ of 12 to 20 hours as determined by dosing said pharmaceutical composition to a subject of a fasted, single dose, human pharmacokinetic study. In other aspects of the embodiment, said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted human pharmacokinetic study. In some aspects of the embodiment, the pharmaceutical composition has a plasma concentration profile for said drug characterized by a dC/dT of less than 1.4 ng/ml/hr per mg of said drug over the first 2 hours after dosing as determined by dosing said pharmaceutical composition to a subject of a fasted, single dose, human pharmacokinetic study. In some aspects of the embodiment, the pharmaceutical composition has a plasma concentration profile for said drug characterized by a dC/dT of less than 1.0 ng/ml/hr per mg of said drug over the first 2 hours after dosing as determined by dosing said pharmaceutical composition to a subject of a fasted, single dose, human pharmacokinetic study. In some aspects of the embodiment, said plasma concentration profile for said drug is further characterized by an $AUC_{0-inf}$ that provides AUC equivalence to IR.

Some embodiments of the invention are directed to a method of administering a pharmaceutical composition to a human patient, comprising administering to said the human patient orally, once daily, a therapeutically effective dose of pharmaceutical composition, wherein said pharmaceutical composition consists of (i) a drug selected from the group consisting of brivaracetam, divalproex, lacosamide, levetiracetam, oxcarbazepine, vigabatrin, and pharmaceutically acceptable salts of any of the foregoing, and (ii) at least one excipient, wherein at least one of said at least one excipients modifies the release of said drug to provide an extended release form, wherein said pharmaceutical composition has a plasma concentration profile for said drug characterized by a $T_{max}$ of 8 to 20 hours and a dC/dT of less than 1 µg/ml/hr over the first 2 hours after dosing, both as determined by dosing said pharmaceutical composition to a subject of a fasted, single dose, human pharmacokinetic study. In some aspects of the embodiment, the drug is selected from the group consisting of brivaracetam, lacosamide, levetiracetam, and pharmaceutically acceptable salts of any of the foregoing. In some embodiments of the method, the drug is lacosamide. In some aspects of the embodiment, the therapeutically effective dose is 300 to 900 mg, 400 to 800 mg, or 450 to 800 mg of said drug. In some embodiments of the method, at least one of said at least one excipients modifies the release of said drug to provide a delayed release form. In some aspects of the embodiment, the pharmaceutical composition has a plasma concentration profile for said drug characterized by a $T_{max}$ of 12 to 20 hours as determined by dosing the pharmaceutical composition to a subject of a fasted, single dose, human pharmacokinetic study. In some aspects of the embodiment, said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted human pharmacokinetic study. In some aspects of the embodiment, the pharmaceutical composition has a plasma concentration profile for the drug characterized by a dC/dT of less than 0.6 µg/ml/hr over the first 2 hours after dosing as determined by dosing the pharmaceutical composition to a subject of a fasted, single dose, human pharmacokinetic study. In some aspects of the embodiment, the pharmaceutical composition has a plasma concentration profile for the drug characterized by a dC/dT of less than 0.3 µg/ml/hr over the first 2 hours after dosing as determined by dosing the pharmaceutical composition to a subject of a fasted, single dose, human pharmacokinetic study. In some aspects of the embodiment, wherein said plasma concentration profile for said drug is further characterized by an $AUC_{0-inf}$ that provides AUC equivalence to IR.

Another embodiment of the invention is directed to a method of administering a pharmaceutical composition to a human patient, comprising administering to the human patient orally, once daily, at a predetermined administration time, a therapeutically effective dose of the pharmaceutical composition, wherein the pharmaceutical composition comprises (i) a drug selected from the group consisting of brivaracetam, divalproex, lacosamide, levetiracetam, oxcarbazepine, vigabatrin, and pharmaceutically acceptable salts of any of the foregoing, and (ii) at least one excipient, wherein at least one of the at least one excipients modifies the release of the drug to provide an extended release form, wherein the predetermined administration time is a time determined from a fasted, human pharmacokinetic study of the pharmaceutical composition and the predetermined time is a time at which once daily dosing of the pharmaceutical composition to a human subject of the pharmacokinetic study provides a C-ave-day that is 20% to 100% greater than C-ave-night, wherein C-ave-day is the average plasma concentration of the drug determined over the period from 9:00 am to 6:00 pm and C-ave-night is the average plasma concentration of the drug determined over the period from 11:00 pm to 8:00 am. In some aspects of the embodiment, the drug is selected from the group consisting of brivaracetam, lacosamide, levetiracetam, and pharmaceutically acceptable salts of any of the foregoing. In some embodiments of the method, the drug is lacosamide. In some aspects of the embodiment, the therapeutically effective dose is 300 to 900 mg, 400 to 800 mg, or 450 to 800 mg of the drug. In some embodiments of the method, at least one of the at least one excipients modifies the release of the drug to provide a delayed release form. In some aspects of the embodiment, the predetermined administration time is 0-4 hours before bedtime. In some aspects of the embodiment, the predetermined administration time is between 8 pm and 12 am. In some aspects of the embodiment, the predetermined administration time is 0-3 hours after waking. In some aspects of the embodiment, the predetermined administration time is between 5 am and 9 am. In some aspects of the embodiment, the predetermined time is a time at which once daily dosing of the pharmaceutical composition to a human subject of the pharmacokinetic study provides a steady state plasma concentration profile characterized by a C-ave-day that is 30% to 100% greater than C-ave-night, wherein C-ave-day is the average plasma concentration of the drug determined over the period from 9:00 am to 6:00 pm and C-ave-night is the average plasma concentration of the drug determined over the period from 11:00 pm to 8:00 am. In some aspects of the embodiment, the pharmaceutical composition has a plasma concentration profile for the drug characterized by a $T_{max}$ of 8 to 20 hours as determined by dosing the pharmaceutical composition to a subject of a fasted, single dose, human pharmacokinetic study. In some aspects of the embodiment, the pharmaceutical composition has a plasma concentration profile for the drug characterized by a $T_{max}$ of 12 to 20 hours as determined by dosing the pharmaceutical composition to a subject of a fasted, single dose, human pharmacokinetic study. In some aspects of the embodiment, the pharmaceutical composition has a plasma concentration profile for the drug characterized by a $T_{max}$ of 5 to 10 hours as determined by dosing the pharmaceutical composition to a subject of a fasted, single dose, human pharmacokinetic study. In some aspects of the embodiment, said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted human pharmacokinetic study. In some aspects of the embodiment, said pharmaceutical composition has a plasma concentration profile for said drug as determined by dosing said pharmaceutical composition to a subject of a fasted, single dose, human pharmacokinetic study characterized by an $AUC_{0-inf}$ for said drug that provides AUC equivalence to IR. Another embodiment of the invention is directed to a method of administering a pharmaceutical composition to a human patient, comprising administering to the human patient orally, once daily, a therapeutically effective dose of the pharmaceutical composition, wherein the pharmaceutical composition comprises (i) a drug selected from the group consisting of brivaracetam, divalproex, lacosamide, levetiracetam, oxcarbazepine, vigabatrin, and pharmaceutically acceptable salts of any of the foregoing, and (ii) at least one excipient, wherein at least one of the at least one excipients modifies the release of the drug to provide an extended release form, wherein the pharmaceutical composition has a dissolution profile characterized by three or more of the following: (a) less than 10% release at 1 hour, (b) less than 15% release at 2 hours, (c) less than 25% release at 4 hours, (d) at least 35% release at 9 hours, (e) at least 65% at 12 hours, wherein the dissolution is carried out in 900 mL simulated gastric fluid (pH 1.2) at 37±0.5° C. for the first two hours, followed by 900 mL simulated intestinal fluid (pH 6.8) at 37±0.5° C. for the subsequent four hours, followed by 900 mL phosphate buffer (pH 7.5) at 37±0.5° C. for the subsequent 18 hours, wherein all dissolution is performed in a USP Apparatus 1 (Basket), with a rotational speed of 100 rpm, and wherein the pharmaceutical composition has a plasma concentration profile for the drug characterized by a $T_{max}$ of 8 to 20 hours as determined by dosing the pharmaceutical composition to a subject of a fasted, single dose, human pharmacokinetic study. In some aspects of the embodiment, the drug is selected from the group consisting of brivaracetam, lacosamide, levetiracetam, and pharmaceutically acceptable salts of any of the foregoing. In some embodiments of the method, the drug is lacosamide. In some aspects of the embodiment, the therapeutically effective dose is 300 to 900 mg, 400 to 800 mg, or 450 to 800 mg of the drug. In some embodiments of the method, at least one of the at least one excipients modifies the release of the drug to provide a delayed release form. In some aspects of the embodiment, the pharmaceutical composition has a plasma concentration profile for the drug characterized by a $T_{max}$ of 12 to 20 hours as determined by dosing the pharmaceutical composition to a subject of a fasted, single dose, human pharmacokinetic study. In some aspects of the embodiment, said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted human pharmacokinetic study. In some embodiments, said plasma concentration profile for said drug is further characterized by an $AUC_{0-inf}$ that provides AUC equivalence to IR.

Another embodiment of the invention is a pharmaceutical composition for oral administration to a human, comprising (i) 50 mg to 900 mg of a drug selected from the group consisting of brivaracetam, divalproex, lacosamide, levetiracetam, oxcarbazepine, vigabatrin, and pharmaceutically acceptable salts of any of the foregoing, and (ii) at least one excipient, wherein at least one of the at least one excipients modifies the release of the drug to provide an extended release form, wherein pharmaceutical composition has a plasma concentration profile for the drug characterized by a $pAUC_{0-4}$ that is less than 4% of $AUC_{0-inf}$ for the drug as determined by dosing the pharmaceutical composition to a subject of a fasted, single dose, human pharmacokinetic study by a $pAUC_{0-4}$ that is less than 4% of $AUC_{0-inf}$ for the drug of the plasma concentration profile. In some aspects of the embodiment, the pharmaceutical composition has a plasma concentration profile for the drug characterized by a $pAUC_{4-8}$ that is less than 14% of $AUC_{0-inf}$ for the drug as determined by dosing the pharmaceutical composition to a subject of a fasted, single dose, human pharmacokinetic study. In some aspects of the embodiment, the drug is selected from the group consisting of brivaracetam, lacosamide, levetiracetam, and pharmaceutically acceptable salts of any of the foregoing. In some embodiments of the composition, the drug is lacosamide. In some aspects of the embodiment, the composition comprises 150 to 900 mg, 200 to 800 mg, 225 to 800, or 250 to 800 mg of the drug. In some embodiments of the composition, at least one of the at least one excipients modifies the release of said drug to provide a delayed release form. In some aspects of the embodiment, wherein said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted human pharmacokinetic study. In some aspects of the embodiment, said plasma concentration profile for said drug is further characterized by an $AUC_{0-inf}$ that provides AUC equivalence to IR.

Another embodiment of the invention is directed to a pharmaceutical composition for oral administration to a human, comprising (i) 50 mg to 900 mg of a drug selected from the group consisting of brivaracetam, divalproex, lacosamide, levetiracetam, oxcarbazepine, vigabatrin, and pharmaceutically acceptable salts of any of the foregoing, and (ii) at least one excipient, wherein at least one of the at least one excipients modifies the release of the drug to provide an extended release form, wherein the pharmaceutical composition has a plasma concentration profile for the drug characterized by a $pAUC_{4-8}$ that is less than 8% of $AUC_{0-inf}$ for the drug as determined by dosing the pharmaceutical composition to a subject of a fasted, single dose, human pharmacokinetic study. In some aspects of the embodiment, the drug is selected from the group consisting of brivaracetam, lacosamide, levetiracetam, and pharmaceutically acceptable salts of any of the foregoing. In some embodiments of the composition, the drug is lacosamide. In some aspects of the embodiment, the composition comprises 150 to 900 mg, 200 to 800 mg, 225 to 800 mg or 250 to 800 mg of the drug. In some embodiments of the composition, at least one of the at least one excipients modifies the release of the drug to provide a delayed release form. In some embodiments, said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted pharmacokinetic study.

In some of the above embodiments, said plasma concentration profile for said drug is further characterized by an $AUC_{0-inf}$ that provides AUC equivalence to IR.

Another embodiment of the invention is directed to a pharmaceutical composition for oral administration to a human, comprising (i) 50 mg to 900 mg of a drug selected from the group consisting of brivaracetam, divalproex, lacosamide, levetiracetam, oxcarbazepine, vigabatrin, and pharmaceutically acceptable salts of any of the foregoing, and (ii) at least one excipient, wherein at least one of the excipients modifies the release of the drug to provide an extended release form, wherein the pharmaceutical composition has a plasma concentration profile for the drug characterized by a $T_{max}$ of 8 to 20 hours as determined by dosing the pharmaceutical composition to a subject of a fasted, single dose, human pharmacokinetic study, and wherein said pharmaceutical composition has a steady state plasma concentration profile for said drug upon once daily dosing of said pharmaceutical composition characterized by a swing of 75% to 200%, as determined by dosing said pharmaceutical composition to a subject of a fasted human pharmacokinetic study. In some aspects of the embodiment, the drug is selected from the group consisting of brivaracetam, lacosamide, levetiracetam, and pharmaceutically acceptable salts of any of the foregoing. In some embodiments of the composition, the drug is lacosamide. In some aspects of the embodiment, the composition comprises 150 to 900 mg, 200 to 800 mg, 225 to 800 mg or 250 to 800 mg of the drug. In some embodiments of the composition, at least one of the at least one excipients modifies the release of drug to provide a delayed release form. In some aspects of the embodiment, the pharmaceutical composition has a plasma concentration profile for said drug characterized by a $T_{max}$ of 12 to 20 hours as determined by dosing the pharmaceutical composition to a subject of a fasted, single dose, human pharmacokinetic study. In some embodiments, said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted human pharmacokinetic study. In some embodiments, said pharmaceutical composition has a steady state plasma concentration profile for said drug upon once daily dosing of said pharmaceutical composition characterized by a swing of 50% to 100%, as determined by dosing said pharmaceutical composition to a subject of a fasted human pharmacokinetic study. In some embodiments, said pharmaceutical composition has a steady state plasma concentration profile for said drug upon once daily dosing of said pharmaceutical composition characterized by a swing of 60% to 200%, as determined by dosing said pharmaceutical composition to a subject of a fasted human pharmacokinetic study. In some aspects of the embodiment, said plasma concentration profile for said drug is further characterized by an $AUC_{0-inf}$ that provides AUC equivalence to IR.

Yet another embodiment of the invention is directed to a pharmaceutical composition for oral administration to a human, comprising (i) 50 mg to 900 mg of a drug selected from the group consisting of brivaracetam, divalproex, lacosamide, levetiracetam, oxcarbazepine, vigabatrin, and pharmaceutically acceptable salts of any of the foregoing, and (ii) at least one excipient, wherein at least one of the at least one excipients modifies the release of the drug to provide an extended release form, wherein the pharmaceutical composition has a plasma concentration profile for the drug characterized by a $T_{max}$ of 8 to 20 hours and a dC/dT of less than 2.2 ng/ml/hr per mg of the drug over the first 2 hours after dosing, both as determined by dosing the pharmaceutical composition to a subject of a fasted, single dose, human pharmacokinetic study. In some aspects of the embodiment, the drug is selected from the group consisting of brivaracetam, lacosamide, levetiracetam, and pharmaceutically acceptable salts of any of the foregoing. In some embodiments of the composition, the drug is lacosamide. In some aspects of the embodiment, the composition comprises 150 to 900 mg, 200 to 800 mg, 225 to 800 mg or 250 to 800 mg of the drug. In some embodiments of the composition, at least one of the at least one excipients modifies the release of the drug to provide a delayed release form. In some aspects of the embodiment, the pharmaceutical composition has a plasma concentration profile for the drug characterized by a $T_{max}$ of 12 to 20 hours as determined by dosing the pharmaceutical composition to a subject of a fasted, single dose, human pharmacokinetic study. In some aspects of the embodiment, said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted human pharmacokinetic study. In some aspects of the embodiment, the pharmaceutical composition has a plasma concentration profile for the drug characterized by a dC/dT of less than 1.4 ng/ml/hr per mg of the drug over the first 2 hours after dosing as determined by dosing the pharmaceutical composition to a subject of a fasted, single dose, human pharmacokinetic study. In some aspects of the embodiment, the pharmaceutical composition has a plasma concentration profile for the drug characterized by a dC/dT of less than 1.0 ng/ml/hr per mg of the drug over the first 2 hours after dosing as determined by dosing the pharmaceutical composition to a subject of a fasted, single dose, human pharmacokinetic study. In some of these embodiments, said plasma concentration profile for said drug is further characterized by an $AUC_{0-inf}$ that provides AUC equivalence to IR.

One embodiment of the invention is directed to a pharmaceutical composition for oral administration to a human, comprising (i) 50 mg to 900 mg of a drug selected from the group consisting of brivaracetam, divalproex, lacosamide, levetiracetam, oxcarbazepine, vigabatrin, and pharmaceutically acceptable salts of any of the foregoing, and (ii) at least one excipient, wherein at least one of the at least one excipients modifies the release of the drug to provide an extended release form, wherein pharmaceutical composition has a plasma concentration profile for the drug characterized by a $T_{max}$ of 8 to 20 hours and a dC/dT of less than 1 μg/ml/hr over the first 2 hours after dosing, both as determined by dosing the pharmaceutical composition to a subject of a fasted, single dose, human pharmacokinetic study. In some embodiments of the invention, the drug is selected from the group consisting of brivaracetam, lacosamide, levetiracetam, and pharmaceutically acceptable salts of any of the foregoing. In some embodiments of the composition, the drug is lacosamide. In some aspects of the embodiment, the composition comprises 150 to 900 mg, 200 to 800 mg, 225 to 800 mg or 250 to 800 mg of the drug. In some embodiments of the composition, at least one of the at least one excipients modifies the release of the drug to provide a delayed release form. In some embodiments, the pharmaceutical composition has a plasma concentration profile for the drug characterized by a $T_{max}$ of 12 to 20 hours as determined by dosing the pharmaceutical composition to a subject of a fasted, single dose, human pharmacokinetic study. In some embodiments, wherein said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted human pharmacokinetic study. In some embodiments, the pharmaceutical composition has a plasma concentration profile for the drug characterized by a dC/dT of less than 0.6 μg/ml/hr over the first 2 hours after dosing as determined by dosing the pharmaceutical composition to a subject of a fasted, single dose, human pharmacokinetic study. In some aspects of the embodiment, the pharmaceutical composition has a plasma concentration profile for the drug characterized by a dC/dT of less than 0.3 μg/ml/hr over the first 2 hours after dosing as determined by dosing the pharmaceutical composition to a subject of a fasted, single dose, human pharmacokinetic study. In some of these embodiments, said plasma concentration profile for said drug is further characterized by an $AUC_{0-inf}$ that provides AUC equivalence to IR.

Another embodiment of the invention is directed to a pharmaceutical composition for oral administration to a human, comprising (i) 50 mg to 900 mg of a drug selected from the group consisting of brivaracetam, divalproex, lacosamide, levetiracetam, oxcarbazepine, vigabatrin, and pharmaceutically acceptable salts of any of the foregoing, and (ii) at least one excipient, wherein at least one of the at least one excipients modifies the release of the drug to provide an extended release form, wherein the pharmaceutical composition has a dissolution profile characterized by three or more of the following: (a) less than 10% release at 1 hour, (b) less than 15% release at 2 hours, (c) less than 25% release at 4 hours, (d) at least 35% at 9 hours, (e) at least 65% at 12 hours, wherein the dissolution is carried out in 900 mL simulated gastric fluid (pH 1.2) at 37±0.5° C. for the first two hours, followed by 900 mL simulated intestinal fluid (pH 6.8) at 37±0.5° C. for the subsequent four hours, followed by 900 mL phosphate buffer (pH 7.5) at 37±0.5° C. for the subsequent 18 hours, wherein all dissolution is performed in a USP Apparatus 1 (Basket), with a rotational speed of 100 rpm, and wherein the pharmaceutical composition has a plasma concentration profile for the drug characterized by a $T_{max}$ of 8 to 20 hours as determined by dosing the pharmaceutical composition to a subject of a fasted, single dose, human pharmacokinetic study. In some embodiments of the invention, the drug is selected from the group consisting of brivaracetam, lacosamide, levetiracetam, and pharmaceutically acceptable salts of any of the foregoing. In some embodiments of the composition, the drug is lacosamide. In some aspects of the embodiment, the composition comprises 150 to 900 mg, 200 to 800 mg, 225 to 800 mg or 250 to 800 mg of the drug. In some embodiments of the composition, at least one of the at least one excipients modifies the release of the drug to provide a delayed release form. In some aspects of the embodiment, the pharmaceutical composition has a plasma concentration profile for the drug characterized by a $T_{max}$ of 12 to 20 hours as determined by dosing the pharmaceutical composition to a subject of a fasted, single dose, human pharmacokinetic study. In some embodiments, wherein said pharmaceutical composition has a steady state plasma concentration profile for said drug upon once daily dosing of said pharmaceutical composition as determined by dosing said pharmaceutical composition characterized by a $T_{max,ss}$ of 10 to 20 hours, as determined by dosing said pharmaceutical composition to a subject of a fasted human pharmacokinetic study. In some aspects of the embodiment, said plasma concentration profile for said drug is further characterized by an $AUC_{0-inf}$ that provides AUC equivalence to IR.

DETAILED DESCRIPTION OF THE INVENTION

Figure 1A:
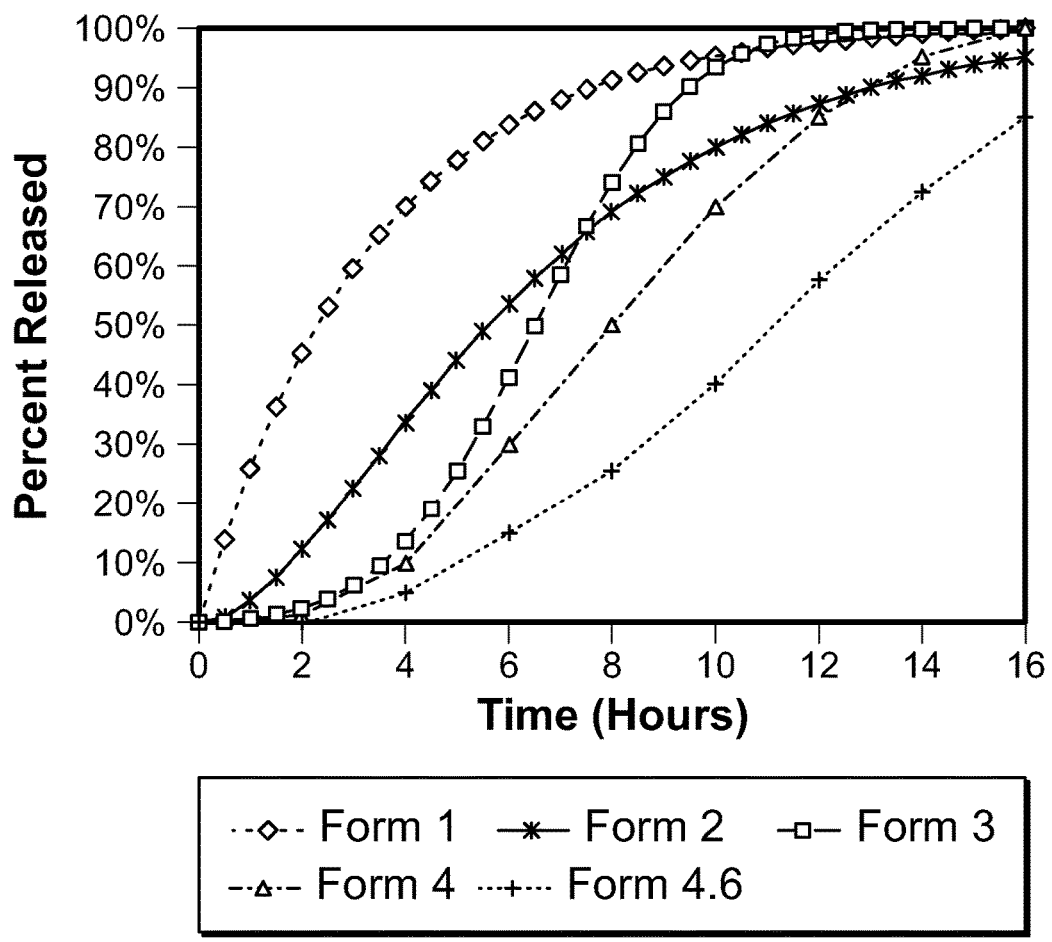
FIG. 1A is a graph depicting the dissolution profiles of ER lacosamide formulations Form 1, Form 2, Form 3, Form 4, and Form 4.6.

The present invention provides compositions and methods for primary or adjunctive therapy for treating or preventing any disease or disorder for which an anti-epilepsy drug is prescribed, such as epilepsy, seizure-based disorders including myoclonic seizures in myoclonic epilepsy, primary generalized tonic-clonic seizures in patients with idiopathic generalized epilepsy, partial onset seizures, status epilepticus, acute mania management, paroxysmal kinesigenic choreoathetosis, phasic spasticity in multiple sclerosis, Landau-Kleffner syndrome, migraine treatment or prophylaxis, pediatric migraine, Meige syndrome, late-onset seizures in patients with Alzheimer's disease, anxiety disorders, severe myoclonic epilepsy of infancy, tardive dyskinesia, lumbar radiculopathy, late onset myoclonic epilepsy in Down syndrome, atypical pain syndromes, neuropathic pain, and Alzheimer's disease. In some embodiments, the present methods treat epilepsy. In some embodiments, the present methods treat seizure-based disorders.

Exemplary compositions include brivaracetam, divalproex sodium, lacosamide, levetiracetam, oxcarbazepine, valproic acid, or vigabatrin in an extended release form.

Compositions of the invention also include, but are not limited to, formulations of brivaracetam, divalproex sodium, valproic acid, felbamate, lacosamide, lamotrigine, levetiracetam, oxcarbazepine, pregabalin, tiagabine, and vigabatrin. Preferred are formulations of brivaracetam, divalproex sodium, valproic acid, lacosamide, levetiracetam, oxcarbazepine, pregabalin, tiagabine, and vigabatrin. Most preferred are formulations of levetiracetam, brivaracetam, lacosamide, oxcarbazepine and valproic acid for administration once daily.

Suitable AEDs for the compositions may be those with half-lives of 4 to 20 hours, preferably 6 to 18 hours, more preferably 7 to 17 hours. Suitable AEDs for the compositions are typically well absorbed after oral administration in an immediate release form, e.g., the bioavailability of AEDs in immediate release compositions is greater than 70%, preferably greater than 80%, more preferably greater than 90%, and even more preferably greater than 95%. Suitable AEDs for the compositions when administered orally as immediate release compositions will typically provide a time to peak plasma concentration, $T_{max}$, of less than 8 hours, preferably less than 6 hours, more preferably less than 5 hours.

In some embodiments, the invention provides an anti-epileptic formulation that is administered once daily and has a pharmacokinetic profile with diurnal variations, with a $T_{1/2}$ between 4 and 15 hours, preferably between 4 and 12 hours.

Some compositions described herein enable administration of a therapeutically effective amount of a selected AED. The therapeutically effective amount may be less than the amount typically indicated for an immediate release form, e.g. 50% of the amount typically required when in an immediate release form. In another embodiment, the daily dose of an AED for a patient in need thereof will be comparable to, or equal to, the daily dose of an immediate release form of the same drug substance. In another embodiment, the daily dose of an AED for a patient in need thereof will be greater than the daily dose of an immediate release form of the same drug substance, e.g. 125%, 150%, 175%, 200%, 250% (e.g. preferably 150 to 200%) of the amount of the same AED as ordinarily dosed to a patient on a daily basis. Due to the characteristics of the compositions, greater doses of a particular AED are well tolerated.

In some embodiments, the tolerability of the AED is improved relative to a comparable dose of an immediate release form of said AED. As used herein, unless expressly stated otherwise, improvement in tolerability means the reduction in incidence and/or severity of adverse effects associated with the administration of a composition comprising the AED relative to the incidence and/or severity of adverse effects associated with administration of the same dose of an immediate release form of said AED. In some embodiments, the improvement in tolerability may include reduced adverse effects associated with administration regimen of the compositions described herein. In some embodiments, the improvement in tolerability may include reduced adverse effects associated with the properties of the compositions described herein. Thus, reduction in the incidence and/or severity of adverse events may be accomplished with the methods and compositions described herein. In some embodiments, administration of a composition with the diurnal plasma concentration profiles described herein reduces the incidence and/or severity of sleep disturbances as compared to an IR form of the same AED at the same daily dose administered two or more times per day. In some embodiments, administration of a composition with the reduced dC/dt characteristics described herein reduces the incidence and/or severity of adverse effects as compared to an IR form of the same AED at the same dose. In some embodiments, the increased tolerability is associated with reduced incidence and/or severity of eye disorder adverse events such as diplopia or blurred vision. In some embodiments, the increased tolerability is associated with reduced incidence and/or severity of nervous system disorder adverse events such as dizziness, headache, ataxia, somnolence, tremor, nystagmus, balance disorders, paresthesia, paresthesia oral, or memory impairment; in preferred embodiments, the increased tolerability is associated with reduced incidence and/or severity of dizziness; in preferred embodiments, the increased tolerability is associated with reduced incidence and/or severity of headache; in preferred embodiments, the increased tolerability is associated with reduced incidence and/or severity of paresthesia or paresthesia oral. In some embodiments, the increased tolerability is associated with reduced incidence and/or severity of vertigo. In some embodiments, the increased tolerability is associated with reduced incidence and/or severity of nausea. In some embodiments, the increased tolerability is associated with reduced incidence and/or severity of vomiting. In some embodiments, the increased tolerability is associated with reduced incidence and/or severity of hypoesthesia oral. In some embodiments, the improvement in tolerability enables the increase in daily dose of the AED as compared to an immediate release form. In some embodiments, the improvement in tolerability associated with the diurnal profile resulting from administration of the compositions or the C-ave-day to C-ave-night ratio resulting from the predetermined administration time, enables the once daily administration, preferably at doses higher than those employed with immediate release forms of the same AED Anti-epileptic drugs suitable for the compositions and methods described herein include those administered in immediate release form at daily doses of up to 3000 mg, however drugs of higher potency are preferred. The compositions are suitable for administration of up to 3000 mg AED per day, 2500 mg AED per day, 2000 mg AED per day, 1500 mg AED per day, 1200 mg AED per day, preferably up to 1000 mg per day, more preferably up to 800 mg per day, even more preferably up to 600 mg per day, up to 500 mg per day, up to 400 mg per day, up to 300 mg per day, up to 250 mg per day, or up to 200 mg per day. Depending upon the composition and the daily dose of drug, compositions may be administered in one or more unit dosage forms. In some embodiments the composition of the invention is administered as one unit dosage form. In some embodiments the composition of the invention is administered as two unit dosage forms. In some embodiments the composition of the invention is administered as three unit dosage forms. In some embodiments the composition of the invention is administered as four unit dosage forms. Compositions are administered orally once or twice per day, preferably once per day.

In embodiments comprising lacosamide or a pharmaceutically acceptable salt thereof as the AED, the daily dose of lacosamide or pharmaceutically acceptable salt thereof may be 200 to 900 mg per day, 250 to 850 mg per day, 300 to 800 mg per day, 350 to 800 mg per day, 400 to 800 mg per day, 450 to 800 mg per day, 500 to 800 mg per day, 350 to 750 mg per day, 400 to 750 mg per day, 450 to 750 mg per day, 500 to 750 mg per day, 350 to 700 mg per day, 400 to 700 mg per day, 450 to 700 mg per day, 500 to 700 mg per day, 350 to 650 mg per day, 400 to 650 mg per day, 450 to 650 mg per day, 500 to 650 mg per day, 350 to 600 mg per day, 400 to 600 mg per day, 450 to 600 mg per day, or 500 to 600 mg per day. In preferred aspects of this embodiment, the daily dose of lacosamide or pharmaceutically acceptable salt thereof may be 400 to 800 mg per day. In preferred aspects of this embodiment, the daily dose of lacosamide or pharmaceutically acceptable salt thereof may be 450 to 800 mg per day. In preferred aspects of this embodiment, the daily dose of lacosamide or pharmaceutically acceptable salt thereof may be 450 to 700 mg per day. In preferred aspects of this embodiment, the compositions comprising lacosamide or pharmaceutically acceptable salts thereof are administered orally, once daily.

As used herein, references to lacosamide, levetiracetam, brivaracetam, oxcarbazepine, divalproex sodium, valproic acid, vigabatrin and other AEDs are intended to encompass pharmaceutically acceptable salts thereof, and, optionally, prodrugs or polymorphs thereof.

As used herein, except where specified as otherwise, "extended release" includes "controlled release", "modified release", "sustained release", "timed release", "delayed release", and also mixtures of delayed release, immediate release, enteric coated, etc. with each of the above.

As used herein, except where specified as otherwise, "delayed release" compositions include dosage forms containing a delayed release coating over an immediate release and/or extended release composition.

As used herein, fasted, single dose human pharmacokinetic study means a fasted study in one or more healthy subjects to determine the pharmacokinetic characteristics of the composition being tested. The study may include a reference composition such as an oral, immediate release dosage form of the same drug substance typically with the same dose. Where a reference composition is included, the study design may be a parallel or crossover study design. Design parameters for such studies are well known an also included in various FDA guidances such as those referenced herein, including, but not limited to the 2002 FDA Guidance: Waiver of In Vivo Bioavailability and Bioequivalence Studies for Immediate-Release Solid Oral Dosage Forms Based on a Biopharmaceutics Classification System, and the 2003 Guidance for Industry: Bioavailability and Bioequivalence Studies for Orally Administered Drug Products—General Considerations. The output of such single dose human pharmacokinetic studies typically includes plasma concentration data for the drug substance (and active metabolites, if any) from blood samples collected at times specified in the study protocol. These plasma concentration data may then be used to construct a plasma concentration profile from which the pharmacokinetic parameters described herein may be determined.

As used herein, except where specified as otherwise, "bioavailability" is 100% multiplied by the $AUC_{0-\infty}$ for a drug in a composition (e.g., 'Test' formulation) divided by the $AUC_{0-\infty}$ for an equivalent dose of the same drug in an immediate release form (e.g., 'Reference' formulation), both as determined from a fasted, single dose, human pharmacokinetic study. In preferred embodiments, the bioavailability of compositions described herein is "AUC equivalence to IR" which, as used herein, means that for an equivalent dose of the same drug, the 90% confidence interval for the ratio (multiplied by 100%) of the geometric least-squares mean ("GLSM") for the $AUC_{0-\infty}$ for the drug of the composition to the GLSM for the $AUC_{0-\infty}$ for the same drug in an immediate release oral form is between 80% to 125%, inclusive.

As used herein, except where specified as otherwise, "$T_{1/2}$", the "elimination half-life", "terminal-phase half-life", "plasma half-life" and "pharmacokinetic half-life" refer to the half-life of the disappearance of drug from the plasma.

As used herein, except where specified as otherwise, "$T_{max}$" refers to the median $T_{max}$ observed from the subjects included in a bioavailability or bioequivalence study. It should be understood, however, the $T_{max}$ determined from a simulation refers to a mean $T_{max}$. Similarly, except where specified as otherwise, "$T_{max,ss}$" refers to the median $T_{max,ss}$, when the formulation has been dosed to steady state, and the $T_{max,ss}$ determined from a simulation refers to a mean $T_{max,ss}$.

As used herein, except where specified as otherwise, "$T_{lag}$" is the time delay between drug administration and first observed concentration above the limit of quantification in plasma.

As used herein, except where specified as otherwise, "$C_{min}$", "$C_{max}$", "$C_{min,ss}$", "$C_{max,ss}$" and AUC values determined over various time periods each refer to mean values.

As used herein, except where specified as otherwise, "swing" is $100\%*(C_{max,ss}-C_{min,ss})/C_{min,ss}$.

As used herein, except where specified as otherwise, "PTF" is the peak trough fluctuation for a specified drug in plasma at steady state. It is determined as $100\%*(C_{max,ss}-C_{min,ss})/(AUC_{tau,ss}/tau)$, wherein $AUC_{tau,ss}$ is the steady state AUC over the dosing interval, tau. As used herein, except where specified as otherwise, a subject of a human pharmacokinetic study shall include one or more subjects of said human pharmacokinetic study. In cases where tau is 24 hours, $AUC_{tau,ss}$ is $AUC_{0-24}$ at steady state.

As used herein, dC/dt over a specified time period is the change in mean plasma concentration of the drug substance from the beginning of the specified time period to the end of said specified time period divided by the length of the time period, determined from a plasma concentration profile from a fasted, single dose, human pharmacokinetic study (unless specified otherwise); the units for dC/dt are mass/volume/time such as ng/ml/hr. Where specified, the dC/dt values may be reported per dose; in these instances, the dC/dt values are divided by the dose to provide a dC/dt per mg of drug. Also in other instances, the dC/dt values are compared to those determined for a reference composition, typically an oral, immediate release form of the drug substance; in such cases, to minimize variability in the plasma concentration profiles from which the dC/dt values are determined, the extended release composition and the reference composition are each administered orally to subjects in a fasted, single dose, oral human pharmacokinetic study.

As used herein, the terms "C-ave-day" and "C-ave-night" are average plasma concentration values for the drug substance determined over specified time periods from a steady state plasma concentration profile wherein administration of the composition is at a predetermined time or within a specified time period such as once daily at 8:00 am.

In some embodiments, C-ave-day is the average AED plasma concentration determined within any four to twelve hour period between the hours of 5 am and 8 pm, such as the average AED plasma concentration determined within any four, five, six, seven, eight, nine, ten, eleven or twelve hour period between the hours of 5 am and 8 pm (e.g. a seven-hour period). In a preferred embodiment, C-ave-day is determined over the period from 9 am to 4 pm. In a preferred embodiment, C-ave-day is determined over the period from 9 am to 6 pm. In some embodiments, C-ave-night is the average AED plasma concentration determined within any four to twelve hour period between the hours of 8 pm and 9 am, such as the average AED plasma concentration as measured within any four, five, six, seven, eight, nine, ten, eleven or twelve hour period between the hours of 8 pm and 9 am (e.g. a nine-hour period). In a preferred embodiment, C-ave-night is determined over the period from 11 pm to 8 am. In a preferred embodiment, C-ave-night is determined over the period from 11 pm to 6 am.

The steady state plasma concentration profile may be determined from (i) a multi-dose human pharmacokinetic study of the pharmaceutical composition or from (ii) a multi-dose model based on a fasted, single-dose human pharmacokinetic study (prepared using WinNonlin version 5.3 or higher, or comparable method) or from (iii) a multi-dose simulation of the human pharmacokinetics based on the dissolution profiles of the pharmaceutical composition prepared using GastroPlus version 9.0 or higher. Of these three, (ii) is a preferred method.

As used herein, except where specified as otherwise, "about" refers to a value within 10% of the value shown. For example, a $T_{max}$ of about 10 hours would also include values from 9.0 to 11.0, unless specified otherwise.

As used herein, the transitional term "comprising" is inclusive or open-ended and does not exclude additional, unrecited elements or method steps. Thus, as used herein, "comprising" includes within its metes and bounds "consisting essentially" of and "consisting of," as defined herein. Accordingly, disclosure of embodiments and aspects "comprising" subject matter herein includes embodiments and aspects "consisting essentially of" and "consisting of," the recited subject matter.

As used herein, the transitional phrase "consisting essentially of" limits the scope of a claim to the specified subject matter, materials or steps and those that do not materially affect the basic and novel characteristic(s).

As used herein, the transitional phrase "consisting of" limits the recited subject matter to the specified matter, elements, steps, or ingredients, and excludes any subject matter, element, step, or ingredient not specified.

As used herein, except where specified as otherwise, a fractional AUC over a specified period of time is equivalent to a pAUC over the same period of time divided by $AUC_{0-inf}$ (i.e. $AUC_{0-\infty}$) or, for steady state calculations, $AUC_{24}$ (i.e. $AUC_{0-24}$), and multiplied by 100%.

As used herein, single dose, fasted, human pharmacokinetic studies are clinical studies performed in accordance to the FDA Guidance documents i.e. 2002 FDA Guidance for Industry: Food Effect Bioavailability and Fed Bioequivalence Studies and/or analogous EMEA Guidelines. Such studies may be performed using either parallel or crossover designs, typically in healthy subjects. For fasted studies, study drug is typically administered following an overnight fast of at least 10 hours; no food should be allowed for at least 4 hours post-dose, and water can be allowed as desired except for one hour before and after drug administration. Blood samples are taken at predetermined times (relative to dosing) and analyzed using validated methods to determine the levels of drug (and active metabolites as appropriate).

As used herein, fasted human pharmacokinetic studies include both single dose, fasted, human pharmacokinetic studies and multiple dose, fasted, human pharmacokinetic studies. Multiple dose, fasted, human pharmacokinetic studies are performed in accordance to the FDA Guidance documents and/or analogous EMEA Guidelines. Pharmacokinetic parameters for steady state values may be determined directly from multiple dose, fasted, human pharmacokinetic studies or may be conveniently determined by extrapolation of single dose data using standard methods or industry standard software such as WinNonlin version 5.3 or higher.

As used herein, chronosynchronous means that the therapeutic composition provides a therapeutically effective dose of the drug substance with increased exposure over time periods in which need is greater, such as during the peak periods of partial onset seizure activity, and less exposure at time in which the need is lower, such as during sleep periods when partial onset seizure activity may be reduced. In this instance, exposure may be determined from partial AUCs at steady state or average plasma concentrations over specified time periods at steady state.

In some embodiments, the chronosynchronous profile provides a therapeutically effective plasma concentration of the AED such as lacosamide at $C_{min,ss}$ and a substantially higher plasma concentration at $T_{max,ss}$ to provide greater efficacy at a time when the therapeutic need is greater, e.g. a time when seizure activity is more frequent or more pronounced. Preferably, the $C_{min,ss}$ is sufficient to reduce the frequency and/or severity of seizures during the the time that the plasma concentration is lower. Preferably, the predetermined administration time selected as described herein provides for the $C_{min,ss}$ to occur during a period of reduced seizure activity as well as providing for the $C_{max,ss}$ to occur during a period of increased seizure activity. Some embodiments, the composition for use in the described methods is adapted for the generation of a diurnal profile which, upon reaching steady state, provides a higher concentration during the waking hours of the day than the sleeping hours of the night. The compositions may be adapted for evening administration, e.g. administration 0 to 4 hours before bedtime, or for morning administration by the methods provided herein. For example, a composition of an AED such as lacosamide may be formulated according to the methods below to provide an extended release formulation that upon once daily administration 0 to 4 hours before bedtime provides a steady state $C_{min}$ ($C_{min,ss}$) during the night while the subject sleeps and a steady state $C_{max}$ ($C_{max,ss}$) in the middle of the day, e.g., between the hours of 9 am and 3 pm. Such formulations may have a single dose median $T_{max}$ of 11 to 20 hours and/or steady state $T_{max}$ between 11 and 18 hours.

In some embodiments, the $T_{max}$ for the composition, as determined from a single dose human pharmacokinetic study in the fasted state, may be 11 to 20 hours, 11 to 18 hours, 11 to 16 hours, 12 to 20 hours, 12 to 18 hours, 12 to 16 hours, 13 to 20 hours, 13 to 18 hours, 13 to 16 hours, 14 to 20 hours, 14 to 18 hours, or 15 to 20 hours. In some embodiments, the steady state $T_{max}$ ($T_{max,ss}$), as determined from a multiple dose fasted human pharmacokinetic study of 11 to 18 hours, 11 to 16 hours, 12 to 18 hours, 12 to 16 hours, 13 to 18 hours, 13 to 16 hours. In some embodiments, both $T_{max}$ and $T_{max,ss}$ are within the aforementioned ranges.

In some embodiments, the composition providing $C_{min,ss}$ at night and $C_{max,ss}$ in the middle of the day steady are administered in the morning, typically between 0 and 1, 2, 3 hours after the subject awakes for the day's activities. Such compositions may provide a $T_{max}$, as determined from a single dose, fasted, human pharmacokinetic study of 3 to 5 hours.

In some embodiments of any of the above aspects, the steady state plasma concentration profile following multiple administrations to a human subject of the composition once daily is characterized by an average plasma concentration lacosamide concentration during the day ("C-ave-day", defined as the average day time plasma concentration for said drug as determined from a fasted, human PK study) that is 1.1 to 2.0 times the average lacosamide concentration during the night ("C-ave-night", defined as the average nighttime lacosamide plasma concentration as determine from a fasted, human PK study). In some embodiments, the ratio of C-ave-day/C-ave-night at steady state is within one of the ranges 1.2 to 2.0, 1.2 to 1.9, 1.3 to 1.9, 1.3 to 1.8, 1.3 to 1.7, 1.3 to 1.6, 1.4 to 2.0, 1.4 to 1.9, 1.4 to 1.8, 1.4 to 1.7, 1.5 to 2.0, 1.5 to 1.9, 1.5 to 1.8, 1.5 to 1.7, 1.6 to 2.0, or 1.6 to 1.9. In some embodiments, the ratio of C-ave-day/C-ave-night at steady state is 1.3, 1.35, 1.4, 1.45, 1.5, 1.55, 1.6, 1.65, 1.7, 1.75, 1.8, 1.85, or 1.9. In some embodiments, the C-ave-day is the average lacosamide plasma concentration as measured between the hours of 5 am, 6 am, 7 am, 8 am or 9 am to the hours of 4 pm, 5 pm, 6 pm, 7 pm or 8 pm and the C-ave-night is the average lacosamide plasma concentration as measured between the hours of 8 pm, 9 pm, 10 pm or 11 pm to the hours of 5 am, 6 am, 7 am, 8 am or 9 am. In some embodiments, the C-ave-day is the average lacosamide plasma concentration as measured within any four to twelve hour period between the hours of 5 am and 8 pm; and the C-ave-night is the average lacosamide plasma concentration as measured within any four to twelve hour period between the hours of 8 pm and 9 am. In some embodiments, the C-ave-day is the average lacosamide plasma concentration as measured within any four, five, six, seven, eight, nine, ten, eleven or twelve hour period between the hours of 5 am and 8 pm; and the C-ave-night is the average lacosamide plasma concentration as measured within any four, five, six, seven, eight, nine, ten, eleven or twelve hour period between the hours of 8 pm and 9 am. In a preferred embodiment, the C-ave-day to C-ave-night ratio is 1.2 to 2.0, wherein C-ave-day is determined over the period from 9 am to 4 pm and C-ave-night is determined over the period from 11 pm to 8 am. In a more preferred embodiment, the C-ave-day to C-ave-night ratio is 1.2 to 1.8, wherein C-ave-day is determined over the period from 9 am to 4 pm and C-ave-night is determined over the period from 11 pm to 8 am.

In another preferred embodiment, the C-ave-day to C-ave-night ratio is 1.2 to 2.0, wherein C-ave-day is determined over the period from 9 am to 6 pm and C-ave-night is determined over the period from 11 pm to 8 am. In some embodiments, the C-ave-day and C-ave-night values are determined from steady state plasma concentration profiles wherein the dosing time is at 8 am. In some embodiments, the C-ave-day and C-ave-night values are determined from steady state plasma concentration profiles adjusted to a predetermined administration time, wherein said predetermined administration time is a time for which the C-ave-day and C-ave-night values provide the recited ratio. In a more preferred embodiment, the C-ave-day to C-ave-night ratio is 1.4 to 2.0, wherein C-ave-day is determined over the period from 9 am to 6 pm and C-ave-night is determined over the period from 11 pm to 8 am.

In some embodiments, the C-ave-day is about 20%, 25%, 35%, 45%, 60%, 80%, 100% higher than C-ave-night. In some embodiments, the C-ave-day is about 20% to about 80% higher than C-ave-night, preferably about 20% to about 50% higher than C-ave-night. In some embodiments, the C-ave-day and C-ave-night values are determined from steady state plasma concentration profiles wherein the dosing time is at 8 am. In some embodiments, the C-ave-day and C-ave-night values are determined from steady state plasma concentration profiles adjusted to a predetermined administration time, wherein said predetermined administration time is a time for which the C-ave-day is greater than C-ave-night by the recited percentage. In some embodiments, the C-ave-day is about 30% to 150% higher than C-ave-night. In some embodiments, the C-ave-day is about 40% to 130% higher than C-ave-night. In some embodiments, the C-ave-day is about 50% to 120% higher than C-ave-night. In come embodiments, the C-ave-day is about 50% to 110% higher than C-ave-night. In some embodiments, the C-ave-day is about 50% to 100% higher than C-ave-night. In some embodiments, the C-ave-day is about 60% to 100% higher than the C-ave-night. In preferred embodiments the C-ave-day is determined over the period from 9 am to 4 pm, 5 pm, 6 pm, 7 pm; preferably over the period from 9 am to 6 pm. In preferred embodiments, C-ave-night is determined over the period from 11 pm to 6 am, 7 am, 8 am, 9 am; preferably over the period from 11 pm to 8 am.

In some embodiments of the invention, the composition is administered once daily at a predetermined administration time. In such embodiments, the predetermined administration time may be determined, based on a steady state plasma concentration profile, to provide pharmacokinetic parameters disclosed herein that are related to specific times of day, including C-ave-day, C-ave-night, and pAUCs at specific times of day. For example, the predetermined administration time providing a C-ave-day/C-ave-night ratio of 1.4 to 2.0 could be a time within 6 am to 9 am for a composition with a relatively short time to $T_{max}$; alternatively the predetermined administration time could be a time with 8 pm to 11 pm for a composition providing a $T_{max,ss}$ of 12 to 14 hours. A steady state plasma concentration profile of the drug of the composition may be determined as described herein. By adjusting the time of administration, also as described herein, the C-ave-day and C-ave-night values may be readily determined and a predetermined administration time which provides the pAUC values or C-ave-day to C-ave-night ratio or increase in C-ave-day relative to C-ave-night may also be readily determined. Certain compositions may provide diurnal variation that is insufficient to meet these parameters, regardless of the time of administration; other compositions may provide sufficient diurnal variation, but may provide pAUC values or C-ave-day or C-ave-night values meeting the requirements of the invention only if the predetermined administration times would require waking a patient to administer the compositions. In preferred embodiments, the predetermined administration time is a time during the normal waking hours of a patient, such as 5 am, 6 am, 7 am, 8 am, 9 am, 10 am, 5 pm, 6 pm, 7 pm, 8 pm, 9 pm, 10 pm, 11 pm, or 12 am. In one embodiment, administration of a single dose of the composition to a human subject provides a plasma concentration profile characterized by: a fractional AUC from 0 to 4 hours that is less than 5%, and preferably less than 3% of $AUC_{0-inf}$; a fractional AUC from 0 to 8 hours that is about 5 to 15%, and preferably about 8 to 12% of $AUC_{0-inf}$; a fractional AUC from 0 to 12 hours that is about 10 to 40%, and preferably about 15 to 30% of $AUC_{0-inf}$; a fractional AUC from 0 to 18 hours that is about 25 to 60%, and preferably about 30 to 50% of $AUC_{0-inf}$; and a fractional AUC from 0 to 24 hours that is about 40 to 75%, and preferably about 50 to 70% of $AUC_{0-inf}$.

In another embodiment, a once daily oral administration of the composition to a human subject provides a steady state plasma concentration profile characterized by: a fractional AUC from 0 to 4 hours that is about 2 to 25%, and preferably about 5 to 20% of $AUC_{24}$; a fractional AUC from 0 to 8 hours that is about 15 to 50%, and preferably about 20 to 40% of $AUC_{24}$; a fractional AUC from 0 to 12 hours that is about 30 to 70%, and preferably about 40 to 60% of $AUC_{24}$: and a fractional AUC from 0 to 18 hours that is about 60 to 95%, and preferably about 75 to 90% of $AUC_{24}$.

In some embodiments of any of the above aspects, a once daily oral administration of the composition to a human subject provides a steady state plasma concentration profile characterized by: a fractional AUC from 0 to 8 hours that is about 15 to 40%, and preferably about 20 to 32% of $AUC_{24}$; a fractional AUC from 8 to 16 hours that is about 30 to 50%, and preferably about 35 to 45% of $AUC_{24}$; and a fractional AUC from 16 to 24 hours that is about 20 to 35%, and preferably about 25 to 33% of $AUC_{24}$.

In some embodiments of any of the above aspects, a once daily oral administration of the composition to a human subject provides a steady state plasma concentration profile characterized by: a fractional AUC from 0 to t (where t is any two-hour increment post administration within a 24 hour period) that is between 80 to 125% of the corresponding fractional AUC from 0 to t of the immediate release formulation.

In some embodiments, a once daily oral administration of the composition to a human subject provides a steady state plasma concentration profile characterized by one or more of the following: (i) a fractional AUC from 8 AM to 10 AM that is between 80 to 125% of the immediate release formulation, and preferably between 90 to 110% of the immediate release formulation; (ii) a fractional AUC from 10 AM to 12 noon that is between 80 to 125% of the immediate release formulation, and preferably between 90 to 110% of the immediate release formulation; (iii) a fractional AUC from 12 noon to 2 PM that is between 80 to 125% of the immediate release formulation, and preferably greater than 100% of the immediate release formulation; (iv) a fractional AUC from 2 PM to 4 PM that is between 80 to 125% of the immediate release formulation, and preferably greater than 100% of the immediate release formulation; (v) a fractional AUC from 4 PM to 8 PM that is between 80 to 125% of the immediate release formulation, and preferably greater than 100% of the immediate release formulation; (vi) a fractional AUC from 8 PM to 12 AM that is between 50 to 100% of the immediate release formulation, and preferably less than 80% of the immediate release formulation; (vii) a fractional AUC from 12 AM to 8 AM that is between 80 to 125% of the immediate release formulation, and preferably less than 100% of the immediate release formulation. In some embodiments, 3 or more of these fractional AUC conditions are met. In some embodiments, 5 or more of these fractional AUC conditions are met. In some embodiments, 6 or more of these fractional AUC conditions are met. In other embodiments, at least one of conditions (iv) and (v) are met and at least one of conditions (vi) and (vii) are met.

Swing is defined as a percentage equal to (100%)*$(C_{max,ss}-C_{min,ss})/C_{min,ss}$. It is a measure of the peak to trough difference in the course of one dosing interval. Thus, it is a measure of the diurnal variation provided from dose to dose. In some embodiments, the swing for a once daily administered composition, as determined from a fasted human pharmacokinetic study, is 45%, 50%, 55%, 60%, 65% 70% to 58%, 63%, 68%, 73%, 78%, 83%, 88%, 93%, 98%, 103%, 108%, 113%, 128%, 140%, 150%, 160%, 180%, 200%; preferably 60% to 160%, 60% to 128%, 65% to 128%, 65 to 98%; more preferably 65 to 78%. In some embodiments, a composition administered once daily has a single dose $T_{max}$ of 14 to 20 hours and a swing of 63% to 77%; in another embodiment, a composition administered once daily has a single dose $T_{max}$ of 14 to 20 hours, a $T_{max,ss}$ of 13 to 17 hours, and a swing of 63% to 77%. In another embodiment, once daily administration of the composition provides a steady state plasma concentration profile characterized by a $T_{max,ss}$ of 10 to 18 hours, preferably 12 to 18 hours, and a swing of 80% to 180%, preferably 85% to 160%. In some embodiments, the composition is administered orally, once daily at a predetermined administration time and the steady state plasma concentration profile is characterized by a swing of 80% to 160% and a peak plasma concentration is during the period from 9 am to 3 pm. In such embodiments, the diurnal variation also results in a reduced plasma concentration at night such that the C-ave-day to C-ave night ratio is 1.2 to 2.0, preferably 1.4 to 2.0.

The dC/dt is the rate at which the drug in the composition is absorbed in a human over a defined period of time. It is conveniently determined over a defined time period from the plasma concentration profile of a human pharmacokinetic study. Except as specified otherwise, dC/dt values are determined from a single dose, fasted, human pharmacokinetic study. It is convenient to express the rate in absolute terms (e.g., ng/ml/hr per mg drug substance over a specified time) or as a fraction of the dC/dt for an immediate release composition of the same drug substance. In some embodiments, the dC/dt over the period from 0 to 1.4 hours is less than 15% of the dC/dt of an IR form of the same drug at the same dose in an immediate release form over the same time period; preferably, the dC/dt is less than 10%, is less than 5%, is less than 3%, 2%, 1.5% of the dC/dt for the IR form of the drug. In some embodiments, the dC/dt over the period from 0 to 2, 3, 4 hours is less than 15% of the dC/dt of an IR form of the same drug at the same dose in an immediate release form over the same time period; preferably, the dC/dt is less than 12%, is less than 10%, is less than 8%, 6%, 4%, 2%, 1.5% of the dC/dt for the IR form of the drug.

In some embodiments, the dC/dt over the first 2, 3, 4 hours after administration is less than 0.8, 0.6, 0.5, 0.4, 0.3, 0.2, 0.1 µg/ml/hr. In some embodiments, the composition comprises lacosamide and the dC/dt for lacosamide over the first 4 hours after administration of the composition is less than 0.5 µg/ml/hr.

The maximum slope ("max slope") over a defined period of time after administration of a single dose of the composition in a fasted human pharmacokinetic study is therefore a useful pharmacokinetic parameter. In some embodiments, the max slope is determined over the period from administration, $T_0$, to $T_{max}$. In another embodiment, the max slope is determined over the period from $T_0$ to a specified time, t. In some embodiments, the max slope is determined as the maximum slope over a time interval of not less than 2, 3, 4 hours within the period from administration to a specified time, t, using standard methods for determining slopes from models of the concentration profile over the time period from $T_0$ to t (e.g. simple linear or non-linear least squares regression, or symmetric difference quotient, Simpson method, or Trapezium rule). In some embodiments, the max slope for a lacosamide composition is determined as the maximum slope over 3 hour intervals from administration to 12 hours after administration using non-linear regression model of the plasma concentration profile from a single dose, fasted, human pharmacokinetic study. In some embodiments, the max slope is less than 4 ng/ml/hr per mg drug; preferably less than 3 ng/ml/hr per mg drug; more preferably less than 2.5 ng/ml/hr per mg drug. In some embodiments, the max slope for a lacosamide composition over a 3 hour interval in the period from administration to 24 hours after administration, the max slope is less than 2.4 ng/ml/hr per mg lacosamide; preferably less than 2.1 ng/ml/hr per mg lacosamide; more preferably less than 1.8 ng/ml/hr per mg lacosamide. In some embodiments, the max slope over a 3 hour interval in the period from T0 to 24 hours after administration, the max slope is about 1.0 to 2.0 ng/ml/hr per mg lacosamide, preferably 1.4 to 1.9 ng/ml/hr per mg lacosamide. Importantly, the maximum slope of a composition may be reduced for compositions with reduced bioavailability; in preferred embodiments, the max slope is adjusted for bioavailability to provide an "adjusted max slope" (i.e., max slope/bioavailability=max slope achieved for a composition with bioavailability equivalent to 100% of an IR form of the same drug).

In some embodiments described herein a lacosamide composition is administered to a patient 0 to 4 hours prior to bedtime. In some embodiments, the lacosamide composition is administered to a patient from 0 to 3, 0 to 2, or 0 to 1 hours prior to bedtime. In some embodiments, the lacosamide composition is administered to a patient from 0 to 240 minutes, from 0 to 180 minutes, e.g., from 0 to 120 minutes, from 0 to 60 minutes, from 0 to 45 minutes, from 0 to 30 minutes, from 0 to 15 minutes or from 0 to 10 minutes prior to bedtime. In some embodiments, the lacosamide composition is administered to a patient from 60 to 240 minutes, from 60 to 180 minutes, from 60 to 120 minutes or from 60 to 90 minutes prior to bedtime.

Unless otherwise specified herein, the term "bedtime" has the normal meaning of a time when a person retires for the primary sleep period during a twenty-four hour period of time. While for the general populace, bedtime occurs at night, there are patients, such as those who work nights, for whom bedtime occurs during the day. Thus, in some embodiments, bedtime may be anytime during the day or night.

In some embodiments, herein a lacosamide composition is administered to a patient in the morning, i.e., 0 to 3 hours after waking for the day, preferably, 0 to 1, 0 to 2 hours after waking for the day. By the term "waking for the day" we mean the time at which the subject rises to begin the day's activities. While for many people, waking for the day is typically between the hours of 5 am and 9 am, for some it may be earlier or later in the day or even in the night depending upon an individual's normal sleep routine.

It is to be understood that administration to a patient includes administration by a healthcare professional and/or self-administration by the patient.

In some embodiments, the invention provides a method of reducing adverse effects associated with administration of lacosamide to a human subject in need thereof. The method comprises administering a therapeutically effective dose of lacosamide in an oral, extended release form to a subject once per day, zero to 1, 2, 3, or 4 hours before bedtime. A therapeutically effective dose of lacosamide may be 50 mg, 75 mg, 100 mg, 125 mg, 150 mg, 175 mg 200 mg, 225 mg 250 mg, 275 mg, 300 mg to about 200 mg, 225 mg, 250 mg, 275 mg, 300 mg, 325 mg, 350 mg, 375 mg, 400 mg per day, 600 mg per day, 650 mg per day, 700 mg per day, 750 mg per day, 800 mg per day, 850 mg per day, or 900 mg per day. Some embodiments, the amount of lacosamide administered once daily is 100 mg to 400 mg, 200 to 400 mg, 225 mg to 375 mg, 250 mg to 375 mg per day, 400 to 600 mg per day, 500 to 700 mg per day, or 600 to 800 mg per day.

Some embodiments provide a method of treating a subject with a seizure disorder comprising administering a therapeutically effective dose of lacosamide in an oral, extended release form to a subject once per day, zero to 1, 2, 3 hours before bedtime. In some embodiments, the composition for administration 0 to 4 hours before bedtime provides a single dose $T_{max}$ of 10 to 20 hours as determined from a single dose, fasted, human pharmacokinetic study and/or a $T_{max,ss}$ of 10, 11, or 12 hours to 16, 18, or 20 hours as determined from a fasted human pharmacokinetic study.

Some embodiments provide a method of treating a subject with a seizure disorder comprising administering a therapeutically effective dose of lacosamide in an oral, extended release form to a subject once per day to 1, 2, 3, 4 hours after waking for the day. In some embodiments, the composition for administration to 1, 2, 3, 4 hours after waking for the day provides a $T_{max}$ less than 8, 7, 6, 5 hours, preferably 3 to 6, 3 to 5 hours after administration as determined from a single dose, fasted, human pharmacokinetic study.

The method comprises administration of a controlled release lacosamide composition in 1, 2, 3, or 4 unit dosage forms once daily; preferably 1 or 2 unit dosage forms.

In some embodiments, administration of lacosamide according to a method described herein provides a peak plasma concentration, $C_{max}$, that is less than the $C_{max}$ for an immediate release form of lacosamide as determined from a single dose, fasted, human pharmacokinetic study, and the time from administration to $C_{max}$, $T_{max}$, that is 8, 9, 10, 11, 12, 13, 14 hours to 13, 14, 16, 18, 20, 22, 24 hours;

preferably 10 hours to 20 hours, more preferably 11 hours to 18 hours such that administration zero to 1, 2, 3, 4 hours before bedtime provides a peak concentration at steady state that is in the middle of the following day. Administration according to methods described herein provides a reduction in adverse effects and/or may increase tolerability, compliance, or adherence to the treatment regimen.

Lacosamide compositions described herein may be used in treatment regimens with other known anti-epileptic drugs.

Making Controlled Release Formulations

In some embodiments, pharmaceutical compositions are prepared by combining an AED, such as lacosamide, with one or more additional ingredients which, when administered to a subject, cause the AED, such as lacosamide to be released at a targeted concentration range over a specified period of time. The AED, such as lacosamide is released at more slowly from the compositions than the AED, such as lacosamide is released from an immediate release (IR) dosage form. The slower release results in a reduced rate of absorption, providing a dC/dt that is significantly reduced relative to the IR dosage form of the same strength.

The precise slope for a given individual will vary according to the AED, such as lacosamide composition being used or other factors, such as whether the patient has eaten or not. For other doses, e.g., those mentioned above, the slopes vary directly in relationship to dose. The determination of initial slopes of plasma concentration is described, for example, by U.S. Pat. No. 6,913,768, or U.S. Pat. No. 8,389,578 hereby incorporated by reference.

Using the formulations described herein, therapeutic levels may be achieved while minimizing debilitating side-effects that are usually associated with immediate release formulations. Furthermore, as a result of the increase in the time to reach peak plasma level and the extended period of time at the therapeutically effective plasma level, the dosage frequency may be reduced to, for example, once daily dosing, thereby improving patient compliance and adherence.

It has been found surprisingly that the frequency of adverse effects is associated with the rapid rate of increase in plasma concentration of an AED such as lacosamide after administration of an immediate release form of the drug may be decreased or lessened in severity using the methods and compositions described herein. For example, side effects including, but not limited to, psychosis, dizziness, and cognitive deficits associated with the administration of an AED, such as lacosamide may be lessened in severity and frequency through the use of these controlled-release methods that reduce the max slope, $pAUC_{0-4}$, $pAUC_{4-8}$, or dC/dT of the drug.

Formulations for each active pharmaceutical ingredient may then be evaluated in human studies to determine the pharmacokinetic characteristics, including dC/dt, $C_{max}$, $T_{max}$, AUC, $T_{1/2}$, max slope, etc. of such formulations using methods known to the skilled artisan. Techniques for determining pharmacokinetic characteristics for a given formulation are routine in the art. Combination compositions may be conveniently prepared either by combining the desired quantities of formulations for each drug composition, blending and filling into hard gelatin capsules the desired quantity for each dosage form. Alternatively, combination compositions may be conveniently prepared filling desired quantities of each of the drug compositions directly into hard gelatin capsules using automated filling machines.

For a specified range a physician or other appropriate health professional will typically determine the best dosage for a given patient, according to his sex, age, weight, pathological state, and other parameters. In some cases, it may be necessary to use dosage outside of the range stated in pharmaceutical packaging insert to treat a subject. Those cases will be apparent to the prescribing physician.

In some embodiments, the compositions achieve therapeutic levels while minimizing debilitating side-effects that are usually associated with immediate release formulations. In some embodiments, the extended release compositions enable once daily administration of the AED, thereby improving patient compliance and adherence.

Modes of Administration

The composition may be administered in an oral formulation. In some embodiments, the lacosamide may be formulated to provide controlled, extended release (as described herein). For example, a pharmaceutical composition that provides controlled release of the lacosamide causes the agent to be released at a targeted rate for a specified period of time.

The preparation of pharmaceutical or pharmacological compositions are known to those of skill in the art in light of the present disclosure. General techniques for formulation and administration are found in "Remington: The Science and Practice of Pharmacy, Twentieth Edition," Lippincott Williams & Wilkins, Philadelphia, Pa. Tablets, capsules, pills, powders, granules, dragees, and slurries, are examples of such formulations.

"Pharmaceutically or Pharmacologically Acceptable" includes molecular entities and compositions that do not produce adverse, allergic or other untoward reaction when administered to an animal, or a human, as appropriate. "Pharmaceutically Acceptable Carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. "Pharmaceutically Acceptable Salts" include acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Formulations for Oral Administration

The brivaracetam, divalproex sodium, lacosamide, levetiracetam, oxcarbazepine, valproic acid, vigabatrin or other agent may be provided in a controlled, extended release form. In one example, at least 50%, 90%, 95%, 96%, 97%, 98%, 99%, or even in excess of 99% of the lacosamide is provided in an extended release dosage form. In another example, at least 50%, 90%, 95%, 96%, 97%, 98%, 99%, or even in excess of 99% of the brivaracetam is provided in an extended release dosage form. In another example, at least 50%, 90%, 95%, 96%, 97%, 98%, 99%, or even in excess of 99% of the levetiracetam is provided in an extended release dosage form. In another example, at least 50%, 90%, 95%, 96%, 97%, 98%, 99%, or even in excess of 99% of the oxcarbazepine is provided in an extended release dosage form. In another example, at least 50%, 90%, 95%, 96%, 97%, 98%, 99%, or even in excess of 99% of the divalproex sodium is provided in an extended release dosage form. In another example, at least 50%, 90%, 95%, 96%, 97%, 98%, 99%, or even in excess of 99% of the valproic acid is provided in an extended release dosage form. In another example, at least 50%, 90%, 95%, 96%, 97%, 98%, 99%, or even in excess of 99% of the vigabatrin is provided in an extended release dosage form. If desired, the release of the lacosamide, brivaracetam, levetiracetam, oxcarbazepine, divalproex sodium, valproic acid, or the vigabatrin may be monophasic or multiphasic (e.g., biphasic).

The pharmacokinetic half-lives of lacosamide is about 13 hours. Thus, suitable formulations may be conveniently selected to achieve the desired profiles over an extended period (preferably from 12 to 24 hours) thereby maintaining an optimal concentration range to maximize therapeutic benefit while minimizing adverse effects.

The pharmacokinetic half-life of brivaracetam is about 7-8 hours. Thus, suitable formulations may be conveniently selected to achieve the desired profiles over an extended period (preferably over 24 hours) thereby maintaining an optimal concentration range to maximize therapeutic benefit while minimizing adverse effects.

The pharmacokinetic half-life of levetiracetam is about 7 hours. Thus, suitable formulations may be conveniently selected to achieve the desired profiles over an extended period (preferably over 24 hours) thereby maintaining an optimal concentration range to maximize therapeutic benefit while minimizing adverse effects.

The pharmacokinetic half-life of oxcarbazepine is about 20 hours. Thus, suitable formulations may be conveniently selected to achieve the desired profiles over an extended period (preferably from 24-36) thereby maintaining an optimal concentration range to maximize therapeutic benefit while minimizing adverse effects.

The pharmacokinetic half-life of divalproex sodium is about 15 hours. Thus, suitable formulations may be conveniently selected to achieve the desired profiles over an extended period (preferably from 15 to 24 hours) thereby maintaining an optimal concentration range to maximize therapeutic benefit while minimizing adverse effects.

The pharmacokinetic half-life of valproic acid is about 9-16 hours. Thus, suitable formulations may be conveniently selected to achieve the desired profiles over an extended period (preferably from 15 to 24 hours) thereby maintaining an optimal concentration range to maximize therapeutic benefit while minimizing adverse effects.

The pharmacokinetic half-life of vigabatrin is about 10 hours. Thus, suitable formulations may be conveniently selected to achieve the desired profiles over an extended period (preferably from 12 to 24 hours) thereby maintaining an optimal concentration range to maximize therapeutic benefit while minimizing adverse effects.

Extended Release Formulations

Extended release compositions suitable for use in the method can be made using a variety of extended release technologies, such as those described in the patent publications referenced herein, which publications are incorporated herein by reference in their entireties. In some embodiments, the extended release form is a pellet in capsule dosage form. In some embodiments, the pellets comprise a pellet core, which is coated with at least one drug layer and at least one extended release coating layer. In some embodiments, the pellets are coated with at least one drug layer, an intermediate layer such as a seal coat and an extended release coating layer. In some embodiments, the pellet, the drug layer or both comprise one or more binders.

In some embodiments, the dosage unit comprises a plurality of coated pellets. In some embodiments, the pellets have a diameter of for example, 300 to 1700 microns, in some cases 500 to 1200 microns. The pellets will comprise, for example, inert substrates, such as sugar spheres, microcrystalline cellulose (MCC) spheres, starch pellets. In some embodiments, pellets can be prepared by other processes such as pelletization, extrusion, spheronization, etc. or combinations thereof. The core pellets may comprise the AED (e.g. brivaracetam, divalproex sodium, lacosamide, levetiracetam, oxcarbazepine, valproic acid, or vigabatrin and pharmaceutically acceptable excipients thereof).

Delayed Release Formulations

In some embodiments, at least a portion of the anti-epileptic composition is formulated in a delayed release formulation. Per the United States Pharmacopeia (USP), delayed-release tablets are enteric-coated to delay release of the medication until the tablet has passed through the stomach to prevent the drug from being destroyed or inactivated by gastric juices or where it may irritate the gastric mucosa. In contrast, extended-release tablets are "formulated in such a manner to make the contained medicament available over an extended period of time following ingestion." Some delayed release formulations may be in the form of capsules, caplets, or tablets.

In some embodiments, the delayed release formulation provides a 1 hour, 2 hour, 4 hour, 6 hour, or 8 hour release of the active ingredient. In some embodiments, the delay in release is between 1 and 3 hours, between 1 and 4 hours, between 1 and 5 hours, between 1 and 6 hours, between 1 and 7 hours, between 1 and 8 hours, between 2 and 3 hours, between 2 and 4 hours, between 2 and 5 hours, between 2 and 6 hours, between 2 and 7 hours, between 2 and 8 hours, between 2 and 9 hours, between 2 and 10 hours, between 3 and 4 hours, between 3 and 5 hours, between 3 and 6 hours, between 3 and 7 hours, between 3 and 8 hours, between 3 and 9 hours, between 3 and 10 hours, between 4 and 5 hours, between 4 and 6 hours, between 4 and 7 hours, between 4 and 8 hours, between 4 and 9 hours, between 4 and 10 hours, between 5 and 6 hours, between 5 and 7 hours, between 5 and 8 hours, between 5 and 9 hours, between 5 and 10 hours, between 6 and 7 hours, between 6 and 8 hours, between 6 and 9 hours, between 6 and 10 hours, 7 and 8 hours, between 7 and 9 hours, between 7 and 10 hours, between 8 and 9 hours, between 8 and 10 hours, or between 9 and 10 hours. Preferably, the delay in release is between 2 and 6 hours.

In some embodiments, only a portion of the active ingredient is a delayed release formulation. In some embodiments, 90%, 85%, 80%, 75%, 70%, 65%, 60%, 55%, 50%, 45%, 40%, 35%, 30%, 25%, 20%, 15%, 10% or 5% of the active ingredient is a DR formulation. In other embodiments, between 1-25%, between 10-25%, between 10-30%, between 10-40%, between 10-50%, between 25-50%, between 25-75%, between 20-40%, between 20-50%, between 20-75%, between 30-60%, between 40-75%, between 50-75%, between 60-85%, between 70-90%, or between 80-95% of the active ingredient is a DR formulation.

In other embodiments, 100% of the anti-epileptic agent is formulated for delayed release. In some embodiments a portion of the anti-epileptic agent is formulated for delayed release, and the balance of the anti-epileptic agent is formulated for extended release.

Release Profile

The compositions prepared as described herein release the drug substance over a prolonged period of time after administration to a human subject. Similarly, the compositions may be tested for release of the drug substance in vitro using standard methods. For example, lacosamide compositions described herein may be dissolved using a USP type 1 or type 2 apparatus to provide a release profile over time. In embodiments with pH dependent coatings, dissolution of the compositions are done in the type 1 apparatus with the protocol described herein. When using a type 1 (basket) apparatus, the dissolution may be performed in 900 ml 0.1 N HCl for 2 hours followed by dissolution in the same volume of USP phosphate buffer, pH 6.8; the dissolution is performed at 37.0±0.5° C. and 100 rpm. Alternatively, the dissolution may be performed at 37.0±0.5° C. and 100 rpm using the following dissolution media: 900 ml simulated gastric fluid (pH 1.2) for 2 hours, followed by 900 ml simulated intestinal fluid (pH 6.8) for 4 hours, followed by 900 ml USP phosphate buffer at pH 7.5 for 18 hours. In embodiments without pH dependent coatings (i.e., without delayed release, enteric coating) dissolutions of the compositions may be done in the type 1 apparatus or the type 2 apparatus with the protocol described herein; preferably, dissolutions for embodiments without pH dependent coatings are performed with the type 2 apparatus. When using a type 2 (paddle) apparatus, the dissolution may be performed in 900 ml 0.1N HCl; the dissolution is performed at 37.0±0.5° C. and 50 rpm. The samples for analysis may be taken over 16 to 24 hours at time points such as 1 hour, 2 hours, 3 hours, 4 hours, 6 hours, 8 hours, 10 hours, 12 hours, 16 hours, 20 hours, 24 hours.

Some embodiments, compositions described herein have dissolution profiles (using the apparatus and protocol appropriate to the presence or absence of delayed release coating as describe above) characterized by at least two of the following: (i) less than 10% of the drug substance in 1 hour, preferably less than 5% in 1 hour, or more preferably not more than 3.6% of the drug substance in 1 hour; (ii) less than 15% of the drug substance in 2 hours, preferably less than 12% in 2 hours, more preferably less than 9% in 2 hours, and even more preferably not more than 6% in 2 hours; (iii) less than 26% of the drug substance in 4 hours, preferably less than 22% in 4 hours, more preferably, less than 18% in four hours, and even more preferably not more than 15% in four hours; (iv) less than 42% of the drug substance in 6 hours, preferably less than 36% in 6 hours, more preferably less than 32% in 6 hours, and even more preferably not more than 28% in 6 hours; or (v) at least 50% of the drug substance in 12 hours, preferably more than 63% in 12 hours, more preferably more than 77% in 12 hours. In some embodiments, at least 3 of the aforementioned criteria are met. In some embodiments, all of the aforementioned criteria are met. In some embodiments, compositions have dissolutions profiles characterized by release of 0% to 9% of the drug substance at 2 hours, 3% to 24% of the drug substance at 4 hours, and 85% to 100% of the drug substance at 16 hours. In some embodiments, compositions have dissolutions profiles characterized by release of 0% to 9% of the drug substance at 2 hours, 3% to 19% of the drug substance at 4 hours, 12% to 41% at 6 hours, and 85% to 100% of the drug substance at 16 hours.

Coated Pellets

The pellet cores are coated with the active ingredient, e.g., brivaracetam, divalproex sodium, lacosamide, levetiracetam, oxcarbazepine, valproic acid, or vigabatrin or pharmaceutically acceptable salts and/or polymorphs thereof. In some embodiments, in addition to the active ingredient, the pellets also comprise one or more binders, such as for example hydroxypropyl methyl cellulose, copovidone, povidone, hydroxypropyl cellulose, hydroxyethyl cellulose, methyl cellulose, carboxymethyl cellulose etc. In some embodiments, the pellets also contain one or more additional excipients, such as anti-tack agents (e.g. talc, magnesium stearate etc.)

In some embodiments, the pellets cores are coated with a drug layer comprising active ingredient, and optionally one or more binders, anti-tack agents and/or solvents by conventional coating techniques such as fluidized bed coating, pan coating.

Intermediate Layer Coating

In some embodiments, the pellets are coated with an intermediate layer, such as a seal coat. In some embodiments, the seal coat is adapted to prevent ingredients in the extended release coating from interacting with ingredients in the pellet core, to prevent migration of the ingredients in the pellet core from diffusing out of the pellet core into the extended release layer, etc. As described herein, the seal coat can comprise one or more film forming polymers including but not limited to hydroxypropylmethyl cellulose (HPMC), copovidone, povidone, polyvinylpyrrolidone, hydroxypropyl cellulose, hydroxyethyl cellulose, methyl cellulose, carboxymethyl cellulose or any combination thereof and the like.

The seal coat can further comprise other additives like plasticizers, such as, propylene glycol, triacetin, polyethylene glycol, tributyl citrate and optionally anti-tacking agents, such as, magnesium stearate, calcium silicate, magnesium silicate, and colloidal silicon dioxide or talc.

Apart from plasticizers and anti-tacking agents as mentioned above, the seal coat can optionally contain buffers, colorants, opacifiers, surfactants or bases, which are known to those skilled in the art.

Seal coating can be applied to the core using conventional coating techniques such as fluidized bed coating, pan coating etc. In some embodiments, the drug coated pellets cores are coated with a seal coat layer that optionally comprises one or more binders, anti-tack agents and/or solvents by fluidized bed coating or pan coating.

Binders

In some embodiments, the pellet cores, the intermediate coating layer, or both may comprise one or more binders (e.g., film forming polymers). Suitable binders for use herein include, e.g.: alginic acid and salts thereof cellulose derivatives such as carboxymethylcellulose, methylcellulose (e.g., Methocel), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone®® CL, Kollidon® CL, Polyplasdone® XL-10), larch arabogalactan, Veegum®, polyethylene glycol, waxes, sodium alginate, and the like.

Extended Release Coating

The pellets may be coated with an extended release coating. The extended release coating is adapted to delay release of the drug from the coated drug cores for a period of time after introduction of the dosage form into the use environment. In some embodiments, the extended release coating includes excipients. Examples of non-pH dependent extended release polymers include ethyl cellulose, hydroxypropylmethyl cellulose, hydroxyethyl cellulose, hydroxypropyl cellulose, carboxymethyl cellulose, copolymer of ethyl acrylate, methyl methacrylate (e.g., Eudragit® RS), etc. Examples of pH dependent extended release excipients include methacrylic acid copolymers, hydroxypropylmethyl cellulose acetate succinate, hydroxypropylmethyl cellulose phthalate, and cellulose acetate phthalate etc. The extended release coating may also include a pore former, such as povidone, polyethylene glycol, hydroxypropyl cellulose, hydroxypropylmethyl cellulose, etc., sugars such as sucrose, mannitol, lactose, and salts, such as sodium chloride, sodium citrate, etc., a plasticizer, such as acetylated citrated esters, acetylated glycerides, castor oil, citrate esters, dibutylsebacate, glyceryl monostearate, diethyl phthalate, glycerol, medium chain triglycerides, propylene glycol, polyethylene glycol. The extended release coating may also include one or more additional excipients, such as lubricants (e.g., magnesium stearate, talc etc.).

Extended release coating can be applied using conventional coating techniques such as fluidized bed coating, pan coating etc. The drug coated pellets cores, which optionally comprise a seal coat, are coated with the extended release coating by fluidized bed coating.

Extended Release Excipients (Coating Polymers)

As described herein, exemplary extended release excipients include, but are not limited to, insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkyl celluloses such as hydroxypropyl cellulose, hydroxypropylmethyl cellulose, sodium carboxymethyl cellulose, and cross-linked acrylic acid polymers like Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain embodiments, the plastic material can be a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain other embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In still other embodiments, the acrylic polymer is an acrylic resin lacquer such as that which is commercially available from Rohm Pharma under the trade name Eudragit®. In further embodiments, the acrylic polymer comprises a mixture of two acrylic resin lacquers commercially available from Rohm Pharma under the trade names Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit RL30D and 1:40 in Eudragit® RS30D. The mean molecular weight is about 150,000. Eudragit® S-100 and Eudragit® L-100 are also suitable for use herein. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain an extended release formulation having a desirable dissolution profile. One skilled in the art will recognize that other acrylic polymers may also be used, such as, for example, Eudragit® L.

Pore Formers

In some embodiments, the extended release coating includes a pore former. Pore formers suitable for use in the extended release coating can be organic or inorganic agents, and include materials that can be dissolved, extracted or leached from the coating in the environment of use. Examples of pore formers include but are not limited to organic compounds such as mono-, oligo-, and polysaccharides including sucrose, glucose, fructose, mannitol, mannose, galactose, lactose, sorbitol, pullulan, dextran; polymers soluble in the environment of use such as water-soluble hydrophilic polymers, such as povidone, crospovidone, polyethylene glycol, hydroxypropyl cellulose, hydroxypropylmethyl cellulose, hydroxyalkyl celluloses, carboxyalkyl celluloses, cellulose ethers, acrylic resins, polyvinylpyrrolidone, cross-linked polyvinylpyrrolidone, polyethylene oxide, carbowaxes, Carbopol®, and the like, diols, polyols, polyhydric alcohols, polyalkylene glycols, polyethylene glycols, polypropylene glycols, or block polymers thereof, polyglycols, poly(a-Q) alkylenediols; inorganic compounds such as alkali metal salts, lithium carbonate, sodium chloride, sodium bromide, potassium chloride, potassium sulfate, potassium phosphate, sodium acetate, sodium citrate, suitable calcium salts, and the like. In certain embodiments, plasticizers can also be used as a pore former.

Delayed Release Coating

The pellets can be coated with a delayed release coating. The delayed release coating as defined in United States Pharmacopeia (USP) refers to an enteric coating to delay the release of drug until it has passed through the stomach and to release the drug in the desired segments of small or large intestine. The release mechanism is controlled by the dissolution of the film at different pHs located in different regions of the intestine. It provides an initial delay for releasing the drug with minimum alteration on the release rate (immediate release or extended release) once the pellets reach target release zone in the intestine. The period for the initial delay as well as the following drug release rate can be varied by changing the film thickness and/or the ratio of polymer combinations. Examples of delayed release polymers include, but not limited to, polymethacrylates and derivatives (methacrylic acid and ethylacrylate derivatives: Eudragit® L100-55, L100 or S100, or any combination), cellulose esters and derivatives (hydroxypropylmethyl cellulose acetate succinate, hydroxypropylmethyl cellulose phthalate, cellulose acetate trimellitate, and cellulose acetate phthalate etc.), and polyvinyl derivatives (polyvinyl acetate phthalate).

The pH-dependent DR film can contain pH-independent, time-release polymers to create blocks for controlling the rate of drug release. Example excipients include, but not limited to, copolymer of ethyl acrylate, methyl methacrylate (e.g., Eudragit® RS or RL, or combination of the two polymers) and cellulose derivatives (ethyl cellulose, hydroxypropyl methyl cellulose, hydroxyethyl cellulose, etc.). The acrylic polymer comprises a mixture of two acrylic resin lacquers commercially available from Rohm Pharma under the trade names Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D.

A plasticizer in the film includes, but not limited to, acetylated citrated esters, acetylated glycerides, castor oil, citrate esters, dibutyl sebacate, glyceryl monostearate, diethyl phthalate, glycerol, medium chain triglycerides, propylene glycol, polyethylene glycol, etc. A lubricant in the film includes, but not limited to, magnesium stearate, talc etc.

Compositions characterized by a delayed release greater than 2 hours may be prepared using a higher coat weight comprising Eudragit L100. In other embodiments, a delayed release greater than 2 hours may be achieved using a mixture of polymers, e.g., Eudragit L100 and S100. Capsules The extended release (ER) or extended release/delayed release pellets may be introduced into a suitable capsule by using an encapsulator equipped with pellet dosing chamber. The capsule sizes may be 00, 00EL, 0, 0EL, 1, 1EL, 2, 2EL, 3, 4 or 5. A particularly suitable composition that provides ideal pharmacokinetic properties and plasma concentration profiles is a pellet-in-capsule composition that comprises a plurality of pellets, typically having a diameter of about 500 µm to 1.2 mm, and preferably about 700 µm to 1000 µm, where each pellet comprises a core comprising brivaracetam, divalproex sodium, lacosamide, levetiracetam, oxcarbazepine, valproic acid, or vigabatrin and a binder, and an extended release coating surrounding the core that extends release of the pharmaceutically active compound so as to provide the desired pharmacokinetic properties and plasma concentration profiles described above.

In some embodiments, the pellets in the pellet-in-capsule are in a size 0 or smaller, preferably a size 1 or smaller capsule. Mean pellet diameters in some embodiments may be in a range of 500 µm to 1200 µm, e.g., from 500 µm to 1100 µm, from 500 µm to 1000 µm, from 500 µm to 900 µm, from 500 µm to 800 µm, from 500 µm to 700 µm, from 600 µm to 1100 µm, from 600 µm to 1000 µm, from 600 µm to 900 µm, from 600 µm to 800 µm, from 600 µm to 700 µm, from 700 µm to 1100 µm, from 700 µm to 1000 µm, from 700 µm to 900 µm, or from 700 µm to 800 µm. In some embodiments the mean particle diameters are, ±10%, e.g.: 500 µm, 550 µm, 600 µm, 650 µm, 700 µm, 750 µm, 800 µm, 850 µm, 900 µm, 950 µm, 1000 µm, 1050 µm, 1100 µm, 1150 µm or 1200 µm.

One suitable composition is a pellet-in-capsule composition wherein each pellet comprises a core that comprises a core seed with a mixture of brivaracetam, divalproex sodium, lacosamide, levetiracetam, oxcarbazepine, valproic acid, or vigabatrin and a binder coated onto the core seed, and an extended release coating surrounding the core comprising ethyl cellulose, a pore forming agent such as hydroxypropyl methyl cellulose or povidone, and a plasticizer. In some embodiments, the pellets may further comprise a seal coating between the pellet core and the extended release coating. The pellets are formulated using methods known in the art, such as those described in Example 1 below. In a specific embodiment, based on the combined weight of the pellet core and extended release coating, the brivaracetam, divalproex sodium, lacosamide, levetiracetam, oxcarbazepine, valproic acid, or vigabatrin is present in amounts from 20-80 wt %, 45-70 wt %, 40-50 wt %, 45-55 wt %, 50-60 wt %, 55-65 wt %, 60-70 wt %, 65-75 wt %, 70-80 wt %, or 40 to 60 wt %, the binder, which is preferably hydroxypropyl methyl cellulose, copovidone, or mixtures thereof, is present in amounts from 1 to 25 wt %, the core seed, preferably a sugar sphere (nonpareil) or microcrystalline cellulose seed (e.g., Celphere®), is present in amounts from 8 to 25 wt %, the ethyl cellulose is present in amounts from 10 to 20 wt %, the pore forming agent, preferably povidone, is present in amounts from 1 to 4 wt %, and the plasticizer is present in amounts from 1 to 4 wt %. In another specific embodiment, based on the combined weight of the pellet core and extended release coating, the brivaracetam, divalproex sodium, lacosamide, levetiracetam, oxcarbazepine, valproic acid, or vigabatrin is present in amounts from 50 to 70 wt %, the binder, which is preferably hydroxypropyl methyl cellulose, copovidone, or mixtures thereof, is present in amounts from 1 to 25 wt %, the core seed, preferably a sugar sphere (nonpareil) or microcrystalline cellulose seed (e.g., Celphere®), is present in amounts from 5 to 15 wt %, the ethyl cellulose is present in amounts from 1 to 15 wt %, the pore forming agent, preferably povidone, is present in amounts from 0.25 to 4 wt %, and the plasticizer is present in amounts from 0.25 to 4 wt %. In a preferred embodiment, the AED is 45-70 wt % of the composition.

Additional embodiments are illustrated in the Table 1, below, entitled "Various lacosamide ER Capsule Size 1 Formulations." By means of methods and compositions described herein, formulations can be made that achieve the desired dissolution characteristics and target pharmacokinetic profiles described herein. More specifically, therapeutically effective doses of lacosamide can be administered once nightly in no more than two size 1 (or smaller, e.g., size 2 or 3) capsules using the manufacturing methods and compositions that have been described herein to achieve these results. In particular, higher drug loading can be achieved using compositions and manufacturing methods described herein. In some embodiments, higher drug loading may be achieved, with the required dissolution profile, using smaller core pellet sizes and concomitantly increased drug layering on smaller cores, but with no change in the extended release coat. In some embodiments, using alternative manufacturing approaches described herein, e.g., extrusion and spheronization, even higher drug loads can be achieved to realize the desired dissolution profile, enabling high lacosamide drug loads with suitable pharmacokinetic profiles, resulting in compositions that are therapeutically more effective, and at least as well tolerated, and can be filled in relatively small sized capsules (e.g., size 1, 2 or 3), enabling ease of administration to patients.

TABLE 1

Various Lacosamide ER Capsule Size 1 Formulations

| Lacosamide Strength (m) | Manufacture Method | Inert Core Pellet Size (mm) | Active Drug % w/w | Extended Release Coating % w/w | Bulk Density (g/cm³) | % Fill in Size 1 Capsule |
|---|---|---|---|---|---|---|
| 50 mg | Fluid bed coating | 0.3-0.5 | 40-50% | 10-30% | 0.6-1.0 | 60-70% |
| 60 mg | Fluid bed Coating | 0.3-0.5 | 40-50% | 10-30% | 0.6-1.0 | 60-70% |
| 75 mg | Fluid bed coating | 0.3-0.5 | 45-50% | 10-30% | 0.6-1.0 | 80-90% |
| 100 mg | Fluid bed coating | 0.3-0.5 | 50-55% | 10-30% | 0.6-1.0 | 80-90% |
| 125 mg | Fluid bed coating | 0.2-0.3 | 50-55% | 10-30% | 0.6-1.0 | 80-90% |
| 150 mg | Fluid bed coating | 0.2-0.3 | 50-65% | 10-30% | 0..55-1.0 | 80-90% |
| 150 mg | Extrusion spheronization, pan or fluidized bed coating | N/A | 55-75% | 10-30% | 0.6-1.0 | 65-75% |
| 175 mg | Extrusion spheronization, pan or fluidized bed coating | N/A | 55-75% | 10-30% | 0.6-1.0 | 75-85% |
| 200 mg | Extrusion spheronization, pan or fluidized bed coating | N/A | 55-75% | 10-30% | 0.6-1.0 | 80-90% |
| 225 mg | Extrusion spheronization, pan or fluidized bed coating | N/A | 55-75% | 10-30% | 0.6-1.0 | 85-95% |

For larger capsules, such as size 00 or 00el, strengths of 250 mg, 275 mg, 300 mg, or 325 mg may be filled.

Additional embodiments are illustrated in Table 2, below, entitled "Various Brivaracetam ER Capsule Size 1 Formulations." By means of methods and compositions described herein, formulations can be made that achieve the desired dissolution characteristics and target pharmacokinetic profiles described herein. More specifically, therapeutically effective doses of brivaracetam can be administered once nightly in no more than two size 1 (or smaller, e.g., size 2 or 3) capsules using the manufacturing methods and compositions that have been described herein to achieve these results. In particular, higher drug loading can be achieved using compositions and manufacturing methods described herein. In some embodiments, higher drug loading may be achieved, with the required dissolution profile, using smaller core pellet sizes and concomitantly increased drug layering on smaller cores, but with no change in the extended release coat. In some embodiments, using alternative manufacturing approaches described herein, e.g., extrusion and spheronization, even higher drug loads can be achieved to realize the desired dissolution profile, enabling high brivaracetam drug loads with suitable pharmacokinetic profiles, resulting in compositions that are therapeutically more effective, and at least as well tolerated, and can be filled in relatively small sized capsules (e.g., size 1, 2 or 3), enabling ease of administration to patients.

TABLE 2

Brivaracetam ER Capsule Size 1 Formulations

| Brivaracetam Strength (mg) | Manufacture Method | Inert Core Pellet Size (mm) | Active Drug % w/w | Extended Release Coating % w/w | Bulk Density (g/cm³) | % Fill in Size 1 Capsule |
|---|---|---|---|---|---|---|
| 50 mg | Fluid bed coating | 0.3-0.5 | 40-50% | 6-30% | 0.6-1.0 | 60-70% |
| 60 mg | Fluid bed coating | 0.3-0.5 | 40-50% | 6-30% | 0.6-1.0 | 60-70% |
| 75 mg | Fluid bed coating | 0.3-0.5 | 45-50% | 6-30% | 0.6-1.0 | 80-90% |
| 100 mg | Fluid bed coating | 0.3-0.5 | 50-55% | 6-30% | 0.6-1.0 | 80-90% |
| 125 mg | Fluid bed coating | 0.2-0.3 | 50-55% | 6-30% | 0.6-1.0 | 80-90% |
| 150 mg | Extrusion spheronization, pan or fluidized bed coating | N/A | 55-75% | 6-30% | 0.6-1.0 | 65-75% |
| 175 mg | Extrusion spheronization, pan or fluidized bed coating | N/A | 55-75% | 6-30% | 0.6-1.0 | 75-85% |
| 200 mg | Extrusion spheronization, pan or fluidized bed coating | N/A | 55-75% | 6-30% | 0.6-1.0 | 80-90% |
| 225 mg | Extrusion spheronization, pan or fluidized bed coating | N/A | 55-75% | 6-30% | 0.6-1.0 | 85-95% |

The formulation techniques described for lacosamide and brivaracetam could be applied to other AEDs One or both agents of the combination may additionally be prepared as described in U.S. Pat. No. 4,897,268, involving a biocompatible, biodegradable microcapsule delivery system. Thus, the lacosamide may be formulated as a composition containing a blend of free-flowing spherical particles obtained by individually microencapsulating quantities of lacosamide, for example, in different copolymer excipients which biodegrade at different rates, therefore releasing lacosamide into the circulation at a predetermined rates. A quantity of these particles may be of such a copolymer excipient that the core active ingredient is released quickly after administration, and thereby delivers the active ingredient for an initial period. A second quantity of the particles is of such type excipient that delivery of the encapsulated ingredient begins as the first quantity's delivery begins to decline. A third quantity of ingredient may be encapsulated with a still different excipient which results in delivery beginning as the delivery of the second quantity beings to decline. The rate of delivery may be altered, for example, by varying the lactide/glycolide ratio in a poly(D, L-lactide-co-glycolide) encapsulation. Other polymers that may be used include polyacetal polymers, polyorthoesters, polyesteramides, polycaprolactone and copolymers thereof, polycarbonates, polyhydroxybuterate and copolymers thereof, polymaleamides, copolyaxalates and polysaccharides.

In some embodiments, the lacosamide, brivaracetam, may be provided in a controlled or extended release form with or without an immediate release component in order to maximize the therapeutic benefit of each, while reducing unwanted side effects associated with each. When these drugs are provided in an oral form without the benefit of controlled or extended release components, they are released and transported into the body fluids over a period of minutes to several hours. Thus, compositions may contain a lacosamide and a sustained release component, such as a coated sustained release matrix, a sustained release matrix, or a sustained release bead matrix. In one example, lacosamide (e.g., 5-80 mg) is formulated without an immediate release component using a polymer matrix (e.g., Eudragit), Hydroxypropyl methyl cellulose (HPMC) and a polymer coating (e.g., Eudragit). Such formulations are compressed into solid tablets or granules or formed into pellets for capsules or tablets. Optionally, a coating such as Opadry® or Surelease® is used.

Optionally, the brivaracetam, divalproex sodium, lacosamide, levetiracetam, oxcarbazepine, valproic acid, or vigabatrin is prepared using the OROS® technology, described for example, in U.S. Pat. Nos. 6,919,373, 6,923, 800, 6,929,803, 6,939,556, and 6,930,128, all of which are hereby incorporated by reference. This technology employs osmosis to provide precise, controlled drug delivery for up to 24 hours and can be used with a range of compounds, including poorly soluble or highly soluble drugs. OROS® technology can be used to deliver high drug doses meeting high drug loading requirements. By targeting specific areas of the gastrointestinal tract, OROS® technology may provide more efficient drug absorption and enhanced bioavailability. The osmotic driving force of OROS® and protection of the drug until the time of release eliminate the variability of drug absorption and metabolism often caused by gastric pH and motility.

Alternatively, the combination may be prepared as described in U.S. Pat. No. 5,395,626 features a multilayered controlled release pharmaceutical dosage form. The dosage form contains a plurality of coated particles wherein each has multiple layers about a core containing an lacosamide and/or the brivaracetam whereby the drug containing core and at least one other layer of drug active is overcoated with a controlled release barrier layer therefore providing at least two controlled releasing layers of a water soluble drug from the multilayered coated particle.

By way of example, extended release oral formulation can be prepared using additional methods known in the art. For example, a suitable extended release form of the either active pharmaceutical ingredient or both may be a matrix tablet composition. Suitable matrix forming materials include, for example, waxes (e.g., carnauba, bees wax, paraffin wax, ceresine, shellac wax, fatty acids, and fatty alcohols), oils, hardened oils or fats (e.g., hardened rapeseed oil, castor oil, beef tallow, palm oil, and soya bean oil), and polymers (e.g., hydroxypropyl cellulose, polyvinylpyrrolidone, hydroxypropyl methyl cellulose, and polyethylene glycol). Other suitable matrix tabletting materials are microcrystalline cellulose, powdered cellulose, hydroxypropyl cellulose, ethyl cellulose, with other carriers, and fillers. Tablets may also contain granulates, coated powders, or pellets. Tablets may also be multi-layered. Multi-layered tablets are especially suitable when the active ingredients have markedly different pharmacokinetic profiles. Optionally, the finished tablet may be coated or uncoated.

The coating composition typically contains an insoluble matrix polymer (approximately 15-85% by weight of the coating composition) and a water soluble material (e.g., approximately 15-85% by weight of the coating composition). Optionally an enteric polymer (approximately 1 to 99% by weight of the coating composition) may be used or included. Suitable insoluble matrix polymers include ethyl cellulose, cellulose acetate butyrate, cellulose acetates, polymethacrylates containing quaternary ammonium groups or other pharmaceutically acceptable polymers. Suitable water soluble materials include polymers such as polyethylene glycol, hydroxypropyl cellulose, hydroxypropyl methyl cellulose, polyvinylpyrrolidone, polyvinyl alcohol, and monomeric materials such as sugars (e.g., lactose, sucrose, fructose, mannitol and the like), salts (e.g., sodium chloride, potassium chloride and the like), organic acids (e.g., fumaric acid, succinic acid, lactic acid, and tartaric acid), and mixtures thereof. Suitable enteric polymers include hydroxypropyl methyl cellulose, acetate succinate, hydroxypropyl methyl cellulose, phthalate, polyvinyl acetate phthalate, cellulose acetate phthalate, cellulose acetate trimellitate, shellac, zein, and polymethacrylates containing carboxyl groups.

The coating composition may be plasticized according to the properties of the coating blend such as the glass transition temperature of the main agent or mixture of agents or the solvent used for applying the coating compositions. Suitable plasticizers may be added from 0 to 50% by weight of the coating composition and include, for example, diethyl phthalate, citrate esters, polyethylene glycol, glycerol, acetylated glycerides, acetylated citrate esters, dibutylsebacate, and castor oil. If desired, the coating composition may include a filler. The amount of the filler may be 1% to approximately 99% by weight based on the total weight of the coating composition and may be an insoluble material such as silicon dioxide, titanium dioxide, talc, kaolin, alumina, starch, powdered cellulose, MCC, or polacrilin potassium.

The coating composition may be applied as a solution or latex in organic solvents or aqueous solvents or mixtures thereof. If solutions are applied, the solvent may be present in amounts from approximate by 25-99% by weight based on the total weight of dissolved solids. Suitable solvents are water, lower alcohol, lower chlorinated hydrocarbons, ketones, or mixtures thereof. If latexes are applied, the solvent is present in amounts from approximately 25-97% by weight based on the quantity of polymeric material in the latex. The solvent may be predominantly water.

The pharmaceutical composition described herein may also include a carrier such as a solvent, dispersion media, coatings, antibacterial and antifungal agents, isotonic and absorption delaying agents. The use of such media and agents for pharmaceutically active substances is well known in the art. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates. The composition may also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, may also be used as a carrier. In some embodiments, lactose and/or casein are not preferred components of the composition. In some embodiments of any of the aspects described herein, the composition does not contain lactose, casein, or both.

Additional methods for making controlled release formulations are described in, e.g., U.S. Pat. Nos. 5,422,123; 5,601,845; 5,912,013; and 6,194,000, all of which are hereby incorporated by reference.

If desired, the agents may be provided in a kit. The kits include a therapeutically effective dose of an agent for treating epilepsy or other seizure-related conditions. The dosage forms may be packaged on blister cards for daily administration convenience and to improve adherence.

Indications Suitable for Treatment

Any subject experiencing or at risk of experiencing a seizure-related disorder, including myoclonic seizures in myoclonic epilepsy, primary generalized tonic-clonic seizures in patients with idiopathic generalized epilepsy, partial onset seizures, status epilepticus, acute mania management, paroxysmal kinesigenic choreoathetosis, phasic spasticity in multiple sclerosis, Landau-Kleffner syndrome, migraine treatment or prophylaxis, pediatric migraine, Meige syndrome, late-onset seizures in patients with Alzheimer's disease, anxiety disorders, severe myoclonic epilepsy of infancy, tardive dyskinesia, lumbar radiculopathy, late onset myoclonic epilepsy in Down syndrome, neuropathic pain, atypical pain syndromes, and Alzheimer's disease may be treated with compounds and methods described herein. Preferably, the methods of the invention treat subjects experiencing or at risk of partial-onset seizures.

A subject of the invention may be experiencing or at risk of experiencing the seizure-related disorder. The subject may be diagnosed with a seizure-related disorder.

References to methods of treatment herein can include methods of prevention.

Administration of the Compositions

Immediate release formulations of an AED such as lacosamide (e.g., Vimpat) are typically administered at low doses (e.g., 100 mg/day) and progressively administered at increasing dose over time to reach a steady state serum concentration that is therapeutically effective. According to the manufacturer's recommendation, Vimpat, an immediate release formulation of lacosamide, is first administered to subjects at a dose of 50 mg twice daily. Doses are increased weekly by 100 mg/day to a daily dose of 200-400 mg/day.

Using a sustained release formulation (at a constant daily dose of 200 mg, for example), a therapeutically effective steady state concentration may be achieved substantially sooner, without using a dose escalating regimen or reducing the escalation to one step (e.g. 200 mg/day for 1 week followed by 400 mg/day thereafter). Furthermore, the slope during each absorption period for the sustained release formulation is less (i.e. not as steep) than the slope for the immediate release form of an AED such as lacosamide. Accordingly, the dC/dt of the sustained release formulation is reduced relative to the immediate release formulation. Based on this model, a sustained release formulation of an AED such as lacosamide may be administered to a subject in an amount that is approximately the full strength dose (or that effectively reaches a therapeutically effective dose) from the onset of therapy and throughout the duration of treatment. Accordingly, a dose escalation may not be required. Alternatively, the sustained release formulation of an AED such as lacosamide may be titrated at an accelerated schedule compared to immediate release lacosamide (e.g. 200 or 300 mg/day for 1 week followed by 400 or 600 mg/day thereafter; or 150 mg/day for 1 week, followed by 300 mg/day for 1 week, followed by 600 mg/day thereafter).

The recommended dose of immediate release lacosamide (e.g. VIMPAT®) for the treatment of partial onset seizures is 100 mg to 200 mg twice daily (200 mg to 400 mg a day, VIMPAT package insert). There is no prescribing information on the time of day VIMPAT should be taken. Data from published literature suggests that, in partial onset seizures, a greater number of seizures may occur between 9 AM and 6 PM. Based on the known PK profile of immediate release lacosamide, it is expected that a BID regimen of immediate release AED such as lacosamide lacosamide would provide a pulsatile plasma profile that is out of sync with this seizure pattern (i.e., a morning dose may provide some coverage for part of the period where there is a high seizure burden, but the evening dose would occur outside of this window) resulting in long periods of time throughout the day where there is high seizure susceptibility and low plasma concentration. Additionally, an evening dose of IR AED such as lacosamide would provide higher levels of the AED lacosamide on board during the nighttime hours when the need for seizure control is reduced. Thus, a sustained release formulation of an AED such as lacosamide that provides sustained and high plasma levels between 9 AM and 6 PM will provide better seizure control.

Drug Ranges for the Drug

The inventors have found surprisingly that a therapeutically effective dose of an AED such as lacosamide administered less than 4 hours before bedtime in an extended release form with the pharmacokinetic characteristics described herein provides a reduction in adverse effects associated with therapy with the AED As described herein, the unit doses of an AED such as lacosamide administered as described herein are generally higher than the ranges normally prescribed for immediate release compositions of the AED. For example, the recommended dose of lacosamide for the treatment of epilepsy is 100 mg to 200 mg immediate release lacosamide administered twice daily. In clinical trials, higher doses appeared to provide greater benefit in subjects who were able to tolerate the high doses, although the higher doses were associated with increased adverse reactions and a higher rate of dropouts. As described herein, doses of 50 to 600 mg (or up to 800 mg) of lacosamide may be administered for treatment of patients, and methods and compositions described herein may comprise once-nightly administration of a dose as defined of up to 400, 500, 600 mg, 700 mg, or 800 mg once nightly, i.e., after 4 p.m. and/or within 4 hours of bedtime. In additional embodiments the administration of such higher doses may be in the form of 1, 2, 3 or 4 capsules of size 00, 0, 1 or 2 in the normal or EL format administered once nightly.

In some embodiment of any of the aspects described herein, a total daily lacosamide dose of 50 mg to 600 mg is administered as a once nightly formulation after 4 p.m. and/or within 4 hours of bedtime. In some embodiments, the once nightly dose of lacosamide administered exceeds 300 mg per day. In various specific embodiments, the once nightly dose of lacosamide or pharmaceutically acceptable salt thereof may be 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 295 mg, 290 mg to 315 mg, 310 mg to 335 mg, 330 mg to 355 mg, 350 mg to 375 mg, 370 mg to 395 mg, 390 mg to 415 mg, 410 mg to 435 mg, 430 mg to 455 mg, 450 mg to 475 mg, 470 mg to 495 mg, 490 mg to 515 mg, 510 mg to 535 mg, 530 mg to 555 mg, 550 mg to 575 mg, 570 mg to 595 mg, 590 mg to 600 mg, 590 to 620 mg, 600 to 625 mg, 620 to 645 mg, 640 to 665 mg, 650 to 675 mg, 670 to 695 mg, 690 to 725 mg, 700 to 750 mg, 725 to 775 mg, or 750 to 800 mg.

In specific embodiments described herein, a subject's entire daily dose of an AED such as lacosamide is administered once, during a period of less than about four, three, two or one hours before bedtime (i.e., after 4 p.m. and/or the time at which the subject wishes to go to sleep for the night). In some embodiments of any of the above aspects, administration of the composition to a patient results in a significant reduction in symptoms.

In some embodiments, herein a an AED such as lacosamide composition is administered to a patient in the morning, i.e., 0 to 3 hours after waking for the day, preferably, 0 to 1, 0 to 2 hours after waking for the day. By the term "waking for the day" we mean the time at which the subject rises to begin the day's activities. While for many people, waking for the day is typically between the hours of 5 am and 9 am, for some it may be earlier or later in the day or even in the night depending upon an individual's normal sleep routine.

Suitable plasticizers include medium chain triglycerides, diethyl phthalate, citrate esters, polyethylene glycol, glycerol, acetylated glycerides, castor oil, and the like. The pellets are filled into capsules to provide the desired strength of an AED such as lacosamide. An advantage of this composition is it provides the desired release properties that make the composition suitable for administration during said period before bedtime. A further advantage is that the extended release coating is sufficiently durable so that the capsule can be opened and the pellets sprinkled onto food for administration to patients who have difficulty swallowing pills, without adversely affecting the release properties of the composition. When the composition is administered by sprinkling onto food, it may be sprinkled on a soft food such as applesauce or chocolate pudding, which is consumed within 30 minutes, and preferably within 15 minutes. A yet further advantage of the above described composition is that it has very good batch-to-batch reproducibility and shelf-life stability.

A suitable pellet-in-capsule composition may have the above in vitro dissolution properties and/or any of the above-described pharmacokinetic properties (e.g., in vivo release profile, $T_{max}$, $pAUC_{0-4}$, $pAUC_{4-8}$, $C_{max}/C_{min}$ ratio, max slope, dC/dt, swing, C-ave-day/C-ave-night ratio, PTF, etc.) to make the composition suitable for administration in said period before bedtime. The composition may be further characterized by providing a $C_{max}$ of 8-21 ng/ml per mg of lacosamide and an $AUC_{0-inf}$ of 200-550 ng*h/mL per mg of lacosamide after oral administration of a single dose of the capsule to a human subject in a fasted state. A suitable pellet-in-capsule composition is further characterized by a steady state plasma concentration in which once nightly oral administration of the capsule to a human subject provides a $C_{max}$ of 12 to 36 ng/ml per mg of lacosamide, a $C_{min}$ of 6 to 15 ng/ml per mg of lacosamide, and an $AUC_{0-24}$ of 200-550 ng*h/mL per mg of lacosamide.

Other Extended Release Dosage Forms

The person of skill in the art will recognize that other embodiments of extended release compositions may be envisioned, in addition to the capsule formulation described above. Such other embodiments include extended release solid dosage forms, such as tablets, capsules, gel caps, powders, pellets, beadlets, etc. Included in such extended release compositions are those that have the release characteristics and in vivo pharmacokinetic profiles suitable for employment in methods described herein. In some embodiments, the person skilled in the art may employ, with appropriate adjustment of design characteristics to achieve the necessary pharmacokinetic profile described herein, the extended release technology described in U.S. Pat. No. 5,358,721, to Guittard et al., or U.S. Pat. No. 6,217,905, to Edgren et al., each of which disclose an oral osmotic dosage form of lacosamide, and each of which is incorporated herein by reference in its entirety. In other embodiments, the person of skill in the art may employ, again with appropriate adjustment of design characteristics, the technology described in U.S. Pat. No. 6,194,000, to Smith et al. or U.S. Patent Appl. Publication Nos. US 2006/0252788, US 2006/0189694, US 2006/0142398, US 2008/0227743 and US2011/0189273, all to Went et al., each of which disclose the administration of an NMDA receptor antagonist, optionally in controlled release form, and each of which is incorporated herein by reference in its entirety.

Manufacturing Considerations

Compositions may be prepared as extended release coated pellets. These compositions may be prepared, for example, in a fluidized bed processor. In such examples, the AED, such as lacosamide, is combined with water and, optionally, other excipients such as binders and/or anti-tacking agents.

The drug layering suspension or solution used in the fluidized bed processor should have a solids content ranging from 15 to 45% w/w, preferably 20% to 35%, more preferably 25% to 35%. Some AEDs, such as lacosamide, have modest solubility in aqueous systems (about 20 mg/ml), and the drug loading is expected to be significant, i.e., 10% to 60% of an extended release pellet composition. To avoid very long processing times, the lacosamide content in the aqueous suspension will be beyond the solubility limit.

Thus for drug layering suspensions for the fluidized bed drug coating, the AED, such as lacosamide, should have defined particle characteristics to i) provide a suspension with high solids content to reduce the coating time, ii) provide a suspension that does not clog the spray nozzles within the fluidized bed coater, iii) provide a uniform suspension to maximize the homogeneity of the product.

The particle size for the AED, such as lacosamide, should be small enough to avoid clogging the spray nozzles and to be atomized in the fluidized bed apparatus. This may be achieved with lacosamide which is either amorphous or crystalline with a length that is less than 3 times the width.

The particle size should be small enough to pass through the fluidized bed spray system without clogging and preferably less than 150 urn, more preferably less than 100 urn, even more preferably less than 75 urn and most preferably less than 50 urn in size. Passing the material through a sieve of an appropriate size is the typical method to ensure the material size, e.g., a 100 mesh sieve will permit material that is less than 149 urn to pass through. The lacosamide particle size may be reduced by milling or other methods and equipment known to the skilled artisan. The suspension to be used in a fluidized bed processor may require agitation or mixing and temperature control of the suspension to maintain homogeneity during the coating process.

In such examples, an extended release coating is then added to the drug coated particles to provide a composition with a release profile as described herein. The ER coated particles may then be encapsulated to provide dosage forms suitable for administration to a subject in need thereof.

Alternatively, coated particles may be prepared by adding an extended release coating to granules of lacosamide prepared by mixing lacosamide with excipients, extruding the composition and spheronizing the extruded composition. The extended release coating may be added in a fluidized bed processor or by other methods known in the art.

EXAMPLES

Example 1: Lacosamide Extended Release Formulations

Lacosamide extended release coated pellet compositions designed for nighttime administration are prepared using the components and relative amounts shown in the table below. For each composition, the drug coating solution is prepared by adding HPMC 5 cps and Copovidone to isopropyl alcohol with continuous stirring. Purified water is added to this dispersion and stirring continued until a clear solution is formed. Drug (lacosamide) is then added to this binder solution and stirring continued until the drug is completely dissolved. Finally, talc is added and dispersed uniformly by stirring.

Celphere beads (screen sizes #35 to #50 i.e., 300 to 500 micron) are loaded in a Wurster coating unit. The drug coating dispersion is sprayed onto the beads followed by a period of drying. The resulting drug coated pellets are sieved to retain the fraction between screens #18 and #24 (approximately 700 μm to 1000 μm diameter).

The seal coating solution is prepared by adding HPMC 5 cps to isopropyl alcohol with continuous stirring. Purified water is added to this dispersion and stirring continued until a clear solution is formed. Talc is added and dispersed uniformly by stirring. The sieved drug coated pellets are loaded in a Wurster coating unit. The seal coating dispersion is sprayed over the drug coated pellets followed by a period of drying to remove the residual solvent and water in the pellets. The resulting seal coated pellets are sieved to retain the fraction between screens #18 and #24.

The ER coating solution is prepared by dissolving ethyl cellulose (viscosity 7 cps) in isopropyl alcohol and purified water and stirring until a clear solution is formed. Povidone K-90 is then dissolved in this clear solution followed by addition of plasticizer Miglyol 812N with continuous stirring to form a clear solution. The sieved seal coated pellets are loaded in a Wurster coating unit. The ER coating solution is sprayed over the seal coated pellets followed by a period of drying to affect the ER coat and remove the residual solvent and water in the pellets. After drying, magnesium stearate is spread on the top bed of the coated pellets in the annulus region followed by recirculation of the pellets in the Wurster unit to blend the magnesium stearate with the coated pellets. The resulting ER coated pellets are sieved to retain the fraction between screens #18 and #24.

The desired weight of the ER coated pellets containing the unit dose are filled into empty #1 hard gelatin capsule shell (size #1 for 100 mg strength) using an encapsulator equipped with pellet dosing chamber. For the composition shown in the table below, 237 mg pellets contain 100 mg lacosamide.

TABLE EX 1

Lacosamide ER Composition

| Component | Function | Combined w/wof capsule |
| --- | --- | --- |
| Pellet Core | | |
| Lacosamide | Active | 42.17% |
| Microcrystalline cellulose spheres (Celphere ®) | Core seeds | 14.04% |
| Hydroxypropyl methyl cellulose USP | Binder/Coating polymer | 18.95% |
| Copovidone | Binder | 2.98% |
| Extended Release Coating | | |
| Ethyl cellulose | Coating polymer | 12.97% |
| Povidone | Pore former | 1.96% |
| Medium chain triglycerides | Plasticizer | 1.55% |
| Talc USP | Anti-tack | 5.25% |
| Magnesium Stearate NF | Lubricant | 0.13% |
| Isopropyl alcohol | Solvent | 1 |
| Water | Solvent | 1 |

[1] Removed upon drying

Example 2: Extended Release Lacosamide Formulations

Lacosamide extended release coated pellet compositions designed for once daily administration are prepared using the components and relative amounts shown below. For each composition, the drug coating suspension is prepared by adding HPMC 5 cps to purified water with continuous stirring until a clear solution is formed. Drug (lacosamide) is then added to this binder solution with continuous stirring until a well-dispersed drug suspension is formed.

Celphere beads (300 to 500 micron) are loaded in a Wurster coating unit. The drug coating dispersion is sprayed onto the beads followed by a period of drying.

The ER coating solution is prepared by dissolving ethyl cellulose (viscosity 7 cps) in isopropyl alcohol and purified water. Hydroxypropyl methyl cellulose is dissolved in the solution followed by addition of plasticizer, diethyl phthalate. The sieved drug coated pellets are loaded in a Wurster coating unit. The ER coating solution is sprayed over the drug coated pellets followed by a period of drying to affect the ER coat and remove the residual solvent and water in the pellets. The resulting ER coated pellets are sieved.

The desired weight of the ER coated pellets containing the unit dose are filled into empty #0 hard gelatin capsule shell (200 mg strength) using an encapsulator equipped with pellet dosing chamber.

TABLE EX 2A

ER Lacosamide Form 1 comprises the following:

| Component | Function | Combined w/w of capsule |
|---|---|---|
| Active-loaded pellets | | |
| Lacosamide | Active | 53.58% |
| Microcrystalline cellulose spheres (Celphere ®) | Core seeds | 13.02% |
| Hydroxypropyl methyl cellulose | Binder/Coating polymer | 13.40% |
| Purified water | Solvent | —[1] |
| ER-coated pellets | | |
| Ethyl cellulose | Coating polymer | 13.33% |
| Hydroxypropyl methyl cellulose | Pore former | 3.33% |
| Diethyl phthalate | Plasticizer | 3.34% |
| Isopropyl alcohol | Solvent | —[1] |
| Purified water | Solvent | —[1] |

[1] removed during process

TABLE EX 2B

ER Lacosamide Form 2

| Component | Function | Combined w/w of capsule |
|---|---|---|
| Active-loaded pellets | | |
| Lacosamide | Active | 54.49% |
| Microcrystalline cellulose spheres (Celphere ®) | Core seeds | 13.24% |
| Hydroxypropyl methyl cellulose | Binder/Coating polymer | 13.63% |
| Purified water | Solvent | —[1] |
| ER-coated pellets | | |
| Ethyl cellulose | Coating polymer | 13.56% |
| Hydroxypropyl methyl cellulose | Pore former | 3.39% |
| Diethyl phthalate | Plasticizer | 1.70% |
| Isopropyl alcohol | Solvent | —[1] |
| Purified water | Solvent | —[1] |

[1] removed during process

Form 3 is formulated as Form 1+3-hr DR.

TABLE EX 2C

ER Lacosamide Form 3

| Component | Function | Combined w/w of capsule |
|---|---|---|
| Active-loaded pellets | | |
| Lacosamide | Active | 47.42% |
| Microcrystalline cellulose spheres (Celphere ®) | Core seeds | 11.52% |
| Hydroxypropyl methyl cellulose | Binder/Coating polymer | 11.86% |
| Purified water | Solvent | —[1] |
| ER-coated pellets | | |
| Ethyl cellulose | Coating polymer | 11.80% |
| Hydroxypropyl methyl cellulose | Pore former | 2.95% |
| Diethyl phthalate | Plasticizer | 2.95% |
| Isopropyl alcohol | Solvent | —[1] |
| Purified water | Solvent | —[1] |
| DR-coated pellets | | |
| Methacrylic Acid and Ethyl Acrylate Copolymer | Coating polymer | 8.85% |
| Talc | Plasticizer | 1.77% |

TABLE EX 2C-continued

ER Lacosamide Form 3

| Component | Function | Combined w/w of capsule |
|---|---|---|
| Triethyl citrate | Anti-tack | 0.88% |
| Purified water | Solvent | —[1] |

[1] removed during process

Example 3: ER Lacosamide Formulations with Partial Delayed Release Components Lacosamide extended release coated pellet compositions designed for nighttime administration are prepared using the components and relative amounts shown below. For each composition, the drug coating suspension is prepared by adding HPMC 5 cps to purified water with continuous stirring until a clear solution is formed. Drug (lacosamide) is then added to this binder solution with continuous stirring until a well-dispersed drug suspension is formed.

Celphere beads (300 to 500 micron) are loaded in a Wurster coating unit. The drug coating dispersion is sprayed onto the beads followed by a period of drying.

The ER coating solution is prepared by dissolving ethyl cellulose (viscosity 7 cps) in isopropyl alcohol and purified water. Hydroxypropyl methyl cellulose is dissolved in the solution followed by addition of plasticizer, diethyl phthalate. The sieved drug coated pellets are loaded in a Wurster coating unit. The ER coating solution is sprayed over the drug coated pellets followed by a period of drying to affect the ER coat and remove the residual solvent and water in the pellets. The resulting ER coated pellets are then sieved.

The delayed-release (DR) coating dispersion is prepared by mixing water, triethyl citrate, and talc with methacrylic acid and ethyl acrylate copolymer aqueous dispersion. The sieved ER coated pellets are loaded in a Wurster coating unit. The DR coating solution is sprayed over the ER coated pellets followed by a period of drying. The resulting DR/ER coated pellets are then sieved.

The desired weight of the DR/ER coated pellets containing the unit dose are filled into empty #0 hard gelatin capsule shell (200 mg strength) using an encapsulator equipped with pellet dosing chamber.

TABLE EX 3A

ER Lacosamide Formulation 2 + 2 Hour Delayed Release

| Component | Function | Combined w/w of capsule |
|---|---|---|
| Lacosamide | Active | 48.22% |
| Microcrystalline cellulose spheres (Celphere ®) | Core seeds | 11.72% |
| Hydroxypropyl methyl cellulose USP | Binder/Coating polymer/pore former | 15.06% |
| Ethyl cellulose | Coating polymer | 12.00% |
| Diethyl phthalate | Plasticizer | 1.5% |
| Methacrylic Acid and Ethyl Acrylate Copolymer | Coating polymer | 8.85% |
| Talc | Plasticizer | 1.77% |
| Triethyl citrate | Anti-tack | 0.88% |
| Isopropyl alcohol | Solvent | —[1] |
| Water | Solvent | —[1] |

[1] removed during processing

An ER lacosamide formulation characterized by a longer delayed release, i.e., 4 hours comprises a higher DR coating level, resulting in an approximate 20% weight increase in the ER pellets.

TABLE EX 3B

ER Lacosamide Formulation 4 hour Delayed Release

| Component | Function | Combined w/w of capsule |
|---|---|---|
| Active-loaded pellets | | |
| Lacosamide | Active | 41.96% |
| Microcrystalline cellulose spheres (Celphere ®) | Core seeds | 10.20% |
| Hydroxypropyl methyl cellulose | Binder/Coating polymer | 10.50% |
| Purified water | Solvent | —[1] |
| ER-coated pellets | | |
| Ethyl cellulose | Coating polymer | 10.44% |
| Hydroxypropyl methyl cellulose | Pore former | 2.60% |
| Diethyl phthalate | Plasticizer | 1.31% |
| Isopropyl alcohol | Solvent | —[1] |
| Purified water | Solvent | —[1] |
| DR-coated pellets | | |
| Methacrylic Acid and Ethyl Acrylate Copolymer | Coating polymer | 17.69% |
| Talc | Plasticizer | 3.54% |
| Triethyl citrate | Anti-tack | 1.77% |
| Purified water | Solvent | —[1] |

[1]removed during processing

Example 4: Brivaracetam Coated Pellet Formulations

Brivaracetam extended release coated pellet compositions designed for nighttime administration are prepared using the components and relative amounts shown in the table below. For each composition, the drug coating solution is prepared by adding HPMC 5 cps and Copovidone to isopropyl alcohol with continuous stirring. Purified water is added to this dispersion and stirring continued until a clear solution is formed. Drug (brivaracetam) is then added to this binder solution and stirring continued until the drug is completely dissolved. Finally, talc is added and dispersed uniformly by stirring.

Celphere beads (screen sizes #35 to #50 i.e., 300 to 500 micron) are loaded in a Wurster coating unit. The drug coating dispersion is sprayed onto the beads followed by a period of drying. The resulting drug coated pellets are sieved to retain the fraction between screens #18 and #24 (approximately 700 μm to 1000 μm diameter).

The seal coating solution is prepared by adding HPMC 5 cps to isopropyl alcohol with continuous stirring. Purified water is added to this dispersion and stirring continued until a clear solution is formed. Talc is added and dispersed uniformly by stirring. The sieved drug coated pellets are loaded in a Wurster coating unit. The seal coating dispersion is sprayed over the drug coated pellets followed by a period of drying to remove the residual solvent and water in the pellets. The resulting seal coated pellets are sieved to retain the fraction between screens #18 and #24. Portions of these seal coated pellets are used to make extended release formulations as described below. Also, a first portion of these seal coated pellets is also retained as an immediate release form of brivaracetam. For the retained portion, magnesium stearate is spread on the top bed of the coated pellets in the annulus region followed by recirculation of the pellets in the Wurster unit to blend the magnesium stearate with the coated pellets to provide immediate release brivaracetam pellets ("Form A"). The desired weight of the Form A pellets containing the unit dose are filled into empty #1 hard gelatin capsule shells (size #1 for 100 mg strength) using an encapsulator equipped with a pellet dosing chamber. For the Form A composition described in the table below, 197 mg pellets contain 100 mg brivaracetam.

The ER coating solution is prepared by dissolving ethyl cellulose (viscosity 7 cps) in isopropyl alcohol and purified water and stirring until a clear solution is formed. Povidone K-90 is then dissolved in this clear solution followed by addition of plasticizer Miglyol 812N with continuous stirring to form a clear solution. The sieved seal coated pellets are loaded in a Wurster coating unit. The ER coating solution is sprayed over one portion of the seal coated pellets to provide a faster release composition (about 8% coat weight, "Form B") and over another portion of the pellets to provide a slower release composition (about 17% coat weight, "Form C"), in each case followed by a period of drying to affect the ER coat and remove the residual solvent and water in the pellets. After drying, magnesium stearate is spread on the top bed of the coated pellets in the annulus region followed by recirculation of the pellets in the Wurster unit to blend the magnesium stearate with the coated pellets. The resulting ER coated pellets from each of the sub-batches are sieved to retain the fraction between screens #18 and #24.

The desired weight of the ER coated pellets containing the unit dose are filled into empty #1 hard gelatin capsule shell (size #1 for 100 mg strength) using an encapsulator equipped with pellet dosing chamber. For the Form Band Form C pellets shown in the table below, 100 mg brivaracetam is contained in 216 pellets and 250 pellets, respectively.

TABLE EX 4

Brivaracetam compositions

| | | Combined w/w of Capsule | | |
|---|---|---|---|---|
| Component | Function | Form A | Form B | Form C |
| Brivaracetam | Active | 50.65% | 46.40% | 39.97% |
| Microcrystalline cellulose spheres (Celphere ®) | Core seeds | 16.86% | 15.45% | 14.57% |
| Hydroxypropyl methyl cellulose USP | Binder/Coating polymer | 22.76% | 20.85% | 19.67% |
| Copovidone | Binder | 3.58% | 3.28% | 3.09% |
| Ethyl cellulose | Coating polymer | — | 6.60% | 13.46% |
| Povidone | Pore former | — | 1.00% | 2.03% |
| Medium chain triglycerides | Plasticizer | — | 0.79% | 1.61% |
| Talc USP | Anti-tack | 6.01% | 5.50% | 5.24% |
| Magnesium Stearate NF | Lubricant | 0.13% | 0.13% | 0.13% |
| Isopropyl Alcohol | Solvent | —[1] | —[1] | —[1] |
| Water | Solvent | —[1] | —[1] | —[1] |

[1]Removed upon drying

Example 5: Dissolution of Lacosamide Formulations

USP method <711> and Ph. Eur. 2.9.3, respectively, refer to an in vitro dissolution test for pharmaceutical composition. A rotating basket apparatus 1 as described in method <711> of the Us Pharmacopeoeia (edition 33) and chapter 2.9.3 of the Pharmacopoeia European (edition 6.8), respectively, with 900 mL dissolution media at 37±0.5° C. at a stirring speed of 100 rpm is used to determine the in vitro release of lacosamide from solid lacosamide formulations. Initially, the dissolution media is 0.1 N HCl; after 2 hours, the media is changed to 0.1 molar sodium phosphate buffer at pH 6.8 (same volume and temperature). Samples are taken for analysis at predetermined time points (as shown in the table below). The amount of lacosamide released at any time is determined via UV spectrometric detection. The values of replicate samples from separate dissolution baths (N=6) are averaged for each time point.

Figure 1B:
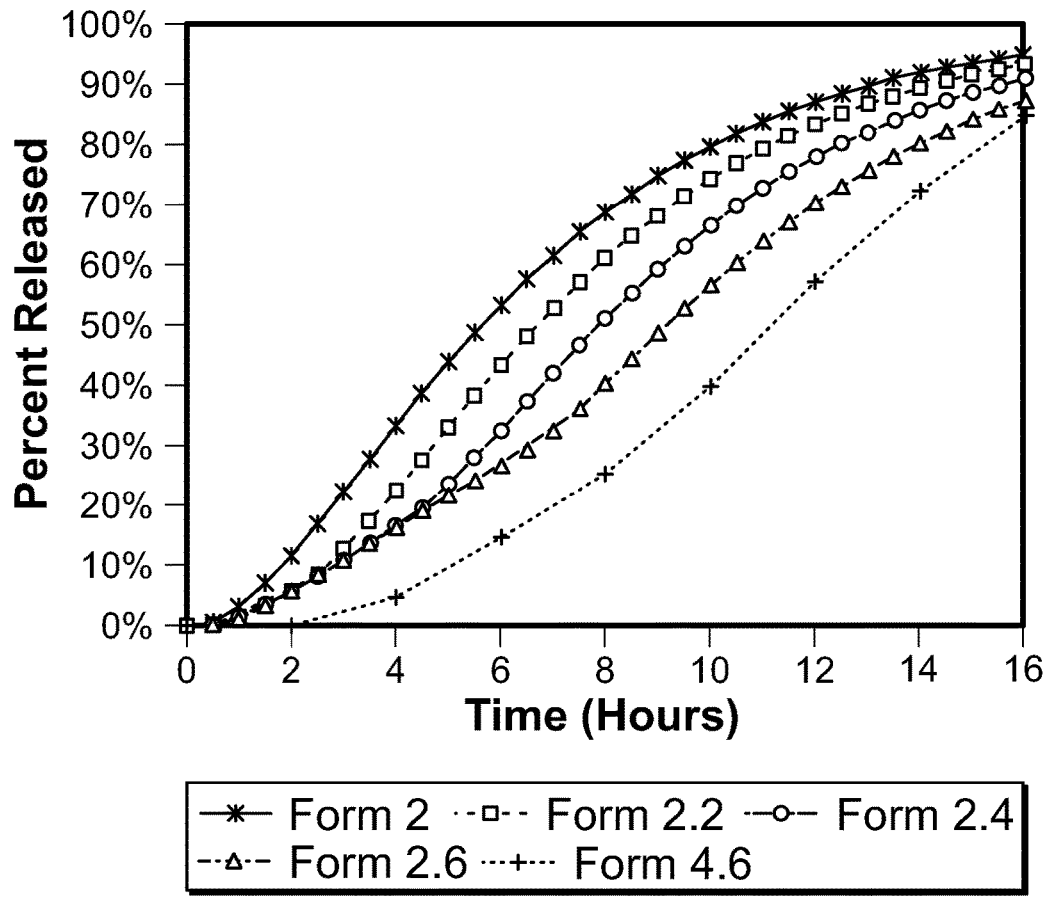
FIG. 1B is a graph depicting the dissolution profiles of ER lacosamide formulations Form 2, Form 2.2, Form 2.4, Form 2.6, and Form 4.6.
Figure 1C:
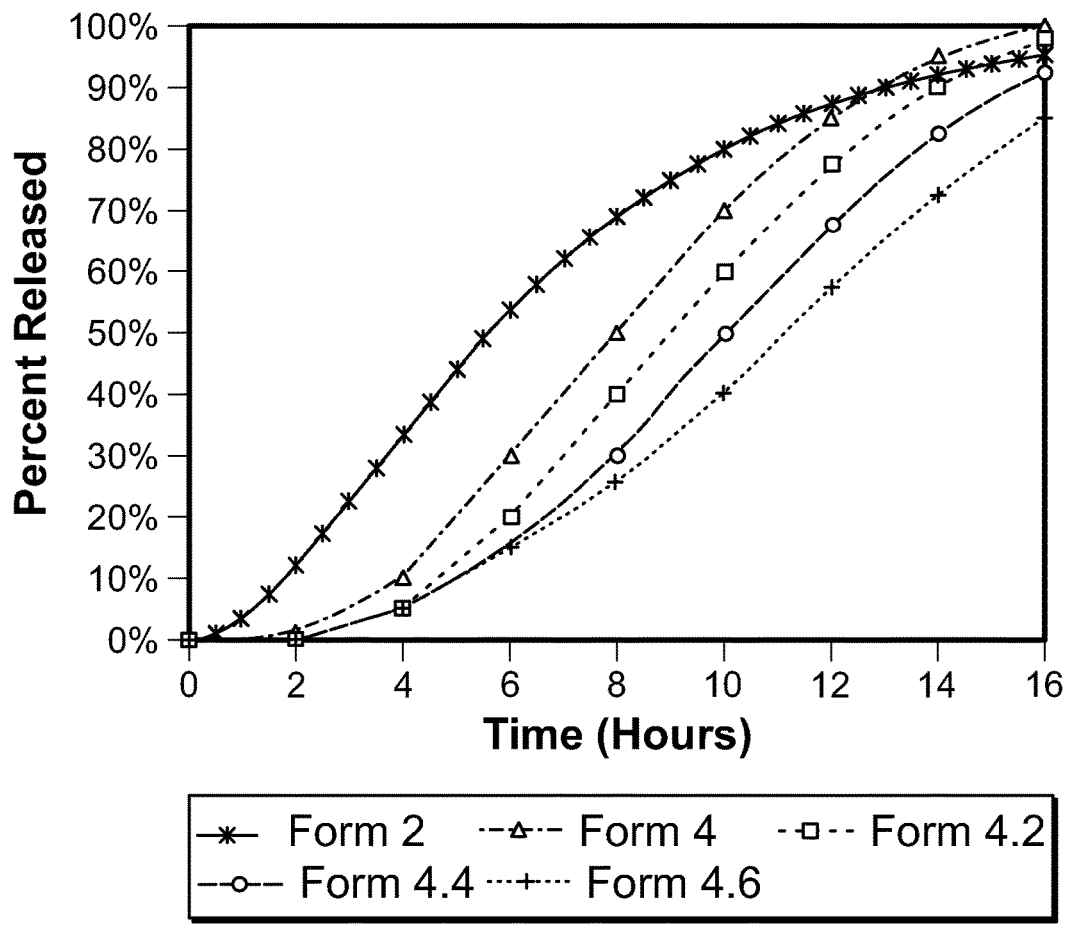
FIG. 1C is a graph depicting the dissolution profiles of ER lacosamide formulations Form 2, Form 4, Form 4.2, Form 4.4, and Form 4.6.

The dissolution rates for Formulations 1, 2, Form 2.2 (a 50:50 mixture of Form 2 and Form 2 with an additional 2 hour DR coat), Form 2.4, (a 50:50 mixture of Form 2 and Form 2 with an increased DR coat), Form 2.6 (a 50:50 mixture of Form 2 and Form 2 with an even greater DR coat), Form 3, Form 4, Form 4.2 (a 50:50 mixture of Form 4 and Form 4 with an additional 2 hour DR coat), Form 4.4, (a 50:50 mixture of Form 4 and Form 4 with an increased DR coat), and Form 4.6 (a 50:50 mixture of Form 4 and Form 4 with an even greater DR coat) are shown in the following Tables and in FIGS. 1A-1C:

TABLE EX 5A

Dissolution Table 1

| Time | Percent Released | | | | |
|---|---|---|---|---|---|
| (hr) | Form 1 | Form 2 | Form 2.2 | Form 2.4 | Form 2.6 |
| 1 | 26 | 3.6 | 1.8 | 1.8 | 1.8 |
| 2 | 45 | 12 | 6.0 | 6.0 | 6.0 |
| 4 | 70 | 33 | 22.8 | 16.8 | 16.8 |
| 6 | 84 | 54 | 44 | 33 | 27 |
| 8 | 91 | 69 | 61 | 51 | 40 |
| 10 | 95 | 80 | 74 | 67 | 57 |
| 12 | 97 | 87 | 84 | 78 | 70 |
| 16 | 99 | 95 | 94 | 91 | 87 |

TABLE EX 5B

Dissolution Table 2

| Time | Percent Released | | | | |
|---|---|---|---|---|---|
| (hr) | Form 3 | Form 4 | Form 4.2 | Form 4.4 | Form 4.6 |
| 1 | 0.6 | 0 | 0 | 0 | 0 |
| 2 | 2.3 | 1.0 | 0.0 | 0.0 | 0.0 |
| 4 | 14 | 10 | 5.5 | 5.0 | 5.0 |
| 6 | 41 | 30 | 20 | 16 | 15 |
| 8 | 74 | 50 | 40 | 30 | 26 |
| 10 | 93 | 70 | 60 | 50 | 40 |
| 12 | 99 | 85 | 78 | 68 | 58 |
| 16 | 100 | 100 | 98 | 92 | 85 |

Example 6: Dissolution of Brivaracetam Formulations

The in vitro dissolution profiles for compositions described herein containing brivaracetam are performed according to USP <711> using a rotating basket apparatus 1 with 900 mL 0.1 molar phosphate buffer pH 6.8 at a stirring speed of 100 rpm at 37±0.5° C. The analytical assay of the samples is performed using GC or another method known in the art.

Example 7: Extended Release Formulation Made by Extrusion Spheronization

Extended release compositions designed for nighttime administration are prepared using the components and relative amounts shown in the table below and the manufacturing process described below.

A blend of drug substance, microcrystalline cellulose and lactose monohydrate is prepared and a wet mass is prepared in a high shear granulator using an aqueous solution of povidone. The wet mass is extruded using 1 mm sieve and extruded mass is spheronized using a spheronizer. The pellets are dried in a tray drier to yield core pellets. The core pellets are coated with extended release coating solution in a pan coater. The desired weight of the ER coated pellets containing the unit dose is filled into empty 1 hard gelatin capsule shell (150 mg strength) using an encapsulator equipped with pellet dosing chamber. In vitro dissolution profiles for the compositions are performed using the methods described herein.

TABLE EX 7

AED Capsule Compositions

| | | Combined w/w % of Capsule | |
|---|---|---|---|
| Component | Function | Lacosamide | Brivaracetam |
| Pellet Core | | | |
| Drug substance | Active | 58.40% | 52.87% |
| Microcrystalline cellulose | Diluent | 17.31% | 20.78% |
| Lactose monohydrate | Diluent | 5.70% | 6.84% |
| Povidone | Binder | 0.59% | 0.71% |
| Water | Solvent | 1 | 1 |
| Extended Release Coating | | | |
| Ethyl cellulose | Coating polymer | 14.83% | 15.58% |
| Polyethylene glycol | Pore former | 1.48% | 1.56% |
| Dibutyl sebacate | Plasticizer | 1.69% | 1.76% |
| Ethanol | Solvent | 1 | 1 |

1 Removed upon drying

Example 8: Pharmacokinetic Measurement of the Formulation of Lacosamide ER Compared to IR Lacosamide Objective: The primary objective of the study is to evaluate the pharmacokinetic profile, safety and tolerability of a prototype formulation of ER Lacosamide (as prepared in Examples 1-3), relative to a 100 mg IR Lacosamide tablet (VIMPAT®) given as single doses to healthy adult subjects under fasting conditions.

Study design: This is a Phase 1, randomized, single dose, open-label, two-period, two-treatment crossover, fasting pharmacokinetic study in which single 200 mg doses of lacosamide ER prepared according to Example 1 are compared to single 200 mg doses of marketed lacosamide IR tablets (VIMPAT®).

Methods: Subjects are admitted to the unit for the first period of dosing within 21 days of study screening. There is a 7 day washout between dosing in period 1 and 2. In each dosing period subjects are dosed on the day after checking into the unit and discharged 72 hours post dose. A final follow up end of study is conducted within 14 days of dosing in the second period.

After an overnight fast, the formulation is administered to the subjects with 240 mL of water while they are in a sitting position. Blood samples are collected at 0 (pre-dose), 1, 2, 3, 4, 6, 7, 8, 9, 10, 11, 12, 13, 14, 15, 16, 18, 24, 30, 36, 48, 60, 72 hours following each dose. Plasma samples are assayed for lacosamide by a validated liquid chromatography/tandem mass spectroscopy (LC/MS/MS) method. Pharmacokinetic parameters are calculated using a non-compartmental analysis with WinNonlin software (version 5.3 or higher; Pharsight Corporation).

An analysis of variance (ANOVA) is performed on the natural logarithms of $C_{max}$ and $AUC_{0-\infty}$ determined from the data following a single dose of study drug using linear mixed effects model. The model includes sequence, period, and regimen as fixed effects and subject with sequence as random effect. Ratio of ER to IR for both AUC (relative bioavailability for ER formulation) and $C_{max}$ is calculated. (Adverse events are monitored throughout the study. Vital signs (pulse rate, blood pressure and body temperature), clinical laboratory measures (biochemistry, hematology, and urinalysis) and ECGs are collected at various times during the study.

The PK results from this study demonstrate the ER form provides an increased $T_{max}$ (in the range of 11 to 19 hours vs about 1.5 hours for VIMPAT), a reduced $C_{max}$ on a dose proportionate basis (about 2.5 to 3.5 µg/ml for the ER form versus more than 5 µg/ml for the IR form), and an $AUC_{0-\infty}$ that is bioequivalent to the IR form (i.e. 80-125% of the IR form on an equivalent dose basis).

Example 9: Simulation of ER and IR Lacosamide PK Profiles

Dissolution profiles for immediate release and extended release compositions of lacosamide were used to model plasma concentration profiles with the software package GastroPlus, version 9.0. Physicochemical and Biopharmaceutical properties for lacosamide were first determined using ADMET Predictor v. 7.2. The GastroPlus model with those parameters was then tested against published lacosamide data to verify suitability for estimating plasma profiles for compositions described herein. The release profile for Form 4 and an immediate release form were input into the GastroPlus model and the single dose and multiple dose plasma concentrations were determined. Linear interpolation was used to determine intervening data points to generate plasma profiles with uniform time intervals of 0.1 hours. The plasma concentration curves were then used to determine PK parameters for the compositions, including $C_{max}$, $T_{max}$, $AUC_{0-\infty}$, dC/dt from 0 to 1.4 hours ($T_{max}$ for the IR composition). Multi-dose models were also generated to determine the steady state PK parameters for these compositions.

Figure 2A:
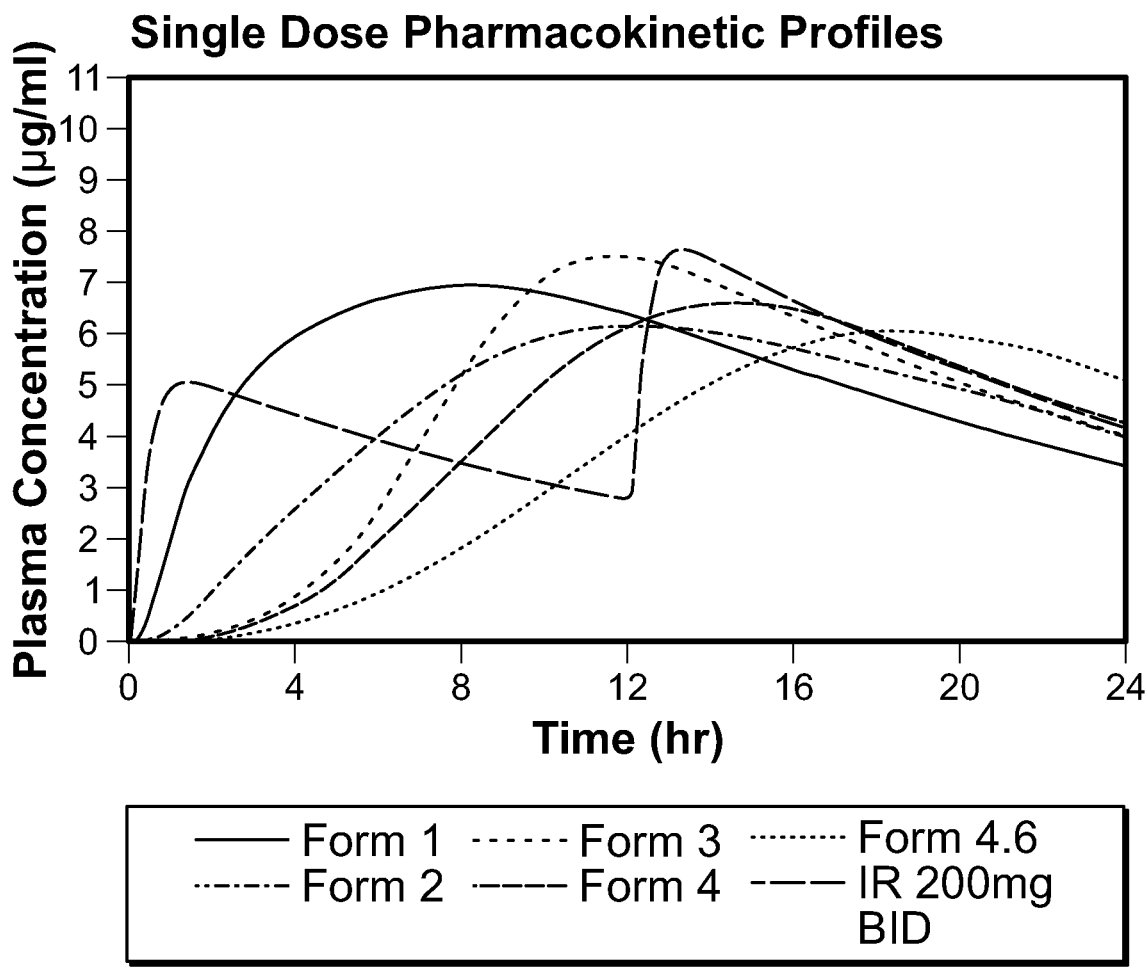
FIG. 2A is a graph depicting the plasma profiles for single dose administration of lacosamide formulations Form 1, Form 2, Form 3, Form 4, Form 4.6, and BID dosing of an IR lacosamide formulation simulated using GastroPlus, version 9.0.
Figure 2B:
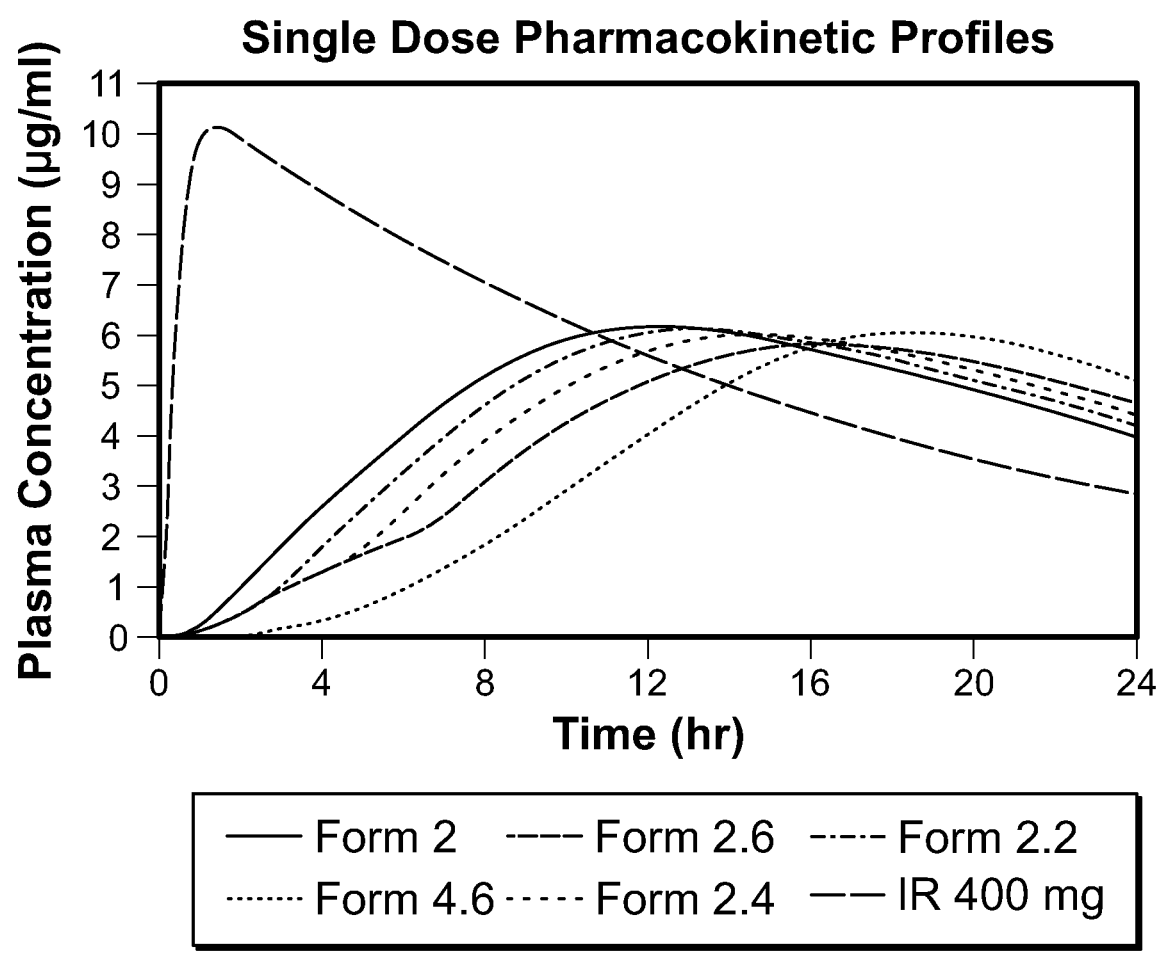
FIG. 2B is a graph depicting the plasma profiles for single dose administration of 400 mg lacosamide in formulations Form 2, Form 2.2, Form 2.4, Form 2.6, Form 4.6, and single dose administration of 400 mg lacosamide in an IR form simulated using GastroPlus, version 9.0.
Figure 2C:
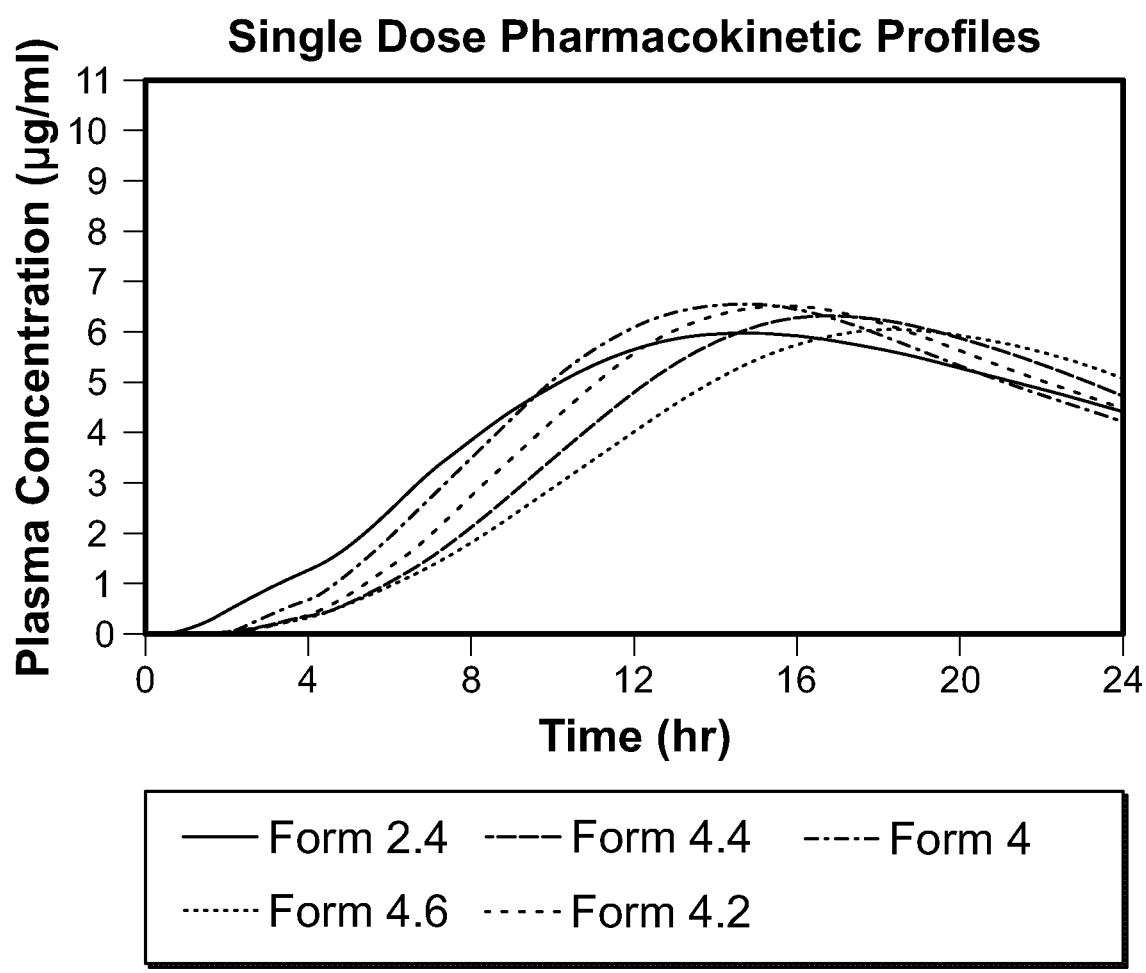
FIG. 2C is a graph depicting the plasma profiles for single dose administration of lacosamide formulations Form 2.4, Form 4, Form 4.2, Form 4.4, and Form 4.6 simulated using GastroPlus, version 9.0.
Figure 3A:
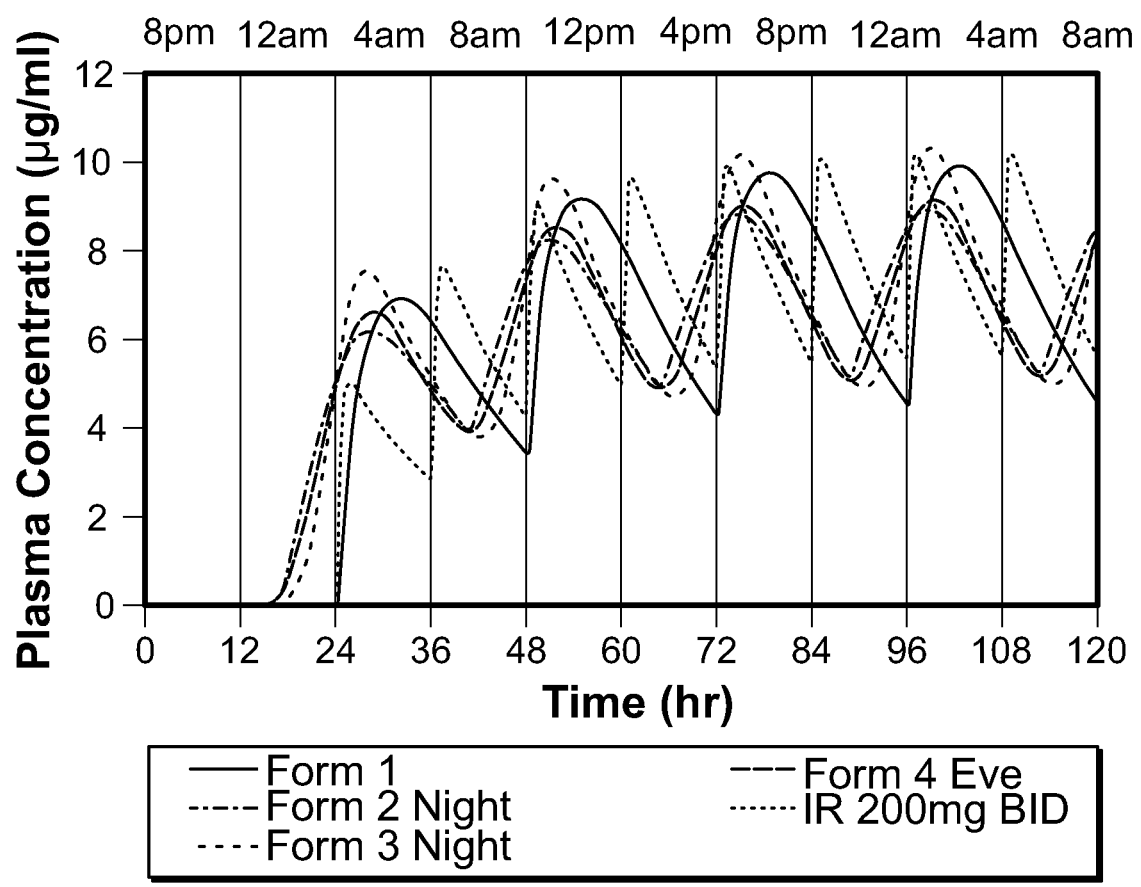
FIG. 3A is a graph shown over the multiple dose time period of 0 to 144 hours showing the steady state plasma profiles for single dose (400 mg) administration of lacosamide formulation Form 1 once daily at 8 am, Form 2 once nightly at 12 am, Form 3 once nightly at 12 am, Form 4 once nightly at 10 pm, Form 4.6 once nightly at 10 pm, and 200 mg BID dosing (8 am and 8 pm) of an IR lacosamide formulation simulated using GastroPlus, version 9.0.
Figure 3B:
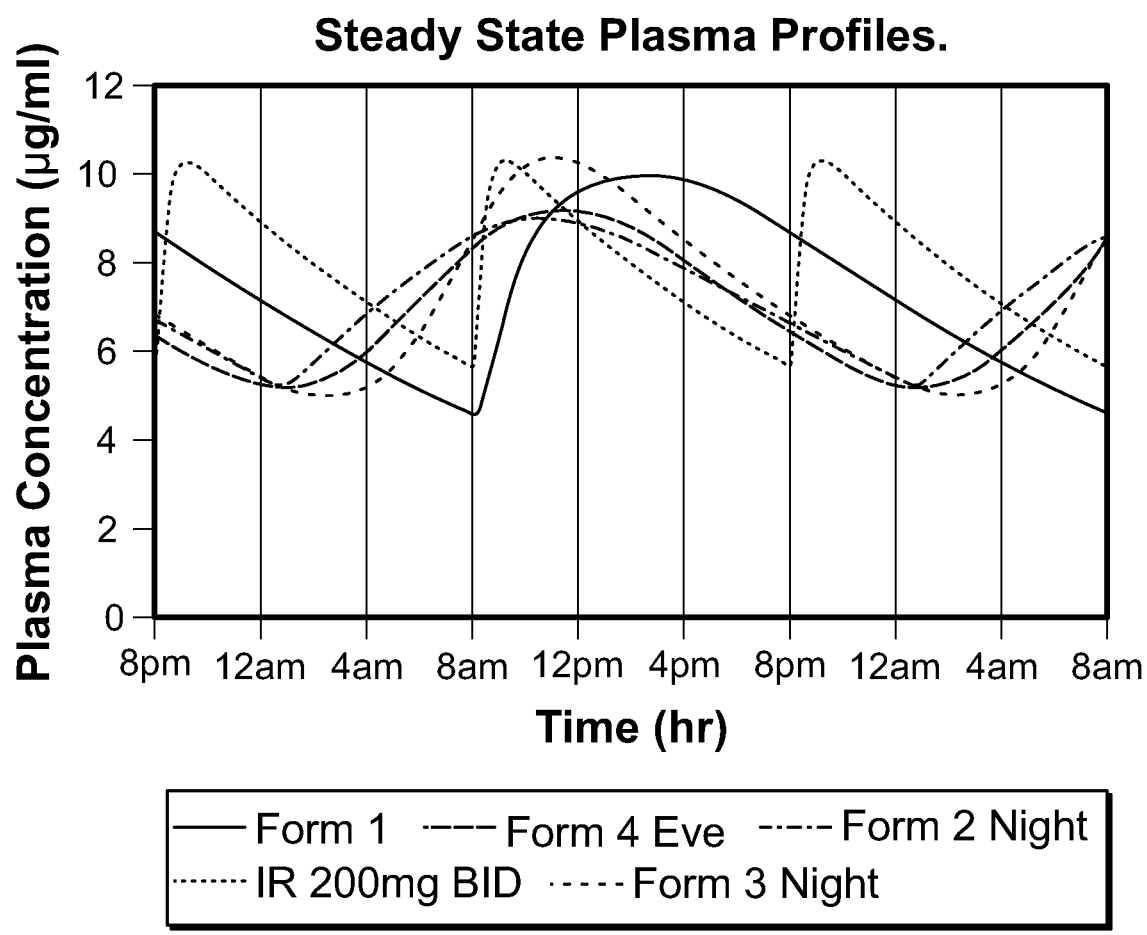
FIG. 3B is the same data as FIG. 3A, limiting the x-axis scale to the 36 hour window beginning at 8 pm on day 5.
Figure 3C:
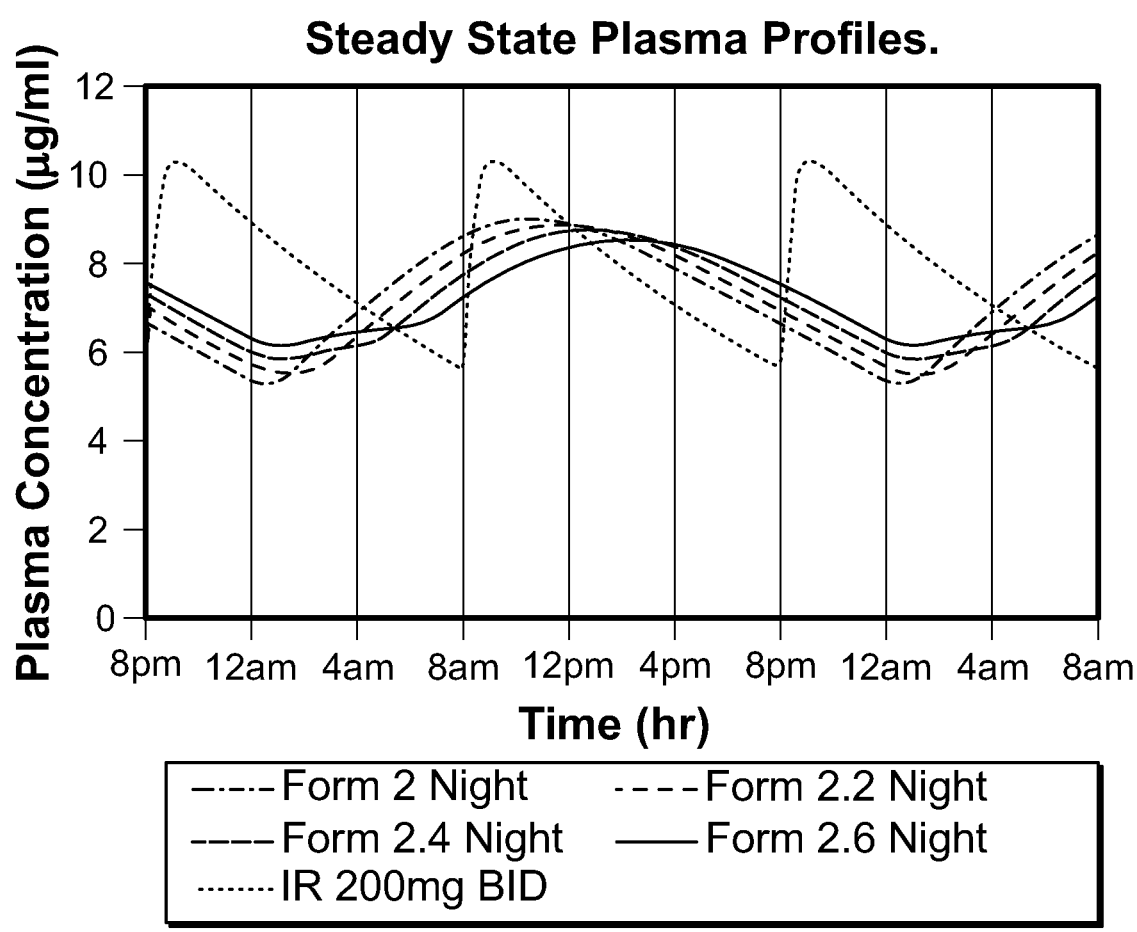
FIG. 3C is a graph depicting the steady state plasma profiles for single dose (400 mg) administration of lacosamide formulations Form 2, Form 2.2, Form 2.4, Form 2.6 each once nightly at 12 am, and 200 mg BID dosing (8 am and 8 pm) of an IR lacosamide formulation simulated using GastroPlus, version 9.0.
Figure 3D:
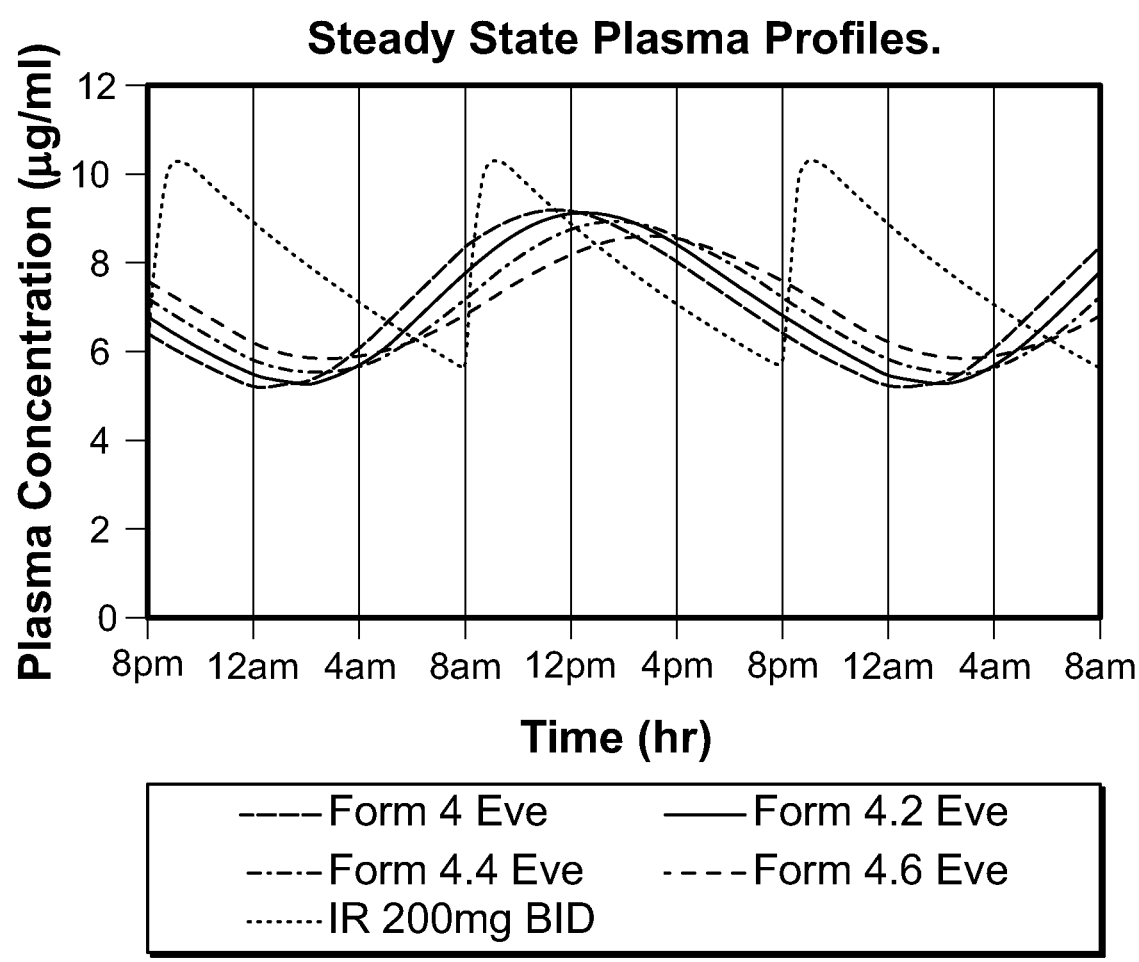
FIG. 3D is a graph depicting the steady state plasma profiles for single dose (400 mg) administration of lacosamide formulations Form 4, Form 4.2, Form 4.4, Form 4.6 each once nightly at 10 pm, and 200 mg BID dosing (8 am and 8 pm) of an IR lacosamide formulation simulated using GastroPlus, version 9.0.

The study results from the simulation of 400 mg Form 4 administered once daily and 200 mg IR administered twice daily (at 12 hour intervals) are provided in the table below and in FIG. 2A. The IR results are based on the first dose (i.e. 200 mg). The Form 4 results were also based on the first dose, however, the dose was 400 mg. Comparison of the dose normalized values for $C_{max}$, AUC and dC/dt show the Form 4 $AUC_{0-\infty}$ is 91% of the IR $AUC_{0-\infty}$, the ER $C_{max}$ is 65% of the IR $C_{max}$, and the dC/dt is 0.6% of the IR dC/dt. The $T_{max}$ of Form 4 is 14.5 hours, while the $T_{max}$ for the IR form is 1.4 hours.

TABLE EX 9

PK Properties of Lacosamide Compositions

|  | Form 4 | IR | Form 4/IR |
|---|---|---|---|
| $C_{max}$ (µg/ml) | 6.6 | 5.1 |  |
| $C_{max}$/mg (µg/ml/mg) | 0.016 | 0.025 | 65% |
| $AUC_{0-\infty}$ (µg*hr/ml) | 172.8 | 94.9 |  |
| $AUC_{0-\infty}$/mg (µg*hr/ml/mg) | 0.432 | 0.475 | 91% |
| dC/dt (µg/ml/hr) | 0.043 | 3.62 |  |
| dC/dt/mg (µg/ml/hr/mg) | 0.00011 | 0.0181 | 0.6% |
| $T_{max}$ (hr) | 14.5 | 1.4 |  |

Example 10: Steady State Plasma Concentrations for Lacosamide

The steady state plasma lacosamide concentrations for the compositions shown in FIGS. 1A-1C were simulated according to the method of Example 9 using GastroPlus, version 9.0. The plasma concentration profiles were indexed to a specific dosing schedules as shown here. The dosing for ER forms was 400 mg once daily. For Form 1, the dosing was simulated at 8 am; for Forms 2, 2.2, 2.4, 2.6, and Form 3, the dosing was simulated once nightly at 12 am; for Forms 4, 4.2, 4.4, and 4.6, the dosing was simulated once nightly at 10 pm. The dosing for the IR form was 200 mg BID at 8 am and 8 pm.

The plasma profiles at steady state are shown in FIGS. 3A, 3B, 3C, and 3D. As illustrated in the Figures, the minimum concentrations for all but Form 1 and the IR form occur during the night between about 12 am and about 4 am; for Form 1, the minimum occurs about 8 am, the time of dosing; and for the IR formulation, the two minimums also occur near the time of dosing, i.e., 8 am and 8 pm. Conversely all of the ER compositions provide a $C_{max,ss}$ between about 10 am and 4 pm (10 to 18 hours after last administration), while the IR formulation provides $C_{max,ss}$ at around 9:30 am and 9:30 pm.

Example 11: Steady State Plasma Profiles with Modified Dosing Regimens

The plasma concentration profile for single dose administration of the IR form was dose adjusted for administration according to the label for VIPAT, then by superposition, the dosing of 100 mg BID for 1 week (starting at 8 am on day 1), followed by dosing of 150 mg BID for 1 week, followed by the maintenance dose of 200 mg BID. The multi dose plasma concentration profiles for Form 4.2 administration and Form 3 as 400 mg QD was plotted as a function of time starting with the first dose at 10 pm and 12 am, respectively, following the day 1 dosing for the IR form.

Figure 4:
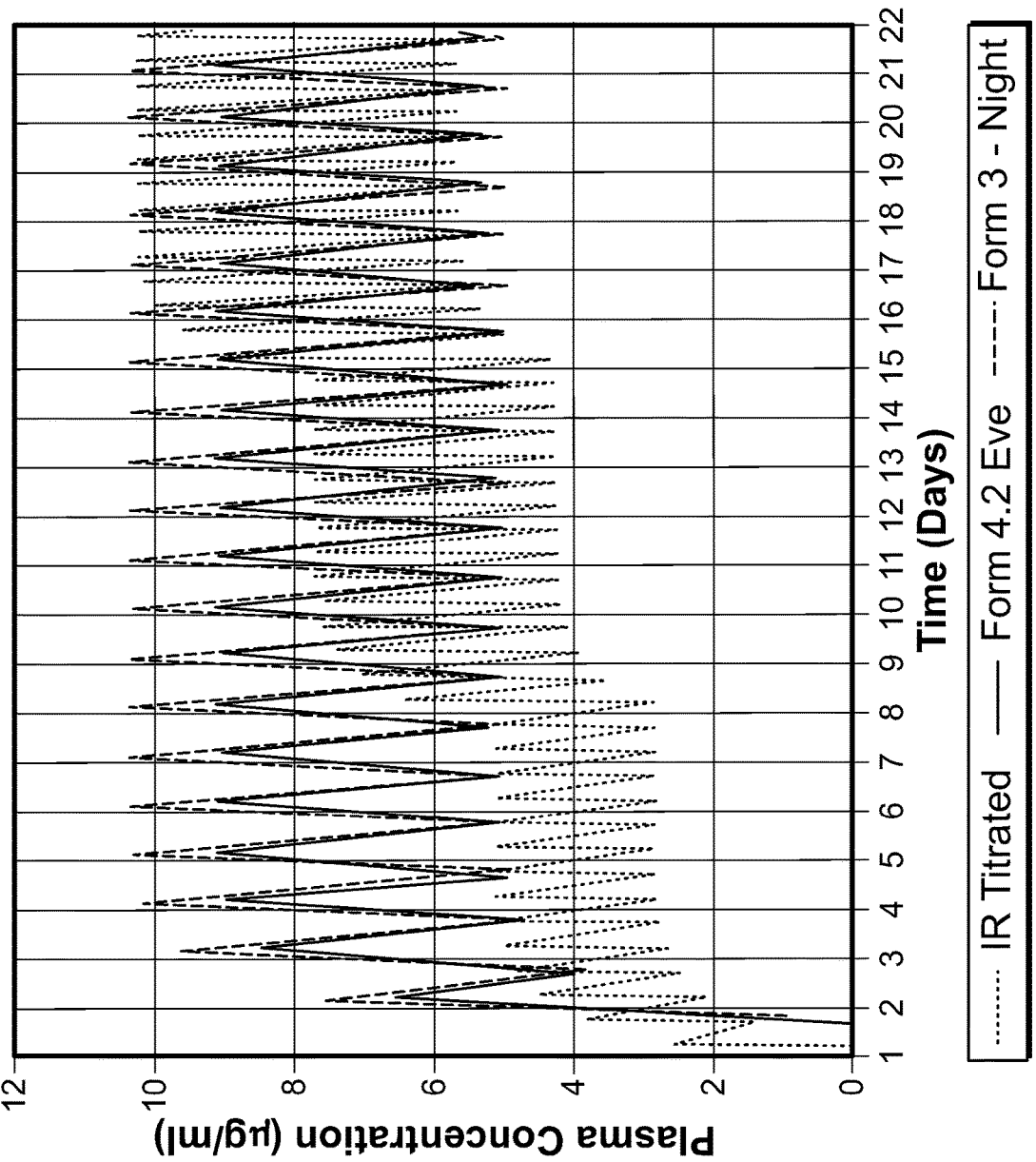
FIG. 4 is a graph depicting the administration of two controlled release lacosamide compositions and an immediate release composition of lacosamide with dose titration.

The results of the simulation are shown in FIG. 4. As can be seen in the figure, the IR administration begins before the controlled release form administration on day 1 and, using the administration protocol from the VIMPAT label, achieves a steady state profile at 200 mg BID about 18 days after initiation of therapy. Conversely, the controlled release forms administered once nightly with no titration, achieved steady state about 4 days after initiation of therapy. Therapeutically effective levels are achieved about 14 days earlier for these controlled release formulation regimens than for the IR regimen.

Example 12: Rotarod Study to Determine the Effects of Lacosamide (LCM) on Motor Coordination in Mice A pharmacokinetic (PK)-pharmacodynamic (PD) study is performed in mice to evaluate the effects of lacosamide on motor coordination using the rotarod test following single intravenous (IV) or oral (PO) doses. The objective of this study is to demonstrate that decreasing the rate of rise of plasma concentration of lacosamide results in a reduction in CNS side effects. PK Phase For the PK phase, male CD-1 mice were assigned to treatment groups according to the study design in Table Ex 12 below. Lacosamide was prepared as a solution in 0.9% saline, at concentrations indicated in Table Ex 12. IV dosing was done via tail vein injection and oral delivery was done with oral gavage tube. Dosing levels by each route are as shown in Table Ex 12.

TABLE EX 12

Study Design for Pharmacokinetic Sampling

| Group | Route | Dose of LCM (mg/kg) | Dose concentration (mg/mL) | Plasma collection times (min) | N per collection time |
|---|---|---|---|---|---|
| 1 | IV | 10 | 2 | 5, 15, 30, 60, 120, 240, 480, 720 | 4 mice/plasma collection time |
| 2 | IV | 30 | 6 | 5, 15, 30, 60, 120, 240, 480, 720 | 4 mice/plasma collection time |
| 3 | PO | 30 | 3 | 5, 15, 30, 60, 120, 240, 480, 720 | 4 mice/plasma collection time |
| 4 | PO | 90 | 9 | 5, 15, 30, 60, 120, 240, 480, 720 | 4 mice/plasma collection time |

Results

The $C_{max}$ of lacosamide after a single 10 mg/kg IV dose was comparable to the $C_{max}$ after a single 30 mg/kg oral dose (~15 μg/mL), while $C_{max}$ values following a single 30 mg/kg IV dose was comparable to those following a 90 mg/kg oral dose (~40 μg/mL). The $T_{max}$ values varied based on the route of administration (<5 to ~15 min by the IV and oral routes, respectively), showing that the $C_{max}$ was reached more slowly in the animals in the PO groups than the IV groups.

PD Phase

The rotarod (Ugo Basile, Germany) is a device that allows for quantitative measurement of motor coordination in rodents. Animals are pre-trained prior to testing on the rotarod.

24 hours prior to the test day, mice are trained to run on the accelerating rotarod for at least 120 s in two consecutive trials. The mice are given up to 12 trials to achieve this performance criterion. Any mice not meeting this criterion are excluded from the test study.

Mice are randomized to treatment groups (vehicle; IV: 3, 10 30 mg/kg; PO: 10, 30, 90 mg/kg). On the day of the test, the animals are dosed with test article and placed on the rotarod 5 minutes post-dosing. The rotarod is accelerated from 0-40 rpm over a 5 minute session, using the built-in function of the equipment. The rotarod test is repeated for each mouse at 15, 30 and 60 minutes post-drug administration. Animals that stay on the rotarod are assigned a run-time of 300 seconds. The time that each animal stays on the rotarod prior to falling is automatically recorded as the animal's fall latency.

The latency to fall time on the rotarod recorded for each animal is reported at each time point post-dose. Latency to fall is averaged (±SEM) across the 10 animals in each treatment group at each time point. Lacosamide groups are compared against vehicle-treated means to determine if there is a significant effect of lacosamide treatment on rotarod performance.

Results

By the same route of administration (IV or PO), an increase in dose results in a corresponding decrease in the latency to fall time on the rotarod, indicative that an increase in dose results in greater CNS impairment. However, at doses that produce equivalent $C_{max}$ by different routes of administration but different $T_{max}$ (e.g. 30 mg/kg IV and 90 mg/kg PO), administration by PO which results in a reduced rate of rise results in greater latency to fall on the rotarod (less impairment) compared to administration by IV.

Example 13: Pharmacokinetic Study of Lacosamide Administered by Continuous Subcutaneous Infusion to Rats for 7 Days The objective of this study is to demonstrate that the PK profile from a standard regimen of 200 mg IR lacosamide BID in humans, along with a novel PK profile of 400 mg ER lacosamide QD, can be replicated in rats using programmable subcutaneous infusion pumps.

Jugular vein cannulated male and female Sprague Dawley rats weighing between 240-260 grams are used for this study. Rats are implanted with programmable infusion pumps (iPRECIO SMP-200).

Simulated IR BID Dosing

Rats are assigned to 2 groups consisting of 4 rats each. Both groups are dosed identically using the same infusion protocol but the blood collection times for each group differ. Animals are allocated into the treatment groups to ensure similar distribution of body weights across all groups (+/− 10% difference in mean body weight between groups). Two different infusion rates are employed over a 12 hour period to achieve a simulated BID profile and the infusion protocol is repeated every 12 hours for 7 days. The solution in the programmable pump is refilled every 3 days. Approximately 0.10 mL blood is collected from each rat via a jugular cannula at the time-points specified in Table Ex 13. The actual plasma collection time are recorded for each animal. The last collection time is the terminal time point for each animal.

TABLE EX 13A

Study Design and Infusion Protocol for Simulated BID dosing

| Group | Number of animals | Dose Period[2] | Dose rate/rat[1] (mg/h/rat) | Concentration in pump (mg/mL) | Pump Flow rate (μL/h) | Plasma Collection Times (hours) |
|---|---|---|---|---|---|---|
| 1 | 4 | 0-2 h | 0.59 | 20 | 29.5 | 1, 4, 8, 14, 20, 84, 144, 158 |
|   |   | 2-12 h | 0.12 | 20 | 6 | |
| 2 | 4 | 0-2 h | 0.59 | 20 | 29.5 | 2, 6, 12, 18, 24, 98, 156, 168 |
|   |   | 2-12 h | 0.12 | 20 | 6 | |

[1]Lacosamide dose estimates are based on average animal body weight of 250 g
[2]Pump infusion protocol is repeated every 12 hours for a total of 7 days Simulated ER QD Dosing Rats are assigned to three groups consisting of 4 rats each. All three groups are dosed identically using the same infusion protocol but blood collection times for each group will be different. The iPRECIO pump is programmed to provide two different infusion rates over a 24 hour period to achieve a simulated QD profile and the infusion protocol will be repeated every 24 hours for 7 days. The pump is refilled every 3 days. Animals are allocated into the treatment groups to ensure similar distribution of body weights across both groups (+/−10% difference in mean body weight between groups). Approximately 0.10 mL blood is collected from each rat via a jugular cannula at the time-points specified in Table Ex 13B. The actual plasma collection time is recorded for each animal. The last collection time point is the terminal point for each animal.

TABLE EX 13B

Study Design and Infusion Protocol for Simulated QD dosing

| Group | Number of animals | Dose Period[2] | Dose rate/rat[1] (mg/h/rat) | Concentration in pump (mg/mL) | Pump Flow rate (µL/h) | Plasma Collection Times (hours) |
|---|---|---|---|---|---|---|
| 1 | 4 | 0-12 h | 0.30 | 20 | 15 | 3, 9, 15, 21, 30, |
|   |   | 12-24 h | 0.15 | 20 | 7.5 | 42, 96, 156 |
| 2 | 4 | 0-12 h | 0.30 | 20 | 15 | 6, 12, 18, 24, 36, |
|   |   | 12-24 h | 0.15 | 20 | 7.5 | 48, 144, 168 |

[1]Lacosamide dose estimates are based on average animal body weight of 250 g
[2]Pump infusion protocol is repeated every 12 hours for a total of 7 days The following parameters are calculated:
Individual and mean plasma concentrations over time (ng/mL)
The plasma lacosamide concentration at each time point tabulated for each animal by group, and the mean (and SD) concentration for each group
The mean (and SD) concentrations for each group plotted as a function of time.
Descriptive PK parameters, such as but not limited to, $AUC_{0-24h}$ (ng×h/mL), $AUC_{0-24}$ (i.e. $AUC,ss$; ng×h/mL), $C_{ave,ss}$ (ng/mL), $C_{min,ss}$ (m/mL) and $C_{max,ss}$ (m/mL) are calculated for individual animals and the mean (and SD) is tabulated by group.

Results

The PK parameters ($C_{max}$, $T_{max}$, $T_{1/2}$, AUC) of 200 mg IR lacosamide BID and 400 mg ER lacosamide QD in humans can be replicated in rats using programmable subcutaneous infusion pumps.

Example 14. Comparison of the Effect of Lacosamide Administered as an IR or an ER Infusion Profile on Motor Coordination and CNS Behavioral Effects in Rats The primary objective of this study is compare the CNS side effects of lacosamide when delivered as a subcutaneous infusion in rats to simulate a once-a day extended release (ER) dosing profile or a twice a day (BID) immediate release (IR) dosing profile in humans. The example investigates reducing the rate of rise of plasma concentrations with the ER profile compared to the IR profile results in reduced CNS impairment. CNS side effects are measured as an impairment of motor coordination in rodents using the rotarod. Performance of rodents in a battery of neurobehavioral tests conducted during the infusion period are used as secondary endpoints as measures of CNS impairment.

Groups of rats are implanted subcutaneously with programmable pumps that administer lacosamide as an infusion for 7 days. The infusion protocols are designed to produce pharmacokinetic profiles of lacosamide similar to that of IR lacosamide administered twice-a-day (BID) to humans (IR profile) or an extended release profile administered once-a-day (QD) to humans (ER profile) at varying doses administered as IR BID or ER QD.

The 400 mg/day ER and IR (BID) doses in humans are predicted to yield steady-state plasma $C_{max}$ and $C_{min}$ of 10.2-11.2 µg/mL and 5.1-7.1 µg/mL. In this study, dosing for rats designed to achieve these plasma levels is referred to as 400 mg/day human equivalent dose ("HED"). For the 600 mg/day HED (300 mg BID dose) and 800 mg/day HED (400 mg BID dose) the targeted $C_{max}$ values to be achieved are 14.5 µg/mL and 18.4 µg/mL, respectively.

Rats are pre-trained on the rotarod prior to testing and assigned to groups based on their body weights. Groups of rats are implanted with pumps and tested on the rotarod prior to initiation of lacosamide infusion, and at time points that correspond to the $C_{max}$, $C_{min}$ during the initial infusion phase and at steady state.

Following the period of acclimation, rats are surgically implanted with subcutaneous programmable pumps (iPRECIO), per the manufacturer's instructions. Prior to implantation, pumps are pre-programmed and filled with sterile 0.9% saline according to the manufacturer's instructions. Implantation is done under anesthesia by using aseptic techniques.

Three days following pump implantation surgery, rats are pre-trained on the rotarod and assigned to treatment groups based on their body weights.

Infusion of lacosamide commences on day four post-pump implantation surgery. Baseline measurements are made on the rotarod on Day 4. Immediately thereafter, saline in the iPRECIO pumps is withdrawn and the pump is refilled with lacosamide solution (25 mg/mL in 0.9% saline). Pumps are refilled during the 7 day period as necessary, through the access port of the iPRECIO pump.

Twenty four hours prior to the first test day (on day 3 post-pump implantation), rats are trained to run on the accelerating rotarod for at least 120 s in two consecutive trials. The rats are given up to 12 trials to achieve this performance criterion. Any rats not meeting this criterion are excluded from the test study. Once rats achieve this criterion, they are considered fully trained and returned to their home cage. The acceleration on the rotarod is the same as that used during test day (0-40 rpm over a 5 mins).

On the test day at the specified time point, rats are placed on the rotarod and the rotarod is accelerated from 0-40 rpm over a 5 minute session, using the built-in function of the equipment. Each rat is run only once at each time point. A rat that has been incorrectly placed on the rotarod and falls off in less than 5 seconds may be re-run at the discretion of the experimenter, who is blinded to the identity of the treatment groups. Animals that stay on the rotarod for the entire session are assigned a run-time of 300 seconds. The time that each animal stays on the rotarod prior to falling is automatically recorded as the animal's fall latency.

A series of additional tests are conducted to characterize the CNS adverse events for the IR and ER profiles. These include neurobehavioral tests to assess an assortment of cognitive and motor function.

Results

By a given infusion protocol, time spent on the rotarod can decrease in a dose-dependent manner, such that the impairment produced by the 800 mg/day HED is greater than that produced at the 400 mg/day HED when comparing data at $C_{max}$.

Surprisingly, for a given dose level, comparison of time spent on the rotarod for rats treated with the IR versus ER infusion protocol at $C_{max}$ show that rats in the IR profile have a significantly reduced time spent on the rotarod (i.e. greater impairment) compared to those in the ER group. These results show that at similar plasma $C_{max}$ concentrations, slowing the rate of rise of the plasma lacosamide concentration via an ER profile results in a significantly reduced impairment on the rotarod.

Similar results are observed with other secondary endpoints tested. Overall, when assessed by multiple measures, the results demonstrate a consistent benefit in reducing CNS impairment by reducing the rate of rise of plasma concentrations with the ER profile compared to the IR profile.

Example 15. Comparison of the Effect of Lacosamide Administered as an IR or an ER Profile on Motor Coordination in Rats The primary objective of this study was to compare the CNS side effects of lacosamide when delivered as a continuous infusion to rats to simulate an extended release (ER) plasma profile or as a bolus to simulate an immediate release (IR) plasma profile. It is hypothesized that reducing the rate of rise of plasma concentrations with the ER profile compared to the IR profile results in reduced CNS impairment. CNS side effects were measured as an impairment of motor coordination in rodents using the rotarod. The rotarod (Ugo Basile, Italy) is a device that allows for quantitative measurement of motor coordination in rodents. Animals experiencing CNS side effects such as dizziness would fall off the rotarod faster than normal animals.

Rats were pre-trained on the rotarod prior to testing and animals that did not meet the training criterion (at least 120 seconds time on rotarod in two consecutive trials) were excluded from the study. An acceleration protocol was used for training and test sessions, wherein the rotarod was accelerated from 0-40 rpm over a 5 minute session. All rats were then surgically implanted subcutaneously with programmable pumps (iPRECIO, Durect Corporation, Cupertino, Calif.), per the manufacturer's instructions, under anesthesia and using aseptic techniques.

Three days following pump implantation surgery, all rats were tested on the rotarod to obtain baseline performance values. Rats were assigned to treatment groups such that the mean time spent on the rotarod was similar for each group. Four groups of rats were utilized in this study, with 8-10 rats per group:

| Group | Profile | Treatment | Route/Method |
|---|---|---|---|
| 1 | ER | Vehicle | IP via programmable pump |
| 2 | ER | Lacosamide | IP via programmable pump |
| 3 | IR | Vehicle | IP via bolus injection |
| 4 | IR | Lacosamide | IP via bolus injection |

To reproduce the plasma profile of ER lacosamide (ER profile, group 2), rats were administered lacosamide as a continuous infusion into the intraperitoneal (IP) space. The infusion protocol was designed to produce a linear rise of lacosamide plasma concentration with a $T_{max}$ of 18 hours. The total pump infusion duration was 18 hours. Control animals (group 1) were infused with vehicle (20% N-methyl-2-pyrrolidone, NMP) using the same infusion protocol. To reproduce the immediate release (IR) profile (group 4), rats were implanted with programmable pumps containing vehicle (20% NMP) and were given an IP bolus of lacosamide with an expected $T_{max}$ of 0.5 hours. Control animals (group 3) were implanted with pumps containing vehicle and were given an IP bolus of vehicle. The slope of the rate of rise of plasma concentration of the ER profile was designed to be ≤10% of the slope of the IR profile, while keeping the target $C_{max}$ for both the ER and IR profiles similar (~20 μg/mL).

Immediately following the 18 hour pump infusion for the ER groups, or 1 hour after IP injection for the IR groups, rats were placed on the rotarod and the rotarod was accelerated from 0-40 rpm over a 5 minute session, using the built-in function of the equipment. Animals that stayed on the rotarod for the entire session were assigned a run-time of 300 seconds. The time that each animal stayed on the rotarod prior to falling was automatically recorded. Immediately after the rotarod test, the rats were euthanized and blood was collected to determine the lacosamide plasma concentration.

In order to fully elucidate the plasma concentration-time profile of lacosamide administered by the ER and IR protocols, two groups of PK satellite rats (n=4 each) were administered lacosamide using identical protocols to groups 2 and 4 above to reproduce the ER and IR profiles, respectively. Blood was collected at varying time points and the plasma lacosamide concentrations were determined. No rotarod testing was performed on the PK satellite rats.

Results

Pharmacokinetic analysis of the PK satellite groups demonstrated that the ER infusion protocol resulted in a slow and linear rate of rise of plasma lacosamide concentration with a median $T_{max}$ of 15 hours, whereas the IP bolus resulted in a rapid rise in plasma lacosamide concentration with a median $T_{max}$ of 0.75 hours. The $C_{max}$ for the ER and IR profiles in the PK satellite rats were similar (19 and 22 μg/mL, respectively). The ER profile resulted in a 98% reduction in the rate of the rise (slope) of lacosamide plasma concentration compared to IR (1.4 μg/mL/h for the ER profile compared to 62 μg/mL/h for the IR profile, Table X). While the ER and IR profiles produced similar $C_{max}$ values, due to the 18 hour infusion time required to produce the ER profile, rats administered lacosamide by the ER profile received ~6-fold higher dose and had 12-fold higher exposure ($AUC_{0-18h}$) compared to rats administered lacosamide by the IR profile (Table 15).

TABLE 15

Lacosamide pharmacokinetic parameters from PK satellite rats

| Parameter | Group 2 (ER) | Group 4 (IR)* | ER/IR Ratio |
|---|---|---|---|
| $C_{max}$ (µg/ml) | 19 | 22 | 0.9 |
| Slope (µg/ml/hr)* | 1.4 | 62 | 0.022 |
| Dose (mg/kg) | 122 | 19 | 6.4 |
| $AUC_{0-18}$ (µg*hr/ml)** | 217 | 18 | 12 |

*Slope calculated from initiation of drug administration
**AUC calculated based on 18 hour infusion for ER profile To confirm that plasma concentrations were similar between the rats treated with lacosamide by the ER and IR profile and tested on the rotarod (groups 2 and 4, respectively), plasma lacosamide concentrations were determined for these groups subsequent to rotarod testing. Analysis of the plasma taken immediately after rotarod testing demonstrated that lacosamide levels were similar for group 2 (ER profile) and group 4 (IR profile), approximately 19 µg/mL for both groups, and also similar to lacosamide levels in the PK satellite rats (Table 15.

Figure 9:
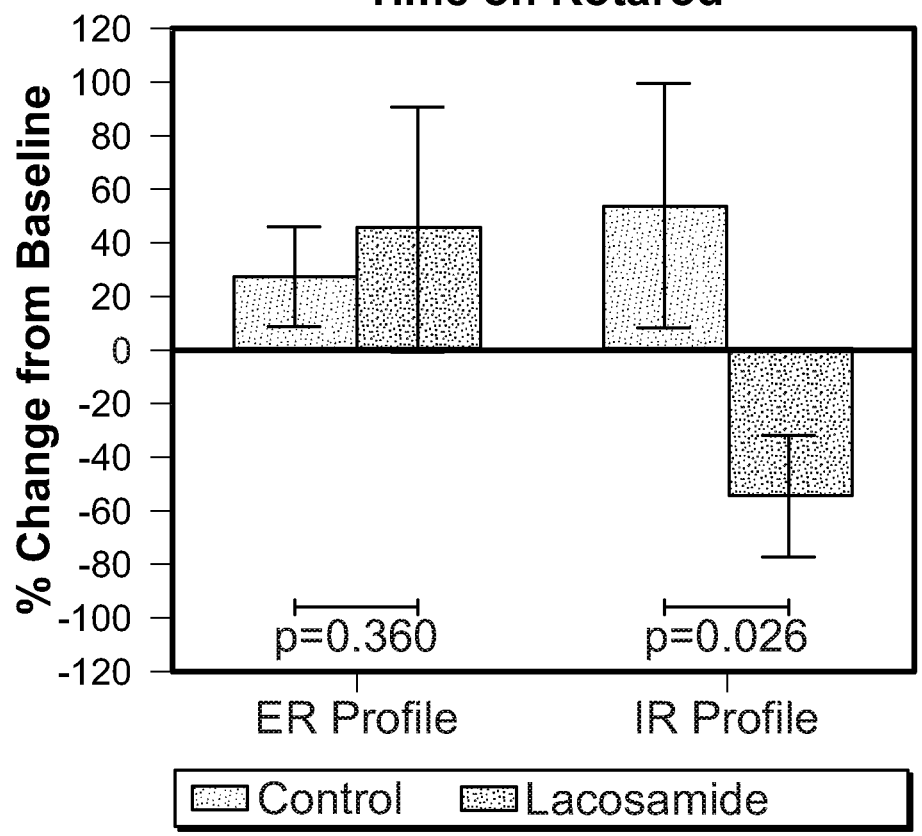
FIG. 9 is a chart depicting the effect of the lacosamide dosing regimen on the performance of the test animals on the rotarod.

Surprisingly, when dosed to achieve the same $C_{max}$, comparison of time spent on the rotarod showed that rats dosed with the IR profile had greater impairment when compared to vehicle controls than those dosed with the ER profile. Specifically, when compared to the baseline rotarod values, rats treated with lacosamide using the ER profile (group 2) showed an increase in time on the rotarod of 45% after drug treatment, compared to a 27% increase in rotarod values for vehicle treated rats (group 1), see FIG. 9. The percent change from baseline in time on the rotarod was not statistically different (p>0.05) between the lacosamide ER group (group 2) and the vehicle ER group (group 1). In contrast, rats administered an IP bolus of lacosamide to produce the IR profile (group 4) showed a 55% reduction in time on the rotarod from baseline values, whereas the matched vehicle controls (group 3) showed a 54% increase. For the IR groups, the difference in percent change from baseline between the lacosamide treated (group 4) and vehicle (group 3) groups was statistically significant (p=0.026).

These results shows that at similar plasma $C_{max}$ concentrations, slowing the rate of rise of the plasma lacosamide concentration via an ER profile results in a significantly reduced impairment on the rotarod. Furthermore, these results demonstrate that, by reducing the rate of rise, it is possible to administer a higher dose of lacosamide and provide greater exposure without inducing significant impairment.

Example 16. Comparison of the Effect of Brivaracetam Administered as an IR or an ER Profile on Motor Coordination in Rats The primary objective of this study is to compare the CNS side effects of brivaracetam when delivered as a continuous infusion to rats to simulate an extended release (ER) plasma profile or as a bolus to simulate an immediate release (IR) plasma profile. It is hypothesized that reducing the rate of rise of plasma concentrations with the ER profile compared to the IR profile results in reduced CNS impairment. CNS side effects are measured as an impairment of motor coordination in rodents using the rotarod. The rotarod (Ugo Basile, Italy) is a device that allows for quantitative measurement of motor coordination in rodents. Animals experiencing CNS side effects such as dizziness would fall off the rotarod faster than normal animals.

Rats are pre-trained on the rotarod prior to testing and animals that did not meet the training criterion (at least 120 seconds time on rotarod in two consecutive trials) are excluded from the study. An acceleration protocol is used for training and test sessions, wherein the rotarod is accelerated from 0-40 rpm over a 5 minute session. All rats are then surgically implanted subcutaneously with programmable pumps (iPRECIO, Durect Corporation, Cupertino, Calif.), per the manufacturer's instructions, under anesthesia and using aseptic techniques.

Three days following pump implantation surgery, all rats are tested on the rotarod to obtain baseline performance values. Rats are assigned to treatment groups such that the mean time spent on the rotarod was similar for each group. Four groups of rats are utilized in this study, with 8-10 rats per group:

| Group | Profile | Treatment | Route/Method |
|---|---|---|---|
| 1 | ER | Vehicle | IP via programmable pump |
| 2 | ER | Brivaracetam | IP via programmable pump |
| 3 | IR | Vehicle | IP via bolus injection |
| 4 | IR | Brivaracetam | IP via bolus injection |

To reproduce the plasma profile of ER brivaracetam (ER profile, group 2), rats are administered brivaracetam as a continuous infusion into the intraperitoneal (IP) space. The infusion protocol is designed to produce a linear rise of brivaracetam plasma concentration with a $T_{max}$ of >10 hours. Control animals (group 1) are infused with vehicle using the same infusion protocol. To reproduce the immediate release (IR) profile (group 4), rats are implanted with programmable pumps containing vehicle and are given an IP bolus of brivaracetam that results in a $T_{max}$ of <1 hour. Control animals (group 3) were implanted with pumps containing vehicle and were given an IP bolus of vehicle. The slope of the rate of rise of plasma concentration of the ER profile is designed to be ≤10% of the slope of the IR profile, while keeping the target $C_{max}$ for both the ER and IR profiles similar.

Approximately 30 minutes following the $T_{max}$ for the ER or IR profile, rats are placed on the rotarod and the rotarod is accelerated from 0-40 rpm over a 5 minute session, using the built-in function of the equipment. Animals that stay on the rotarod for the entire session are assigned a run-time of 300 seconds. The time that each animal stays on the rotarod prior to falling is automatically recorded. Immediately after the rotarod test, the rats are euthanized and blood is collected to determine the brivaracetam plasma concentration.

In order to fully elucidate the plasma concentration-time profile of brivaracetam administered by the ER and IR protocols, two groups of PK satellite rats are administered brivaracetam using identical protocols to groups 2 and 4 above to reproduce the ER and IR profiles, respectively. Blood is collected at varying time points and the plasma brivaracetam concentrations are determined. No rotarod testing is performed on the PK satellite rats.

Results

Pharmacokinetic analysis of the PK satellite groups demonstrated that the ER infusion protocol results in a slow and linear rate of rise of plasma brivaracetam concentration which is <10% of the rate of rise of the IR profile. The $C_{max}$ for the ER and IR profiles in the PK satellite rats are similar.

When dosed to achieve the same $C_{max}$, comparison of time spent on the rotarod shows greater impairment for rats dosed with the IR profile than those dosed with the ER profile (when each are compared to vehicle controls). Specifically, in rats treated using the ER profile, the change from baseline in time on the rotarod is not different between brivaracetam treated and vehicle animals. In contrast, rats administered an IP bolus of brivaracetam to produce the IR profile have greater reduction in time on the rotarod than matched vehicle controls.

These results show that at similar plasma $C_{max}$ concentrations, slowing the rate of rise of the plasma brivaracetam concentration via an ER profile results in a significantly reduced impairment on the rotarod. Furthermore, these results demonstrate that, by reducing the rate of rise, it is possible to administer a higher dose of brivaracetam and provide greater exposure without inducing significant impairment.

Example 17: Lacosamide Coated Pellet Formulations

Lacosamide extended release coated pellet compositions, Formulations A, B, C, D, were prepared using the components and relative amounts shown in the table below. For each composition, the drug coating suspension was prepared by combining the active pharmaceutical ingredient with Hypromellose USP in purified water. This suspension was applied onto microcrystalline cellulose spheres in a Wurster fluidized bed processor to provide immediate release cores shown in the table below. An extended release coating solution was prepared by dissolving ethyl cellulose, Hypromellose USP, and diethyl phthalate in isopropyl alcohol and purified water. The extended release coating was then applied to the immediate release cores in a Wurster fluidized bed processor to providing extended release pellets described in the table below. For Formulations B, C, and D, an additional delayed release coating was added; the delayed release coating suspensions were prepared by combining the methylacrylic acid and methyl methacrylate copolymer(s) with triethyl citrate, talc, isopropyl alcohol and purified water. These coating suspensions were then applied to the extended release coated pellets in a Wurster fluidized bed processor to the levels indicated in the table below. The coated pellets were subsequently machine encapsulated into size 00 hard gelatin capsules at a strength of 200 mg lacosamide

TABLE 17

Compositions of Lacosamide MR Capsules, 200 mg, Formulation A-D

| Component | Functionality | A Amount per unit (mg/capsule) | B Amount per unit (mg/capsule) | C Amount per unit (mg/capsule) | D Amount per unit (mg/capsule) |
|---|---|---|---|---|---|
| Immediate-release core | | | | | |
| Lacosamide | Active Pharmaceutical Ingredient | 200.00 | 200.00 | 200.00 | 200.00 |
| Hypromellose, USP | Binder | 50.01 | 50.01 | 50.01 | 50.01 |
| Microcrystalline Cellulose Spheres, NF | Inert spherical core | 48.58 | 48.58 | 48.58 | 48.58 |
| Purified Water, USP[1] | Coating solvent | — | — | — | — |
| Extended-release membrane | | | | | |
| Ethylcellulose, NF | Rate-controlling polymer | 25.97 | 25.95 | 20.76 | 31.14 |
| Hypromellose, USP | Pore former | 6.48 | 6.49 | 5.20 | 7.79 |
| Diethyl Phthalate, NF | Plasticizer | 4.87 | 4.88 | 3.90 | 5.85 |
| Purified Water, USP[1] | Coating solvent | — | — | — | — |
| Isopropyl Alcohol, USP[1] | Coating solvent | — | — | — | — |
| Delayed-release membrane | | | | | |
| Methacrylic Acid and Methyl Methacrylate Copolymer (1:1), NF | Rate-controlling polymer | — | 0.00 | 2.81 | 0.00 |
| Methacrylic Acid and Methyl Methacrylate Copolymer (1:2), NF | Rate-controlling polymer | — | 25.84 | 22.45 | 26.41 |
| Triethyl Citrate, NF | Plasticizer | — | 2.59 | 2.53 | 2.64 |
| Talc, USP | Glidant | — | 5.17 | 5.06 | 5.29 |
| Isopropyl Alcohol, USP[1] | Coating solvent | — | — | — | — |
| Acetone, USP[1] | Coating solvent | — | — | — | — |
| Purified Water, USP[1] | Coating solvent | — | — | — | — |
| TOTAL | | 335.92 | 369.51 | 361.30 | 377.72 |

[1]Removed during process

Example 18: Dissolution Profiles of Lacosamide Compositions

Figure 5:
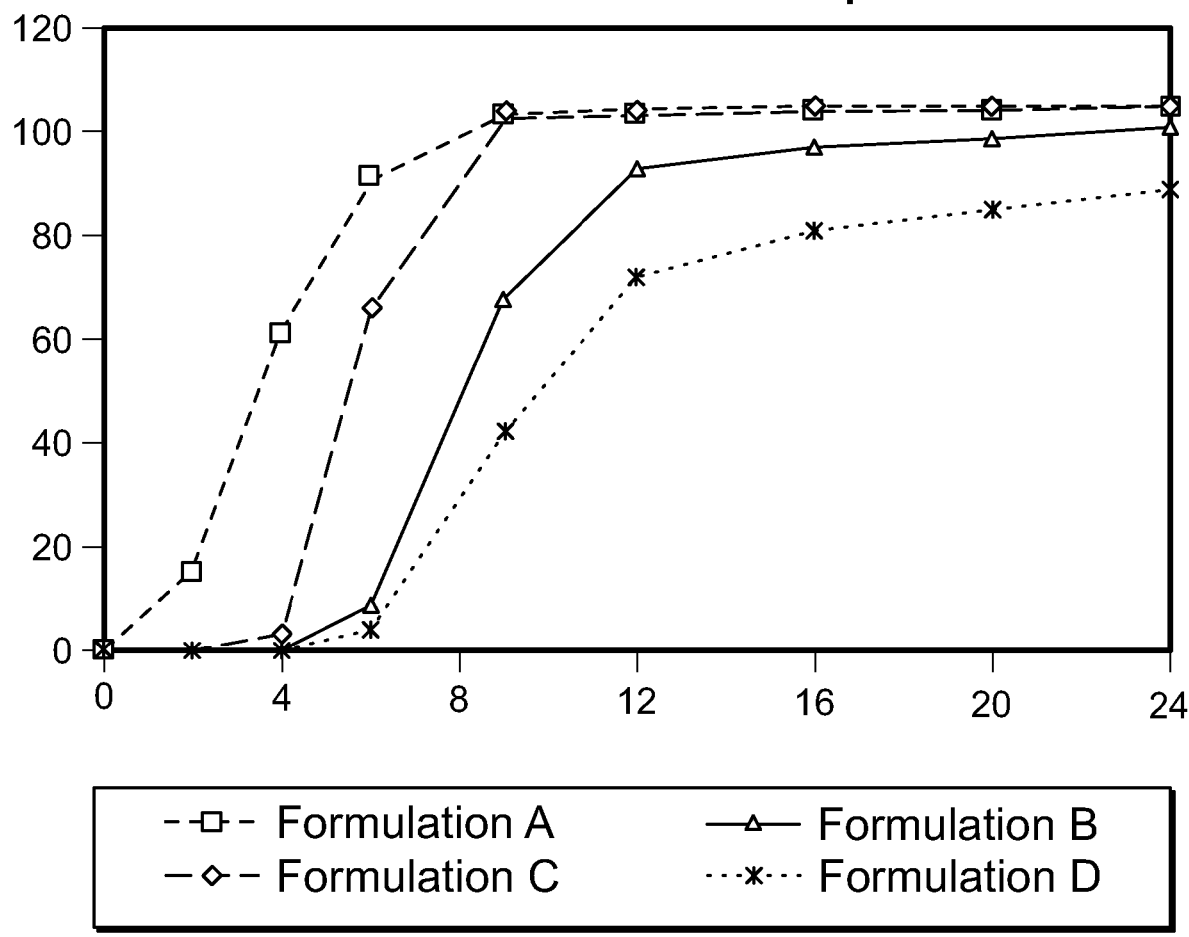
FIG. 5 is a graph depicting the dissolution profiles of Example 18.

The dissolution profiles for the lacosamide formulations prepared according to Example 17 above were determined as described in USP method <711> of the US Pharmacopoeia (edition 33 and chapter 2.9.3 of the Pharmacopoeia European (edition 6.8). Briefly, a rotating basket apparatus as described in the aforementioned references was used with 900 mL of dissolution media at 37.0±0.5° C. at a stirring speed of 100 rpm to determine the in vitro release of the lacosamide. Initially, the dissolution media was simulated gastric fluid (pH 1.2); after two hours at pH 1.2, the media was changed to simulated intestinal fluid (pH 6.8); after four hours at pH 6.8, the media was changed to phosphate buffer (pH 7.5) for the final 18 hours. Samples were taken at the time points shown in the table below and the amount of lacosamide released was determined by UV spectrometric detection. The mean dissolution percentages for each formulation at the specified times are provided in the table below and in FIG. 5.

TABLE 18

Dissolution profiles for Lacosamide Compositions

| Time (hr) | Formulation A | Formulation B | Formulation C | Formulation D |
|---|---|---|---|---|
| 0 | 0 | 0 | 0 | 0 |
| 2 | 15 | 0 | 0 | 0 |
| 4 | 61 | 0 | 3 | 0 |
| 6 | 91 | 9 | 66 | 4 |
| 9 | 103 | 68 | 104 | 42 |
| 12 | 103 | 93 | 104 | 72 |
| 16 | 104 | 97 | 105 | 81 |
| 20 | 104 | 99 | 105 | 85 |
| 24 | 105 | 101 | 105 | 89 |

Example 19: Simulation of Lacosamide Plasma Concentration Profiles

Figure 6:
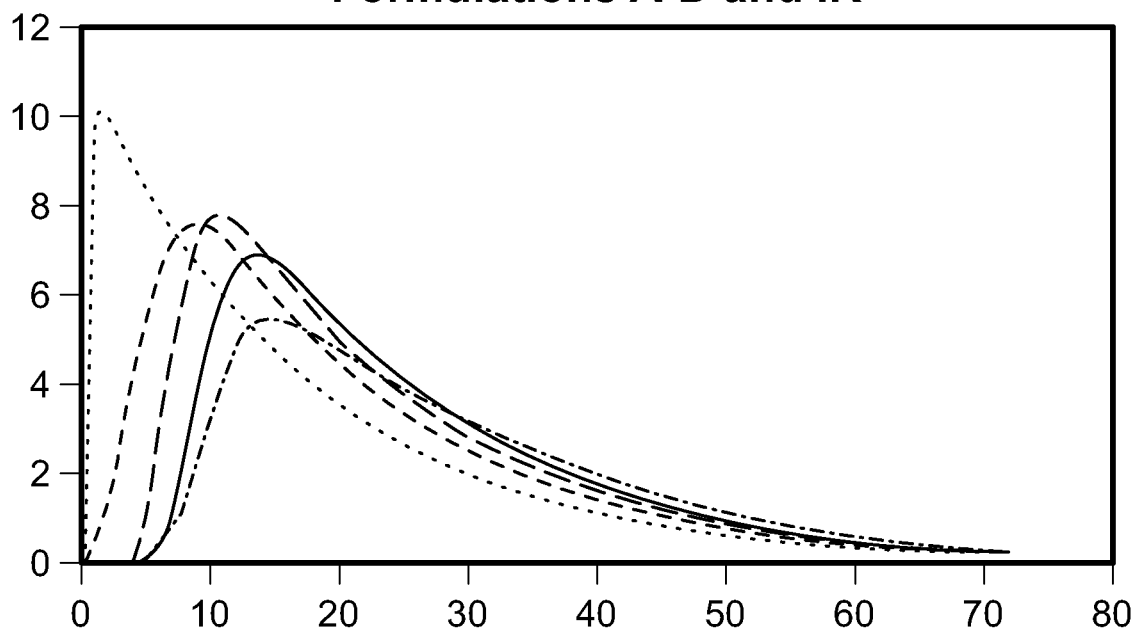
FIG. 6 is a graph depicting the plasma concentration profiles of the Example 19.
Figure 7A:
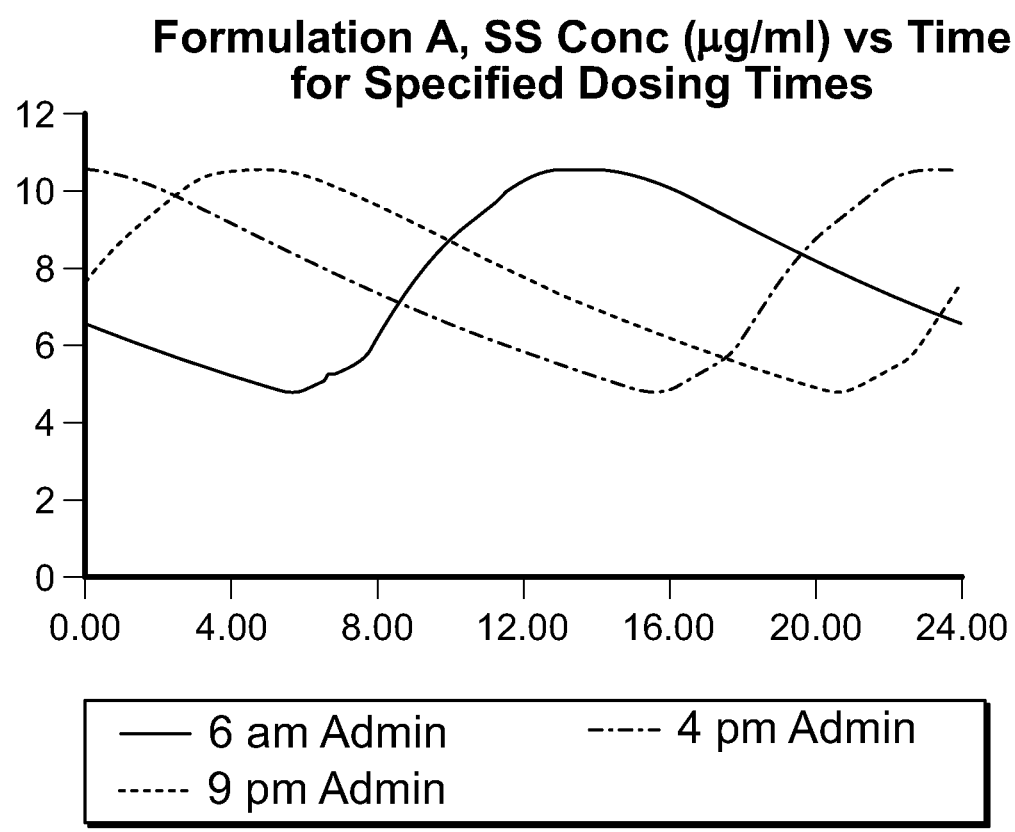
FIG. 7A is a graph depicting steady state profiles of Formulation A administered at different times.
Figure 7B:
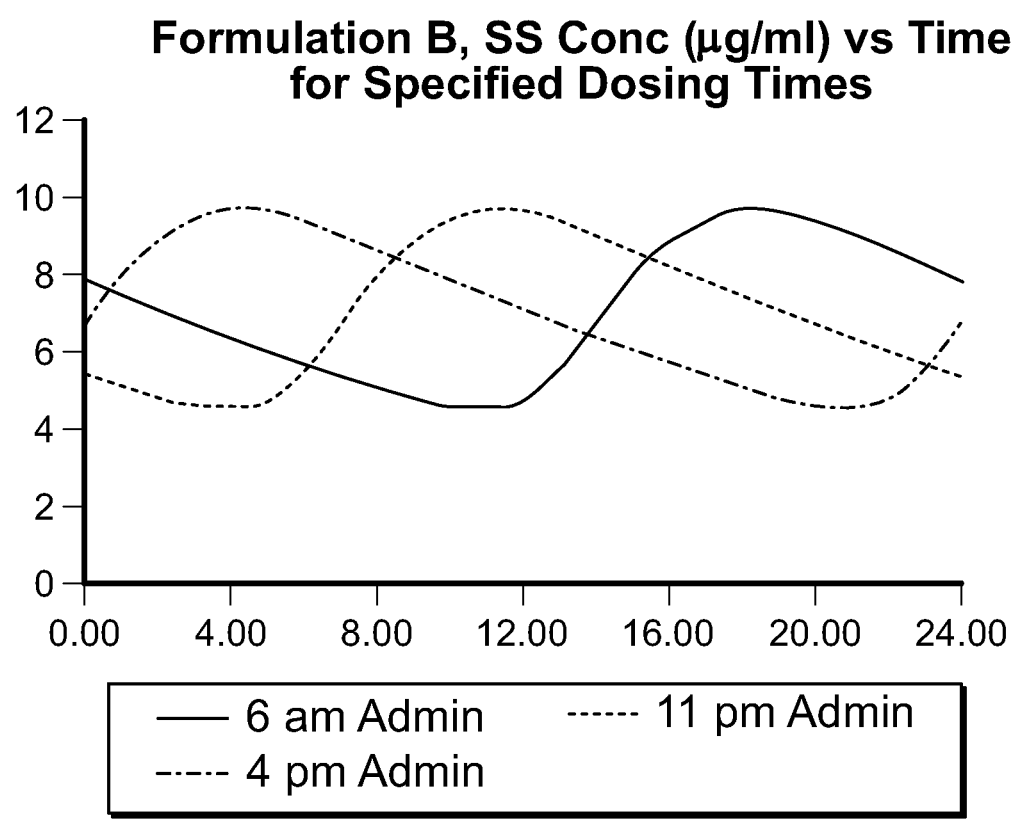
FIG. 7B is a graph depicting steady state profiles of Formulation B administered at different times.
Figure 7C:
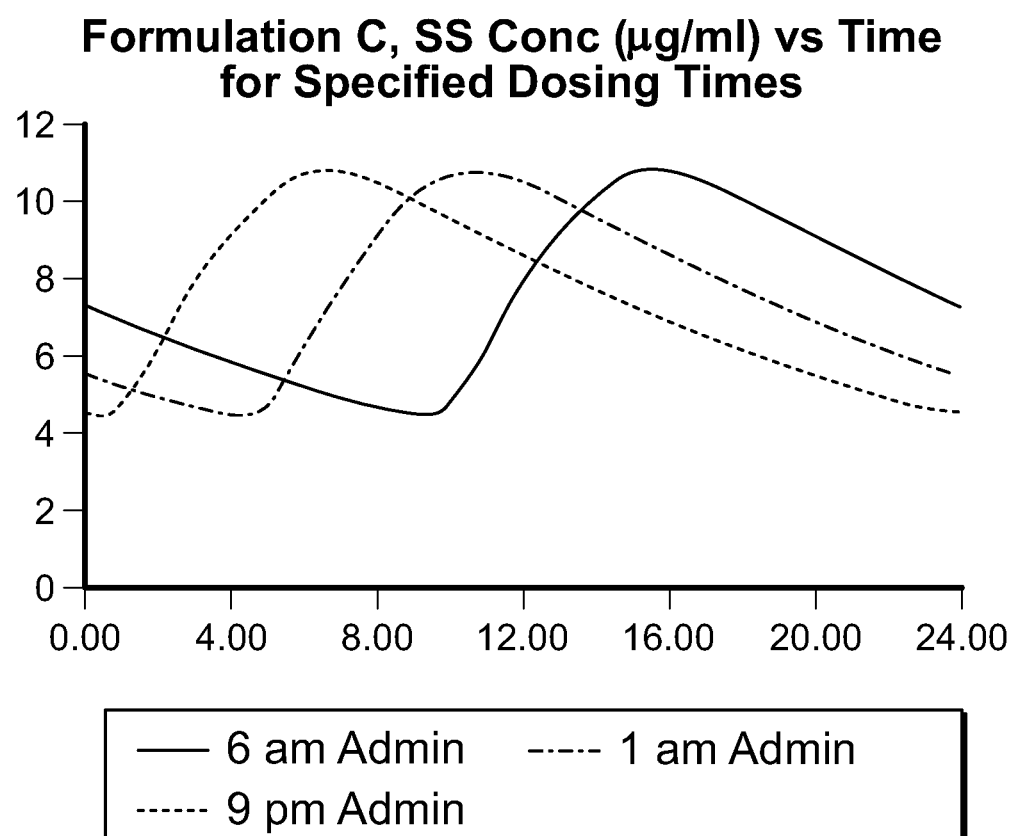
FIG. 7C is a graph depicting steady state profiles of Formulation C administered at different times.
Figure 7D:
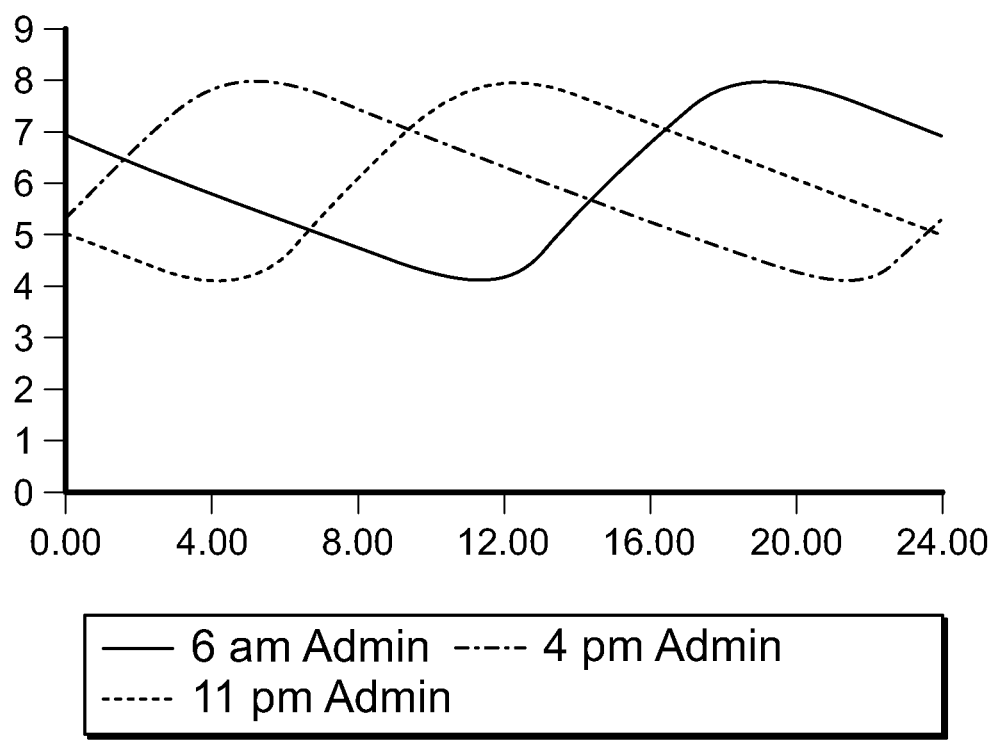
FIG. 7D is a graph depicting steady state profiles of Formulation D administered at different times.

Dissolution profiles for the lacosamide compositions shown in Example 18 above were used to model plasma concentration profiles with the software package GastroPlus, version 9.0 as described in Example 9 above for single doses at 400 mg. The plasma concentration curves were then used to determine PK parameters for the compositions, including $C_{max}$, $T_{max}$, $AUC_{0-\infty}$, $AUC_{0-4}$, $AUC_{4-8}$, and dC/dt from 0 to 1.4, 2, 3, 4 hours. These parameters were also determined from the plasma concentration curve for the immediate release lacosamide formulation of Example 9, adjusted to a single dose of 400 mg. The plasma concentration curves based on the models from GastroPlus are shown in FIG. 6. As shown in the table below, when compared to the immediate release formulations, the modified release formulations all provide delayed $T_{max}$ values and provides AUC equivalence to IR. The $pAUC_{0-4}$ values are substantially lower than the IR $pAUC_{0-4}$ value; the $pAUC_{4-8}$ and $pAUC_{0-8}$ values for Formulation B, Formulation C, and Formulation D are also much lower than the corresponding values for IR and Formulation A. The dC/dT values over each of the time periods shown in the table are 50% or less than the corresponding IR value; and over the first 1.2, 2, or 3 hours after administration of a single dose of the compositions or an equivalent dose of the IR formulation, the dC/dT for the formulations of the compositions are less than 33% of the corresponding values. The dC/dT values for Formulation B, Formulation C, and Formulation D are all less than 5% of the corresponding IR value.

TABLE 19A

Single Dose PK Parameters

| | IR | Form. A | Form. B | Form. C | Form. D |
|---|---|---|---|---|---|
| $T_{max}$ (h) | 1.4 | 9.1 | 13.3 | 10.5 | 14.4 |
| $C_{max}$ (µg/ml) | 10.1 | 7.6 | 6.9 | 7.9 | 5.5 |
| $AUC_{0-inf}$ (µg*hr/ml) | 190.3 | 186.0 | 170.6 | 181.2 | 156.0 |
| % of IR | | 98% | 90% | 95% | 82% |
| $pAUC_{0-4}$ (µg*hr/ml) | 35.01 | 6.99 | 0.00 | 0.19 | 0.00 |
| Fractional AUC (%) | 18% | 4% | 0% | 0% | 0% |
| $pAUC_{4-8}$ (µg*hr/ml) | 31.73 | 25.42 | 2.93 | 12.89 | 1.57 |
| Fractional AUC (%) | 17% | 14% | 2% | 7% | 1% |
| $pAUC_{0-8}$ (µg*hr/ml) | 66.74 | 32.42 | 2.93 | 13.08 | 1.57 |
| Fractional AUC (%) | 35% | 17% | 2% | 7% | 1% |
| dC/dT 0 to 1.4 hr (µg/ml/hr) | 7.25 | 0.65 | 0.00 | 0.00 | 0.00 |
| dC/dT 0 to 2 hr (µg/ml/hr) | 4.97 | 0.67 | 0.00 | 0.00 | 0.00 |
| dC/dT 0 to 3 hr (µg/ml/hr) | 3.13 | 0.98 | 0.00 | 0.03 | 0.00 |
| dC/dT 0 to 4 hr (µg/ml/hr) | 2.22 | 1.11 | 0.00 | 0.05 | 0.00 |

Multi-dose plasma concentration profiles for the IR and modified release formulations each dosed once daily at 400 mg per day were also generated from GastroPlus. Additionally, a multi-dose plasma concentration profile for the IR formulation dosed at 200 mg BID was generated from GastroPlus. These multi-dose plasma concentration profiles were extended to 6 days to provide a steady state profile for the final day; the steady state profiles were used to determine the steady state PK parameters for the compositions, including $T_{max,ss}$, $C_{max,ss}$, $C_{min,ss}$, $AUC_{0-24}$, swing and PTF. As shown in the table below, each of the formulations of Example 17 provide a $T_{max,ss}$ that is substantially greater than the IR $T_{max,ss}$. The $T_{max,ss}$ for Formulation B and Formulation D are both greater than 12 hours, consistent with suitability for night time administration once daily. The swing values and PTF values for the formulations of the Example 17 are greater than the swing provided by the BID and QD dosing regimens for IR.

TABLE 19B

Steady State PK Parameters

| | IR-BID | IR-QD | Form. A | Form. B | Form. C | Form. D |
|---|---|---|---|---|---|---|
| $T_{max,ss}$ (h) | 1.2 | 1.3 | 8 | 12.7 | 10.1 | 13.4 |
| $C_{max,ss}$ (µg/ml) | 10.3 | 13.7 | 10.6 | 9.8 | 10.8 | 8.0 |
| $C_{min,ss}$ (µg/ml) | 5.7 | 3.8 | 4.8 | 4.6 | 4.5 | 4.1 |
| $AUC_{0-24}$ (µg*hr/ml) | 190.2 | 190.3 | 186.0 | 170.6 | 181.2 | 146.1 |
| % of IR-QD | 100% | 100% | 98% | 90% | 95% | 77% |
| $C_{max,ss}/D$ (ng/ml/mg) | 25.8 | 34.1 | 26.4 | 24.4 | 27.1 | 20.0 |
| $C_{min,ss}/D$ (ng/ml/mg) | 14.1 | 9.5 | 11.9 | 11.5 | 11.1 | 10.2 |

TABLE 19B-continued

| | Steady State PK Parameters | | | | | |
|---|---|---|---|---|---|---|
| | IR-BID | IR-QD | Form. A | Form. B | Form. C | Form. D |
| $AUC_{0-24}/D$ (ng*hr/ml/mg) | 475.6 | 475.6 | 465.1 | 426.5 | 453.0 | 365.3 |
| Swing $(C_{max,\,ss}\text{-}C_{min,\,ss})/$ $C_{min,\,ss}$ (%) | 83% | 260% | 122% | 112% | 143% | 95% |
| PTF $((C_{max,\,ss}\text{-}C_{min,\,ss})/$ $(AUC_{0-24}/\text{tau}))$ | 59% | 124% | 75% | 73% | 84% | 64% |

Figure 8:
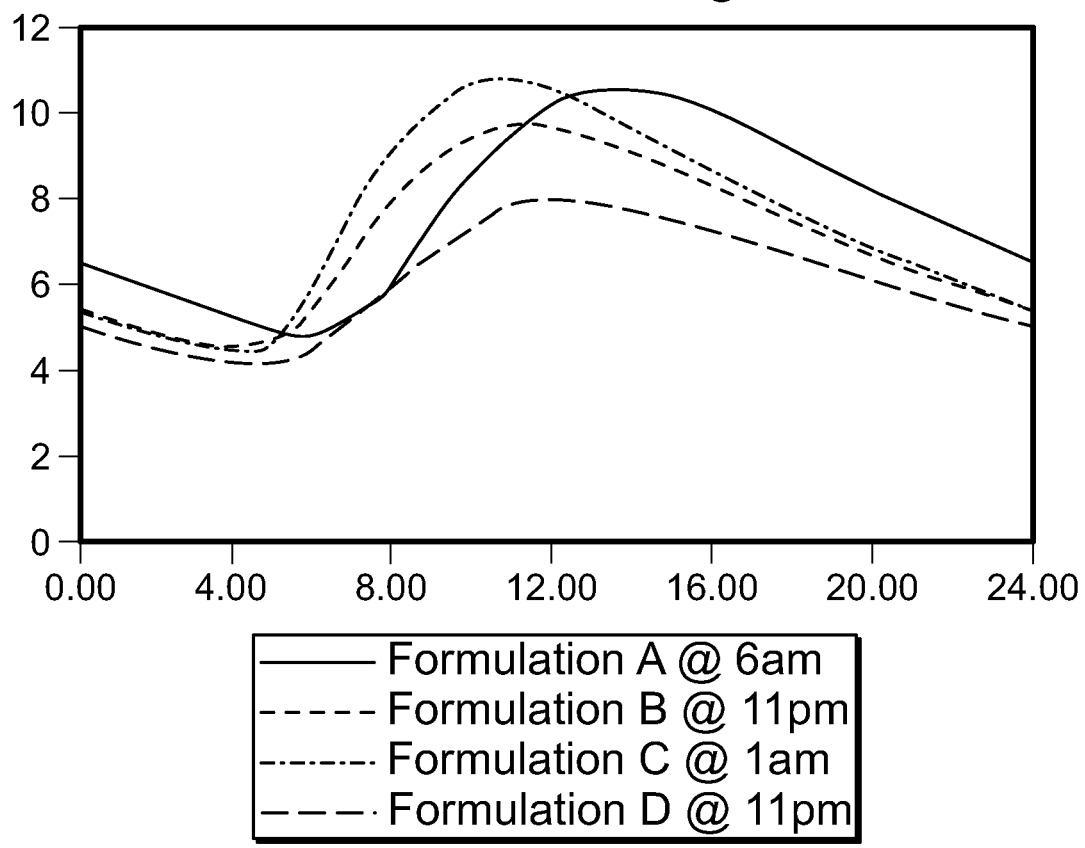
FIG. 8 is a graph depicting steady state profiles of Formulations A-D administered at specified times to provide $T_{max,ss}$ in the period of about 10 am to 2 pm.

Example 20: Steady State Lacosamide Plasma Profiles with Modified Dosing Regimens The steady state plasma concentration profiles prepared in the previous example were based on once daily, oral dosing of the modified release lacosamide compositions at 8:00 am. By adjusting the dosing time the $C_{max,ss}$ and $C_{min,ss}$ were also shifted as shown in FIGS. 7A to 7D. The C-ave-day and C-ave night averages were determined over the periods of 9 am to 6 pm and 11 pm to 8 am, respectively, for various administration times to determine the optimum administration times for each of the compositions, i.e., the time at which C-ave-day is 50% to 100% greater than C-ave-night. As shown in the table below, Formulation A provides a substantially higher C-ave-day than C-ave-night when administered in the morning hours (e.g., 6 am to 9 am); similarly Formulation B and Formulation D provide a substantially higher C-ave-day than C-ave-night when administered in the evening hours (e.g., 8 pm to 11 pm). None of the formulations from Example 17 provided a C-ave-day that met the 50% to 100% criteria when administration times were between 9 am and 8 pm. Formulation C met the criteria when administered late at night (i.e., at or after midnight). Importantly, each of the Formulations of Example 17 could be dosed at a predetermined administration time to provide a C-ave-day that is greater than C-ave-night by 50% to 100%. Furthermore, once daily dosing at these predetermined administration times typically led to steady state peak concentrations from about 10 am to about 2 pm as shown in FIG. 8. These periods of increased exposure are thus designed to be chronosynchronous with an increased partial onset seizure frequency during the late morning to mid-day hours.

TABLE 20

Does Daily Dosing Within the Time Period Provide C-ave-day increase of 50-100% over C-ave-night?

| Dosing Time | Formulation A | Formulation B | Formulation C | Formulation D |
|---|---|---|---|---|
| 6 am to 9 am | Yes | No | No | No |
| 9 am to 8 pm | No | No | No | No |
| 8 pm to 11 pm | No | Yes | No | Yes |
| 11 pm to 2 am | No | Yes | Yes | Yes |

Example 21: Single Dose Pharmacokinetic Study of Lacosamide Compositions

Objective: The primary objective of the study was to evaluate the pharmacokinetic profile, safety and tolerability of prototype modified release formulations of lacosamide (as prepared in Example 17 above), relative to IR Lacosamide tablets (VIMPAT®) given as single doses to healthy adult subjects under fasting conditions.

Study design: This was a Phase 1, randomized, single dose, open-label, three-period, two-parallel group, balanced crossover, fasting pharmacokinetic study in which single 400 mg doses of lacosamide ER prepared according to Example 17 were compared to single 400 mg doses of marketed lacosamide IR tablets (VIMPAT®). Within each group, as illustrated in Table 21A below, individuals were randomly assigned to a "sequence" and received two of the modified release formulations and the immediate release formulation over the three treatment periods.

Methods: Subjects were screened within 14 days of the first dose of the first treatment period. Qualified subjects entered the clinic one day prior to the first dose (first treatment period) and were confined within the clinic until completion of the 7 day safety follow-up after the third dose (third treatment period). Each treatment period of 7 days consisted of dosing on the first day, followed by sampling, starting from the time of dose. In each treatment period, the subjects were administered a single, oral dose at approximately 8:00 (after an overnight fast of at least 10 hours). Safety monitoring and study drug tolerability assessments (adverse events, vital signs, clinical laboratory parameters) were conducted throughout the study for all subjects. Pharmacokinetic blood samples were collected to measure plasma lacosamide concentrations.

While confined to the clinic (once day before first dose through the study completion) subjects followed a standard meal schedule. At each dosing time, the study drug (either one of the 4 formulations prepared according to Example 17 or IR lacosamide) was administered as a single dose containing 400 mg lacosamide with 240 mL of noncarbonated, room-temperature water. Subjects were required to refrain from drinking water for the hour prior to receiving the dose and for one hour after receiving the dose. Subjects were allowed to eat 4 hours after dosing. Subjects were required to remain in a sitting or semi-supine position for at least 2 hours after each study drug administration in each treatment period (other than any protocol-required assessments conducted by the site staff); thereafter subjects were allowed to engage in non-strenuous activities. Following each treatment period dose, subjects were required to complete study assessments and scheduled blood draws from day 1 through day 7.

Plasma lacosamide concentrations were measured for the following time points in each treatment period: Pre-dose (0), 0.25, 0.5, 1, 1.5, 2, 3, 4, 5, 6, 7, 8, 9, 10, 11, 12, 13, 14, 15, 16, 18, 20, 24, 30, 36, 48, and 72 hours post dose. Adverse events were reported for each subject throughout each treatment period. Clinical laboratory tests (hematology, clinical chemistry, and urinalysis) were completed for each subject at check-in, day 2 (36 hour time point), during and on the last day of each treatment period. Vital signs were collected at screening, check-in, prior to study drug dosing and 6, 8, 24, 36, and 72 hours post dose and at the end of each treatment period. Electrocardiograms were recorded and assessed at screening and baseline and at 2 hours, 12 hours, at day 1 prior to dose for each treatment period and at the end of study.

TABLE 21A

Treatment Sequences

|  | Treatment Period A | Treatment Period B | Treatment Period C |
|---|---|---|---|
| GROUP 1 | | | |
| Sequence 1 | 1* | 2 | IR |
| Sequence 2 | IR | 1 | 2 |
| Sequence 3 | 2 | IR | 1 |
| Sequence 4 | IR | 2 | 1 |
| Sequence 5 | 2 | 1 | IR |
| Sequence 6 | 1 | IR | 2 |
| GROUP 2 | | | |
| Sequence 7 | 3 | 4 | IR |
| Sequence 8 | IR | 3 | 4 |
| Sequence 9 | 4 | IR | 3 |
| Sequence 10 | IR | 4 | 3 |
| Sequence 11 | 4 | 3 | IR |
| Sequence 12 | 3 | IR | 4 |

*1, 2, 3, 4, and IR refer to Formulation A, Formulation B, Formulation C, Formulation D, and the IR lacosamide tablets, respectively Twenty-four subjects meeting the study criteria were randomly assigned to the 12 sequences of the two parallel study groups. Of these, 22 completed the three treatment periods. The two subjects not completing the study were exited from the study before Treatment Period C for reasons unrelated to study drugs.

Samples for lacosamide concentration measurement were quantified using a validated liquid chromatography/tandem mass spectroscopy (LC/MS/MS) method.

Figure 10:
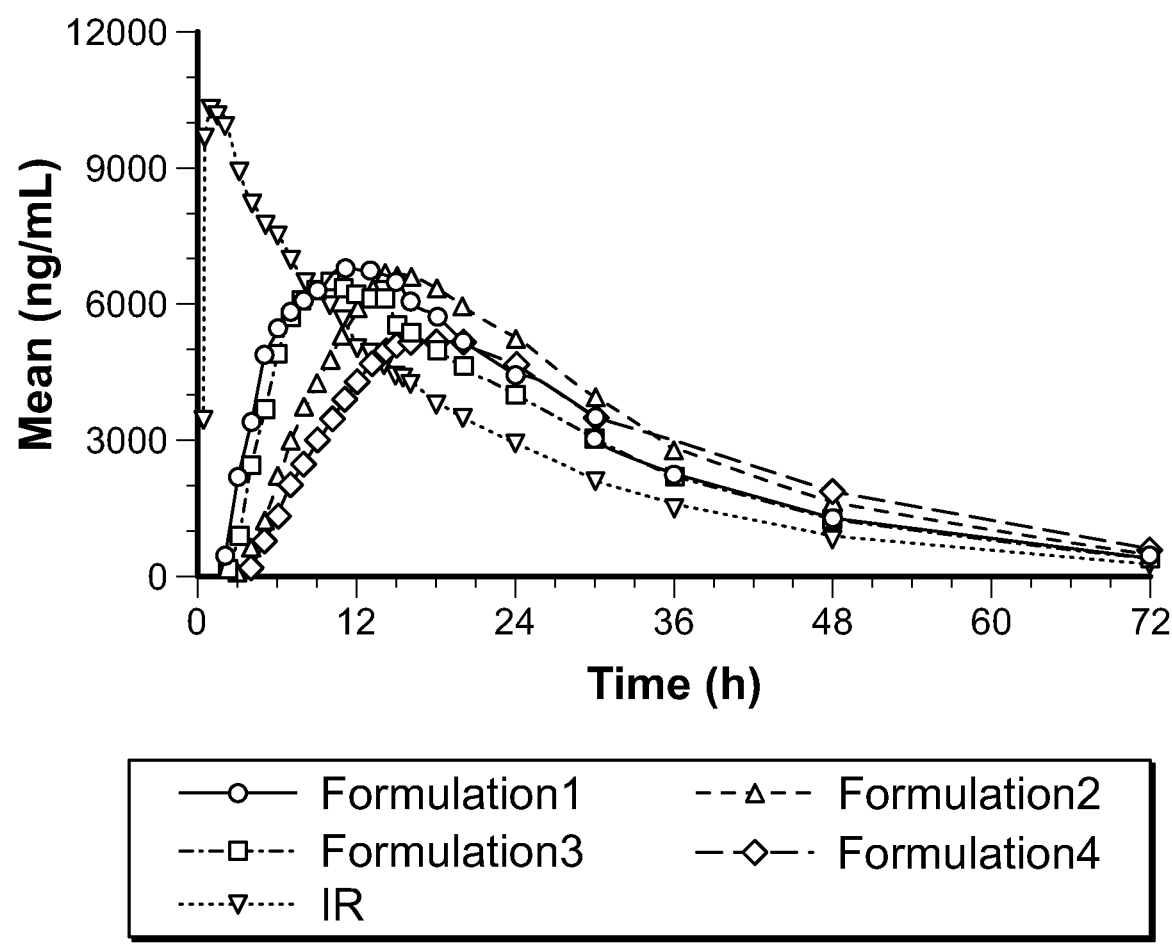
FIG. 10 is a graph depicting the plasma concentration profiles of the study drugs of Example 21. Formulation1 of the figure is the plasma concentration profile for Formulation A of Example 21; Formulation2 of the figure is the plasma concentration profile for Formulation B of Example 21; Formulation3 of the figure is the plasma concentration profile for Formulation C of Example 21; Formulation4 of the figure is the plasma concentration profile for Formulation D of Example 21; IR of the figure is the plasma concentration profile for the IR lacosamide of Example 21.

Results: Plasma concentrations for the four test formulations, when compared to the IR lacosamide tablets, confirmed delayed $T_{max}$ and reduced $C_{max}$, generally consistent with the GastroPlus results of Example 19. A graph of the mean lacosamide plasma concentrations vs time for the four test formulations and IR is shown in FIG. 10.

The safety results from this study are shown in Table 21B below. The lacosamide compositions prepared according to Example 17 had fewer adverse events than an equivalent dose of the IR lacosamide composition. Of the adverse events observed, hypoaesthesia oral was observed in 11 of 24 (45.8%) of the subjects receiving the IR lacosamide and only 1 of 12 (8.3%) of the subjects receiving Formulation B; similarly, dizziness was observed in 8 of 24 (33.3%) of subjects receiving the IR lacosamide and only 1 of 12 (8.3%) subjects receiving Formulation A, 1 of 12 (8.3%) subjects receiving Formulation B, 1 of 12 (8.3%) subjects receiving Formulation C, and 1 of 10 (10.0%) subjects receiving Formulation D. For a given adverse event, no more than one subject in any of the experimental formulations reported the event.

TABLE 21B

Incidence of Subjects with Adverse Events within 24 hours after dosing

| System Organ Class Preferred Term | Form. A (N = 12) | Form. B (N = 12) | Form. C (N = 12) | Form. D (N = 10) | IR Form (N = 24) |
|---|---|---|---|---|---|
| Subjects with At Least One Adverse Event within 24 Hours | 2 (16.7%) | 4 (33.3%) | 2 (16.7%) | 1 (10.0%) | 15 (62.5%) |
| Not Coded | 0 (0.0%) | 0 (0.0%) | 0 (0.0%) | 0 (0.0%) | 2 (8.3%) |
| Hypoaesthesia Nose | 0 (0.0%) | 0 (0.0%) | 0 (0.0%) | 0 (0.0%) | 1 (4.2%) |
| Paresthesia Periorbital | 0 (0.0%) | 0 (0.0%) | 0 (0.0%) | 0 (0.0%) | 1 (4.2%) |
| Ear and labyrinth disorders | 0 (0.0%) | 0 (0.0%) | 0 (0.0%) | 0 (0.0%) | 2 (8.3%) |
| Ear discomfort | 0 (0.0%) | 0 (0.0%) | 0 (0.0%) | 0 (0.0%) | 1 (4.2%) |
| Tinnitus | 0 (0.0%) | 0 (0.0%) | 0 (0.0%) | 0 (0.0%) | 1 (4.2%) |
| Eye disorders | 0 (0.0%) | 0 (0.0%) | 1 (8.3%) | 1 (10.0%) | 1 (4.2%) |
| Diplopia | 0 (0.0%) | 0 (0.0%) | 0 (0.0%) | 0 (0.0%) | 1 (4.2%) |
| Vision blurred | 0 (0.0%) | 0 (0.0%) | 1 (8.3%) | 1 (10.0%) | 0 (0.0%) |
| Gastrointestinal disorders | 1 (8.3%) | 2 (16.7%) | 0 (0.0%) | 0 (0.0%) | 13 (54.2%) |
| Dry mouth | 0 (0.0%) | 1 (8.3%) | 0 (0.0%) | 0 (0.0%) | 0 (0.0%) |
| Dysphagia | 0 (0.0%) | 0 (0.0%) | 0 (0.0%) | 0 (0.0%) | 1 (4.2%) |
| Hypoaesthesia oral | 0 (0.0%) | 1 (8.3%) | 0 (0.0%) | 0 (0.0%) | 11 (45.8%) |
| Nausea | 1 (8.3%) | 0 (0.0%) | 0 (0.0%) | 0 (0.0%) | 1 (4.2%) |
| Paraesthesia oral | 0 (0.0%) | 0 (0.0%) | 0 (0.0%) | 0 (0.0%) | 2 (8.3%) |
| General disorders and administration site conditions | 0 (0.0%) | 1 (8.3%) | 0 (0.0%) | 0 (0.0%) | 1 (4.2%) |
| Fatigue | 0 (0.0%) | 1 (8.3%) | 0 (0.0%) | 0 (0.0%) | 0 (0.0%) |
| Feeling hot | 0 (0.0%) | 0 (0.0%) | 0 (0.0%) | 0 (0.0%) | 1 (4.2%) |
| Musculoskeletal and connective tissue disorders | 0 (0.0%) | 0 (0.0%) | 0 (0.0%) | 0 (0.0%) | 1 (4.2%) |
| Myalgia | 0 (0.0%) | 0 (0.0%) | 0 (0.0%) | 0 (0.0%) | 1 (4.2%) |
| Nervous system disorders | 1 (8.3%) | 1 (8.3%) | 2 (16.7%) | 1 (10.0%) | 10 (41.7%) |
| Altered state of consciousness | 0 (0.0%) | 0 (0.0%) | 0 (0.0%) | 0 (0.0%) | 1 (4.2%) |
| Disturbance in attention | 0 (0.0%) | 0 (0.0%) | 0 (0.0%) | 0 (0.0%) | 1 (4.2%) |
| Dizziness | 1 (8.3%) | 1 (8.3%) | 1 (8.3%) | 1 (10.0%) | 8 (33.3%) |
| Headache | 0 (0.0%) | 0 (0.0%) | 0 (0.0%) | 1 (10.0%) | 0 (0.0%) |
| Hypoaesthesia | 0 (0.0%) | 0 (0.0%) | 1 (8.3%) | 0 (0.0%) | 1 (4.2%) |
| Somnolence | 0 (0.0%) | 0 (0.0%) | 0 (0.0%) | 0 (0.0%) | 2 (8.3%) |
| Respiratory, thoracic and mediastinal disorders | 1 (8.3%) | 0 (0.0%) | 0 (0.0%) | 0 (0.0%) | 1 (4.2%) |
| Pharyngeal paraesthesia | 0 (0.0%) | 0 (0.0%) | 0 (0.0%) | 0 (0.0%) | 1 (4.2%) |
| Rhinorrhoea | 1 (8.3%) | 0 (0.0%) | 0 (0.0%) | 0 (0.0%) | 0 (0.0%) |
| Sneezing | 1 (8.3%) | 0 (0.0%) | 0 (0.0%) | 0 (0.0%) | 0 (0.0%) |

1: For each formulation, adverse events are tabulated once based on their first occurrence post dose administration.

ENUMERATED EMBODIMENTS

Embodiment 1. A method of administering a pharmaceutical composition to a human patient, comprising administering to said human patient orally, once daily, a therapeutically effective dose of said pharmaceutical composition,
- wherein said pharmaceutical composition comprises (i) a drug selected from the group consisting of brivaracetam, divalproex, lacosamide, levetiracetam, oxcarbazepine, vigabatrin, and pharmaceutically acceptable salts of any of the foregoing, and (ii) at least one excipient,
- wherein at least one of said at least one excipients modifies the release of said drug to provide an extended release form,
- wherein said pharmaceutical composition has a plasma concentration profile for said drug characterized by a $pAUC_{0-4}$ that is less than 4% of $AUC_{0-inf}$ for said drug as determined by dosing said pharmaceutical composition to a subject of a fasted, single dose, human pharmacokinetic study.

Embodiment 2. The method of embodiment 1, wherein said pharmaceutical composition has a plasma concentration profile for said drug characterized by a $pAUC_{4-8}$ that is less than 14% of $AUC_{0-inf}$ for said drug as determined by dosing said pharmaceutical composition to a subject of a fasted, single dose, human pharmacokinetic study.

Embodiment 3. The method of embodiment 1, wherein said drug is selected from the group consisting of brivaracetam, lacosamide, levetiracetam, and pharmaceutically acceptable salts of any of the foregoing.

Embodiment 4. The method of embodiment 1, wherein said drug is lacosamide.

Embodiment 5. The method of embodiment 1, wherein said therapeutically effective dose is 300 to 900 mg of said drug.

Embodiment 6. The method of embodiment 1, wherein said therapeutically effective dose is 400 to 800 mg of said drug.

Embodiment 7. The method of embodiment 1, wherein said therapeutically effective dose is 450 to 800 mg of said drug.

Embodiment 8. The method of embodiment 1, wherein at least one of said at least one excipients modifies the release of said drug to provide a delayed release form.

Embodiment 9. The method of embodiment 1, wherein said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted pharmacokinetic study.

Embodiment 10. The method of embodiment 1, wherein said plasma concentration profile for said drug is further characterized by an $AUC_{0-inf}$ that provides AUC equivalence to IR.

Embodiment 11. A method of administering a pharmaceutical composition to a human patient, comprising administering to said human patient orally, once daily, a therapeutically effective dose of said pharmaceutical composition,
- wherein said pharmaceutical composition comprises (i) a drug selected from the group consisting of brivaracetam, divalproex, lacosamide, levetiracetam, oxcarbazepine, vigabatrin, and pharmaceutically acceptable salts of any of the foregoing, and (ii) at least one excipient,
- wherein at least one of said at least one excipients modifies the release of said drug to provide an extended release form,
- wherein said pharmaceutical composition has a plasma concentration profile for said drug characterized by a $pAUC_{4-8}$ that is less than 8% of $AUC_{0-inf}$ for said drug as determined by dosing said pharmaceutical composition to a subject of a fasted, single dose, human pharmacokinetic study.

Embodiment 12. The method of embodiment 11, wherein said drug is selected from the group consisting of brivaracetam, lacosamide, levetiracetam, and pharmaceutically acceptable salts of any of the foregoing.

Embodiment 13. The method of embodiment 11, wherein said drug is lacosamide.

Embodiment 14. The method of embodiment 11, wherein said therapeutically effective dose is 300 to 900 mg of said drug.

Embodiment 15. The method of embodiment 11, wherein said therapeutically effective dose is 400 to 800 mg of said drug.

Embodiment 16. The method of embodiment 11, wherein said therapeutically effective dose is 450 to 800 mg of said drug.

Embodiment 17. The method of embodiment 11, wherein at least one of said at least one excipients modifies the release of said drug to provide a delayed release form.

Embodiment 18. The method of embodiment 11, wherein said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted human pharmacokinetic study.

Embodiment 19. The method of embodiment 11, wherein said plasma concentration profile for said drug is further characterized by an $AUC_{0-inf}$ that provides AUC equivalence to IR.

Embodiment 20. A method of administering a pharmaceutical composition to a human patient, comprising administering to said human patient orally, once daily, a therapeutically effective dose of said pharmaceutical composition,
- wherein said pharmaceutical composition comprises (i) a drug selected from the group consisting of brivaracetam, divalproex, lacosamide, levetiracetam, oxcarbazepine, vigabatrin, and pharmaceutically acceptable salts of any of the foregoing, and (ii) at least one excipient,
- wherein at least one of said excipients modifies the release of said drug to provide an extended release form,
- wherein said pharmaceutical composition has a plasma concentration profile for said drug characterized by a $T_{max}$ of 8 to 20 hours as determined by dosing said pharmaceutical composition to a subject of a fasted, single dose, human pharmacokinetic study, and
- wherein said pharmaceutical composition has a steady state plasma concentration profile for said drug upon once daily dosing of said pharmaceutical composition characterized by a swing of 40% to 200%, as determined by dosing said pharmaceutical composition to a subject of a fasted human pharmacokinetic study.

Embodiment 21. The method of embodiment 20, wherein said drug is selected from the group consisting of brivaracetam, lacosamide, levetiracetam, and pharmaceutically acceptable salts of any of the foregoing.

Embodiment 22. The method of embodiment 20, wherein said drug is lacosamide.

Embodiment 23. The method of embodiment 20, wherein said therapeutically effective dose is 300 to 900 mg of said drug.

Embodiment 24. The method of embodiment 20, wherein said therapeutically effective dose is 400 to 800 mg of said drug.

Embodiment 25. The method of embodiment 20, wherein said therapeutically effective dose is 450 to 800 mg of said drug.

Embodiment 26. The method of embodiment 20, wherein at least one of said at least one excipients modifies the release of said drug to provide a delayed release form.

Embodiment 27. The method of embodiment 20, wherein said pharmaceutical composition has a plasma concentration profile for said drug characterized by a $T_{max}$ of 12 to 20 hours as determined by dosing said pharmaceutical composition to a subject of a fasted, single dose, human pharmacokinetic study.

Embodiment 28. The method of embodiment 20, wherein said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted pharmacokinetic study.

Embodiment 29. The method of embodiment 20, wherein said pharmaceutical composition has a steady state plasma concentration profile for said drug upon once daily dosing of said pharmaceutical composition characterized by a swing of 50% to 100%, as determined by dosing said pharmaceutical composition to a subject of a fasted pharmacokinetic study.

Embodiment 30. The method of embodiment 20, wherein said pharmaceutical composition has a steady state plasma concentration profile for said drug upon once daily dosing of said pharmaceutical composition characterized by a swing of 60% to 200%, as determined by dosing said pharmaceutical composition to a subject of a fasted human pharmacokinetic study.

Embodiment 31. The method of embodiment 20, wherein said plasma concentration profile for said drug is further characterized by an $AUC_{0-inf}$ that provides AUC equivalence to IR.

Embodiment 32. A method of administering a pharmaceutical composition to a human patient, comprising administering to said human patient orally, once daily, a therapeutically effective dose of said pharmaceutical composition,
wherein said pharmaceutical composition comprises (i) a drug selected from the group consisting of brivaracetam, divalproex, lacosamide, levetiracetam, oxcarbazepine, vigabatrin, and pharmaceutically acceptable salts of any of the foregoing, and (ii) at least one excipient,
wherein at least one of said at least one excipients modifies the release of said drug to provide an extended release form,
wherein said pharmaceutical composition has a plasma concentration profile for said drug characterized by a $T_{max}$ of 8 to 20 hours and a dC/dT of less than 2.2 ng/ml/hr per mg of said drug over the first 2 hours after dosing, both as determined by dosing said pharmaceutical composition to a subject of a fasted, single dose, human pharmacokinetic study.

Embodiment 33. The method of embodiment 32, wherein said drug is selected from the group consisting of brivaracetam, lacosamide, levetiracetam, and pharmaceutically acceptable salts of any of the foregoing.

Embodiment 34. The method of embodiment 32, wherein said drug is lacosamide.

Embodiment 35. The method of embodiment 32, wherein said therapeutically effective dose is 300 to 900 mg of said drug.

Embodiment 36. The method of embodiment 32, wherein said therapeutically effective dose is 400 to 800 mg of said drug.

Embodiment 37. The method of embodiment 32, wherein said therapeutically effective dose is 450 to 800 mg of said drug.

Embodiment 38. The method of embodiment 32, wherein at least one of said at least one excipients modifies the release of said drug to provide a delayed release form.

Embodiment 39. The method of embodiment 32, wherein said pharmaceutical composition has a plasma concentration profile for said drug characterized by a $T_{max}$ of 12 to 20 hours as determined by dosing said pharmaceutical composition to a subject of a fasted, single dose, human pharmacokinetic study.

Embodiment 40. The method of embodiment 32, wherein said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted human pharmacokinetic study.

Embodiment 41. The method of embodiment 32, wherein said pharmaceutical composition has a plasma concentration profile for said drug characterized by a dC/dT of less than 1.4 ng/ml/hr per mg of said drug over the first 2 hours after dosing as determined by dosing said pharmaceutical composition to a subject of a fasted, single dose, human pharmacokinetic study.

Embodiment 42. The method of embodiment 32, wherein said pharmaceutical composition has a plasma concentration profile for said drug characterized by a dC/dT of less than 1.0 ng/ml/hr per mg of said drug over the first 2 hours after dosing as determined by dosing said pharmaceutical composition to a subject of a fasted, single dose, human pharmacokinetic study.

Embodiment 43. The method of embodiment 32, wherein said plasma concentration profile for said drug is further characterized by an $AUC_{0-inf}$ that provides AUC equivalence to IR.

Embodiment 44. A method of administering a pharmaceutical composition to a human patient, comprising administering to said human patient orally, once daily, a therapeutically effective dose of said pharmaceutical composition,
wherein said pharmaceutical composition consists of (i) a drug selected from the group consisting of brivaracetam, divalproex, lacosamide, levetiracetam, oxcarbazepine, vigabatrin, and pharmaceutically acceptable salts of any of the foregoing, and (ii) at least one excipient,
wherein at least one of said at least one excipients modifies the release of said drug to provide an extended release form, wherein said pharmaceutical composition has a plasma concentration profile for said drug characterized by a $T_{max}$ of 8 to 20 hours and a dC/dT of less than 1 μg/ml/hr over the first 2 hours after dosing, both as determined by dosing said pharmaceutical composition to a subject of a fasted, single dose, human pharmacokinetic study.

Embodiment 45. The method of embodiment 44, wherein said drug is selected from the group consisting of brivaracetam, lacosamide, levetiracetam, and pharmaceutically acceptable salts of any of the foregoing.

Embodiment 46. The method of embodiment 44, wherein said drug is lacosamide.

Embodiment 47. The method of embodiment 44, wherein said therapeutically effective dose is 300 to 900 mg of said drug.

Embodiment 48. The method of embodiment 44, wherein said therapeutically effective dose is 400 to 800 mg of said drug.

Embodiment 49. The method of embodiment 44, wherein said therapeutically effective dose is 450 to 800 mg of said drug.

Embodiment 50. The method of embodiment 44, wherein at least one of said at least one excipients modifies the release of said drug to provide a delayed release form.

Embodiment 51. The method of embodiment 44, wherein said pharmaceutical composition has a plasma concentration profile for said drug characterized by a $T_{max}$ of 12 to 20 hours as determined by dosing said pharmaceutical composition to a subject of a fasted, single dose, human pharmacokinetic study.

Embodiment 52. The method of embodiment 44, wherein said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted human pharmacokinetic study.

Embodiment 53. The method of embodiment 44, wherein said pharmaceutical composition has a plasma concentration profile for said drug characterized by a dC/dT of less than 0.6 μg/ml/hr over the first 2 hours after dosing as determined by dosing said pharmaceutical composition to a subject of a fasted, single dose, human pharmacokinetic study.

Embodiment 54. The method of embodiment 44, wherein said pharmaceutical composition has a plasma concentration profile for said drug characterized by a dC/dT of less than 0.3 μg/ml/hr over the first 2 hours after dosing as determined by dosing said pharmaceutical composition to a subject of a fasted, single dose, human pharmacokinetic study.

Embodiment 55. The method of embodiment 44, wherein said plasma concentration profile for said drug is further characterized by an $AUC_{0-inf}$ that provides AUC equivalence to IR.

Embodiment 56. A method of administering a pharmaceutical composition to a human patient, comprising administering to said human patient orally, once daily, at a predetermined administration time, a therapeutically effective dose of said pharmaceutical composition,
wherein said pharmaceutical composition comprises (i) a drug selected from the group consisting of brivaracetam, divalproex, lacosamide, levetiracetam, oxcarbazepine, vigabatrin, and pharmaceutically acceptable salts of any of the foregoing, and (ii) at least one excipient,
wherein at least one of said at least one excipients modifies the release of said drug to provide an extended release form,
wherein said predetermined administration time is a time determined from a fasted, human pharmacokinetic study of said pharmaceutical composition and said predetermined time is a time at which once daily dosing of the pharmaceutical composition to a human subject of said pharmacokinetic study provides a steady state plasma concentration profile characterized by a C-ave-day that is 20% to 100% greater than C-ave-night, wherein C-ave-day is the average plasma concentration of said drug determined over the period from 9:00 am to 6:00 pm and C-ave-night is the average plasma concentration of said drug determined over the period from 11:00 pm to 8:00 am.

Embodiment 57. The method of embodiment 56, wherein said drug is selected from the group consisting of brivaracetam, lacosamide, levetiracetam, and pharmaceutically acceptable salts of any of the foregoing.

Embodiment 58. The method of embodiment 56, wherein said drug is lacosamide.

Embodiment 59. The method of embodiment 56, wherein said therapeutically effective dose is 300 to 900 mg of said drug.

Embodiment 60. The method of embodiment 56, wherein said therapeutically effective dose is 400 to 800 mg of said drug.

Embodiment 61. The method of embodiment 56, wherein said therapeutically effective dose is 450 to 800 mg of said drug.

Embodiment 62. The method of embodiment 56, wherein at least one of said at least one excipients modifies the release of said drug to provide a delayed release form.

Embodiment 63. The method of embodiment 56, wherein said predetermined administration time is 0-4 hours before bedtime.

Embodiment 64. The method of embodiment 56, wherein said predetermined administration time is between 8 pm and 12 am.

Embodiment 65. The method of embodiment 56, wherein said predetermined administration time is 0-3 hours after waking.

Embodiment 66. The method of embodiment 56, wherein said predetermined administration time is between 5 am and 9 am.

Embodiment 67. The method of embodiment 56, wherein said predetermined time is a time at which once daily dosing of the pharmaceutical composition to a human subject of said pharmacokinetic study provides a steady state plasma concentration profile characterized by a C-ave-day that is 30% to 100% greater than C-ave-night, wherein C-ave-day is the average plasma concentration of said drug determined over the period from 9:00 am to 6:00 pm and C-ave-night is the average plasma concentration of said drug determined over the period from 11:00 pm to 8:00 am.

Embodiment 68. The method of embodiment 56, wherein said pharmaceutical composition has a plasma concentration profile for said drug characterized by a $T_{max}$ of 8 to 20 hours as determined by dosing said pharmaceutical composition to a subject of a fasted, single dose, human pharmacokinetic study.

Embodiment 69. The method of embodiment 56, wherein said pharmaceutical composition has a plasma concentration profile for said drug characterized by a $T_{max}$ of 12 to 20 hours as determined by dosing said pharmaceutical composition to a subject of a fasted, single dose, human pharmacokinetic study.

Embodiment 70. The method of embodiment 56, wherein said pharmaceutical composition has a plasma concentration profile for said drug characterized by a $T_{max}$ of 5 to 10 hours as determined by dosing said pharmaceutical composition to a subject of a fasted, single dose, human pharmacokinetic study.

Embodiment 71. The method of embodiment 56, wherein said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted human pharmacokinetic study.

Embodiment 72. The method of embodiment 56, wherein said pharmaceutical composition has a plasma concentration profile for said drug as determined by dosing said pharmaceutical composition to a subject of a fasted, single dose, human pharmacokinetic study characterized by an $AUC_{0-inf}$ for said drug that provides AUC equivalence to IR.

Embodiment 73. A method of administering a pharmaceutical composition to a human patient, comprising administering to said human patient orally, once daily, a therapeutically effective dose of said pharmaceutical composition,
wherein said pharmaceutical composition comprises (i) a drug selected from the group consisting of brivaracetam, divalproex, lacosamide, levetiracetam, oxcarbazepine, vigabatrin, and pharmaceutically acceptable salts of any of the foregoing, and (ii) at least one excipient,
wherein at least one of said at least one excipients modifies the release of said drug to provide an extended release form,
wherein said pharmaceutical composition has a dissolution profile characterized by three or more of the following: (a) less than 10% release at 1 hour, (b) less than 15% release at 2 hours, (c) less than 25% release at 4 hours, (d) at least 35% release at 9 hours, (e) at least 65% at 12 hours, wherein said dissolution is carried out in 900 mL simulated gastric fluid (pH 1.2) at 37±0.5° C. for the first two hours, followed by 900 mL simulated intestinal fluid (pH 6.8) at 37±0.5° C. for the subsequent four hours, followed by 900 mL phosphate buffer (pH 7.5) at 37±0.5° C. for the subsequent 18 hours, wherein all dissolution is performed in a USP Apparatus 1 (Basket), with a rotational speed of 100 rpm, and
wherein said pharmaceutical composition has a plasma concentration profile for said drug characterized by a $T_{max}$ of 8 to 20 hours as determined by dosing said pharmaceutical composition to a subject of a fasted, single dose, human pharmacokinetic study.

Embodiment 74. The method of embodiment 73, wherein said drug is selected from the group consisting of brivaracetam, lacosamide, levetiracetam, and pharmaceutically acceptable salts of any of the foregoing.

Embodiment 75. The method of embodiment 73, wherein said drug is lacosamide.

Embodiment 76. The method of embodiment 73, wherein said therapeutically effective dose is 300 to 900 mg of said drug.

Embodiment 77. The method of embodiment 73, wherein said therapeutically effective dose is 400 to 800 mg of said drug.

Embodiment 78. The method of embodiment 73, wherein said therapeutically effective dose is 450 to 800 mg of said drug.

Embodiment 79. The method of embodiment 73, wherein at least one of said at least one excipients modifies the release of said drug to provide a delayed release form.

Embodiment 80. The method of embodiment 73, wherein said pharmaceutical composition has a plasma concentration profile for said drug characterized by a $T_{max}$ of 12 to 20 hours as determined by dosing said pharmaceutical composition to a subject of a fasted, single dose, human pharmacokinetic study.

Embodiment 81. The method of embodiment 73, wherein said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted human pharmacokinetic study.

Embodiment 82. The method of embodiment 73, wherein said plasma concentration profile for said drug is further characterized by an $AUC_{0-inf}$ that provides AUC equivalence to IR.

Embodiment 83. A pharmaceutical composition for oral administration to a human, comprising (i) 50 mg to 900 mg of a drug selected from the group consisting of brivaracetam, divalproex, lacosamide, levetiracetam, oxcarbazepine, vigabatrin, and pharmaceutically acceptable salts of any of the foregoing, and (ii) at least one excipient,
wherein at least one of said at least one excipients modifies the release of said drug to provide an extended release form,
wherein pharmaceutical composition has a plasma concentration profile for said drug characterized by a $pAUC_{0-4}$ that is less than 4% of $AUC_{0-inf}$ for said drug as determined by dosing said pharmaceutical composition to a subject of a fasted, single dose, human pharmacokinetic study by a $pAUC_{0-4}$ that is less than 4% of $AUC_{0-inf}$ for said drug of said plasma concentration profile.

Embodiment 84. The composition of embodiment 83, wherein said pharmaceutical composition has a plasma concentration profile for said drug characterized by a $pAUC_{4-8}$ that is less than 14% of $AUC_{0-inf}$ for said drug as determined by dosing said pharmaceutical composition to a subject of a fasted, single dose, human pharmacokinetic study.

Embodiment 85. The composition of embodiment 83, wherein said drug is selected from the group consisting of brivaracetam, lacosamide, levetiracetam, and pharmaceutically acceptable salts of any of the foregoing.

Embodiment 86. The composition of embodiment 83, wherein said drug is lacosamide.

Embodiment 87. The composition of embodiment 83, wherein said composition comprises 150 mg to 900 mg of said drug.

Embodiment 88. The composition of embodiment 83, wherein said composition comprises 200 mg to 800 mg of said drug.

Embodiment 89. The composition of embodiment 83, wherein said composition comprises 225 mg to 800 mg of said drug.

Embodiment 90. The composition of embodiment 83, wherein said composition comprises 250 mg to 800 mg of said drug.

Embodiment 91. The composition of embodiment 83, wherein at least one of said at least one excipients modifies the release of said drug to provide a delayed release form.

Embodiment 92. The composition of embodiment 83, wherein said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted pharmacokinetic study.

Embodiment 93. The composition of embodiment 83, wherein said plasma concentration profile for said drug is further characterized by an $AUC_{0-inf}$ that provides AUC equivalence to IR.

Embodiment 94. A pharmaceutical composition for oral administration to a human, comprising (i) 50 mg to 900 mg of a drug selected from the group consisting of brivaracetam, divalproex, lacosamide, levetiracetam, oxcarbazepine, vigabatrin, and pharmaceutically acceptable salts of any of the foregoing, and (ii) at least one excipient,
wherein at least one of said at least one excipients modifies the release of said drug to provide an extended release form,
wherein said pharmaceutical composition has a plasma concentration profile for said drug characterized by a $pAUC_{4-8}$ that is less than 8% of $AUC_{0-inf}$ for said drug as determined by dosing said pharmaceutical composition to a subject of a fasted, single dose, human pharmacokinetic study.

Embodiment 95. The composition of embodiment 94, wherein said drug is selected from the group consisting of brivaracetam, lacosamide, levetiracetam, and pharmaceutically acceptable salts of any of the foregoing.

Embodiment 96. The composition of embodiment 94, wherein said drug is lacosamide.

Embodiment 97. The composition of embodiment 94, wherein said composition comprises 150 mg to 900 mg of said drug.

Embodiment 98. The composition of embodiment 94, wherein said composition comprises 200 mg to 800 mg of said drug.

Embodiment 99. The composition of embodiment 94, wherein said composition comprises 225 mg to 800 mg of said drug.

Embodiment 100. The composition of embodiment 94, wherein said composition comprises 250 mg to 800 mg of said drug.

Embodiment 101. The composition of embodiment 94, wherein at least one of said at least one excipients modifies the release of said drug to provide a delayed release form.

Embodiment 102. The composition of embodiment 94, wherein said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted human pharmacokinetic study.

Embodiment 103. The composition of embodiment 94, wherein said plasma concentration profile for said drug is further characterized by an $AUC_{0-inf}$ that provides AUC equivalence to IR.

Embodiment 104. A pharmaceutical composition for oral administration to a human, comprising (i) 50 mg to 900 mg of a drug selected from the group consisting of brivaracetam, divalproex, lacosamide, levetiracetam, oxcarbazepine, vigabatrin, and pharmaceutically acceptable salts of any of the foregoing, and (ii) at least one excipient,
wherein at least one of said excipients modifies the release of said drug to provide an extended release form,
wherein said pharmaceutical composition has a plasma concentration profile for said drug characterized by a $T_{max}$ of 8 to 20 hours as determined by dosing said pharmaceutical composition to a subject of a fasted, single dose, human pharmacokinetic study, and
wherein said pharmaceutical composition has a steady state plasma concentration profile for said drug upon once daily dosing of said pharmaceutical composition characterized by a swing of 40% to 200%, as determined by dosing said pharmaceutical composition to a subject of a fasted human pharmacokinetic study.

Embodiment 105. The composition of embodiment 104, wherein said drug is selected from the group consisting of brivaracetam, lacosamide, levetiracetam, and pharmaceutically acceptable salts of any of the foregoing.

Embodiment 106. The composition of embodiment 104, wherein said drug is lacosamide.

Embodiment 107. The composition of embodiment 104, wherein said composition comprises 150 mg to 900 mg of said drug.

Embodiment 108. The composition of embodiment 104, wherein said composition comprises 200 mg to 800 mg of said drug.

Embodiment 109. The composition of embodiment 104, wherein said composition comprises 225 mg to 800 mg of said drug.

Embodiment 110. The composition of embodiment 104, wherein said composition comprises 250 mg to 800 mg of said drug.

Embodiment 111. The composition of embodiment 104, wherein at least one of said at least one excipients modifies the release of said drug to provide a delayed release form.

Embodiment 112. The composition of embodiment 104, wherein said pharmaceutical composition has a plasma concentration profile for said drug characterized by a $T_{max}$ of 12 to 20 hours as determined by dosing said pharmaceutical composition to a subject of a fasted, single dose, human pharmacokinetic study.

Embodiment 113. The composition of embodiment 104, wherein said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted human pharmacokinetic study.

Embodiment 114. The composition of embodiment 104, wherein said pharmaceutical composition has a steady state plasma concentration profile for said drug upon once daily dosing of said pharmaceutical composition characterized by a swing of 50% to 100%, as determined by dosing said pharmaceutical composition to a subject of a fasted human pharmacokinetic study.

Embodiment 115. The composition of embodiment 104, wherein said pharmaceutical composition has a steady state plasma concentration profile for said drug upon once daily dosing of said pharmaceutical composition characterized by a swing of 60% to 200%, as determined by dosing said pharmaceutical composition to a subject of a fasted human pharmacokinetic study.

Embodiment 116. The composition of embodiment 104, wherein said plasma concentration profile for said drug is further characterized by an $AUC_{0-inf}$ that provides AUC equivalence to IR.

Embodiment 117. A pharmaceutical composition for oral administration to a human, comprising (i) 50 mg to 900 mg of a drug selected from the group consisting of brivaracetam, divalproex, lacosamide, levetiracetam, oxcarbazepine, vigabatrin, and pharmaceutically acceptable salts of any of the foregoing, and (ii) at least one excipient,
wherein at least one of said at least one excipients modifies the release of said drug to provide an extended release form,
wherein said pharmaceutical composition has a plasma concentration profile for said drug characterized by a $T_{max}$ of 8 to 20 hours and a dC/dT of less than 2.2 ng/ml/hr per mg of said drug over the first 2 hours after dosing, both as determined by dosing said pharmaceutical composition to a subject of a fasted, single dose, human pharmacokinetic study.

Embodiment 118. The composition of embodiment 117, wherein said drug is selected from the group consisting of brivaracetam, lacosamide, levetiracetam, and pharmaceutically acceptable salts of any of the foregoing.

Embodiment 119. The composition of embodiment 117, wherein said drug is lacosamide.

Embodiment 120. The composition of embodiment 117, wherein said composition comprises 150 mg to 900 mg of said drug.

Embodiment 121. The composition of embodiment 117, wherein said composition comprises 200 mg to 800 mg of said drug.

Embodiment 122. The composition of embodiment 117, wherein said composition comprises 225 mg to 800 mg of said drug.

Embodiment 123. The composition of embodiment 117, wherein said composition comprises 250 mg to 800 mg of said drug.

Embodiment 124. The composition of embodiment 117, wherein at least one of said at least one excipients modifies the release of said drug to provide a delayed release form.

Embodiment 125. The composition of embodiment 117, said pharmaceutical composition has a plasma concentration profile for said drug characterized by a $T_{max}$ of 12 to 20 hours as determined by dosing said pharmaceutical composition to a subject of a fasted, single dose, human pharmacokinetic study.

Embodiment 126. The composition of embodiment 117, wherein said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted human pharmacokinetic study.

Embodiment 127. The composition of embodiment 117, wherein said pharmaceutical composition has a plasma concentration profile for said drug characterized by a dC/dT of less than 1.4 ng/ml/hr per mg of said drug over the first 2 hours after dosing as determined by dosing said pharmaceutical composition to a subject of a fasted, single dose, human pharmacokinetic study.

Embodiment 128. The composition of embodiment 117, wherein said pharmaceutical composition has a plasma concentration profile for said drug characterized by a dC/dT of less than 1.0 ng/ml/hr per mg of said drug over the first 2 hours after dosing as determined by dosing said pharmaceutical composition to a subject of a fasted, single dose, human pharmacokinetic study.

Embodiment 129. The composition of embodiment 117, wherein said plasma concentration profile for said drug is further characterized by an $AUC_{0-inf}$ that provides AUC equivalence to IR.

Embodiment 130. A pharmaceutical composition for oral administration to a human, comprising (i) 50 mg to 900 mg of a drug selected from the group consisting of brivaracetam, divalproex, lacosamide, levetiracetam, oxcarbazepine, vigabatrin, and pharmaceutically acceptable salts of any of the foregoing, and (ii) at least one excipient,
wherein at least one of said at least one excipients modifies the release of said drug to provide an extended release form,
wherein said pharmaceutical composition has a plasma concentration profile for said drug characterized by a $T_{max}$ of 8 to 20 hours and a dC/dT of less than 1 μg/ml/hr over the first 2 hours after dosing, both as determined by dosing said pharmaceutical composition to a subject of a fasted, single dose, human pharmacokinetic study.

Embodiment 131. The composition of embodiment 130, wherein said drug is selected from the group consisting of brivaracetam, lacosamide, levetiracetam, and pharmaceutically acceptable salts of any of the foregoing.

Embodiment 132. The composition of embodiment 130, wherein said drug is lacosamide.

Embodiment 133. The composition of embodiment 130, wherein said composition comprises 150 mg to 900 mg of said drug.

Embodiment 134. The composition of embodiment 130, wherein said composition comprises 200 mg to 800 mg of said drug.

Embodiment 135. The composition of embodiment 130, wherein said composition comprises 225 mg to 800 mg of said drug.

Embodiment 136. The composition of embodiment 130, wherein said composition comprises 250 mg to 800 mg of said drug.

Embodiment 137. The composition of embodiment 130, wherein at least one of said at least one excipients modifies the release of said drug to provide a delayed release form.

Embodiment 138. The composition of embodiment 130, wherein said pharmaceutical composition has a plasma concentration profile for said drug characterized by a $T_{max}$ of 12 to 20 hours as determined by dosing said pharmaceutical composition to a subject of a fasted, single dose, human pharmacokinetic study.

Embodiment 139. The composition of embodiment 130, wherein said pharmaceutical composition has a steady state plasma concentration profile for said drug upon once daily dosing of said pharmaceutical composition as determined by dosing said pharmaceutical composition characterized by a $T_{max,ss}$ of 10 to 20 hours, as determined by dosing said pharmaceutical composition to a subject of a fasted human pharmacokinetic study.

Embodiment 140. The composition of embodiment 130, wherein said pharmaceutical composition has a plasma concentration profile for said drug characterized by a dC/dT of less than 0.6 µg/ml/hr over the first 2 hours after dosing as determined by dosing said pharmaceutical composition to a subject of a fasted, single dose, human pharmacokinetic study.

Embodiment 141. The composition of embodiment 130, wherein said pharmaceutical composition has a plasma concentration profile for said drug characterized by a dC/dT of less than 0.3 µg/ml/hr over the first 2 hours after dosing as determined by dosing said pharmaceutical composition to a subject of a fasted, single dose, human pharmacokinetic study.

Embodiment 142. The composition of embodiment 130, wherein said plasma concentration profile for said drug is further characterized by an $AUC_{0-inf}$ that provides AUC equivalence to IR.

Embodiment 143. A pharmaceutical composition for oral administration to a human, comprising (i) 50 mg to 900 mg of a drug selected from the group consisting of brivaracetam, divalproex, lacosamide, levetiracetam, oxcarbazepine, vigabatrin, and pharmaceutically acceptable salts of any of the foregoing, and (ii) at least one excipient,
wherein at least one of said at least one excipients modifies the release of said drug to provide an extended release form,
wherein said pharmaceutical composition has a dissolution profile characterized by three or more of the following: (a) less than 10% release at 1 hour, (b) less than 15% release at 2 hours, (c) less than 25% release at 4 hours, (d) at least 35% at 9 hours, (e) at least 65% at 12 hours, wherein said dissolution is carried out in 900 mL simulated gastric fluid (pH 1.2) at 37±0.5° C. for the first two hours, followed by 900 mL simulated intestinal fluid (pH 6.8) at 37±0.5° C. for the subsequent four hours, followed by 900 mL phosphate buffer (pH 7.5) at 37±0.5° C. for the subsequent 18 hours, wherein all dissolution is performed in a USP Apparatus 1 (Basket), with a rotational speed of 100 rpm, and
wherein said pharmaceutical composition has a plasma concentration profile for said drug characterized by a $T_{max}$ of 8 to 20 hours as determined by dosing said pharmaceutical composition to a subject of a fasted, single dose, human pharmacokinetic study.

Embodiment 144. The composition of embodiment 143, wherein said drug is selected from the group consisting of brivaracetam, lacosamide, levetiracetam, and pharmaceutically acceptable salts of any of the foregoing.

Embodiment 145. The composition of embodiment 143, wherein said drug is lacosamide.

Embodiment 146. The composition of embodiment 143, wherein said composition comprises 150 mg to 900 mg of said drug.

Embodiment 147. The composition of embodiment 143, wherein said composition comprises 200 mg to 800 mg of said drug.

Embodiment 148. The composition of embodiment 143, wherein said composition comprises 225 mg to 800 mg of said drug.

Embodiment 149. The composition of embodiment 143, wherein said composition comprises 250 mg to 800 mg of said drug.

Embodiment 150. The composition of embodiment 143, wherein at least one of said at least one excipients modifies the release of said drug to provide a delayed release form.

Embodiment 151. The composition of embodiment 143, wherein said pharmaceutical composition has a plasma concentration profile for said drug characterized by a $T_{max}$ of 12 to 20 hours as determined by dosing said pharmaceutical composition to a subject of a fasted, single dose, human pharmacokinetic study.

Embodiment 152. The composition of embodiment 143, wherein said pharmaceutical composition has a steady state plasma concentration profile for said drug upon once daily dosing of said pharmaceutical composition characterized by a $T_{max,ss}$ of 10 to 20 hours, as determined by dosing said pharmaceutical composition to a subject of a fasted human pharmacokinetic study.

Embodiment 153. The composition of embodiment 143, wherein said plasma concentration profile for said drug is further characterized by an $AUC_{0-inf}$ that provides AUC equivalence to IR.

What is claimed is:

1. A method of treating partial onset seizures in a human patient in need thereof, comprising administering to said human patient orally, once daily, a therapeutically effective dose of a pharmaceutical composition, wherein said pharmaceutical composition comprises a plurality of pellets, each pellet comprising:
   (i) a pellet core comprising a drug, wherein the drug is lacosamide or a pharmaceutically acceptable salt thereof;
   (ii) an extended release coating comprising (a) ethylcellulose, (b) povidone or hypromellose, and (c) diethyl phthalate or medium chain triglycerides; and
   (iii) a pH dependent coating comprising at least one polymer comprising methacrylic acid or a methacrylic ester;
   wherein said pharmaceutical composition has a dissolution profile characterized by less than 2.3% release at two hours, and one or more of the following:
   (a) less than 25% release at 4 hours,
   (b) at least 35% release at 9 hours,
   (c) at least 65% release at 12 hours,
   wherein said dissolution is carried out in 900 mL simulated gastric fluid (pH 1.2) at 37±0.5° C. for the first two hours, followed by 900 mL simulated intestinal fluid (pH 6.8) at 37±0.5° C. for the subsequent four hours, followed by 900 mL phosphate buffer (pH 7.5) at 37±0.5° C. for the subsequent 18 hours, wherein all dissolution is performed in a USP Apparatus 1 (Basket), with a rotational speed of 100 rpm; and
   wherein said pharmaceutical composition has a plasma concentration profile for said drug characterized by a $T_{max}$ of 8 to 20 hours as determined by oral administration of a single dose of said pharmaceutical composition to a fasted human subject.

2. The method of claim 1, wherein said therapeutically effective dose is 100 mg to 700 mg of said drug, and said pharmaceutical composition comprises one, two, three, or four unit dosage forms.

3. The method of claim 1, wherein said pharmaceutical composition has a plasma concentration profile for said drug characterized by a $T_{max}$ of 12 to 20 hours as determined by oral administration of a single dose of said pharmaceutical composition to a fasted human subject.

4. The method of claim 1, wherein said pharmaceutical composition has a steady state plasma concentration profile for said drug upon once daily oral administration of said pharmaceutical composition characterized by a $T_{max,ss}$ of 10 to 20 hours, as determined by oral administration of said pharmaceutical composition to a fasted human subject.

5. The method of claim 1, wherein said plasma concentration profile for said drug is further characterized by the $AUC_{0-inf}$ providing AUC equivalence to the same daily dose of an immediate release form.

6. The method of claim 1, wherein said pharmaceutical composition is administered 0 to 4 hours before bedtime.

7. The method of claim 1, wherein said pharmaceutical composition is administered between the hours of 8:00 pm and 12:00 am.

8. The method of claim 1, wherein said pharmaceutical composition comprises one, two, or three unit dosage forms, wherein each unit dosage form comprises 200 mg of lacosamide.

9. The method of claim 1, wherein the administration of the pharmaceutical composition results in a reduced frequency or severity of one or more side effects of lacosamide, as compared to the administration of the same daily dose of an immediate release form of lacosamide or a pharmaceutically acceptable salt thereof.

10. The method of claim 1, wherein the administration of a single dose of the pharmaceutical composition results in a reduced frequency or severity of one or more side effects of lacosamide, as compared to the administration of the same dose of an immediate release form of lacosamide or a pharmaceutically acceptable salt thereof.

11. The method of claim 9, wherein the one or more side effects is psychosis, dizziness, cognitive deficits, headache, ataxia, somnolence, tremor, nystagmus, balance disorder, cardiac complications, vertigo, diplopia, blurred vision, nausea, vomiting, diarrhea, fatigue, gait disturbance, asthenia, depression, pruritus, neutropenia, anemia, tinnitus, constipation, dehydration, dry mouth, irritability, pyrexia, increased incidence of falls, muscle spasms, paresthesia, cognitive disorder, hypoaesthesia, dysarthria, disturbance in attention, cerebellar syndrome, confusion, or mood disorders, or any combinations thereof.

12. The method of claim 10, wherein the one or more side effects is dizziness, headache, somnolence, tremor, nystagmus, cardiac complications, diplopia, blurred vision, nausea, vomiting, diarrhea, fatigue, asthenia, pruritus, tinnitus, constipation, dehydration, dry mouth, irritability, pyrexia, muscle spasms, paresthesia, hypoaesthesia, or confusion, or any combinations thereof.

13. The method of claim 1, wherein the fasted human subject in which the $T_{max}$ is determined is a subject of a fasted, single dose, human pharmacokinetic study.

14. The method of claim 3, wherein the fasted human subject in which the $T_{max}$ is determined is a subject of a fasted, single dose, human pharmacokinetic study.

15. The method of claim 4, wherein the fasted human subject in which the $T_{max,ss}$ is determined is a subject of a fasted human pharmacokinetic study.

16. A method of treating partial onset seizures in a human patient in need thereof, comprising administering to said human patient orally, once daily, a therapeutically effective dose of a pharmaceutical composition, wherein said pharmaceutical composition comprises a plurality of pellets, each pellet comprising:
   (i) a pellet core comprising a drug, wherein the drug is lacosamide or a pharmaceutically acceptable salt thereof;
   (ii) an extended release coating comprising (a) ethylcellulose, (b) povidone or hypromellose, and (c) diethyl phthalate or medium chain triglycerides; and
   (iii) a pH dependent coating comprising at least one polymer comprising methacrylic acid or a methacrylic ester;
   wherein said pharmaceutical composition has a dissolution profile characterized by less than 2.3% release at two hours, and one or more of the following:
   (a) less than 25% release at 4 hours,
   (b) at least 35% release at 9 hours,
   (c) at least 65% release at 12 hours,
   wherein said dissolution is carried out in 900 mL simulated gastric fluid (pH 1.2) at 37±0.5° C. for the first two hours, followed by 900 mL simulated intestinal fluid (pH 6.8) at 37±0.5° C. for the subsequent four hours, followed by 900 mL phosphate buffer (pH 7.5) at 37±0.5° C. for the subsequent 18 hours, wherein all dissolution is performed in a USP Apparatus 1 (Basket), with a rotational speed of 100 rpm; and
   wherein said pharmaceutical composition has a plasma concentration profile for said drug characterized by a median $T_{max}$ of 8 to 20 hours as determined by oral administration of said pharmaceutical composition to human subjects of a fasted, single dose, human pharmacokinetic study.

17. The method of claim 1, wherein the pellet core comprises an inert core and a drug layer.

18. The method of claim 16, wherein the pellet core comprises an inert core and a drug layer.

* * * * *